US006824779B1

(12) United States Patent
Freeman et al.

(10) Patent No.: US 6,824,779 B1
(45) Date of Patent: Nov. 30, 2004

(54) METHODS FOR INHIBITING THE INTERACTION OF B7-2 WITH ITS NATURAL LIGAND

(75) Inventors: Gordon J. Freeman, Brookline, MA (US); Lee M. Nadler, Newton, MA (US); Gary S. Gray, Brookline, MA (US)

(73) Assignees: Dana-Farber Cancer Institute, Inc., Boston, MA (US); Genetics Institute, LLC, Cambridge, MA (US)

( * ) Notice: Subject to any disclaimer, the term of this patent is extended or adjusted under 35 U.S.C. 154(b) by 0 days.

(21) Appl. No.: 09/425,516

(22) Filed: Oct. 22, 1999

Related U.S. Application Data

(63) Continuation of application No. 08/479,744, filed on Jun. 5, 1995, now Pat. No. 6,084,067, which is a continuation-in-part of application No. 08/280,757, filed on Jul. 26, 1994, now Pat. No. 6,130,316, which is a continuation-in-part of application No. 08/109,393, filed on Aug. 19, 1993, now abandoned, which is a continuation-in-part of application No. 08/101,624, filed on Jul. 26, 1993, now Pat. No. 5,942,607, which is a continuation-in-part of application No. 08/147,773, filed on Nov. 3, 1993, now abandoned.

(51) Int. Cl.$^7$ ............................................. A61K 39/395
(52) U.S. Cl. ................................ 424/153.1; 424/130.1; 424/133.1; 424/141.1; 424/143.1; 424/144.1; 424/173.1; 530/387.1; 530/387.3; 530/388.1; 530/388.2; 530/388.22; 530/388.7; 530/388.73
(58) Field of Search .......................... 424/130.1, 133.1, 424/144.1, 173.1; 530/387.1, 388.2, 388.73

(56) References Cited

U.S. PATENT DOCUMENTS

| 5,116,964 A | | 5/1992 | Capon et al. ............... 536/23.5 |
| 5,434,131 A | | 7/1995 | Linsley et al. .................. 514/2 |
| 5,434,141 A | | 7/1995 | Schafer et al. ................ 514/53 |
| 5,747,034 A | * | 5/1998 | de Boer et al. |
| 5,770,197 A | | 6/1998 | Linsley et al. ........... 424/134.1 |
| 5,869,050 A | | 2/1999 | de Boer et al. .......... 424/156.1 |
| 6,071,716 A | | 6/2000 | Freeman et al. ........... 435/69.1 |
| 6,090,914 A | * | 7/2000 | Linsley et al. |

FOREIGN PATENT DOCUMENTS

| WO | WO 92/00092 | 1/1992 |
| WO | WO 93/00431 | 1/1993 |
| WO | WO 94/12520 | 6/1994 |
| WO | WO 95/03408 | 2/1995 |
| WO | WO 95/05464 | 2/1995 |
| WO | WO 95/06738 | 3/1995 |

OTHER PUBLICATIONS

Perrin et al. J. Neuroimmunol. 65:31–39 (1996).*
Blaear et al. J. Immunol. 157:3250–3254 (1996).*
Yi–Qun et al. International Immunology 8:37–44 (1996).*
Debets et al. Immunology Today 15:455–458(1994).*
Coyle et al. Nature Immunology 2:203–209 (2000).*
Skolnick et al. Tibtech 18:34–39 (2000).*
Li et al. Pajas 77:3211–3214 (1980).*
Lederman et al. Molecular Immunology 28:1171–1181 (1991).*
Kahan Current Opinion in Immunology 4:553–560(1992).
Edgington Biotechnology 10:383–389 (1992).
Ngo et al. in The Protein Folding Problem and Tertiary Structure Prediction. Menz et al. (eds.) Birkhawer Boyton 1994.
Sturmhoefer et al. Cancer Research 59:4964–4972 (1999).
Azuma, M. et al., "B70 antigen is a second ligand for CTLA–4 and CD28," *Nature* 366:76–79 (1993).
Azuma, M. et al., "Involvement of CD28 in MHC–unrestricted cytotoxicity mediated by a human natural killer leukemia cell line," *J. Immunol.* 149(4):1115–1123 (1992).
Baskar, S. et al. (1993) "Constitutive Expression of B7 Restores Immunogenicity of Tumor Cells Expressing Truncated Major Histocompatibility Complex Class II Molecules" *Proc. Natl. Acad. Sci. USA* 90:5687–5690.
Bateman, W.J. et al. (1991) "Inducibilty of Class II Major Histocompatability Complex Antigens by Interferon γ Is Associated with Reduced Tumorigenicity in C3H Mouse Fibroblasts Transformed by v–Ki–ras" *J. Exp. Med.* 173:193–196.
Blazar, B.R., "In vivo blockade of CD28/CTLA4: B7/BB1 interaction with CTLA4–Ig reduces lethal murine graft–versus–host disease across the major histocompatibility complex barrier in mice," *Blood* 83(12):3815–3825 (1994).
Boussiotis, V.A. et al. (1993) "Activated Human B Lymphocytes Express Three CTLA–4 Counterreceptors that Costimulate T–Cell Activation" *Proc Natl. Acad. Sci. USA* 90: 11059–11063.
Chen, L. et al. (1992) "Costimulation of Antitumor Immunity by the B7 Counterreceptor For the T Lymphocyte Molecules CD2B and CTLA–4" *Cell* 71:1093–1102.
Classon et al., "The hinge region of the CD8 alpha chain: structure, antigenicity, and utility in expression of immunoglobulin superfamily domains," *Int. Immunol.* 4(2):215–225 (1992).

(List continued on next page.)

*Primary Examiner*—Phillip Gambel
(74) *Attorney, Agent, or Firm*—Lahive & Cockfield LLP; Amy E. Mandragouras; Megan E. Williams

(57) ABSTRACT

The present invention relates to, inter alia, methods for inhibiting the interaction of the B-lymphocyte antigen, B7-2, with its natural ligand on the surface of an immune cell are disclosed. The methods comprise contacting the immune cell with an agent which inhibits B7-2 binding with its natural ligand, to thereby inhibit the interaction. Examples of such agents are provided, and include a soluble form of B7-2, an antibody that recognized B7-2. The method may also include contacting the immune cell with an agent that blocks the interaction of B7-1 with its natural ligand. Further, the method may include contacting the immune cell with an immunomodulating agent, for example, an antibody reactive with CD28, an antibody reactive with CTLA4, an antibody reactive with a cytokine, a CTLA4Ig fusion protein, a CD28Ig fusion protein, and an immunosuppressive drug. Both in vivo and in vitro applications of the method are disclosed.

47 Claims, 34 Drawing Sheets

OTHER PUBLICATIONS

Clements, V.K. et al. (1992) "Invariant Chain Alters The Malignant Phenotype of MHC Class II+ Tumor Cells" *J. of Immunology* 149:2391–2396.

Cole, G.A. et al. (1991) "Rejection of Allogeneic Tumor Is Not Determined by Host Responses to MHC Class I Molecules and is Mediated By CD4−CD8+ T Lymphocytes That Are Not Lytic for the Tumor" *Cellular Immunology* 134:480–490.

Fearon, E.R. et al. (1990) "Interleukin–2 Production By Tumor Cells Bypasses T Helper Function in the Generation of An Antitumor Response" *Cell* 60:397–403.

Freedman, A. S. et al. (1987) "B7, A B Cell–Restricted Antigen That Identifies Preactivated B Cells" *Journal of Immunology* 139(10): 3260–3267.

Freeman et al., "Structure, Expression, and T Cell Costimulatory Activity of the Murine Homologue of the Human B Lymphocyte Activation Antigen B7" Journal Experimental Medicine, vol. 174, pp. 625–631, (1991).

Freeman, G. J. et al. (1989) "B7, A New Member of the Ig Superfamily with Unique Expression on Activated and Neoplastic B Cells" *Journal of Immunology* 143(8): 2714–2722.

Freeman, G., et al., "Cloning of B7–2; A CTLA–4 Counter-Receptor that Costimulates Human T Cell Proliferation," Science, vol. 262, 909–911 (1993).

Galvin, F. et al. (1992) "Murine B7 Antigen Provides A Sufficient Costimulatory Signal For Antigen–Specific and MHC–Restricted T Cell Activation" *J. Immunology* 149:3802–3808.

Gimmi et al., "B–cell surface antigen B7 provides a costimulatory signal that induces T cells to proliferate and secrete interleukin 2" Proceedings of the National Academy of Sciences, vol. 88, pp. 6575–6579, (1991).

Gimmi, C., et al., "Human T–cell Clonal Anergy is Induced by Antigen Presentation in the Absence of B7 Costimulation," Proc. Natl. Acad. Sci. USA, vol. 90, 6586–6590 (1993).

Guo, Y. et al. (1995) "Mutational Analysis and an Alternatively Spliced Product of B7 Defines Its CD28/CTLA4–binding Site on Immunoglobulin C–like Domain" *J. Exp. Med.*, 181:1345–1355.

Harding, F. and Allison, J., "CD28–B7 Interactions Allow the Induction of CD8.sup.+ Cytotoxic T Lymphocytes in the Absence of Exogeneous Help," J. Exp. Med., vol. 177, 1791–1796 (1993).

Harding, F., et al., "CD28–medicated Signalling Co–stimulates Murine T Cells and Prevents Induction of Anergy in T–cell Clones," Nature, vol. 356, 607–609 (1992).

Hollenbaugh and A. Aruffo (1992) "Construction of Immunoglobulin Fusion Proteins" *Immunology Suppl. 4*, Unit 10.19: 1–11.

Inobe, M. et al. (1994) "Identification of an Alternatively Spliced Form of the Murine Homologue of B7", *Biochemical and Biophysical Research Communication* 200(1):443–449.

James, R.F.L. "The effect of class II gene transfection on the tumourigenicity of the H–2K–negative mouse leukaemia cell line K36.16," *Immunology*. Feb. 1991;72(2):213–8.

June, C.H. et al., "The B7 and CD28 receptor families," *Immunol. Today*, Jul. 1994;15(7):321–31.

Lanier, L.L. et al., "CD80 (B7) and CD86 (B70) provide similar costimulatory signals for T cell proliferation, cytokine production, and generation of CTL," *J. Immunol.* Jan. 1, 1995;154(1):97–105.

Lenschow, D.J. et al., "Expression and functional significance of an additional ligand for CTLA–4," *Proc. Natl. Acad. Sci. U. S. A.* Dec. 1, 1993;90(23):11054–8.

Lenschow, D.J. et al., "Long–term survival of xenogeneic pancreatic islet grafts induced by CTLA4lg," *Science*, Aug. 7, 1992;257(5071):789–92.

Linsley, P.S. et al., "Immunosuppression in vivo by a soluble form of the CTLA–4 T cell activation molecule," *Science*, Aug. 7, 1992;257(5071):792–5.

Linsley, P.S. et al., "Binding of the B cell activation antigen B7 to CD28 costimulates T cell proliferation and interleukin 2 mRNA accumulation," *J. Exp. Med.*, Mar. 1, 1991;173(3):721–30.

Lin, H. et al., "Long–term acceptance of major histocompatibility complex mismatched cardiac allografts induced by CTLA4lg plus donor–specific transfusion," *J. Exp. Med.*, Nov. 1, 1993;178(5):1801–6.

Nabavi, N. et al., "Signalling through the MHC class II cytoplasmic domain is required for antigen presentation and induces B7 expression," *Nature* Nov. 19, 1992;360(6401):266–8.

Ostrand–Rosenberg, S. et al., "Costimulation through murine B7 molecule restores immunogenicity of autologous tumor cells expressing truncated MHC class II molecules," *J. Cell Biochem. Suppl.* (Abstract HZ 228) (1993) p. 71.

Ostrand–Rosenberg, S. et al., "Abrogation of tumorigenicity by MHC class II antigen expression requires the cytoplasmic domain of the class II molecule," *J. Immunol.*, Oct. 1, 1991;147(7):2419–22.

Ostrand–Rosenberg, S. et al., "Rejection of mouse sarcoma cells after transfection of MHC class II genes," *J. Immunol.*, May 15, 1990;144(10):4068–71.

Reiser, H. et al., "Murine B7 antigen provides an efficient costimulatory signal for activation of murine T lymphocytes via the T–cell receptor/CD3 complex," *Proc. Natl. Acad. Sci. U. S. A.*, Jan. 1, 1992;89(1):271–5.

Schultz, K. et al., "The role of B cells for in vivo T cell responses to a Friend virus–induced leukemia," *Science*, Aug. 24, 1990;249(4971):921–3.

Schwartz, "A cell culture model for T lymphocyte clonal anergy," *Science* Jun. 15, 1990;248(4961):1349–56.

Southern, S.O. et al., "Induction of the H–2 D antigen during B cell activation," *J. Immunol.* Jan. 1, 1989;142(1):336–42.

Tan, P. et al., "Induction of alloantigen–specific hyporesponsiveness in human T lymphocytes by blocking interaction of CD28 with its natural ligand B7/BB1," *J. Exp. Med.* 1993 ;177(1):165–73.

Townsend, S.E. et al. (1993) "Expression of the T cell costimulatory ligand B7 by a melanoma induces rejection mediated by direct activation of CD8+ T cells," *J Cell Biochem Supp.* 136 (abstr.).

Townsend, S. E. et al., "Emergency hospital admissions and readmissions of patients aged over 75 years and the effects of a community–based discharge scheme," *Health Trends* 1992;24(4):136–9.

Townsend, S. E. et al., "Tumor rejection after direct costimulation of CD8+ T cells by B7–transfected melanoma cells," *Science*, Jan. 15, 1993;259(5093):368–70.

Travis, J. "A stimulating new approach to cancer treatment," *Science* Jan. 15, 1993;259(5093):310–1.

Van der Bruggen, P. et al., "A gene encoding an antigen recognized by cytolytic T lymphocytes on a human melanoma," *Science* Dec. 13, 1991;254(5038):1643–7.

Chen, C., et al., "Monoclonal Antibody 2D10 Recognizes a Novel T Cell Costimulatory Molecule on Activated Murine B Lymphocytes", *J. Immunol. 152*: 2105–2114 (1994).

P, Engel, et al., The B7–2 (B70) CostimulatoryMolecule Expressed by Monocytes and Activated B. Lymphocytes Is the CD86 Differentiation Antigen, Blood, vol. 84(5) 1994: pp 1402–1407.

Freeman, G., et al., "Murine B7–2, an Alternative CTLA4 Counter–receptor that Costimultes T Cell Proliferation and Interleukin 2 Production", *J. Exp. Med. 178*: 2185–2192 (1993).

Freeman, G., et al., "Uncovering of Functional Alternative CTLA–4 Counter–Receptor in B7–Deficient Mice", *Science 262*: 907–909 (1993).

Hathcock, K., et al., "Identification of an Alternative CTLA–4 Ligand Costimulatory for T Cell Activation", *Science 262*: 905–907 (1993).

Nozawa et al., A Novel Monoclonal Antibody (FUN–1) Identifies An Activation Antigen In Cells of The B–Cell Lineage and Reed–Sternberg Cells, Journal of Pathology, vol. 169:309–315 (1993).

Powers, G., et al., "Expression and Functional Analysis of Murine B7 Delineated by a Novel Monoclonal Antibody", *Cell. Immunol. 153*: 298–311 (1994).

* cited by examiner

FIG. 8A

```
  1  CACAGGGTGAAAGCTTGCTTCTCTGCTGCTGTAACAGGACTAGCACAGAGACACGGATGAGTGGGTC     70

71  ATTTCCAGATATTAGGTCACAGCAGAAGCAGCCAAAATGGATCCCCAGTGCACTATGGGACTGAGTAACA   140
                                  M  D  P  Q  C  T  M  G  L  S  N            11

141  TTCTCTTTGTGATGGCCTTCCTGCTCTCTGGTGCTGCCCCTCTGAAGATTCAAGCTTATTTCAATGAGAC   210
 12   I  L  F  V  M  A  F  L  L  S  G  A  A  P  L  K  I  Q  A  Y  F  N  E  T   35
                                            ^                                #

211  TGCAGACCTGCCATGCCAATTTGCAAACTCTCAAACCAAGCCTGAGTGAGCTAGTAGTATTTTGGCAG    280
 36   A  D  L  P  C  Q  F  A  N  S  Q  N  Q  S  L  S  E  L  V  V  F  W  Q     58
                  *                    #

281  GACCAGGAAAACTTGGTTCTGAATGAGGTATACTTAGGCAAAGAGAAATTTGACAGTGTTCATTCCAAGT  350
 59   D  Q  E  N  L  V  L  N  E  V  Y  L  G  K  E  K  F  D  S  V  H  S  K    81

351  ATATGGGCCGCACAAGTTTTGATTCGGACAGTTGGACCCTGAGACTTCACAATCTTCAGATCAAGGACAA  420
 82   Y  M  G  R  T  S  F  D  S  D  S  W  T  L  R  L  H  N  L  Q  I  K  D  K  105
```

FIG. 8B

```
421  GGGCTTGTATCAATGTATCATCATCACAAAAGCCCACAGGAATGATTCGCATCCACCAGATGAATTCT   490
106    G  L  Y  Q  C  I  I  H  H  K  K  P  T  G  M  I  R  I  H  Q  M  N  S     128
                  *
491  GAACTGTCAGTGCTGCTTGCTAACTTCAGTCAACCTGAAATAGTACCAATTTCTAATATAACAGAAAATGTGT   560
129    E  L  S  V  L  A  N  F  S  Q  P  E  I  V  P  I  S  N  I  T  E  N  V     151
                        #
561  ACATAAATTTGACCTGCTCATCTATACACGGTTACCCAGAACCTAAGAAGATGAGTGTTTGCTAAGAAC   630
152    Y  I  N  L  T  C  S  S  I  H  G  Y  P  P  E  P  K  K  M  S  V  L  L  R  T   175
                  #                                                            *
631  CAAGAATTCAACTATCGAGTATGATGGTATTATGCAGAAATCTCAAGATAAGTCACAGAACTGTACGAC   700
176    K  N  S  T  I  E  Y  D  G  I  M  Q  K  S  Q  D  N  V  T  E  L  Y  D     198
              #
701  GTTTCCATCAGCTGTGTCTGTGTTCATTCCCTGATGTTACGAGCAATATGACCATCTTCTGTATTCTGGAAA   770
199    V  S  I  S  L  S  V  S  F  P  D  V  T  S  N  M  T  I  F  C  I  L  E     221
                                                #
771  CTGACAAGACGCGGCTTTATCTTCACCTTTCTCTATAGAGCTTGAGGACCCTCAGCCTCCCCCAGACCA   840
222    T  D  K  T  R  L  L  S  S  P  F  S  I  E  L  E  D  P  Q  P  P  P  D  H   245
                                                          *
```

FIG. 8C

```
841   CATTCCTTGGATTACAGCTGTACTTCCAACAGTTATTATATGTGTGATGGTTTTCTGTCTAATTCTATGG   910
246    I  P  W  I  T  A  V  L  P  T  V  I  I  C  V  M  V  F  C  L  I  L  W    268

911   AATGGAAGAAGAAGAAGCGGCCTCGCAACTCTTATAAATGTGGAACCAACACAATGGAGAGGGAAGAGA   980
269    K  W  K  K  K  K  R  P  R  N  S  Y  K  C  G  T  N  T  M  E  R  E  E    291

981   GTGAACAGACCAAGAAAAGAGAAAATCCATATACCTGAAAGATCTGATGAAGCCCAGCGTGTTTTAA   1050
292    S  E  Q  T  K  K  R  E  K  I  H  I  P  E  R  S  D  E  A  Q  R  V  F  K   315

1051  AAGTTCGAAGACATCTTCATGCGACAAAAGTGATACATGTTTTAATTAAAGAGTAAAGCCCAAAAAAAA   1120
316    S  S  K  T  S  S  C  D  K  S  D  T  C  F  *                             329
```

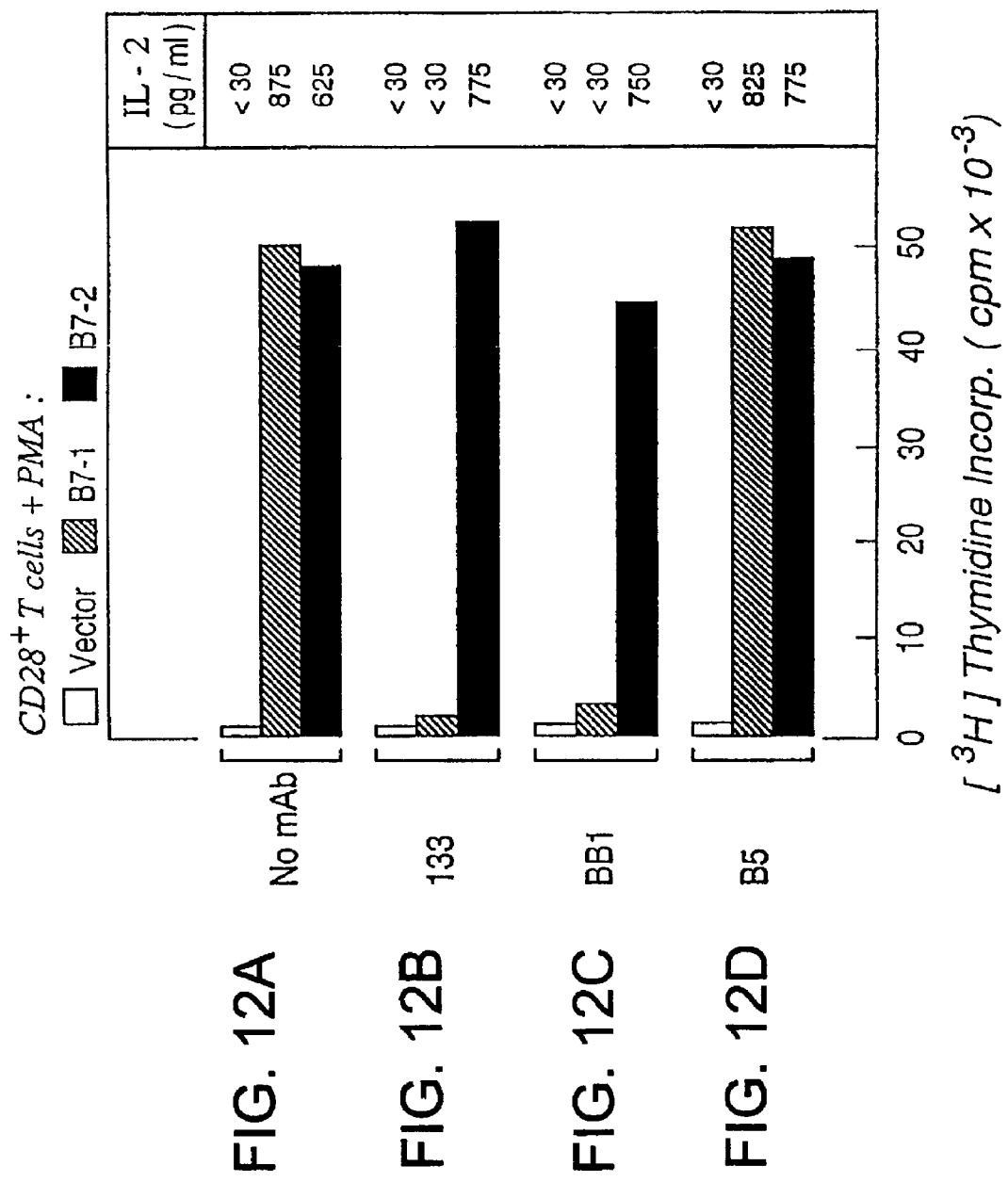

FIG. 13A

```
hB7-1    1 M..GHTRRQGTSPSKCPYLNFFQLLV.LAGLSHFCSGV.IHVTKEVKEVA         46
            |   |                    |  ||| |  |   |  |||| |
hB7-2    1 M.....DPQCTMGLSN......ILFVMAFLLSGA...APLKIQAYFNETA         36
            |                            |  |||
mB7      1 MACNCQLMQDTPLLKFPCPRLILFVLLIRLSQVSSDVDEQLSKSVKDKV          50 hB7-1   47 TLSCGHNVSVEE.LAQTRIYWQKEKKMVLT.MMSGDMNI...WPEYKNRT         91
            ||| |  |    |   ||||| |  | |  |   |     ||||||||
hB7-2   37 DLPCQFANSQNQSLSELVVFWQDQENLVLNEVYLGKEKFDSVHSKYMGRT         86
             |||      |||    |||| |    ||     | |      |  ||
mB7     51 LLPCRY.NSPHEDESEDRIYWQKHDKVVLS.VIAGKLKV...WPEYKNRT         95 hB7-1   92 IFDITNNLSIVILALRPSDEGTYECVVLKYEKDAFKREHLAEVTLSVKAD        141
            ||     || |  |    | |||  | |      |     |  ||  |
hB7-2   87 SFD.SDSWTLRLHNLQIKDKGLYQCIIHHKKPTGMIRIHQMNSELSVLAN        135
             ||  |    |  |    | || |  |     |   | |   |||| |
mB7     96 LYDNTT.YSLIILGLVLSDRGTYSCVVQKKERGTYEVKHLALVKLSIKAD        144 hB7-1  142 FPTPSISDFEIPTSNI.RRIICSTSGGFPEPH....LSWLENGEELNAIN        186
             |||| |   |       ||| ||||||| |     ||||||       
hB7-2  136 FSQPEIVPISNITENVYINLTCSSIHGYPEPKKMSVLLRTKNSTIEYDGI        185
            ||||  |    |        | ||||||||     |  |||  |     
mB7    145 FSTPNITESGNPSADT.KRITCFASGGFPKPR....FSWLENGRELPGIN        189
```

FIG. 13B

```
hB7-1  187 TTVSQDPETELYAVSSKLDFN...MTTNHSFMCLIKYGHLRVNQTFNWNT 233
           |||  |||| ||  |          |  ||| | |||||||  ||| |||
hB7-2  186 MQKSQDNVTELYDVSISLSVSFPDVTSNMTIFCILETDKTRLLSSPFSIE 235
           |||  ||||  |           |  ||| ||||||||   | ||
mB7    190 TTISQDPESELYTISSQLDFN...TTRNHTIKCLIKYGDAHVSEDFTWEK 236 hB7-1  234 TKQEHF.PDNLLPSWAITLISVNGIFVICCLTYCFAPRCRERRRNERLRR 282
                    |   |||| |  |  || |||| | |
hB7-2  236 .LEDPQPPPDHIPWITAVLP....TVIICVMVFCLILWKKKKRPRNSY  280
                     |     |        | ||  |     | |  |  |
mB7    237 PPEDPPPDSKNTLVLFGAGFGAVITVVIVVIIKCFCKHRSCFRRNEA.SR 285 hB7-1  283 ESVRPV*                                          288 hB7-2  281 KCG...TNTMEREESEQTKKRREKIHIPERSDEAQRVFKSSKTSSCDKSDT 327
                     |||
mB7    286 ETNNSLTFGPEEALAEQTVFL*                            306 hB7-2  328 CG*                                              329
```

FIG. 14A

```
     CCCACGCGTCCGGGAGCAAGCAGACGGGTAAGAGTGGCTCCTGTAGGCAGCACGGACTTG
1    ------+---------+---------+---------+---------+---------+ 60
     GGGTGCGCAGGCCCTCGTTCGTCTGCCCATTCTCACCGAGGACATCCGTCGTGCCTGAAC

AACAACCAGACTCCCTGTAGACGTGTTCCAGAACTTACGGAAGCACCCACGATGGACCCCA
61   ------+---------+---------+---------+---------+---------+ 120
     TTGTTGGTCTGAGGGACATCTGCACAAGGTCTTGAATGCCTTCGTGGGTGCTACCTGGGGT
                                                       M  D  P  -

GATGCACCATGGGCTTGGCAATCCTTATCTTTGTGACAGTCTTGCTGATCTCAGATGCTG
121  ------+---------+---------+---------+---------+---------+ 180
     CTACGTGGTACCCGAACCGTTAGGAATAGAAACACTGTCAGAACGACTAGAGTCTACGAC
     R  C  T  M  G  L  A  I  L  I  F  V  T  V  L  L  I  S  D  A  V  -

TTTCCGTGGAGACGCAAGCTTATTTCAATGGACTGCATATCTGCCGTGCCCATTTACAA
181  ------+---------+---------+---------+---------+---------+ 240
     AAAGGCACCTCTGCGTTCGAATAAAGTTACCCTGACGTATAGACGGCACGGGTAAATGTT
     S  V  E  T  Q  A  Y  F  N  G  T  A  Y  L  P  C  P  F  T  K  -

AGGCTCAAAAACATAAGCCTGAGTGAGCTGGTAGTATTTTGGCAGGACCAGCAAAAGTTGG
241  ------+---------+---------+---------+---------+---------+ 300
     TCCGAGTTTTTGTATTCGGACTCACTCGACCATCATAAAACCGTCCTGGTCGTTTTCAACC
     A  Q  N  I  S  L  S  E  L  V  V  F  W  Q  D  Q  Q  K  L  V  -
```

FIG. 14B

```
     TTCTGTACGAGCACTATTGGGCACAGAGAAACTGATAGTGTGAATGCCAAGTACCTGG
301  ----+----+----+----+----+----+----+----+----+----+----+----+ 360
     AAGACATGCTCGTGATAACCCGTGTCTCTTGACTATCACACTTACGGTTCATGGACC
      L   Y   E   H   Y   L   G   T   E   K   L   D   S   V   N   A   K   Y   L   G   -

GCCGCACGAGCTTTGACAGGAACAACTGTCTACGACTTCACAATGTTCAGATCAAGG
361  ----+----+----+----+----+----+----+----+----+----+----+----+ 420
     CGGCGTGCTCGAAACTGTCCTTGTTGACAGGATGCTGAAGTGTTACAAGTCTAGTTCC
      R   T   S   F   D   R   N   N   W   T   L   R   L   H   N   V   Q   I   K   D   -

ACATGGGCTCGTATGATTGTTTATACAAAAAAGCCACCACAGGATCAATTATCCTCC
421  ----+----+----+----+----+----+----+----+----+----+----+----+ 480
     TGTACCCGAGCATACTAACAAATATGTTTTTTCGGTGGTGTCCTAGTTAATAGGAGG
      M   G   S   Y   D   C   F   I   Q   K   K   P   P   T   G   S   I   I   L   Q   -

AACAGACATTAACAGAACTGTCAGTGATCGCCAACTTCAGTGAACCTGAAATAAAACTGG
481  ----+----+----+----+----+----+----+----+----+----+----+----+ 540
     TTGTCTGTAATTGTCTTGACAGTCACTAGCGGTTGAAGTCACTTGGACTTTATTTTGACC
      Q   T   L   I   T   E   L   S   V   I   A   N   F   S   E   P   E   I   K   L   A   -

CTCAGAATGTAACAGGAAATTCTGGCATAAATTTGACCTGCACGTCTAAGCAAGGTCACC
541  ----+----+----+----+----+----+----+----+----+----+----+----+ 600
     GAGTCTTACATTGTCCTTTAAGACCGTATTTAAACTGGACGTGCAGATTCGTTCCAGTGG
      Q   N   V   T   G   N   S   G   I   N   L   T   C   T   S   K   Q   G   H   P   -
```

FIG.14C

```
601  CGAAACCTAAGAAGATGTATTTCTGATAATCAACTAATGAGTATGGTGATAACA
     ----+----|----+----|----+----|----+----|----+----|----+----|  660
     GCTTTGGATTCTTCTACATAAAGACTATTAGTTGATTACTCATACCACTATTGT

K  P  K  K  M  Y  F  L  I  T  N  S  T  N  E  Y  G  D  N  M  -

661  TGCAGATATCACAAGATAATGTCACAGAACTGTTCAGTATCTCCAACAGCCTCTCTCTTT
     ----+----|----+----|----+----|----+----|----+----|----+----|  720
     ACGTCTATAGTGTTCTATTACAGTGTCTTGACAAGTCATAGAGGTTGTCGGAGAGAAA

Q  I  S  Q  D  N  V  T  E  L  F  S  I  S  N  S  L  S  L  S  -

721  CATTCCCGGATGGTGTGTGGCATATGACCGTTGTGTGTTCTGAAACGGAGTCAATGA
     ----+----|----+----|----+----|----+----|----+----|----+----|  780
     GTAAGGGCCTACCACACACCGTATACTGGCAACACACAAGACCTTTGCCTCAGTTACT

F  P  D  G  V  W  H  M  T  V  V  C  V  L  E  T  E  S  M  K  -

781  AGATTTCCTCCAAACCTCTCAATTCACTCAAGAGTTTCCATCTCCTCAAACGTATTGA
     ----+----|----+----|----+----|----+----|----+----|----+----|  840
     TCTAAAGGAGGTTTGGAGAGTTAAAGTGAGTTCTCAAAGGTAGAGGAGTTTGCATAACCT

I  S  S  K  P  L  N  F  T  Q  E  F  P  S  P  Q  T  Y  W  K  -

841  AGGAGATTACAGCTTCAGTTACTGTGGCCCTCCTCCTTGTGATGCTGCTCATCATTGTAT
     ----+----|----+----|----+----|----+----|----+----|----+----|  900
     TCCTCTAATGTCGAAGTCAATGACACCGGGAGGAGGAACACTACGACGAGTAGTAACATA

```
       GTCACAAGAAGCCGAATCAGCTAGCAGCCCAGCAACACAGCCTCTAAGTTAGAGCGGG
901    ---------+---------+---------+---------+---------+---------+  960
       CAGTGTTCTTCGGCTTAGTCGATCGTCGGGTCGTTGTGTCGAGATTCAATCTCGCCC

H  K  K  P  N  Q  P  S  R  P  S  N  T  A  S  K  L  E  R  D  -

ATAGTAACGCTGACAGAGACTATCAACCTGAAGGAACTTGAACCCCAAATTGCTTCAG
961    ---------+---------+---------+---------+---------+---------+ 1020
       TATCATTGCGACTGTCTCTGATAGTTGGACTTCCTTGAACTTGGGGTTTAACGAAGTC

S  N  A  D  R  E  T  I  N  L  K  E  L  E  P  Q  I  A  S  A  -

CAAAACCAAATGCAGAGTGAAGGCAGTGAGAGCCTGAGGAAAGAGTTAAAAATTGCTTTG
1021   ---------+---------+---------+---------+---------+---------+ 1080
       GTTTTGGTTTACGTCTCACTTCCGTCACTCTCGGACTCCTTTCTCAATTTTTAACGAAAC

K  P  N  A  E  *

CCTGAAATAAGAAGTGCAGAGTTTCTCAGAATTCAAAAATGTTCTCAGCTGATTGGAATT
1081   ---------+---------+---------+---------+---------+---------+ 1140
       GGACTTTATTCTTCACGTCTCAAAGAGTCTTAAGTTTTTACAAGAGTCGACTAACCTTAA

CTACAGTTGAATAATTAAAGAAC
1141   ---------+---------+--- 1163
       GATGTCAACTTATTAATTTCTTG
```

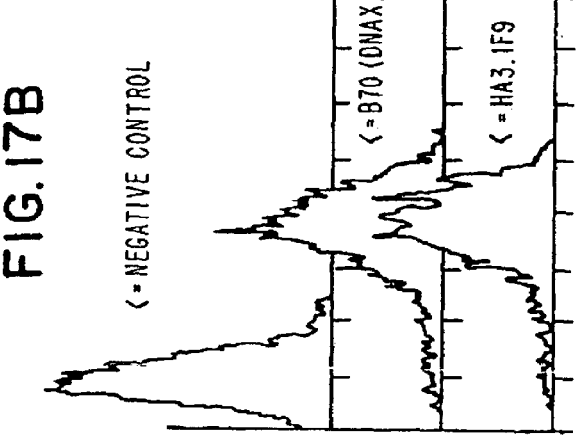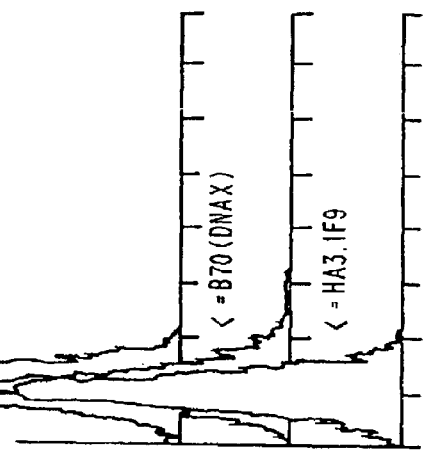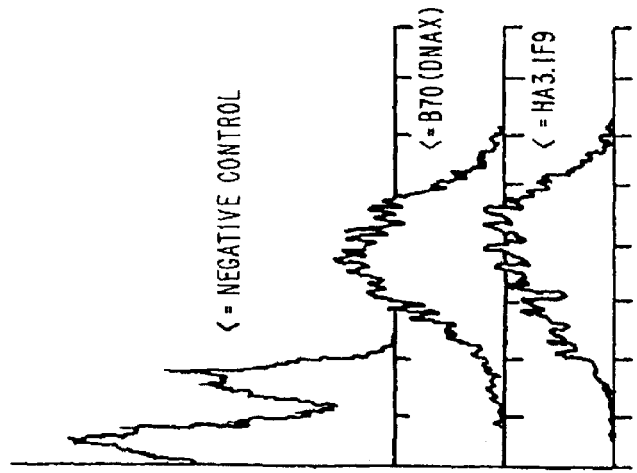

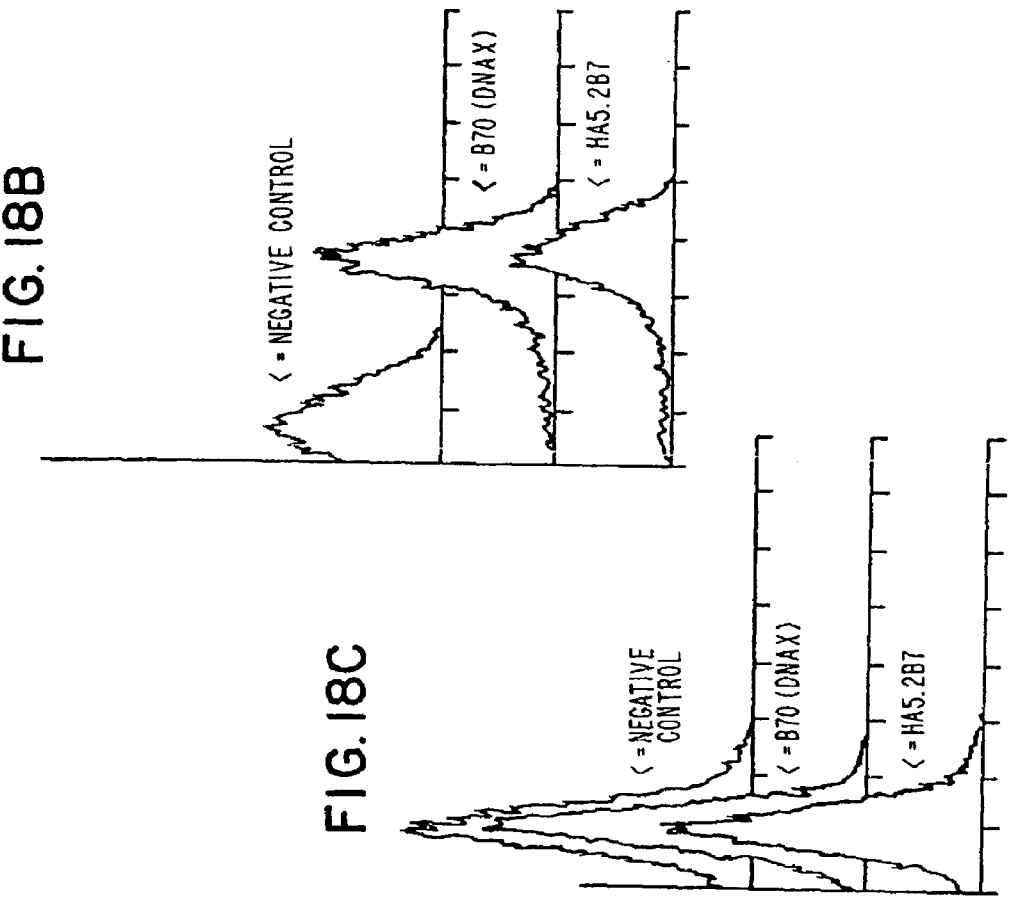
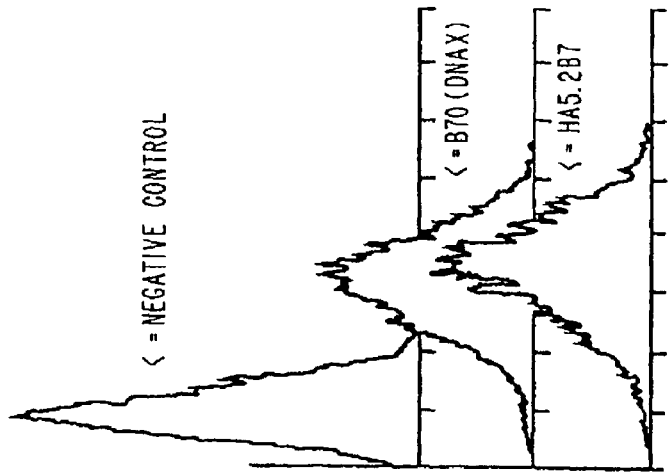
FIG. 18A
FIG. 18B
FIG. 18C

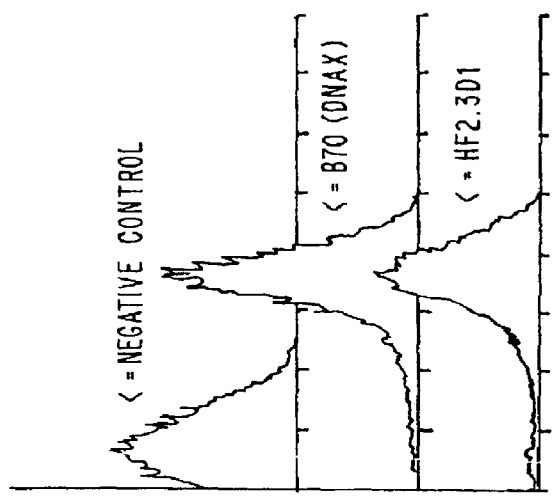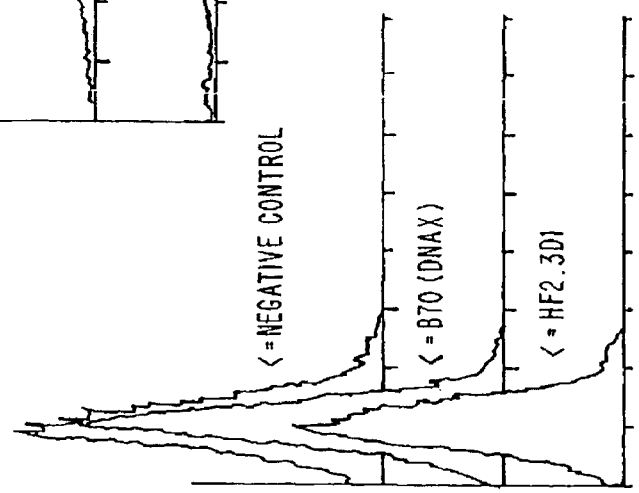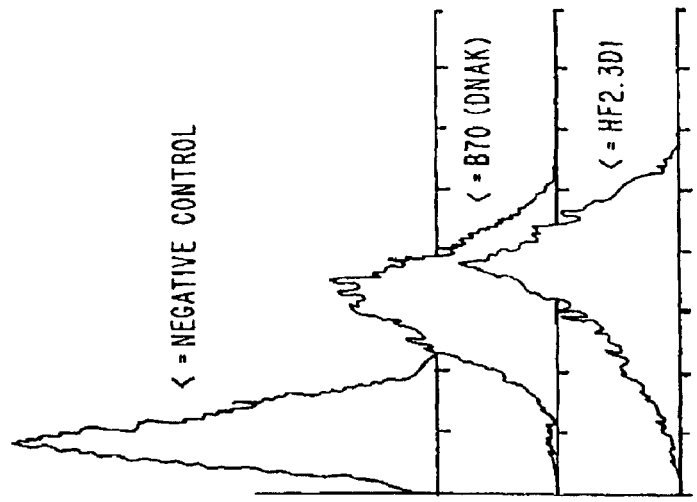

METHODS FOR INHIBITING THE INTERACTION OF B7-2 WITH ITS NATURAL LIGAND

RELATED APPLICATIONS

This application is a continuation application of U.S. Ser. No. 08/479,744, filed on Jun. 5, 1995, now U.S. Pat. No. 6,084,067, which is a continuation-in-part of U.S. Ser. No. 08/280,757, entitled "Novel CTLA4/CD28 Ligands and Uses Therefor" filed Jul. 26, 1994, now U.S. Pat. No. 6,130,316, which is a continuation-in-part of U.S. Ser. No. 08/109,393, entitled "Novel CTLA4/CD28 Ligands and Uses Therefor" filed Aug. 19, 1993, now abandoned, which is a continuation-in-part of U.S. Ser. No. 08/101,624, also entitled "Novel CTLA4/CD28 Ligands and Uses Therefor", filed Jul. 26, 1993, now U.S. Pat. No. 5,942,607. U.S. Ser. No. 08/479,744, now U.S. Pat. No. 6,084,067, is also a continuation-in-part of U.S. Ser. No. 08/147,773, entitled "Tumor Cells Modified To Express B7-2 And B7-3 With Increased Immunogenicity And Uses Therefor" filed Nov. 3, 1993, now abandoned. The contents of each of these applications is incorporated herein by reference.

GOVERNMENT FUNDING

Work described herein was supported under CA-40216-08 awarded by the National Institutes of Health. The U.S. government therefore may have certain rights in this invention.

BACKGROUND OF THE INVENTION

To induce antigen-specific T cell activation and clonal expansion, two signals provided by antigen-presenting cells (APCs) must be delivered to the surface of resting T lymphocytes (Jenkins, M. and Schwartz, R. (1987) *J. Exp. Med.* 165, 302–319; Mueller, D. L., et al. (1990) *J. Immunol.* 144, 3701–3709; Williams, I. R. and Unanue, E. R. (1990) *J. Immunol.* 145, 85–93). The first signal, which confers specificity to the immune response, is mediated via the T cell receptor (TCR) following recognition of foreign antigenic peptide presented in the context of the major histocompatibility complex (MHC). The second signal, termed costimulation, induces T cells to proliferate and become functional (Schwartz, R. H. (1990) *Science* 248, 1349–1356). Costimulation is neither antigen-specific, nor MHC restricted and is thought to be provided by one or more distinct cell surface molecules expressed by APCs (Jenkins, M. K., et al. (1988) *J. Immunol.* 140, 3324–3330; Linsley, P. S., et al. (1991) *J. Exp. Med.* 173, 721–730; Gimmi, C. D., et al., (1991) *Proc. Natl. Acad. Sci. USA.* 88, 6575–6579; Young, J. W., et al. (1992) *J. Clin. Invest.* 90, 229–237; Koulova, L., et al. (1991) *J. Exp. Med.* 173, 759–762; Reiser, H., et al. (1992) *Proc. Natl. Acad. Sci. USA.* 89, 271–275; van-Seventer, G. A., et al. (1990) *J. Immunol.* 144, 4579–4586; LaSalle, J. M., et al., (1991) *J. Immunol.* 147, 774–80; Dustin, M. I., et al., (1989) *J. Exp. Med.* 169, 503; Armitage, R. J., et al. (1992) *Nature* 357, 80–82; Liu, Y., et al. (1992) *J. Exp. Med.* 175, 437–445).

Considerable evidence suggests that the B7 protein, expressed on APCs, is one such critical costimulatory molecule (Linsley, P. S., et al., (1991) *J. Exp. Med.* 173, 721–730; Gimmi, C. D., et al., (1991) *Proc. Nat. Acad. Sci. USA.* 88, 6575–6579; Koulova, L., et al., (1991) *J. Exp. Med.* 173,759–762; Reiser, H., et al. (1992) *Proc. Natl. Acad Sci. USA.* 89, 271–275; Linsley, P. S. et al. (1990) *Proc. Natl. Acad. Sci. USA.* 87, 5031–5035; Freeman, G. J. et al. (1991) *J. Exp. Med.* 174,625–631.). B7 is the counter-receptor for two ligands expressed on T lymphocytes. The first ligand, termed CD28, is constitutively expressed on resting T cells and increases after activation. After signaling through the T cell receptor, ligation of CD28 induces T cells to proliferate and secrete IL-2 (Linsley, P. S., et al. (1991) *J. Exp. Med.* 173, 721–730; Gimmi, C. D., et al. (1991) *Proc. Nat. Acad. Sci. USA.* 88, 6575–6579; Thompson, C. B., et al. (1989) *Proc. Natl. Acad. Sci. USA.* 86, 1333–1337; June, C. H., et al. (1990) *Immunol. Today.* 11, 211–6; Harding, F. A., et al. (1992) *Nature.* 356, 607–609.). The second ligand, termed CTLA4 is homologous to CD28 but is not expressed on resting T cells and appears following T cell activation (Brunet, J. F., et al., (1987) *Nature* 328, 267–270). DNA sequences encoding the human and murine CTLA4 protein are described in Dariavach, et al. (1988) *Eur. J. Immunol.* 18(12), 1901–1905; Brunet, J. F., et al. (1987) supra; Brunet, J. F. et al. (1988) *Immunol. Rev.* 103:21–36; and Freeman, G. J., et al. (1992) *J. Immunol.* 149, 3795–3801. Although B7 has a higher affinity for CTLA4 than for CD28 (Linsley, P. S., et al., (1991) *J. Exp. Med.* 174, 561–569), the function of CTLA4 is still unknown.

The importance of the B7:CD28/CTLA4 costimulatory pathway has been demonstrated in vitro and in several in vivo model systems. Blockade of this costimulatory pathway results in the development of antigen specific tolerance in murine and humans systems (Harding, F. A., et al. (1992) *Nature.* 356, 607–609; Lenschow, D. J., et al. (1992) *Science.* 257, 789–792; Turka, L. A., et al. (1992) *Proc. Natl. Acad. Sci. USA.* 89, 11102–11105; Gimmi, C. D., et al. (1993) *Proc. Natl. Acad. Sci. USA.* 90, 6586–6590; Boussiotis, V., et al. (1993) *J. Exp. Med.* 178, 1753–1763). Conversely, expression of B7 by B7 negative murine tumor cells induces T-cell mediated specific immunity accompanied by tumor rejection and long lasting protection to tumor challenge (Chen, L., et al. (1992) *Cell* 71, 1093–1102; Townsend, S. E. and Allison, J. P. (1993) *Science* 259, 368–370; Baskar, S., et al. (1993) *Proc. Natl. Acad. Sci.* 90, 5687–5690.). Therefore, manipulation of the B7:CD28/CTLA4 pathway offers great potential to stimulate or suppress immune responses in humans.

SUMMARY OF THE INVENTION

This invention pertains to isolated nucleic acids encoding novel molecules which costimulate T cell activation. Preferred costimulatory molecules include antigens on the surface of B lymphocytes, professional antigen presenting cells (e.g., monocytes, dendritic cells, Langerhan cells) and other cells (e.g., keratinocytes, endothelial cells, astrocytes, fibroblasts, oligodendrocytes) which present antigen to immune cells, and which bind either CTLA4, CD28, both CTLA4 and CD28 or other known or as yet undefined receptors on immune cells. Such costimulatory molecules are referred to herein as CTLA4/CD28 binding counter-receptors or B lymphocyte antigens, and are capable of providing costimulation to activated T cells to thereby induce T cell proliferation and/or cytokine secretion. Preferred B lymphocyte antigens include B7-2 and B7-3 and soluble fragments or derivatives thereof which bind CTLA4 and/or CD28 and have the ability to inhibit or induce costimulation of immune cells. In one embodiment, an isolated nucleic acid which encodes a peptide having the activity of the human B7-2 B lymphocyte antigen is provided. Preferably, the nucleic acid is a CDNA molecule having a nucleotide sequence encoding human B7-2, as shown in FIG. 8 (SEQ ID NO:1). In another embodiment, the nucleic acid is a cDNA molecule having a nucleotide sequence encoding murine B7-2, as shown in FIG. 14 (SEQ ID NO:22).

The invention also features nucleic acids which encode a peptide having B7-2 activity and at least about 50%, more preferably at least about 60% and most preferably at least about 70% homologous with an amino acid sequence shown in FIG. 8 (SEQ ID NO:2) or an amino acid sequence shown in FIG. 14 (SEQ ID NO:23). Nucleic acids which encode peptides having B7-2 activity and at least about 80%, more preferably at least about 90%, more preferably at least about 95% and most preferably at least about 98% or at least about 99% homologous with an amino acid sequence shown in FIG. 8 (SEQ ID NO:2) or an amino acid sequence shown in FIG. 14 (SEQ ID NO:23) are also within the scope of the invention. In another embodiment, the peptide having B7-2 activity is encoded by a nucleic acid which hybridizes under high or low stringency conditions to a nucleic acid which encodes a peptide having an amino acid sequence of FIG. 8 (SEQ ID NO:2) or a peptide having an amino acid sequence shown in FIG. 14 (SEQ ID NO:23).

The invention further pertains to an isolated nucleic acid comprising a nucleotide sequence encoding a peptide having B7-2 activity and having a length of at least 20 amino acid residues. Peptides having B7-2 activity and consisting of at least 40 amino acid residues in length, at least 60 amino acid residues in length, at least 80 amino acid residues in length, at least 100 amino acid residues in length or at least 200 or more amino acid residues in length are also within the scope of this invention. Particularly preferred nucleic acids encode a peptide having B7-2 activity, a length of at least 20 amino acid residues or more and at least 50% or greater homology (preferably at least 70%) with a sequence shown in FIG. 8 (SEQ ID NO:2).

In one preferred embodiment, the invention features an isolated DNA encoding a peptide having B7-2 activity and an amino acid sequence represented by a formula:

$X_n\text{-}Y\text{-}Z_m$

In the formula, Y consists essentially of amino acid residues 24–245 of the sequence shown in FIG. 8 (SEQ ID NO:2). $X_n$ and $Z_m$ are additional amino acid residue(s) linked to Y by an amide bond. $X_n$ and $Z_m$ are amino acid residues selected from amino acid residues contiguous to Y in the amino acid sequence shown in FIG. 8 (SEQ ID NO:2). $X_n$ is amino acid residue(s) selected from amino acids contiguous to the amino terminus of Y in the sequence shown in FIG. 8 (SEQ ID NO:2), i.e., selected from amino acid residue 23 to 1. $Z_m$ is amino acid residue(s) selected from amino acids contiguous to the carboxy terminus of Y in the sequence shown in FIG. 8 (SEQ ID NO:2), i.e., selected from amino acid residue 246 to 329. According to the formula, n is a number from 0 to 23 (n=0–23) and m is a number from 0 to 84 (m=0–84). A particularly preferred DNA encodes a peptide having an amino acid sequence represented by the formula $X_n\text{-}Y\text{-}Z_m$, where Y is amino acid residues 24–245 of the sequence shown in FIG. 8 (SEQ ID NO:2) and n=0 and m=0.

The invention also features an isolated DNA encoding a B7-2 fusion protein which includes a nucleotide sequence encoding a first peptide having B7-2 activity and a nucleotide sequence encoding a second peptide corresponding to a moiety that alters the solubility, binding affinity, stability or valency of the first peptide. Preferably, the first peptide having B7-2 activity includes an extracellular domain portion of the B7-2 protein (e.g., about amino acid residues 24–245 of the sequence shown in FIG. 8 (SEQ ID NO:2)) and the second peptide is an immunoglobulin constant region, for example, a human Cγ1 or Cγ4 domain, including the hinge, CH2 and CH3 region, to produce a B7-2 immunoglobulin fusion protein (B7-2Ig)(see Capon et al. (1989) Nature 337, 525–531 and Capon U.S. Pat. No. 5,116,964).

The nucleic acids obtained in accordance with the present invention can be inserted into various expression vectors, which in turn direct the synthesis of the corresponding protein or peptides in a variety of hosts, particularly eucaryotic cells, such as mammalian and insect cell culture, and procaryotic cells such as E. coli. Expression vectors within the scope of the invention comprise a nucleic acid encoding at least one peptide having the activity of a novel B lymphocyte antigen as described herein, and a promoter operably linked to the nucleic acid sequence. In one embodiment, the expression vector contains a DNA encoding a peptide having the activity of the B7-2 antigen and a DNA encoding a peptide having the activity of another B lymphocyte antigen, such as the previously characterized B7 activation antigen, referred to herein as B7-1. Such expression vectors can be used to transfect host cells to thereby produce proteins and peptides, including fusion proteins, encoded by nucleic acids as described herein.

Nucleic acid probes useful for assaying a biological sample for the presence of B cells expressing the B lymphocyte antigens B7-2 and B7-3 are also within the scope of the invention.

The invention further pertains to isolated peptides having the activity of a novel B lymphocyte antigen, including the B7-2 and B7-3 protein antigens. A preferred peptide having B7-2 activity is produced by recombinant expression and comprises an amino acid sequence shown in FIG. 8 (SEQ ID NO: 2). Another preferred peptide having B7-2 activity comprises an amino acid sequence shown in FIG. 14 (SEQ ID NO:23). A particularly preferred peptide having the activity of the B7-2 antigen includes at least a portion of the mature form of the protein, such as an extracellular domain portion (e.g., about amino acid residues 24245 of SEQ ID NO:2) which can be used to enhance or suppress T-cell mediated immune responses in a subject. Other preferred peptides having B7-2 activity include peptides having an amino acid sequence represented by a formula:

$X_n\text{-}Y\text{-}Z_m$

In the formula, Y is amino acid residues selected from the group consisting of: amino acid residues 5568 of the sequence shown in FIG. 8 (SEQ ID NO:2); amino acid residues 81–89 of the sequence shown in FIG. 8 (SEQ ID NO:2); amino acid residues 128–142 of the sequence shown in FIG. 8 (SEQ ID NO:2); amino acid residues 160–169 of the sequence shown in FIG. 8 (SEQ ID NO:2); amino acid residues 188–200 of the sequence shown in FIG. 8 (SEQ ID NO:2); and amino acid residues 269–282 of the sequence shown in FIG. 8 (SEQ ID NO:2). In the formula $X_n$ and $Z_m$ are additional amino acid residue(s) linked to Y by an amide bond and are selected from amino acid residues contiguous to Y in the amino acid sequence shown in FIG. 8 (SEQ ID NO:2). $X_n$ is amino acid residue(s) selected from amino acids contiguous to the amino terminus of Y in the sequence shown in FIG. 8 (SEQ ID NO:2). $Z_m$ is amino acid residue(s) selected from amino acids contiguous to the carboxy terminus of Y in the sequence shown in FIG. 8 (SEQ ID NO:2). According to the formula, n is a number from 0 to 30 (n=0–30) and m is a number from 0 to 30 (m=0–30).

Fusion proteins or hybrid fusion proteins including a peptide having the activity of a novel B lymphocyte antigen (e.g., B7-2, B7-3) are also featured. For example, a fusion protein comprising a first peptide which includes an extracellular domain portion of a novel B lymphocyte antigen fused to second peptide, such as an immunoglobulin constant region, that alters the solubility, binding affinity, stability and/or valency of the first peptide are provided. In one embodiment, a fusion protein is produced comprising a first peptide which includes amino acid residues of an extracellular domain portion of the B7-2 protein joined to a second peptide which includes amino acid residues of a sequence corresponding to the hinge, CH2 and CH3 regions of Cγ1 or Cγ4 to form a B7-2Ig fusion protein. In another embodiment, a hybrid fusion protein is produced comprising a first peptide which includes an extracellular domain portion of the B7–1 antigen and an extracellular domain portion of the B7-2 antigen and a second peptide which includes amino acid residues corresponding to the hinge, CH2 and CH3 of Cγ1 (see e.g., Linsley et al. (1991) *J. Exp. Med.* 1783:721–730; Capon et al. (1989) *Nature* 337, 525–531; and Capon U.S. Pat. No. 5,116,964). In a yet another embodiment, a hybrid fusion protein comprises the immunoglobulin-like variable domain of B7-2, but not the immunoglobulin-like constant domain of B7-2, linked to the constant region of an immunoglobulin molecule. In a preferred embodiment, the B7-2Ig fusion protein includes the variable domain of human B7-2, preferably from about amino acid residue 24 to about amino acid residue 133 of the human B7-2 protein (as shown SEQ ID NO: 2), fused to the constant region of an IgG molecule.

Isolated peptides and fusion proteins of the invention can be administered to a subject to either upregulate or inhibit the expression of one or more B lymphocyte antigens or block the ligation of one or more B lymphocyte antigens to their natural ligand on immune cells, such as T cells, to thereby provide enhancement or suppression of cell-mediated immune responses in vivo.

Another embodiment of the invention provides antibodies, preferably monoclonal antibodies, specifically reactive with a peptide of a novel B lymphocyte antigen or fusion protein as described herein. Preferred antibodies are anti-human B7-2 monoclonal antibodies produced by hybridoma cells HF2.3D1, HA5.2B7 and HA3.1F9. These hybridoma cells have been deposited with the American Type Culture Collection at ATCC Accession No. HB11686 (HF2.3D1), ATCC Accession No. HB11687 (HA5.2B7), and ATCC Accession No. HB11688 (HA3.1F9).

A still further aspect of the invention involves the use of the nucleic acids of the invention, especially the cDNAs, to enhance the immunogenicity of a mammalian cell. In preferred embodiments, the mammalian cell is a tumor cell, such as a sarcoma, a lymphoma, a melanoma, a neuroblastoma, a leukemia or a carcinoma, or an antigen presenting cell, such as a macrophage, which is transfected to allow expression of a peptide having the activity of a novel B lymphocyte antigen of the invention on the surface of the cell. Macrophages that express a peptide having the activity of a B lymphocyte antigen, such as the B7-2 antigen, can be used as antigen presenting cells, which, when pulsed with an appropriate pathogen-related antigen or tumor antigen, enhance T cell activation and immune stimulation.

Mammalian cells can be transfected with a suitable expression vector containing a nucleic acid encoding a peptide having the activity of a novel B lymphocyte antigen, such as the B7-2 antigen, ex vivo and then introduced into the host mammal, or alternatively, cells can be transfected with the gene in vivo via gene therapy techniques. For example, the nucleic acid encoding a peptide having B7-2 activity can be transfected alone, or in combination with nucleic acids encoding other costimulatory molecules. In enhancing the immunogenicity of tumors which do not express Class I or Class II MHC molecules, it may be beneficial to additionally transfect appropriate class I or II genes into the mammalian cells to be transfected with a nucleic acid encoding a peptide having the activity of a B lymphocyte antigen, as described herein.

The invention also provides methods for inducing both general immunosuppression and antigen-specific tolerance in a subject by, for example, blocking the functional interaction of the novel B lymphocyte antigens of the invention, e.g., B7-2 and B7-3, to their natural ligand(s) on T cells or other immune system cells, to thereby block co-stimulation through the receptor-ligand pair. In one embodiment, inhibitory molecules that can be used to block the interaction of the natural human B7-2 antigen to its natural ligands (e.g., CTLA4 and CD28) include a soluble peptide having B7-2 binding activity but lacking the ability to costimulate immune cells, antibodies that block the binding of B7-2 to its ligands and fail to deliver a co-stimulatory signal (so called "blocking antibodies", such as blocking anti-B7-2 antibodies), B7-2-Ig fusion proteins, which can be produced in accordance with the teachings of the present invention, as well as soluble forms of B7-2 receptors, such as CTLA4Ig or CD28Ig. Such blocking agents can be used alone or in combination with agents which block interaction of other costimulatory molecules with their natural ligands (e.g., anti-B7 antibody). Inhibition of T cell responses and induction of T cell tolerance according to the methods described herein may be useful prophylactically, in preventing transplantation rejection (solid organ, skin and bone marrow) and graft versus host disease, especially in allogeneic bone marrow transplantation. The methods of the invention may also be useful therapeutically, in the treatment of autoimmune diseases, allergy and allergic reactions, transplantation rejection, and established graft versus host disease in a subject.

Another aspect of the invention features methods for upregulating immune responses by delivery of a costimulatory signal to T cells through use of a stimulatory form of B7-2 antigen, which include soluble, multivalent forms of B7-2 protein, such as a peptide having B7-2 activity and B7-2 fusion proteins. Delivery of a stimulatory form of B7-2 in conjunction with antigen may be useful prophylactically to enhance the efficacy of vaccination against a variety of pathogens and may also be useful therapeutically to upregulate an immune response against a particular pathogen during an infection or against a tumor in a tumor-bearing host.

The invention also features methods of identifying molecules which can inhibit either the interaction of B lymphocyte antigens, e.g., B7-2, B7-3, with their receptors or interfere with intracellular signalling through their receptors. Methods for identifying molecules which can modulate the expression of B lymphocyte antigens on cells are also provided. In addition, methods for identifying cytokines produced in response to costimulation of T cells by novel B lymphocyte antigens are within the scope of the invention.

BRIEF DESCRIPTION OF THE DRAWINGS

FIG. 8 is the nucleotide and deduced amino acid sequence of the human B lymphocyte antigen B7-2 (hB7-2-clone29).

FIG. 13 shows the sequence homology between the human B7-2 protein (h B7-2) deduced amino acid sequence (SEQ ID NO: 2) and the amino acid sequence of both the human B7-1 protein (h B7-1) (SEQ ID NO: 28 and 29) and the murine B7-1 protein (m B7) (SEQ ID NO: 30 and 31).

FIG. 14 is the nucleotide and deduced amino acid sequence of the murine B7-2 antigen (mB7-2) (SEQ ID NO: 22 and 23).

FIG. 17 depicts flow cytometric profiles of cells stained with an anti-hB7-2 monoclonal antibody, HA3.1F9. Cells stained with the antibody were CHO cells transfected to express human B7-2 (CHO-hB7.2), NIH 3T3 cells transfected to express human B7-2 (3T3-hB7.2) and control transfected NIH 3T3 cells (3T3-neo). The anti-hB7.2 antibody B70 was used as a positive control.

FIG. 18 depicts flow cytometric profiles of cells stained with an anti-hB7-2 monoclonal antibody, HA5.2B7. Cells stained with the antibody were CHO cells transfected to express human B7-2 (CHO-hB7.2), NIH 3T3 cells transfected to express human B7-2 (3T3-hB7.2) and control transfected NIH 3T3 cells (3T3-neo). The anti-hB7.2 antibody B70 was used as a positive control.

FIG. 19 depicts flow cytometric profiles of cells stained with an anti-hB7-2 monoclonal antibody, HF2.3D1. Cells stained with the antibody were CHO cells transfected to express human B7-2 (CHO-hB7.2), NIH 3T3 cells transfected to express human B7-2 (3T3-hB7.2) and control transfected NIH 3T3 cells (3T3-neo). The anti-hB.7.2 antibody B70 was used as a positive control.

DETAILED DESCRIPTION OF THE INVENTION

Figure 1A:
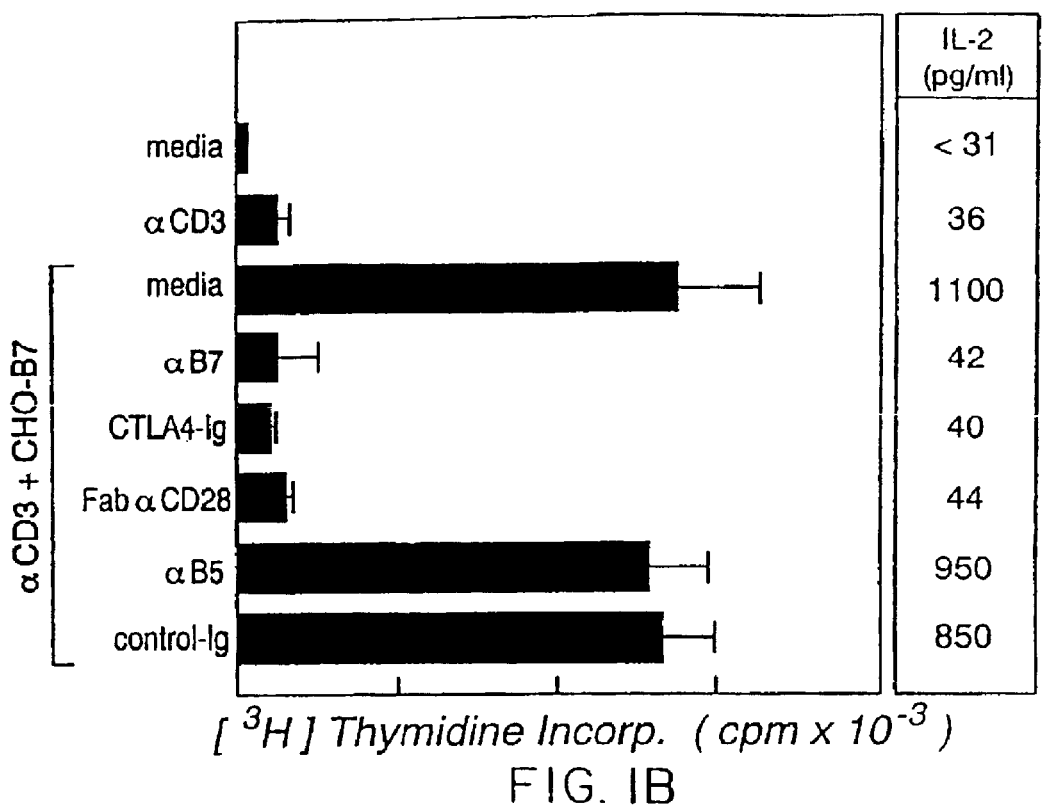
FIGS. 1A–B are graphic representations of the responses of $CD28^+$ T cells, as assessed by $^3$H-thymidine incorporation or IL-2 secretion, to costimulation provided by either B7 (B7-1) transfected CHO cells (panel a) or syngeneic activated B lymphocytes (panel b) cultured in media, anti-CD3 alone, or anti-CD3 in the presence of the following monoclonal antibodies or recombinant proteins: αB7 (133, anti-B7-1); CTLA4Ig; Fab α CD28; control Ig fusion protein (isotype control for CTLA4Ig); or αB5 (anti-B5, the isotype control for anti-B7-1).

In addition to the previously characterized B lymphocyte activation antigen B7 (referred to herein as B7-1), human B lymphocytes express other novel molecules which costimulate T cell activation. These costimulatory molecules include antigens on the surface of B lymphocytes, professional antigen presenting cells (e.g., monocytes, dendritic cells, Langerhan cells) and other cells (e.g., keratinocytes, endothelial cells, astrocytes, fibroblasts, oligodendrocytes) which present antigen to immune cells, and which bind either CTLA4, CD28, both CTLA4 and CD28 or other known or as yet undefined receptors on immune cells. Costimulatory molecules within the scope of the invention are referred to herein as CTLA4/CD28 ligands (counter-receptors) or B lymphocyte antigens. Novel B lymphocyte antigens which provide costimulation to activated T cells to thereby induce T cell proliferation and/or cytokine secretion include the B7-2 (human and murine) and the B7-3 antigens described and characterized herein.

The B lymphocyte antigen B7-2 is expressed by human B cells at about 24 hours following stimulation with either anti-immunoglobulin or anti-MHC class II monoclonal antibody. The B7-2 antigen induces detectable IL-2 secretion and T cell proliferation. At about 48 to 72 hours post activation, human B cells express both B7-1 and a third CTLA4 counter-receptor, B7-3, identified by a monoclonal antibody BB-1, which also binds B7-1 (Yokochi; T., et al. (1982) *J. Immunol.* 128, 823–827). The B7-3 antigen is also expressed on B7-1 negative activated B cells and can costimulate T cell proliferation without detectable IL-2 production, indicating that the B7-1 and B7-3 molecules are distinct. B7-3 is expressed on a wide variety of cells including activated B cells, activated monocytes, dendritic cells, Langerhan cells and keratinocytes. At 72 hours post B cell activation, the expression of B7-1 and B7-3 begins to decline. The presence of these costimulatory molecules on the surface of activated B lymphocytes indicates that T cell costimulation is regulated, in part, by the temporal expression of these molecules following B cell activation.

Accordingly, one aspect of this invention pertains to isolated nucleic acids comprising a nucleotide sequence encoding a novel costimulatory molecule, such as the B lymphocyte antigen, B7-2, fragments of such nucleic acids, or equivalents thereof. The term "nucleic acid" as used herein is intended to include such fragments or equivalents. The term "equivalent" is intended to include nucleotide sequences encoding functionally equivalent B lymphocyte antigens or functionally equivalent peptides having an activity of a novel B lymphocyte antigen, i.e., the ability to bind to the natural ligand(s) of the B lymphocyte antigen on immune cells, such as CTLA4 and/or CD28 on T cells, and inhibit (e.g., block) or stimulate (e.g., enhance) immune cell costimulation. Such nucleic acids are considered equivalents of the human B7-2 nucleotide sequence provided in FIG. 8 (SEQ ID NO:1) and the murine B7-2 nucleotide sequence provided in FIG. 14 (SEQ ID NO:22) and are within the scope of this invention.

In one embodiment, the nucleic acid is a cDNA encoding a peptide having an activity of the B7-2 B lymphocyte antigen. Preferably, the nucleic acid is a cDNA molecule consisting of at least a portion of a nucleotide sequence encoding human B7-2, as shown in FIG. 8 (SEQ ID NO:1) or at least a portion of a nucleotide sequence encoding murine B7-2, as shown in FIG. 14 (SEQ ID NO:22). A preferred portion of the CDNA molecule of FIG. 8 (SEQ ID NO:1) or FIG. 14 (SEQ ID NO:22) includes the coding region of the molecule.

In another embodiment, the nucleic acid of the invention encodes a peptide having an activity of B7-2 and comprising an amino acid sequence shown in FIG. 8 (SEQ ID NO:2) or FIG. 14 (SEQ ID NO:23). Preferred nucleic acids encode a peptide having B7-2 activity and at least about 50% homology, more preferably at least about 60% homology and most preferably at least about 70% homology with an amino acid sequence shown in FIG. 8 (SEQ ID NO:2). Nucleic acids which encode peptides having B7-2 activity and at least about 90%, more preferably at least about 95%, and most preferably at least about 98–99% homologous with a sequence set forth in FIG. 8 (SEQ ID NO:2) are also within the scope of the invention. Homology refers to sequence similarity between two peptides having the activity of a novel B lymphocyte antigen, such as B7-2, or between two nucleic acid molecules. Homology can be determined by comparing a position in each sequence which may be aligned for purposes of comparison. When a position in the compared sequences is occupied by the same nucleotide base or amino acid, then the molecules are homologous at that position. A degree (or percentage) of homology between sequences is a function of the number of matching or homologous positions shared by the sequences.

Another aspect of the invention provides a nucleic acid which hybridizes under high or low stringency conditions to a nucleic acid which encodes a peptide having all or a portion of an amino acid sequence shown in FIG. 8 (SEQ ID NO:2) or a peptide having all or a portion of an amino acid sequence shown in FIG. 14 (SEQ ID NO:23). Appropriate stringency conditions which promote DNA hybridization, for example, 6.0×sodium chloride/sodium citrate (SSC) at about 45° C., followed by a wash of 2.0×SSC at 50° C. are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C. to high stringency conditions, at about 65° C.

Isolated nucleic acids encoding a peptide having an activity of a novel B lymphocyte antigen, as described herein, and having a sequence which differs from nucleotide sequence shown in FIG. 8 (SEQ ID NO:1) or FIG. 14 (SEQ ID NO:22) due to degeneracy in the genetic code are also within the scope of the invention. Such nucleic acids encode functionally equivalent peptides (e.g., a peptide having B7-2 activity) but differ in sequence from the sequence of FIG. 8 or FIG. 14 due to degeneracy in the genetic code. For example, a number of amino acids are designated by more than one triplet. Codons that specify the same amino acid, or synonyms (for example, CAU and CAC are synonyms for histidine) may occur due to degeneracy in the genetic code. As one example, DNA sequence polymorphisms within the nucleotide sequence of a B7-2 (especially those within the third base of a codon) may result in "silent" mutations in the DNA which do not affect the amino acid encoded. However, it is expected that DNA sequence polymorphisms that do lead to changes in the amino acid sequences of the B7-2 antigen will exist within a population. It will be appreciated by one skilled in the art that these variations in one or more nucleotides (up to about 3–4% of the nucleotides) of the nucleic acids encoding peptides having the activity of a novel B lymphocyte antigen may exist among individuals within a population due to natural allelic variation. Any and all such nucleotide variations and resulting amino acid polymorphisms are within the scope of the invention. Furthermore, there may be one or more isoforms or related, cross-reacting family members of the novel B lymphocyte antigens described herein. Such isoforms or family members are defined as proteins related in function and amino acid sequence to a B lymphocyte antigen (e.g., the B7-2 antigen), but encoded by genes at different loci.

A "fragment" of a nucleic acid encoding a novel B lymphocyte antigen is defined as a nucleotide sequence having fewer nucleotides than the nucleotide sequence encoding the entire amino acid sequence of the B lymphocyte antigen and which encodes a peptide having an activity of the B lymphocyte antigen (i.e., the ability to bind to the natural ligand(s) of the B lymphocyte antigen on immune cells, such as CTLA4 and/or CD28 on T cells and either stimulate or inhibit immune cell costimulation). Thus, a peptide having B7-2 activity binds CTLA4 and/or CD28 and stimulates or inhibits a T cell mediated immune response, as evidenced by, for example, cytokine production and/or T cell proliferation by T cells that have received a primary activation signal. In one embodiment, the nucleic acid fragment encodes a peptide of the B7-2 antigen which retains the ability of the antigen to bind CTLA4 and/or CD28 and deliver a costimulatory signal to T lymphocytes. In another embodiment, the nucleic acid fragment encodes a peptide including an extracellular portion of the human B7-2 antigen (e.g., approximately amino acid residues 24–245 of the sequence provided in FIG. 8 (SEQ ID NO:2)) which can be used to bind CTLA4 and/or CD28 and, in monovalent form, inhibit costimulation, or in multivalent form, induce or enhance costimulation.

Preferred nucleic acid fragments encode peptides of at least 20 amino acid residues in length, preferably at least 40 amino acid residues and length, and more preferably at least 60 amino acid residues in length. Nucleic acid fragments which encode peptides of at least 80 amino acid residues in length, at least 100 amino acid residues in length, and at least 200 or more amino acids in length are also within the scope of the invention. Particularly preferred nucleic acid fragments encode a peptide having the activity of human B7-2 and an amino acid sequence represented by a formula:

$X_n\text{-}Y\text{-}Z_m$

In the formula, Y comprises amino acid residues 24–245 of the sequence shown in FIG. 8 (SEQ ID NO:2). $X_n$ and $Z_m$ are additional amino acid residue(s) linked to Y by an amide bond. $X_n$ and $Z_m$ are selected from amino acid residues contiguous to Y in the amino acid sequence shown in FIG. 8 (SEQ ID NO:2). In the formula, $X_n$ is amino acid residue(s) selected from amino acids contiguous to the amino terminus of Y in the sequence shown in FIG. 8 (SEQ ID NO:2), i.e., from amino acid residue 23 to 1. $Z_m$ is amino acid residue(s) selected from amino acids contiguous to the carboxy terminus of Y in the sequence shown in FIG. 8 (SEQ ID NO:2), i.e., from amino acid residue 246 to 329. In addition, in the formula, n is a number from 0 to 23 (n=0–23) and m is a number from 0 to 84 (m=0–84). A particularly preferred peptide has an amino acid sequence represented by the formula $X_n\text{-}Y\text{-}Z_m$ as above, where n=0 and m=0.

Nucleic acid fragments within the scope of the invention include those capable of hybridizing with nucleic acid from other animal species for use in screening protocols to detect novel proteins that are cross-reactive with the B lymphocyte antigens described herein. These and other fragments are described in detail herein. Generally, the nucleic acid encoding a fragment of a B lymphocyte antigen will be selected from the bases coding for the mature protein, however, in some instances it may be desirable to select all or part of a fragment or fragments from the leader sequence or non-coding portion of a nucleotide sequence. Nucleic acids within the scope of the invention may also contain linker sequences, modified restriction endonuclease sites and other sequences useful for molecular cloning, expression or purification of recombinant protein or fragments thereof. These and other modifications of nucleic acid sequences are described in further detail herein.

A nucleic acid encoding a peptide having an activity of a novel B lymphocyte antigen, such as the B7-2 antigen, may be obtained from mRNA present in activated B lymphocytes. It should also be possible to obtain nucleic acid sequences encoding B lymphocyte antigens from B cell genomic DNA. For example, the gene encoding the B7-2 antigen can be cloned from either a cDNA or a genomic library in accordance with protocols herein described. A cDNA encoding the B7-2 antigen can be obtained by isolating total mRNA from an appropriate cell line. Double stranded cDNAs can then prepared from the total mRNA. Subsequently, the cDNAs can be inserted into a suitable plasmid or viral (e.g., bacteriophage) vector using any one of a number of known techniques. Genes encoding novel B lymphocyte antigens can also be cloned using established polymerase chain reaction techniques in accordance with the nucleotide sequence information provided by the invention. The nucleic acids of the invention can be DNA or RNA. A preferred nucleic acid is a cDNA encoding the human B7-2 antigen having the sequence depicted in FIG. 8 (SEQ ID NO:1). Another preferred nucleic acid is a CDNA encoding the murine B7-2 antigen having the sequence shown on FIG. 14 (SEQ ID NO:22).

This invention further pertains to expression vectors containing a nucleic acid encoding at least one peptide having the activity of a novel B lymphocyte antigen, as described herein, operably linked to at least one regulatory sequence. "Operably linked" is intended to mean that the nucleotide acid sequence is linked to a regulatory sequence in a manner which allows expression of the nucleotide sequence (e.g., in cis or trans). Regulatory sequences are art-recognized and are selected to direct expression of the desired protein in an appropriate host cell. Accordingly, the term regulatory sequence includes promoters, enhancers and other expression control elements. Such regulatory sequences are known to those skilled in the art or one described in Goeddel, *Gene Expression Technology: Methods in Enzymology* 185, Academic Press, San Diego, Calif. (1990). It should be understood that the design of the expression vector may depend on such factors as the choice of the host cell to be transfected and/or the type of protein desired to be expressed. In one embodiment, the expression vector includes a nucleic acid encoding at least a portion of the B7-2 protein, such as an extracellular domain portion. In another embodiment, the expression vector includes a DNA encoding a peptide having an activity of the B7-2 antigen and a DNA encoding a peptide having an activity of another B lymphocyte antigen, such as B7-1. cDNAs encoding the human B7-1 and mouse B7-1 antigens are shown in SEQ ID NO:28 and SEQ ID NO:30, respectively. The deduced amino acid sequences of these antigens are also shown in SEQ ID NO:29 and SEQ ID NO:31, respectively. Such expression vectors can be used to transfect cells to thereby produce proteins or peptides, including fusion proteins or peptides encoded by nucleic acid sequences as described herein. These and other embodiments are described in further detail herein.

The invention also features methods of producing peptides having an activity of a novel B lymphocyte antigen. For example, a host cell transfected with a nucleic acid vector directing expression of a nucleotide sequence encoding a peptide having an activity of the B7-2 protein can be cultured in a medium under appropriate conditions to allow expression of the peptide to occur. In addition, one or more expression vectors containing DNA encoding a peptide having an activity of B7-2 and DNA encoding another peptide, such as a peptide having an activity of a second B lymphocyte antigen (e.g., B7-1, B7-3) can be used to transfect a h6st cell to coexpress these peptides or produce fusion proteins or peptides. In one embodiment, a recombinant expression vector containing DNA encoding a B7-2 fusion protein is produced. A B7-2 fusion protein can be produced by recombinant expression of a nucleotide sequence encoding a first peptide having B7-2 activity and a nucleotide sequence encoding second peptide corresponding to a moiety that alters the solubility, affinity, stability or valency of the first peptide, for example, an immunoglobulin constant region. Preferably, the first peptide consists of a portion of the extracellular domain of the human B7-2 antigen (e.g., approximately amino acid residues 24–245 of the sequence shown in FIG. 8 (SEQ ID NO:2)). The second peptide can include an immunoglobulin constant region, for example, a human Cγ1 domain or Cγ4 domain (e.g., the hinge, CH2 and CH3 regions of human IgCγ1, or human IgCγ4, see e.g., Capon et al. U.S. Pat. No. 5,116,964, incorporated herein by reference). A resulting B7-2Ig fusion protein may have altered B7-2 solubility, binding affinity, stability and/or valency (i.e., the number of binding sites available per molecule) and may increase the efficiency of protein purification. Fusion proteins and peptides produced by recombinant technique may be secreted and isolated from a mixture of cells and medium containing the protein or peptide. Alternatively, the protein or peptide may be retained cytoplasmically and the cells harvested, lysed and the protein isolated. A cell culture typically includes host cells, media and other byproducts. Suitable mediums for cell culture are well known in the art. Protein and peptides can be isolated from cell culture medium, host cells, or both using techniques known in the art for purifying proteins and peptides. Techniques for transfecting host cells and purifying proteins and peptides are described in further detail herein.

Particularly preferred human B7-2Ig fusion proteins include the extracellular domain portion or variable region-like domain of human B7-2 coupled to an immunoglobulin constant region. The immunoglobulin constant region may contain genetic modifications which reduce or eliminate effector activity inherent in the immunoglobulin structure. For example, DNA encoding the extracellular portion of human B7-2 (hB7-2), as well as DNA encoding the variable region-like domain of human B7-2 (hB7.2V) or the constant region-like domain of human B7-2 (hB7.2C) can be joined to DNA encoding the hinge, CH2 and CH3 regions of human IgCγ1 and/or IgCγ4 modified by site directed mutagenesis. The preparation and characterization of these fusion proteins is described in detail in Example 7.

In a specific embodiment, the protein of the invention is a variable region form of the B cell activation antigen B7-2. The language "a variable region form of the B cell activation antigen B7-2" is intended to include forms of B7-2 which contain the immunoglobulin-like variable domain of B7-2, but do not comprise the immunoglobulin-like constant domain of B7-2. In a preferred embodiment, the variable region form of B7-2 comprises an amino acid sequence starting at about amino acid position I 8 to 30 and ending about amino acid position 128 to 140 of human B7-2 protein (SEQ ID NO: 2). In a most preferred embodiment, the variable form of B7-2 comprises about amino acids 24 to 133 of human B7-2 protein (SEQ ID NO: 2). The variable region form of B7-2 can further be operatively linked directly to a transmembrane domain, such as the transmembrane domain of B7-2, to form a variable region form of B7-2 that can be expressed on a cell surface. "Operatively" is intended to mean in such a way that the molecule formed by operatively linking two or more domains or peptides is functional. The transmembrane domain of human B7-2 comprises about amino residues 246 to 268 of human 1B7-2 protein. Thus, in one embodiment, the variable region form of B7-2 is operatively linked to a peptide having a first amino acid located between about amino acid residue 238 and about amino acid residue 252, and a last amino acid residue located between about amino acid residue 260 and about amino acid residue 274 of human B7-2 protein of sequence SEQ ID NO: 2. The incorporation of a transmembrane domain in a protein of the invention, allows the protein to be expressed on a cell surface when a nucleic acid encoding the protein is expressed in the cell.

In another embodiment, the variable region form of B7-2 s operatively linked to a cytoplasmic domain, such as a cytoplasmic domain of B7-2. The cytoplasmic domain of human B7-2 comprises about amino acid residues 269 to 329 of human B7-2 protein of SEQ ID NO: 2. Accordingly, in one embodiment, the variable region form of B7-2 is operatively linked to a second B7-2 peptide, having a first amino acid residue located between about amino acids 260 and 275 of human B7-2 and a terminal amino acid residue located between about amino acid 323 to about amino acid 335 of human B7-2 of SEQ ID NO: 2. In another embodiment, a variable region form of B7-2 is operatively linked to a second B7-2 peptide of about amino acid residues 269 to 329 of human B7-2.

In a further embodiment, a variable region form of B7-2 operatively linked to a peptide corresponding to about the transmembrane domain of B7-2 is further operatively linked to a peptide corresponding significantly to the cytoplasmic domain of B7-2. Thus, proteins within the scope of the invention include those comprising an amino acid sequence from about position 24 to about position 133 of SEQ ID NO: 2, operatively linked to an amino acid sequence from about position 246 to about position 268 of SEQ ID NO: 2 (V-region and transmembrane domains). Other proteins within the scope of the invention include those comprising an amino acid sequence from about position 24 to about position 133 of SEQ ID NO: 2, operatively linked to an amino acid sequence from about position 246 to about position 329 of SEQ ID NO: 2 (V-region, transmembrane and cytoplasmic domains). Yet other proteins within the scope of the invention include the leader sequence of B7-2 (e.g. positions 1–23) at the N-terminus. Proteins including other portions of B7-2 protein operatively linked to each other, but not including the immunoglobulin-like constant domain of B7-2, are also within the scope of the invention. In other embodiments, B7-2 proteins that contain an immunoglobulin-like constant domain of B7-2 in the absence of the variable region are contemplated.

A variable region form of B7-2, can also be linked to at least one heterologous polypeptide. The term "heterologous polypeptide" is intended to include any polypeptide, such as a polypeptide that directs the protein of the invention to a specific cellular compartment. In one embodiment, the heterologous polypeptide is a signal peptide that allows for the protein to be secreted from the cell. Another heterologous polypeptide within the scope of the invention is a signal peptide that allows for the protein to be expressed on the surface of the cell. In yet another embodiment, the heterologous polypeptide is a constant region of an immunoglobulin molecule. In an even more preferred embodiment, the heterologous polypeptide comprises the hinge, CH2, and CH3 domains of IgG1, as described herein.

The variable region form of B7-2 can further be attached to a linker polypeptide. A "linker polypeptide" as defined herein includes any polypeptide that bridges two peptides in the protein of the invention. Alternatively, the linker peptide is attached to either or both ends of the protein. Thus, a linker peptide attached to one or both ends of the protein can for example facilitate binding of the protein of the invention to a solid support. The linker peptide can also be a fragment of a bacterial or viral protein.

The fusion proteins described above can be, for example, human or murine. The nucleic acid molecules encoding the above described fusion proteins, as well as expression vectors and host cells expressing the fusion proteins are also within the scope of the invention.

Transfected cells which express peptides having an activity of one or more B lymphocyte antigens (e.g., B7-2, B7-3) on the surface of the cell are also within the scope of this invention. In one embodiment, a host cell such as a COS cell is transfected with an expression vector directing the expression of a peptide having B7-2 activity on the surface of the cell. Such a transfected host cell can be used in methods of identifying molecules which inhibit binding of B7-2 to its counter-receptor on T cells or which interfere with intracellular signaling of costimulation to T cells in response to B7-2 interaction. In another embodiment, a tumor cell such as a sarcoma, a melanoma, a leukemia, a lymphoma, a carcinoma or a neuroblastoma is transfected with an expression vector directing the expression of at least one peptide having the activity of a novel B lymphocyte antigen on the surface of the tumor cell. In some instances, it may be beneficial to transfect a tumor cell to coexpress major histocompatibility complex (MHC) proteins, for example MHC class II α and β chain proteins or an MHC class I α chain protein, and, if necessary, a β2 microglobulin protein. Such transfected tumor cells can be used to induce tumor immunity in a subject. These and other embodiments are described in farther detail herein.

The nucleic acid sequences of the invention can also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

Another aspect of the invention pertains to isolated peptides having an activity of a novel B lymphocyte antigen (e.g., B7-2, B7-3). A peptide having an activity of a B lymphocyte antigen may differ in amino acid sequence from the B lymphocyte antigen, such as the human B7-2 sequence depicted in FIG. 8 (SEQ ID NO:2), or murine B7-2 sequence depicted in FIG. 14 (SEQ ID NO:22), but such differences result in a peptide which functions in the same or similar manner as the B lymphocyte antigen or which has the same or similar characteristics of the B lymphocyte antigen. For example, a peptide having an activity of the B7-2 protein is defined herein as a peptide having the ability to bind to the natural ligand(s) of the B7-2 protein on immune cells, such as CLTA4 and/or CD28 on T cells and either stimulate or inhibit immune cell costimulation. Thus, a peptide having B7-2 activity binds CTLA4 and/or CD28 and stimulates or inhibits a T cell mediated immune response (as evidenced by, for example, cytokine production and/or proliferation by T cells that have received a primary activation signal). One embodiment provides a peptide having B7-2 binding activity, but lacking the ability to deliver a costimulatory signal to T cells. Such a peptide can be used to inhibit or block T cell proliferation and/or cytokine secretion in a subject. Alternatively, a peptide having both B7-2 binding activity and the ability to deliver a costimulatory signal to T cells is used to stimulate or enhance T cell proliferation and/or cytokine secretion in a subject. Various modifications of the B7-2 protein to produce these and other functionally equivalent peptides are described in detail herein. The term "peptide" as used herein, refers to peptides, proteins and polypeptides.

A peptide can be produced by modification of the amino acid sequence of the human B7-2 protein shown in FIG. 8 (SEQ ID NO:2) or the murine B7-2 protein shown in FIG. 14 (SEQ ID NO:23), such as a substitution, addition or deletion of an amino acid residue which is not directly involved in the function of B7-2 (i.e., the ability of B7-2 to bind CTLA4 and/or CD28 and/or stimulate or inhibit T cell costimulation). Peptides of the invention are typically at least 20 amino acid residues in length, preferably at least 40 amino acid residues in length, and most preferably 60 amino acid residues in length. Peptides having B7-2 activity and including at least 80 amino acid residues in length, at least 100 amino acid residues in length, or at least 200 or more amino acid residues in length are also within the scope of the invention. A preferred peptide includes an extracellular domain portion of the human B7-2 antigen (e.g., about amino acid residues 24–245 of the sequence shown in FIG. 8 (SEQ ID NO:2). Other preferred peptides have an amino acid sequence represented by a formula:

$$X_n\text{-}Y\text{-}Z_m$$

where Y is amino acid residues selected from the group consisting of: amino acid residues 55–68 of the sequence shown in FIG. 8 (SEQ ID NO:2); amino acid residues 81–89 of the sequence shown in FIG. 8 (SEQ ID NO:2); amino acid residues 128–142 of the sequence shown in FIG. 8 (SEQ ID NO:2); amino acid residues 160–169 of the sequence shown in FIG. 8 (SEQ ID NO:2); amino acid residues 188–200 of the sequence shown in FIG. 8 (SEQ ID NO:2); and amino acid residues 269–282 of the sequence shown in FIG. 8 (SEQ ID NO:2). In the formula, $X_n$ and $Z_m$ are additional amino acid residues linked to Y by an amide bond. $X_n$ and $Z_m$ are amino acid residues selected from amino acids contiguous to Y in the amino acid sequence shown in FIG.

8 (SEQ ID NO:2). $X_n$ is amino acid residues selected from amino acids contiguous to the amino terminus of Y in the sequence shown in FIG. 8 (SEQ ID NO:2). $Z_m$ is amino acid residues selected from amino acids contiguous to the carboxy terminus of Y in the sequence shown in FIG. 8 (SEQ ID NO:2). According to the formula, n is a number from 0 to 30 (n=0–30) and m is a number from 0 to 30 (m=0–30). A particularly preferred peptide has an amino acid sequence represented by the formula $X_n$-Y-$Z_m$, where n=0 and m=0.

Another embodiment of the invention provides a substantially pure preparation of a peptide having an activity of a novel B lymphocyte antigen such as B7-2 or B7-3. Such a preparation is substantially free of proteins and peptides with which the peptide naturally occurs in a cell or with which it naturally occurs when secreted by a cell.

The term "isolated" as used throughout this application refers to a nucleic acid, protein or peptide having an activity of a novel B lymphocyte antigen, such as B7-2, substantially free of cellular material or culture medium when produced by recombinant DNA techniques, or chemical precursors or other chemicals when chemically synthesized. An isolated nucleic acid is also free of sequences which naturally flank the nucleic acid (i.e., sequences located at the 5' and 3' ends of the nucleic acid) in the organism from which the nucleic acid is derived.

The various peptides, polypeptides, proteins, and fusion proteins of the invention can be prepared as soluble forms. Alternatively, the proteins of the invention can be expressed on the surface of a cell, such as a CHO cell and can be prepared according to methods well known in the art. The proteins of the invention can also be coupled to a solid phase support, such as a bead or a plate. In a specific embodiment, a B7-2Ig fusion protein is attached to a solid phase support, such as a bead, for example a biodegradable bead. In a preferred embodiment, a variable region form of B7-2 is attached to a solid support. In a most preferred embodiment, a B7-2VIg fusion protein comprising an amino acid sequence of about position 24 to 133 of human B7-2Ig (SEQ ID NO: 2) linked to the constant domain of an IgG molecule is attached to a solid phase support.

These molecules can then be attached to a solid phase surface via several possible methods. For example, the proteins of the invention, such as a variable region form of B7-2, can be crosslinked to the beads via covalent modification using tosyl linkage. In this method, the proteins of the invention are typically in 0.05M borate buffer, pH 9.5 and added to tosyl-activated magnetic immunobeads (Dynal Inc., Great Neck, N.Y.) according to manufacturer's instructions. After a 24 hr incubation at 22° C., the beads are collected and washed extensively. It is not mandatory that immunomagnetic beads be used, as other methods are also satisfactory. For example, proteins of the invention may also be immobilized on polystyrene beads or culture vessel surfaces.

It is also possible to attach the proteins, such as B7-2VIg to a solid phase surface through an avidin- or streptavidin-biotin complex. In this particular embodiment, the soluble protein is first crosslinked to biotin and then reacted with the solid phase surface to which avidin or streptavidin molecules are bound. It is also possible to crosslink the protein with avidin or streptavidin and to react these with a solid phase surface that is covered with biotin molecules.

These and other aspects of this invention are described in detail in the following subsections.

I. Isolation of Nucleic Acid From Cell Lines

Suitable cells for use in isolating nucleic acids encoding peptides having an activity of a novel B lymphocyte antigen include cells capable of producing mRNA coding for B lymphocyte antigens (e.g., B7-1, B7-2, B7-3) and appropriately translating the mRNA into the corresponding protein. One source of mRNA is normal human splenic B cells, either resting or activated by treatment with an anti-immunoglobulin antibody or an anti-MHC class II antibody, or from subsets of neoplastic B cells. Expression of the human B7-2 antigen is detectable in resting B cells and in activated B cells, with mRNA levels increasing 4-fold from resting levels following stimulation. Total cellular RNA can be obtained using standard techniques from resting or activated B cells during these intervals and utilized in the construction of a cDNA library.

In addition, various subsets of neoplastic B cells may express B7-2 and B7-3 and can alternatively serve as a source of the mRNA for construction of a cDNA library. For example, tumor cells isolated from patients with non-Hodgkins lymphoma express B7-1 MRNA. B cells from nodular, poorly differentiated lymphoma (NPDL), diffuse large cell lymphoma (LCL) and Burkitt's lymphoma cell lines are also suitable sources of human B7-1 mRNA and, potentially B7-2 and B7-3 mRNA. Myelomas generally express B7-2, but not B7-1 mRNA, and, thus can provide a source of B7-2 mRNA. The Burkitt's lymphoma cell line Raji is one source of B lymphocyte antigen MRNA. Preferably, B7-2 MRNA is obtained from a population of both resting and activated normal human B cells. Activated B cells can be obtained by stimulation over a broad spectrum of time (e.g., from minutes to days) with, for example, an anti-immunoglobulin antibody or an anti-MCH class II antibody.

II. Isolation of mRNA and Construction of cDNA Library

Total cellular mRNA can be isolated by a variety of techniques, e.g., by using the guanidinium-thiocyanate extraction procedure of Chirgwin et al., *Biochemistry* 18, 5294–5299 (1979). According to this method, Poly (A+) mRNA is prepared and purified for use in a cDNA library construction using oligo (dT) cellulose selection. cDNA is then synthesized from the poly(A+) RNA using oligo(dT) priming and reverse transcriptase. Moloney MLV reverse transcriptase (available from Gibco/BRL, Bethesda, Md.) or AMV reverse transcriptase (available from Seikagaku America, Inc., St. Petersburg, Fla.) are preferably employed.

Following reverse transcription, the mRNA/DNA hybrid molecule is converted to double stranded DNA using conventional techniques and incorporated into a suitable vector. The experiments herein employed *E. coli* DNA polymerase I and ribonuclease H in the conversion to double stranded cDNA.

Cloning of the cDNAs can be accomplished using any of the conventional techniques for joining double stranded DNA with an appropriate vector. The use of synthetic adaptors is particularly preferred, since it alleviates the possibility of cleavage of the cDNA with restriction enzyme prior to cloning. Using this method, non-self complementary, kinased adaptors are added to the DNA prior to ligation with the vector. Virtually any adaptor can be employed. As set forth in more detail in the examples below, non-self complementary BstXI adaptors are preferably added to the cDNA for cloning, for ligation into a pCDM8 vector prepared for cloning by digestion with BstXI.

Eucaryotic cDNA can be expressed when placed in the sense orientation in a vector that supplies an appropriate eucaryotic promoter and origin of replication and other elements including enhancers, splice acceptors and/or donor sequences and polyadenylation signals. The cDNAs of the present invention are placed in suitable vectors containing a eucaryotic promoter, an origin of replication functional in *E. coli*, an SV40 origin of replication which allows growth in COS cells, and a cDNA insertion site. Suitable vectors include πH3 (Seed and Aruffo, *Proc. Natl. Acad. Sci.*, 84:3365–3369 (1987)), πH3m (Aruffo and Seed, *Proc. Natl. Acad. Sci.*, 84:8573–8577 (1987)), pCDM7 and pCDM8 (Seed, *Nature*, 329:840–841 (1987), with the pCDM8 vector being particularly preferred (available commercially from Invitrogen, San Diego, Calif.).

III. Transfection of Host Cells and Screening for Novel B Lymphocyte Activation Antigens The thus prepared cDNA library is then used to clone the gene of interest by expression cloning techniques. A basic expression cloning technique has been described by Seed and Aruffo, *Proc. Natl. Acad Sc. USA*, 84:3365–3369 (1987) and Aruffo and Seed, *Proc. Natl. Acad. Sci. USA*, 84:8573–8577 (1987), although modifications to this technique may be necessary.

According to one embodiment, plasmid DNA is introduced into a simian COS cell line (Gluzman, *Cell* 23:175 (1981)) by known methods of transfection (e.g., DEAE-Dextran) and allowed to replicate and express the cDNA inserts. The transfectants expressing B7-1 antigen are depleted with an anti-B7-1 monoclonal antibody (e.g., 133 and B1.1) and anti-murine IgG and IgM coated immunomagnetic beads. Transfectants expressing human B7-2 antigen can be positively selected by reacting the transfectants with the fusion proteins CTLA4Ig and CD28Ig, followed by panning with anti-human Ig antibody coated plates. Although human CTLA4Ig and CD28Ig fusion proteins were used in the examples described herein, given the cross-species reactivity between B7-1 and, for example murine B7-1 it can be expected that other fusion proteins reactive with another cross-reactive species could be used. After panning, episomal DNA is recovered from the panned cells and transformed into a competent bacterial host, preferably *E. coli*. Plasmid DNA is subsequently reintroduced into COS cells and the cycle of expression and panning repeated at least two times. After the final cycle, plasmid DNA is prepared from individual colonies, transfected into COS cells and analyzed for expression of novel B lymphocyte antigens by indirect immunofluorescence with, for example, CTLA4Ig and CD28Ig.

IV. Sequencing of Novel B Lymphocyte Antigens

Plasmids are prepared from those clones which are strongly reactive with the CTLA4Ig and/or CD28Ig. These plasmids are then sequenced. Any of the conventional sequencing techniques suitable for sequencing tracts of DNA about 1.0 kb or larger can be employed.

As described in Example 4, a human B7-2 clone (clone29) was obtained containing an insert of 1,120 base pairs with a single long open reading frame of 987 nucleotides and approximately 27 nucleotides of 3' noncoding sequences (FIG. 8, SEQ ID NO:1). The predicted amino acid sequence encoded by the open reading frame of the protein is shown below the nucleotide sequence in FIG. 8. The encoded human B7-2 protein, is predicted to be 329 amino acid residues in length (SEQ ID NO:2). This protein sequence exhibits many features common to other type I Ig superfamily membrane proteins. Protein translation is predicted to begin at the methionine codon (ATG, nucleotides 107 to 109) based on the DNA homology in this region with the consensus eucaryotic translation initiation site (see Kozak, M. (1987) *Nucl. Acids Res.* 15:8125–8148). The amino terminus of the B7-2 protein (amino acids 1 to 23) has the characteristics of a secretory signal peptide with a predicted cleavage between the alanines at positions 23 and 24 (von Heijne (1987) Nucl. Acids Res. 14:4683). Processing at this site would result in a B7-2 membrane bound protein of 306 amino acids having an unmodified molecular weight of approximately 34 kDa. This protein would consist of an approximate extracellular Ig superfamily V and C like domains of from about amino acid residue 24 to 245, a hydrophobic transmembrane domain of from about amino acid residue 246 to 268, and a long cytoplasmic domain of from about amino acid residue 269 to 329. The homologies to the Ig superfamily are due to the two contiguous Ig-like domains in the extracellular region bound by the cysteines at positions 40 to 110 and 157 to 218. The extracellular domain also contains eight potential N-linked glycosylation sites and, like B7-1, is probably glycosylated. Glycosylation of the human B7-2 protein may increase the molecular weight to about 50–70 kDa. The cytoplasmic domain of human B7-2, while somewhat longer than B7-l, contains a common region of multiple cysteines followed by positively charged amino acids which presumably function as signaling or regulatory domains within an antigen-presenting cell (APC). Comparison of both the nucleotide and amino acid sequences of the human B7-2 with the GenBank and EMBL databases yielded significant homology (about 26% amino acid sequence identity) with human B7-1. Since human B7-1, human B7-2 and murine B7-1 all bind to human CTLA4 and CD28, the homologous amino acids probably represent those necessary to comprise a CTLA4 or CD28 binding sequence. *E. coli* transfected with a vector containing a cDNA insert encoding human B7-2 (clone 29) was deposited with the American Type Culture Collection (ATCC) on Jul. 26, 1993 as Accession No. 69357.

V. Cloning Novel B Lymphocyte Antigens from Other Mammalian Species

The present invention is not limited to human nucleic acid molecules and contemplates that novel B lymphocyte antigen homologues from other mammalian species that express B lymphocyte antigens can be cloned and sequenced using the techniques described herein. B lymphocyte antigens isolated for one species (e.g., humans) which exhibit cross-species reactivity may be used to modify T cell mediated immune responses in a different species (e.g., mice). Isolation of cDNA clones from other species can also be accomplished using human CDNA inserts, such as human B7-2 CDNA, as hybridization probes.

As described in Example 6, a murine B7-2 clone (mB7-2, clone 4) was obtained containing an insert of 1,163 base pairs with a single long open reading frame of 927 nucleotides and approximately 126 nucleotides of 3' noncoding sequences (FIG. 14, SEQ ID NO:22). The predicted amino acid sequence encoded by the open reading frame of the protein is shown below the nucleotide sequence in FIG. 14. The encoded murine B7-2 protein, is predicted to be 309 amino acid residues in length (SEQ ID NO:23). This protein sequence exhibits many features common to other type I Ig superfamily membrane proteins. Protein translation is predicted to begin at the methionine codon (ATG, nucleotides 111 to 113) based on the DNA homology in this region with the consensus eucaryotic translation initiation site (see Kozak, M. (1987) *Nucl. Acids Res.* 15:8125–8148). The amino terminus of the murine B7-2 protein (amino acids 1 to 23) has the characteristics of a secretory signal peptide with a predicted cleavage between the alanine at position 23 and the valine at position 24 (von Heijne (1987) *Nucl. Acids Res.* 14:4683). Processing at this site would result in a murine B7-2 membrane bound protein of 286 amino acids having an unmodified molecular weight of approximately 32 kDa This protein would consist of an approximate extracellular Ig superfamily V and C like domains of from about amino acid residue 24 to 246, a hydrophobic transmembrane domain of from about amino acid residue 247 to 265, and a long cytoplasmic domain of from about amino acid residue 266 to 309. The homologies to the Ig superfamily are due to the two contiguous Ig-like domains in the extracellular region bound by the cysteines at positions 40 to 110 and 157 to 216. The extracellular domain also contains nine potential N-linked glycosylation sites and, like murine B7-1, is probably glycosylated. Glycosylation of the murine B7-2 protein may increase the molecular weight to about 50–70 kDa. The cytoplasmic domain of murine B7-2 contains a common region which has a cysteine followed by positively charged amino acids which presumably functions as signaling or regulatory domain within an APC. Comparison of both the nucleotide and amino acid sequences of murine B7-2 with the GenBank and EMBL databases yielded significant homology (about 26% amino acid sequence identity) with human and murine B7-1. Murine B7-2 exhibits about 50% identity and 67% similarity with its human homologue, hB7-2. *E. coli* (DH106/p3) transfected with a vector (plasmid pmBx4) containing a cDNA insert encoding murine B7-2 (clone 4) was deposited with the American Type Culture Collection (ATCC) on Aug. 18, 1993 as Accession No. 69388.

Nucleic acids which encode novel B lymphocyte antigens from other species, such as the murine B7-2, can be used to generate either transgenic animals or "knock out" animals which, in turn, are useful in the development and screening of therapeutically useful reagents. A transgenic animal (e.g., a mouse) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, murine B7-2 cDNA or an appropriate sequence thereof can be used to clone genomic B7-2 in accordance with established techniques and the genomic sequences used to generate transgenic animals that contain cells which express B7-2 protein. Methods for generating transgenic animals, particularly animals such as mice, have become conventional in the art and are described, for example, in U.S. Pat. Nos. 4,736,866 and 4,870,009. Typically, particular cells would be targeted for B7-2 transgene incorporation with tissue specific enhancers, which could result in T cell costimulation and enhanced T cell proliferation and autoimmunity. Transgenic animals that include a copy of a B7-2 transgene introduced into the germ line of the animal at an embryonic stage can be used to examine the effect of increased B7 expression. Such animals can be used as tester animals for reagents thought to confer protection from, for example, autoimmune disease. In accordance with this facet of the invention, an animal is treated with the reagent and a reduced incidence of the disease, compared to untreated animals bearing the transgene, would indicate a potential therapeutic intervention for the disease.

Alternatively, the non-human homologues of B7-2 can be used to construct a B7-2 "knock out" animal which has a defective or altered B7-2 gene as a result of homologous recombination between the endogenous B7-2 gene and altered B7-2 genomic DNA introduced into an embryonic cell of the animal. For example, murine B7-2 cDNA can be used to clone genomic B7-2 in accordance with established techniques. A portion of the genomic B7-2 DNA (e.g., such as an exon which encodes an extracellular domain) can be deleted or replaced with another gene, such as a gene encoding a selectable marker which can be used to monitor integration. Typically, several kilobases of unaltered flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced DNA has homologously recombined with the endogenous DNA are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for their ability to accept grafts, reject tumors and defend against infectious diseases and can be used in the study of basic immunobiology.

VI. Expression of B Lymphocyte Antigens

Host cells transfected to express peptides having the activity of a novel B lymphocyte antigen are also within the scope of the invention. The host cell may be any procaryotic or eucaryotic cell. For example, a peptide having B7-2 activity may be expressed in bacterial cells such as *E. coli*, insect cells (baculovirus), yeast, or mammalian cells such as Chinese hamster ovary cells (CHO) and NSO cells. Other suitable host cells may be found in Goeddel, (1990) supra or are known to those skilled in the art.

For example, expression in eucaryotic cells such as mammalian, yeast, or insect cells can lead to partial or complete glycosylation and/or formation of relevant inter- or intra-chain disulfide bonds of recombinant protein. Examples of vectors for expression in yeast *S. cerivisae* include pYepSec1 (Baldari. et al., (1987) *EMBO J.* 6:229–234), pMFa (Kuwjan and Herskowitz, (1982) *Cell* 30:933–943), pJRY88 (Schultz et al., (1987) *Gene* 54:113–123), and pYES2 (Invitrogen Corporation, San Diego, Calif.). Baculovirus vectors available for expression of proteins in cultured insect cells (SF 9 cells) include the pAc series (Smith et al., (1983) *Mol. Cell Biol.* 3:2156–2165) and the pVL series (Lucklow, V. A., and Summers, M. D., (1989) *Virology* 170:31–39). Generally, COS cells (Gluzman, Y., (1981) *Cell* 23:175–182) are used in conjunction with such vectors as pCDM8 (Seed, B., (1987) *Nature* 329:840) for transient amplification/expression in mammalian cells, while CHO (dhfi⁻Chinese Hamster Ovary) cells are used with vectors such as pMT2PC (Kaufinan et al. (1987), *EMBO J.* 6:187–195) for stable amplification/expression in mammalian cells. A preferred cell line for production of recombinant protein is the NSO myeloma cell line available from the ECACC (catalog #85110503) and described in Galfre, G. and Milstein, C. ((1981) *Methods in Enzymology* 73(13):3–46; and *Preparation of Monoclonal Antibodies: Strategies and Procedures*, Academic Press, N.Y., N.Y). Vector DNA can be introduced into mammalian cells via conventional techniques such as calcium phosphate or calcium chloride co-precipitation, DEAE-dextran-mediated transfection, lipofectin, or electroporation. Suitable methods for transforming host cells can be found in Sambrook et al. (*Molecular Cloning: A Laboratory Manual*, 2nd Edition, Cold Spring Harbor Laboratory press (1989)), and other laboratory textbooks. When used in mammalian cells, the expression vector's control functions are often provided by viral material. For example, commonly used promoters are derived from polyoma, Adenovirus 2, cytomegalovirus and most frequently, Simian Virus 40.

It is known that a small faction of cells (about 1 out of $10^5$) typically integrate DNA into their genomes. In order to identify these integrants, a gene that contains a selectable marker (i.e., resistance to antibiotics) is generally introduced into the host cells along with the gene of interest. Preferred selectable markers include those which confer resistance to drugs, such as G418, hygromycin and methotrexate. Selectable markers may be introduced on the same plasmid as the gene of interest or may be introduced on a separate plasmid. Cells containing the gene of interest can be identified by drug selection; cells that have incorporated the selectable marker gene will survive, while the other cells die. The surviving cells can then be screened for production of novel B lymphocyte antigens by cell surface staining with ligands to the B cell antigens (e.g., CTLA4Ig and CD28Ig). Alternatively, the protein can be metabolically radiolabeled with a labeled amino acid and immunoprecipitated from cell supernatant with an anti-B lymphocyte antigen monoclonal antibody or a fusion protein such as CTLA4Ig or CD28Ig.

Expression in procaryotes is most often carried out in *E. coli* with vectors containing constitutive or inducible promoters directing the expression of either fusion or non-fusion proteins. Fusion vectors add a number of amino acids usually to the amino terminus of the expressed target gene. Such fusion vectors typically serve three purposes: 1) to increase expression of recombinant protein; 2) to increase the solubility of the target recombinant protein; and 3) to aid in the purification of the target recombinant protein by acting as a ligand in affinity purification. Often, in fusion expression vectors, a proteolytic cleavage site is introduced at the junction of the fusion moiety and the target recombinant protein to enable separation of the target recombinant protein from the fusion moiety subsequent to purification of the fusion protein. Such enzymes, and their cognate recognition sequences, include Factor Xa, thrombin and enterokinase. Typical fusion expression vectors include pGEX (Amrad Corp., Melbourne, Australia), pMAL (New England Biolabs, Beverly, Mass.) and pRITs (Pharmacia, Piscataway, N.J.) which fuse glutathione S-transferase, maltose E binding protein, or protein A, respectively, to the target recombinant protein.

*E. coli* expression systems include the inducible expression vectors pTrc (Amann et al., (1988) Gene 69:301–315) and pET 11 (Studier et al., *Gene Expression Technology: Methods in Enzymology* 185, Academic Press, San Diego, Calif. (1990) 60–89; commercially available from Novagen). In the pTrc vector system, the inserted gene is expressed with a pelB signal sequence by host RNA polymerase transcription from a hybrid trp-lac fusion promoter. After induction, the recombinant protein can be purified from the periplasmic fraction. In the pET 11 vector system, the target gene is expressed as non-fusion protein by transcription from the T7 gn 10-lac 0 fusion promoter mediated by a coexpressed viral RNA polymerase (T7 gn1). This viral polymerase is supplied by host *E. coli* strains BL21(DE3) or HMS174(DE3) from a resident λ prophage harboring a T7 gn1 under the transcriptional control of the lacUV 5 promoter. In this system, the recombinant protein can be purified from inclusion bodies in a denatured form and, if desired, renatured by step gradient dialysis to remove denaturants.

One strategy to maximize recombinant B7-2 expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy would be to alter the nucleic acid sequence of the B7-2 gene or other DNA to be inserted into an expression vector so that the individual codons for each amino acid would be those preferentially utilized in highly expressed *E. coli* proteins (Wada et al., (1992) *Nuc. Acids Res.* 20:2111–2118). Such alteration of nucleic acid sequences of the invention could be carried out by standard DNA synthesis techniques.

Novel B lymphocyte antigens and portions thereof, expressed in mammalian cells or otherwise, can be purified according to standard procedures of the art, including ammonium sulfate precipitation, fractionation column chromatography (e.g. ion exchange, gel filtration, electrophoresis, affinity chromatography, etc.) and ultimately, crystallization (see generally, "Enzyme Purification and Related Techniques", *Methods in Enzymology*, 22:233–577 (1971)). Once purified, partially or to homogeneity, the recombinantly produced B lymphocyte antigens or portions thereof can be utilized in compositions suitable for pharmaceutical administration as described in detail herein.

VII. Modifications of Nucleic Acid and Amino Acid Sequences of the Invention and Assays for B7 Lymphocyte Antigen Activity It will be appreciated by those skilled in the art that other nucleic acids encoding peptides having the activity of a novel B lymphocyte antigen can be isolated by the above process. Different cell lines can be expected to yield DNA molecules having different sequences of bases. Additionally, variations may exist due to genetic polymorphisms or cell-mediated modifications of the genetic material. Furthermore, the DNA sequence of a B lymphocyte antigen can be modified by genetic techniques to produce proteins or peptides with altered amino acid sequences. Such sequences are considered within the scope of the present invention, where the expressed peptide is capable of either inducing or inhibiting activated T cell mediated immune responses and immune function.

A number of processes can be used to generate equivalents or fragments of an isolated DNA sequence. Small subregions or fragments of the nucleic acid encoding the B7-2 protein, for example 1–30 bases in length, can be prepared by standard, synthetic organic chemical means. The technique is also useful for preparation of antisense oligonucleotides and primers for use in the generation of larger synthetic fragments of B7-2 DNA.

Larger subregions or fragments of the genes encoding B lymphocyte antigens can be expressed as peptides by synthesizing the relevant piece of DNA using the polymerase chain reaction (PCR) (Sambrook, Fritsch and Maniatis, 2 *Molecular Cloning; A Laboratory Manual*, Cold Spring Harbor, N.Y., (1989)), and ligating the thus obtained DNA into an appropriate expression vector. Using. PCR, specific sequences of the cloned double stranded DNA are generated, cloned into an expression vector, and then assayed for CTLA4/CD28 binding activity. For example, to express a secreted (soluble) form of the human B7-2 protein, using PCR, a DNA can be synthesized which does not encode the transmembrane and cytoplasmic regions of the protein. This DNA molecule can be ligated into an appropriate expression vector and introduced into a host cell such as CHO, where the B7-2 protein fragment is synthesized and secreted. The B7-2 protein fragment can then readily be obtained from the culture media In another embodiment, mutations can be introduced into a DNA by any one of a number of methods, including those for producing simple deletions or insertions, systematic deletions, insertions or substitutions of clusters of bases or substitutions of single bases, to generate variants or modified equivalents of B lymphocyte antigen DNA. For example, changes in the human B7-2 cDNA sequence shown in FIG. 8 (SEQ ID NO:1) or murine B7-2 cDNA sequence shown in FIG. 14 (SEQ ID NO:22) such as amino acid substitutions or deletions are preferably obtained by site-directed mutagenesis. Site directed mutagenesis systems are well known in the art. Protocols and reagents can be obtained commercially from Amersham International PLC, Amersham, U.K.

Peptides having an activity of a novel B lymphocyte antigen, i.e., the ability to bind to the natural ligand(s) of a B lymphocyte antigen on T cells and either stimulate (amplify) or inhibit (block) activated T cell mediated immune responses, as evidenced by, for example, cytokine production and/or T cell proliferation by T cells that have received a primary activation signal are considered within the scope of the invention. More specifically, peptides that bind to T lymphocytes, for example $CD28^+$ cells, may be capable of delivering a costimulatory signal to the T lymphocytes, which, when transmitted in the presence of antigen and class II MHC, or other material capable of transmitting a primary signal to the T cell, results in activation of cytokine genes within the T cell. Alternatively, such a peptide can be used in conjunction with class I MHC to thereby activate $CD8^+$ cytolytic T cells. In addition, soluble, monomeric forms of the B7-2 protein, may retain the ability to bind to their natural ligand(s) on $CD28^+$ T cells but, perhaps because of insufficient cross-linking with the ligand, fail to deliver the secondary signal essential for enhanced cytokine production and cell division. Such peptides, which provide a means to induce a state of anergy or tolerance in the cells, are also considered within the scope of the invention.

Screening the peptides for those which retain a characteristic B lymphocyte antigen activity as described herein can be accomplished using one or more of several different assays. For example, the peptides can be screened for specific reactivity with an anti-B7-2 monoclonal antibody reactive with cell surface B7-2 or with a fusion protein, such as CTLA4Ig or CD28Ig. Specifically, appropriate cells, such as COS cells, can be transfected with a B7-2 DNA encoding a peptide and then analyzed for cell surface phenotype by indirect immunofluorescence and flow cytometry to determine whether the peptide has B7-2 activity. Cell surface expression of the transfected cells is evaluated using a monoclonal antibody specifically reactive with cell surface B7-2 or with a CTLA4Ig or CD28Ig fusion protein. Production of secreted forms of B7-2 is evaluated using anti-B7-2 monoclonal antibody or CTLA4Ig or CD28 fusion protein for immunoprecipitation.

Other, more preferred, assays take advantage of the functional characteristics of the B7-2 antigen. As previously set forth, the ability of T cells to synthesize cytokines depends not only on occupancy or cross-linking of the T cell receptor for antigen (the "primary activation signal" provided by, for example anti-CD3, or phorbol ester to produce an "activated T cell"), but also on the induction of a costimulatory signal, in this case, by interaction with a B lymphocyte antigen, such as B7-2, B7-1 or B7-3. The binding of B7-2 to its natural ligand(s) on, for example, $CD28^+$ T cells, has the effect of transmitting a signal to the T cell that induces the production of increased levels of cytokines, particularly of interleukin-2, which in turn stimulates the proliferation of the T lymphocytes. Other assays for B7-2 function thus involve assaying for the synthesis of cytokines, such as interleukin-2, interleukin-4 or other known or unknown novel cytokines, and/or assaying for T cell proliferation by $CD28^+$ T cells which have received a primary activation signal.

In vitro, T cells can be provided with a first or primary activation signal by anti-T3 monoclonal antibody (e.g. anti-CD3) or phorbol ester or, more preferably, by antigen in association with class II MHC. T cells which have received a primary activation signal are referred to herein as activated T cells. B7-2 function is assayed by adding a source of B7-2 (e.g., cells expressing a peptide having B7-2 activity or a secreted form of B7-2) and a primary activation signal such as antigen in association with Class II MHC to a T cell culture and assaying the culture supernatant for interleukin-2, gamma interferon, or other known or unknown cytokine. For example, any one of several conventional assays for interleukin-2 can be employed, such as the assay described in *Proc. Natl. Acad. Sci. USA*, 86:1333 (1989) the pertinent portions of which are incorporated herein by reference. A kit for an assay for the production of interferon is also available from Genzyme Corporation (Cambridge, Mass.). T cell proliferation can also be measured as described in the Examples below. Peptides that retain the characteristics of the B7-2 antigen as described herein may result in increased per cell production of cytokines, such as IL-2, by T cells and may also result in enhanced T cell proliferation when compared to a negative control in which a costimulatory signal is lacking.

The same basic functional assays can also be used to screen for peptides having B7-2 activity, but which lack the ability to deliver a costimulatory signal, but in the case of such peptides, addition of the B7-2 protein will not result in a marked increase in proliferation or cytokine secretion by the T cells. The ability of such proteins to inhibit or completely block the normal B7-2 costimulatory signal and induce a state of anergy can be determined using subsequent attempts at stimulation of the T cells with antigen presenting cells that express cell surface B7-2 and present antigen. If the T cells are unresponsive to the subsequent activation attempts, as determined by IL-2 synthesis and T cell proliferation, a state of anergy has been induced. See, e.g., Gimmi, C. D. et al. (1993) *Proc. Natl. Acad. Sci. USA* 90, 6586–6590; and Schwartz (1990) *Science*, 248, 1349–1356, for assay systems that can used as the basis for an assay in accordance with the present invention.

It is possible to modify the structure of a peptide having the activity of a novel B lymphocyte antigen for such purposes as increasing solubility, enhancing therapeutic or prophylactic efficacy, or stability (e.g., shelf life ex vivo and resistance to proteolytic degradation in vivo). Such modified peptides are considered functional equivalents of the B lymphocyte antigens as defined herein. For example, a peptide having B7-2 activity can be modified so that it maintains the ability to co-stimnulate T cell proliferation and/or produce cytokines. Those residues shown to be essential to interact with the CTLA4/CD28 receptors on T cells can be modified by replacing the essential amino acid with another, preferably similar amino acid residue (a conservative substitution) whose presence is shown to enhance, diminish, but not eliminate, or not effect receptor interaction. In addition, those amino acid residues which are not essential for receptor interaction can be modified by being replaced by another amino acid whose incorporation may enhance, diminish, or not effect reactivity.

Another example of modification of a peptide having the activity of a novel B lymphocyte antigen is substitution of cysteine residues preferably with alanine, serine, threonine, leucine or glutamic acid residues to minimize dimerization via disulfide linkages. In addition, amino acid side chains of a peptide having B7-2 activity can be chemically modified. Another modification is cyclization of the peptide.

In order to enhance stability and/or reactivity, peptides having B7-2 activity can be modified to incorporate one or more polymorphisms in the amino acid sequence of the antigen resulting from any natural allelic variation. Additionally, D-amino acids, non-natural amino acids, or non-amino acid analogs can be substituted or added to produce a modified protein within the scope of this invention. Furthermore, the peptides can be modified using polyethylene glycol (PEG) according to the method of A. Sehon and co-workers (Wie et al., supra) to produce a peptide conjugated with PEG. In addition, PEG can be added during chemical synthesis of the peptide. Other modifications of the peptides include reduction/alkylation (Tarr in: *Methods of Protein Microcharacterization*, J. E. Silver ed., Humana Press, Clifton N.J. 155–194 (1986)); acylation (Tarr, supra); chemical coupling to an appropriate carrier (Mishell and Shiigi, eds, *Selected Methods in Cellular Immunology*, W H Freeman, San Francisco, Calif. (1980), U.S. Pat. No. 4,939, 239; or mild formalin treatment (Marsh (1971), *Int. Arch. of Allergy and Appl. Immunol*. 41:199–215).

To facilitate purification and potentially increase solubility of a peptide, it is possible to add an amino acid fusion moiety to the protein backbone. For example, hexa-histidine can be added to the peptide for purification by immobilized metal ion affinity chromatography (Hochuli, E. et al., (1988) *Bio/Technology* 6:1321–1325). In addition, to facilitate isolation of a B lymphocyte antigen free of irrelevant sequences, specific endoprotease cleavage sites can be introduced between the sequences of a fusion moiety and the peptide. It may be necessary to increase the solubility of a peptide by adding functional groups to the peptide, or by omitting hydrophobic regions of the peptide.

VII. Uses of Nucleic Acid Sequences Encoding B Lymphocyte Antigens and Peptides Having B7-2 Activity

A. Molecular Probes

The nucleic acids of this invention are useful diagnostically, for tracking the progress of disease, by measuring the activation status of B lymphocytes in biological samples or for assaying the effect of a molecule on the expression of a B lymphocyte antigen (e.g., detecting cellular mRNA levels). In accordance with these diagnostic assays, the nucleic acid sequences are labeled with a detectable marker, e.g., a radioactive, fluorescent, or biotinylated marker and used in a conventional dot blot or Northern hybridization procedure to probe mRNA molecules of total or poly(A+) RNAs from a biological sample.

B. Antibody Production

The peptides and fusion proteins produced from the nucleic acid molecules of the present invention can also be used to produce antibodies specifically reactive with B lymphocyte antigens. For example, by using a full-length B7-2 protein, or a peptide fragment thereof, having an amino acid sequence based on the predicted amino acid sequence of B7-2, anti-protein/anti-peptide polyclonal antisera or monoclonal antibodies can be made using standard methods. A mammal, (e.g., a mouse, hamster, or rabbit) can be immunized with an immunogenic form of the protein or peptide which elicits an antibody response in the mammal. The immunogen can be, for example, a recombinant B7-2 protein, or fragment thereof, a synthetic peptide fragment or a cell that expresses a B lymphocyte antigen on its surface. The cell can be for example, a splenic B cell or a cell transfected with a nucleic acid encoding a B lymphocyte antigen of the invention (e.g., a B7-2 cDNA) such that the B lymphocyte antigen is expressed on the cell surface. The immunogen can be modified to increase its immunogenicity. For example, techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay can be used with the immunogen as antigen to assess the levels of antibodies.

Following immunization, antisera can be obtained and, if desired, polyclonal antibodies isolated from the sera. To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. For example, the hybridoma technique originally developed by Kohler and Milstein (*Nature (*1975) 256:495–497) as well as other techniques such as the human B-cell hybridoma technique (Kozbar et al., *Immunol. Today* (1983) 4:72), the EBV-hybridoma technique to produce human monoclonal antibodies (Cole et al. *Monoclonal Antibodies in Cancer Therapy* (1985) (Allen R. Bliss, Inc., pages 77–96), and screening of combinatorial antibody libraries (Huse et al., *Science* (1989) 246:1275). Hybridoma cells can be screened immunochemically for production of antibodies specifically reactive with the peptide and monoclonal antibodies isolated.

The term antibody as used herein is intended to include fragments thereof which are also specifically reactive with a peptide having the activity of a novel B lymphocyte antigen or fusion protein as described herein. Antibodies can be fragmented using conventional techniques and the fragments screened for utility in the same manner as described above for whole antibodies. For example, $F(ab')_2$ fragments can be generated by treating antibody with pepsin. The resulting $F(ab')_2$ fragment can be treated to reduce disulfide bridges to produce Fab' fragments. The antibody of the present invention is further intended to include bispecific and chimeric molecules having an anti-B lymphocyte antigen (i.e., B7-2, B7-3) portion.

Particularly preferred antibodies are anti-human B7-2 monoclonal antibodies produced by hybridomas HA3.1F9, HA5.2B7 and HF2.3D1. The preparation and characterization of these antibodies is described in detail in Example 8. Monoclonal antibody HA3.1F9 was determined to be of the IgG1 isotype; monoclonal antibody HA5.2B7 was determined to be of the IgG2b isotype; and monoclonal antibody HF2.3D1 was determined to be of the IgG2a isotype. Hybridoma cells were deposited with the American Type Culture Collection, which meets the requirements of the Budapest Treaty, on Jul. 19, 1994 as ATCC Accession No. HB11688 (hybridoma HA3.1F9), ATCC Accession No. HB11687 (HA5.2B7) and ATCC Accession No. HB11686 (HF2.3D1).

When antibodies produced in non-human subjects are used therapeutically in humans, they are recognized to varying degrees as foreign and an immune response may be generated in the patient. One approach for minimizing or eliminating this problem, which is preferable to general immunosuppression, is to produce chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region which recognizes the gene product of the novel B lymphocyte antigens of the invention. See, for example, Morrison et al., Proc. Natl. Acad. Sci. U.S.A. 81:6851 (1985); Takeda et al., Nature 314:452 (1985), Cabilly et al., U.S. Pat. No. 4,816,567; Boss et al., U.S. Pat. No. 4,816,397; Tanaguchi et al., European Patent Publication EP 171496; European Patent Publication 0173494, United Kingdom Patent GB 2177096B. It is expected that such chimeric antibodies would be less immunogenic in a human subject than the corresponding non-chimeric antibody.

For human therapeutic purposes, the monoclonal or chimeric antibodies specifically reactive with a peptide having the activity of a B lymphocyte antigen as described herein can be further humanized by producing human variable region chimeras, in which parts of the variable regions, especially the conserved framework regions of the antigen-binding domain, are of human origin and only the hypervariable regions are of non-human origin. General reviews of "humanized" chimeric antibodies are provided by Morrison, S. L. (1985) Science 229:1202–1207 and by Oi et al. (1986) BioTechniques 4:214. Such altered immunoglobulin molecules may be made by any of several techniques known in the art, (e.g., Teng et al., Proc. Natl. Acad. Sci. U.S.A., 80:7308–7312 (1983); Kozbor et al., Immunology Today, 4:7279 (198.3); Olsson et al., Meth. Enzymol., 92:3–16 (1982)), and are preferably made according to the teachings of PCT Publication WO92/06193 or EP 0239400. Humanized antibodies can be commercially produced by, for example, Scotgen Limited, 2 Holly Road, Twickenham, Middlesex, Great Britain. Suitable "humanized" antibodies can be alternatively produced by CDR or CEA substitution (see U.S. Pat. No. 5,225,539 to Winter; Jones et al. (1986) Nature 321:552–525; Verhoeyen et al. (1988) Science 239:1534; and Beidler et al. (1988) J. Immunol. 141:40534060). Humanized antibodies which have reduced immunogenicity are preferred for immunotherapy in human subjects. Immunotherapy with a humanized antibody will likely reduce the necessity for any concomitant immunosuppression and may result in increased long term effectiveness for the treatment of chronic disease situations or situations requiring repeated antibody treatments.

As an alternative to humanizing a monoclonal antibody from a mouse or other species, a human monoclonal antibody directed against a human protein can be generated. Transgenic mice carrying human antibody repertoires have been created which can be immunized with a human B lymphocyte antigen, such as B7-2. Splenocytes from these immunized transgenic mice can then be used to create hybridomas that secrete human monoclonal antibodies specifically reactive with a human B lymphocyte antigen (see, e.g., Wood et al. PCT publication WO 91/00906, Kucherlapati et al. PCT publication WO 91/10741; Lonberg et al. PCT publication WO 92/03918; Kay et al. PCT publication 92/03917; Lonberg, N. et al. (1994) Nature 368:856–859; Green, L. L. et al. (1994) Nature Genet. 7:13–21; Morrison, S. L. et al. (1994) Proc. Natl. Acad. Sci. USA 81:6851–6855; Bruggeman et al. (1993) Year Immunol 7:33–40; Tuaillon et al. (1993) Proc. Natl. Acad. Sci. USA 90:3720–3724; and Bruggeman et al. (1991) Eur J Immunol 21:1323–1326).

Monoclonal antibody compositions of the invention can also be produced by other methods well known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies that bind a B lymphocyte antigen of the invention (for descriptions of combinatorial antibody display see e.g., Sastry et al. (1989) Proc. Natl. Acad. Sci. USA 86:5728; Huse et al. (1989) Science 246:1275; and Orlandi et al. (1989) Proc. Natl. Acad. Sci. USA 86:3833). After immunizing an animal with a B lymphocyte antigen, the antibody repertoire of the resulting B-cell pool is cloned. Methods are generally known for directly obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primer to a conserved 3' constant region primer can be used for PCR amplification of the heavy and light chain variable regions from a number of murine antibodies (Larrick et al. (1991) Biotechniques 11:152–156). A similar strategy can also been used to amplify human heavy and light chain variable regions from human antibodies (Larrick et al. (1991) Methods: Companion to Methods in Enzymology 2:106-110).

In an illustrative embodiment, RNA is isolated from activated B cells of, for example, peripheral blood cells, bone marrow, or spleen preparations, using standard protocols (e.g., U.S. Pat. No. 4,683,202; Orlandi, et al. Proc. Natl. Acad. Sci. USA (1989) 86:3833–3837; Sastry et al., Proc. Natl. Acad. Sci. USA (1989) 86:5728–5732; and Huse et al. (1989) Science 246:1275–1281.) First-strand cDNA is synthesized using primers specific for the constant region of the heavy chain(s) and each of the κ and λ light chains, as well as primers for the signal sequence. Using variable region PCR primers, the variable regions of both heavy and light chains are amplified, each alone or in combination, and ligated into appropriate vectors for further manipulation in generating the display packages. Oligonucleotide primers useful in amplification protocols may be unique or degenerate or incorporate inosine at degenerate positions. Restriction endonuclease recognition sequences may also be incorporated into the primers to allow for the cloning of the amplified fragment into a vector in a predetermined reading frame for expression.

The V-gene library cloned from the immunization-derived antibody repertoire can be expressed by a population of display packages, preferably derived from filamentous phage, to form an antibody display library. Ideally, the display package comprises a system that allows the sampling of very large diverse antibody display libraries, rapid sorting after each affinity separation round, and easy isolation of the antibody gene from purified display packages. In addition to commercially available kits for generating phage display libraries (e.g., the Pharmnacia Recombinant Phage

*Antibody System*, catalog no. 27-9400–01; and the Stratagene SurfZAP™ phage display kit, catalog no. 240612), examples of methods and reagents particularly amenable for use in generating a diverse antibody display library can be found in, for example, Ladner et al. U.S. Pat. No. 5,223,409; Kang et al. International Publication No. WO 92/18619; Dower et al. International Publication No. WO 91/17271; Winteret al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1369–1372; Hay et al. (1992) *Hum Antibod Hybridomas* 3:81–85; Huse et al. (1 989) *Science* 246:1275–128 1; Griffiths et al. (1993) *EMBO J* 12:725–734; Hawkins et al. (1992) *J Mol Biol* 226:889–896; Clackson et al. (1991) *Nature* 352:624–628; Gram et al. (1992) *Proc. Natl. Acad. Sci. USA* 89:3576–3580; Garrard et al. (1991) *Bio/Technology* 9:1373–1377; Hoogenboom et al. (1991) *Nucleic Acids Res.* 19:41334137; and Barbas et al. (1991) *Proc. Natl. Acad. Sci. USA* 88:7978–7982.

In certain embodiments, the V region domains of heavy and light chains can be expressed on the same polypeptide, joined by a flexible linker to form a single-chain Fv fragment, and the scFV gene subsequently cloned into the desired expression vector or phage genome. As generally described in McCafferty et al., *Nature* (1990) 348:552–554, complete $V_H$ and $V_L$ domains of an antibody, joined by a flexible $(Gly_4\text{-Ser})_3$ linker can be used to produce a single chain antibody which can render the display package separable based on antigen affinity. Isolated scFV antibodies immunoreactive with a peptide having activity of a B lymphocyte antigen can subsequently be formulated into a pharmaceutical preparation for use in the subject method.

Once displayed on the surface of a display package (e.g., filamentous phage), the antibody library is screened with a B lymphocyte antigen protein, or peptide fragment thereof, to identify and isolate packages that express an antibody having specificity for the B lymphocyte antigen. Nucleic acid encoding the selected antibody can be recovered from the display package (e.g., from the phage genome) and subcloned into other expression vectors by standard recombinant DNA techniques.

The antibodies of the current invention can be used therapeutically to inhibit T cell activation through blocking receptor:ligand interactions necessary for costimulation of the T cell. These so-called "blocking antibodies" can be identified by their ability to inhibit T cell proliferation and/or cytokine production when added to an in vitro costimulation assay as described herein. The ability of blocking antibodies to inhibit T cell functions may result in immunosuppression and/or tolerance when these antibodies are administered in vivo.

C. Protein Purification

The polyclonal or monoclonal antibodies of the current invention, such as an antibody specifically reactive with a recombinant or synthetic peptide having B7-2 activity or B7-3 activity can also be used to isolate the native B lymphocyte antigen from cells. For example, antibodies reactive with the peptide can be used to isolate the naturally-occurring or native form of B7-2 from activated B lymphocytes by immunoaffinity chromatography. In addition, the native form of B7-3 can be isolated from B cells by immunoaffinity chromatography with monoclonal antibody BB-1.

D. Other Therapeutic Reagents

The nucleic acid sequences and novel B lymphocyte antigens described herein can be used in the development of therapeutic reagents having the ability to either upregulate (e.g., amplify) or downregulate (e.g., suppress or tolerize) T cell mediated immune responses. For example, peptides having B7-2 activity, including soluble, monomeric forms of the B7-2 antigen or a B7-2 fusion protein, e.g., B7-2Ig, and anti-B7-2 antibodies that fail to deliver a costimulatory signal to T cells that have received a primary activation signal, can be used to block the B7-2 ligand(s) on T cells and thereby provide a specific means by which to cause immunosuppression and/or induce tolerance in a subject. Such blocking or inhibitory forms of B lymphocyte antigens and fusion proteins and blocking antibodies can be identified by their ability to inhibit T cell proliferation and/or cytokine production when added to an in vitro costimulation assay as previously described herein. In contrast to the monomeric form, stimulatory forms of B7-2, such as an intact cell surface B7-2, retain the ability to transmit the costimulatory signal to the T cells, resulting in an increased secretion of cytokines when compared to activated T cells that have not received the secondary signal.

In addition, fusion proteins comprising a first peptide having an activity of B7-2 fused to a second peptide having an activity of another B lymphocyte antigen (e.g., B7-1) can be used to modify T cell mediated immune responses. Alternatively, two separate peptides having an activity of B lymphocyte antigens, for example, B7-2 and B7-1, or a combination of blocking antibodies (e.g., anti-B7-2 and anti-B7-1 monoclonal antibodies) can be combined as a single composition or administered separately (simultaneously or sequentially), to upregulate or downregulate T cell mediated immune responses in a subject. Furthermore, a therapeutically active amount of one or more peptides having B7-2 activity and or B7-1 activity can be used in conjunction with other immunomodulating reagents to influence immune responses. Examples of other immunomodulating reagents include blocking antibodies, e.g., against CD28 or CTLA4, against other T cell markers or against cytokines, fusion proteins, e.g., CTLA4Ig, or immunosuppressive drugs, e.g., cyclosporine A or FK506.

The peptides produced from the nucleic acid molecules of the present invention may also be useful in the construction of therapeutic agents which block T cell function by destruction of the T cell. For example, as described, secreted forms of a B lymphocyte antigen can be constructed by standard genetic engineering techniques. By linking a soluble form of B7-1, B7-2 or B7-3 to a toxin such as ricin, an agent capable of preventing T cell activation can be made. Infusion of one or a combination of immunotoxins, e.g., B7-2-ricin, B7-1-ricin, into a patient may result in the death of T cells, particularly of activated T cells that express higher amounts of CD28 and CTLA4. Soluble forms of B7-2 in a monovalent form alone may be useful in blocking B7-2 function, as described above, in which case a carrier molecule may also be employed.

Another method of preventing the function of a B lymphocyte antigen is through the use of an antisense or triplex oligonucleotide. For example, an oligonucleotide complementary to the area around the B7-1, B7-2 or B7-3 translation initiation site, (e.g., for B7-1, TGGCCCATGGCTTCAGA, (SEQ ID NO:20) nucleotides 326–309 and for B7-2, GCCAAAATGGATCCCCA (SEQ ID NO:21)), can be synthesized. One or more antisense oligonucleotides can be added to cell media, typically at 200 μg/ml, or administered to a patient to prevent the synthesis of B7-1, B7-2 and/or B7-3. The antisense oligonucleotide is taken up by cells and hybridizes to the appropriate B lymphocyte antigen MRNA to prevent translation. Alternatively, an oligonucleotide which binds double-stranded DNA to form a triplex construct to prevent DNA unwinding and transcription can be used. As a result of either, synthesis of one or more B lymphocyte antigens is blocked.

In a specific embodiment, T cells are obtained from a subject and cultured ex vivo to expand the population of T cells. In a further embodiment the T cells are then administered to a subject. T cells can be stimulated to proliferate in vitro by, for example, providing to the T cells a primary activation signal and a costimulatory signal, as described in detail in the Examples section. A preferred costimulatory molecule for stimulating proliferation of activated T cells, such as T cells stimulated through their T cell receptor, is aB7-2VIg fusion protein. However, other forms of B7-2Ig fusion proteins can also be used to costimulate proliferation of T cells. In a specific embodiment of the invention, activated T cells are costimulated with a B7-2VIg protein, such that a response by the activated T cells is stimulated. In one embodiment T cells are cultured ex vivo according to the method described in PCT Application No. WO 94129436, using B7-2Ig, or more preferably B7-2VIg as the costimulatory molecule. The costimulatory molecule can be soluble, attached to a cell membrane or attached to a solid surface, such as a bead. In a preferred embodiment, a T helper-type 2 (Th2) response is preferentially stimulated.

E. Therapeutic Uses by Downregulation of Immune Responses

Given the structure and function of the novel B lymphocyte antigens disclosed herein, it is possible to downregulate the function of a B lymphocyte antigen, and thereby downregulate immune responses, in a number of ways. Downregulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Downregulating or preventing one or more B lymphocyte antigen functions, e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this manner prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens. For example, it may be desirable to block the function of B7-2 and B7-1, B7-2 and B7-3, B7-1 and B7-3 or B7-2, B7-1 and B7-3 by administering a soluble form of a combination of peptides having an activity of each of these antigens or a blocking antibody (separately or together in a single composition) prior to transplantation. Alternatively, inhibitory forms of B lymphocyte antigens can be used with other suppressive agents such as blocking antibodies against other T cell markers or against cytokines, other fusion proteins, e.g., CTLA4Ig, or immunosuppressive drugs.

The efficacy of particular blocking reagents in preventing organ transplant rejection or GVHD can be assessed using animal models that are predictive of efficacy in humans. The functionally important aspects of B7-1 are conserved structurally between species and it is therefore likely that other B lymphocyte antigens can function across species, thereby allowing use of reagents composed of human proteins in animal systems. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., *Science*, 257: 789–792 (1992) and Turka et al., *Proc. Natl. Acad. Sci. USA*, 89: 11102–11105 (1992). In addition, murine models of GVHD (see Paul ed., *Fundamental Immunology*, Raven Press, New York, 1989, pp. 846–847) can be used to determine the effect of blocking B lymphocyte antigen function in vivo on the development of that disease.

Blocking B lymphocyte antigen function, e.g., by use of a peptide having B7-2 activity alone or in combination with a peptide having B7-1 activity and/or a peptide having B7-3 activity, may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythematosus in MRL/1pr/1pr mice or NZB hybrid mice, murine autoimmune collagen arthritis, diabetes mellitus in NOD mice and BB rats, and murine experimental myasthenia gravis (see Paul ed., *Fundamental Immunology*, Raven Press, New York, 1989, pp. 840–856).

The IgE antibody response in atopic allergy is highly T cell dependent and, thus, inhibition of B lymphocyte antigen induced T cell activation may be useful therapeutically in the treatment of allergy and allergic reactions. An inhibitory form of B7-2 protein, such as a peptide having B7-2 activity alone or in combination with a peptide having the activity of another B lymphocyte antigen, such as B7-1, can be administered to an allergic subject to inhibit T cell mediated allergic responses in the subject. Inhibition of B lymphocyte antigen costimulation of T cells may be accompanied by exposure to allergen in conjunction with appropriate MHC molecules. Allergic reactions may be systemic or local in nature, depending on the route of entry of the allergen and the pattern of deposition of IgE on mast cells or basophils. Thus, it may be necessary to inhibit T cell mediated allergic responses locally or systemically by proper administration of an inhibitory form of B7-2 protein.

Inhibition of T cell activation through blockage of B lymphocyte antigen function may also be important therapeutically in viral infections of T cells. For example, in the acquired immune deficiency syndrome (AIDS), viral replication is stimulated by T cell activation. Blocking B7-2 function could lead to a lower level of viral replication and thereby ameliorate the course of AIDS. In addition, it may also be necessary to block the function of a combination of B lymphocyte antigens i.e., B7-1, B7-2 and B7-3. Surprisingly, HTLV-I infected T cells express B7-1 and B7-2. This expression may be important in the growth of HTLV-I infected T cells and the blockage of B7-1 function together with the function of B7-2 and/or B7-3 may slow the growth of HTLV-I induced leukemias. Alternatively, stimulation of viral replication by T cell activation may be induced by contact with a stimulatory form of B7-2 protein, for such purposes as generating retroviruses (e.g., various HIV isolates) in sufficient quantities for isolation and use.

F. Therapeutic Uses by Upregulation of Immune Responses

Upregulation of a B lymphocyte antigen function, as a means of upregulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. Viral infections are cleared primarily by cytolytic T cells. In accordance with the present invention, it is believed that B7-2 and thus, B7-1 and B7-3 with their natural ligand(s) on T cells may result in an increase in the cytolytic activity of at least some T cells. It is also believed that B7-2, B7-1, and B7-3 are involved in the initial activation and generation of $CD8^+$ cytotoxic T cells. The addition of a soluble peptide having B7-2 activity, alone, or in combination with a peptide having the activity of another B lymphocyte antigen, in a multi-valent form, to stimulate T cell activity through the costimulation pathway would thus be therapeutically useful in situations where more rapid or thorough clearance of virus would be beneficial. These would include viral skin diseases such as Herpes or shingles, in which cases the multi-valent soluble peptide having B7-2 activity or combination of such peptide and/or a peptide having B7-1 activity and/or a peptide having B7-3 activity is delivered topically to the skin. In addition, systemic viral diseases such as influenza, the common cold, and encephalitis might be alleviated by the administration of stimulatory forms of B lymphocyte antigens systemically.

Alternatively, anti-viral immune responses may be enhanced in an infected patient by removing T cells from the patient, costimulating the T cells in vitro with viral antigen-pulsed APCs either expressing a peptide having B7-2 activity (alone or in combination with a peptide having B7-1 activity and/or a peptide having B7-3 activity) or together with a stimulatory form of a soluble peptide having B7-2 activity (alone or in combination with a peptide having B7-1 activity and/or a peptide having B7-3 activity) and reintroducing the in vitro activated T cells into the patient. Another method of enhancing anti-viral immune responses would be to isolate infected cells from a patient, transfect them with a nucleic acid encoding a peptide having the activity of a B lymphocyte antigen as described herein such that the cells express all or a portion of a B lymphocyte antigen on their surface, e.g., B7-2 or B7-3, and reintroduce the transfected cells into the patient. The infected cells would now be capable of delivering a costimulatory signal to, and thereby activate, T cells in vivo.

Stimulatory forms of B lymphocyte antigens may also be used prophylactically in vaccines against various pathogens. Immunity against a pathogen, e.g., a virus, could be induced by vaccinating with a viral protein along with a stimulatory form of a peptide having B7-2 activity or another peptide having the activity of B lymphocyte antigen in an appropriate adjuvant. Alternately, an expression vector which encodes genes for both a pathogenic antigen and a peptide having the activity of a B lymphocyte antigen, e.g., a vaccinia virus expression vector engineered to express a nucleic acid encoding a viral protein and a nucleic acid encoding a peptide having B7-2 activity as described herein, can be used for vaccination. Presentation of B7-2 with class I MHC proteins by, for example, a cell transfected to coexpress a peptide having B7-2 activity and MHC class I α chain protein and $β_2$ microglobulin may also result in activation of cytolytic $CD8^+$ T cells and provide immunity from viral infection. Pathogens for which vaccines may be useful include hepatitis B, hepatitis C, Epstein-Barr virus, cytomegalovirus, HIV-1, HIV-2, tuberculosis, malaria and schistosomiasis.

In another application, upregulation or enhancement of B lymphocyte antigen function may be useful in the induction of tumor immunity. Tumor cells (e.g., sarcoma, melanoma, lymphoma, leukemia, neuroblastoma, carcinoma) transfected with a nucleic acid encoding at least one peptide having the activity of a B lymphocyte antigen, such as B7-2, can be administered to a subject to overcome tumor-specific tolerance in the subject. If desired, the tumor cell can be transfected to express a combination of peptides having the activity of a number of B lymphocyte antigens (e.g., B7-1, B7-2, B7-3). For example, tumor cells obtained from a patient can be transfected ex vivo with an expression vector directing the expression of a peptide having B7-2 activity alone, or in conjunction with a peptide having B7-1 activity and/or B7-3 activity. The transfected tumor cells are returned to the patient to result in expression of the peptides on the surface of the transfected cell. Alternatively, gene therapy techniques can be used to target a tumor cell for transfection in vivo.

The presence of the peptide having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to express sufficient amounts of MHC class I or MHC class II molecules, can be transfected with nucleic acid encoding all or a portion of (e.g., a cytoplasmic-domain truncated portion) of an MHC class I α chain protein and $β_2$ microglobulin protein or an MHC class II α chain protein and an MHC class II β chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Expression of B7-1 by B7 negative murine tumor cells has been shown to induce T cell mediated specific immunity accompanied by tumor rejection and prolonged protection to tumor challenge in mice (Chen, L., et al. (1992) *Cell* 71, 1093–1102; Townsend, S. E. and Allison, J. P. (1993) *Science* 259, 368–370; Baskar, S., et al. (1993)*Proc. Natl. Acad. Sci.* 90, 5687–5690). Thus, the induction of a T cell mediated immune response in a human subject may be sufficient to overcome tumor-specific tolerance in the subject.

In another aspect, a stimulatory form of one or more soluble peptides having an activity of a B lymphocyte antigen can be administered to a tumor-bearing patient to provide a costimulatory signal to T cells in order to induce anti-tumor immunity.

G. Administration of Therapeutic Forms of B Lymphocyte Antigens

The peptides of the invention are administered to subjects in a biologically compatible form suitable for pharmaceutical administration in vivo to either enhance or suppress T cell mediated immune response. By "biologically compatible form suitable for administration in vivo" is meant a form of the protein to be administered in which any toxic effects are outweighed by the therapeutic effects of the protein. The term subject is intended to include living organisms in which an immune response can be elicited, e.g., mammals. Examples of subjects include humans, dogs, cats, mice, rats, and transgenic species thereof. Administration of a peptide having the activity of a novel B lymphocyte antigen as described herein can be in any pharmacological form including a therapeutically active amount of peptide alone or in combination with a peptide having the activity of another B lymphocyte antigen and a pharmaceutically acceptable carrier. Administration of a therapeutically active amount of the therapeutic compositions of the present invention is defined as an amount effective, at dosages and for periods of time necessary to achieve the desired result. For example, a therapeutically active amount of a peptide having B7-2 activity may vary according to factors such as the disease state, age, sex, and weight of the individual, and the ability of peptide to elicit a desired response in the individual. Dosage regima may be adjusted to provide the optimum therapeutic response. For example, several divided doses may be administered daily or the dose may be proportionally reduced as indicated by the exigencies of the therapeutic situation.

The active compound (e.g., peptide) may be administered in a convenient manner such as by injection (subcutaneous, intravenous, etc.), oral administration, inhalation, transdermal application, or rectal administration. Depending on the route of administration, the active compound may be coated in a material to protect the compound from the action of enzymes, acids and other natural conditions which may inactivate the compound.

To administer a peptide having B7-2 activity by other than parenteral administration, it may be necessary to coat the peptide with, or co-administer the peptide with, a material to prevent its inactivation. For example, a peptide having B7-2 activity may be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water emulsions as well as conventional liposomes (Strejan et al., (1984) *J. Neuroimmunol* 7:27).

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active compound (e.g., peptide having B7-2 activity) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., peptide) plus any additional desired ingredient from a previously sterile-filtered solution thereof.

When the active compound is suitably protected, as described above, the protein may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

H. Identification of Cytokines Induced by Costimulation

The nucleic acid sequences encoding peptides having the activity of novel B lymphocyte antigens as described herein can be used to identify cytokines which are produced by T cells in response to stimulation by a form of B lymphocyte antigen, e.g., B7-2. T cells can be suboptimally stimulated in vitro with a primary activation signal, such as phorbol ester, anti-CD3 antibody or preferably antigen in association with an MHC class II molecule, and given a costimulatory signal by a stimulatory form of B7-2 antigen, for instance by a cell transfected with nucleic acid encoding a peptide having B7-2 activity and expressing the peptide on its surface or by a soluble, stimulatory form of the peptide. Known cytokines released into the media can be identified by ELISA or by the ability of an antibody which blocks the cytokine to inhibit T cell proliferation or proliferation of other cell types that is induced by the cytokine. An IL-4 ELISA kit is available from Genzyme (Cambridge MA), as is an IL-7 blocking antibody. Blocking antibodies against IL-9 and IL-12 are available from Genetics Institute (Cambridge, Mass.).

An in vitro T cell costimulation assay as described above can also be used in a method for identifying novel cytokines which may be induced by costimulation. If a particular activity induced upon costimulation, e.g., T cell proliferation, cannot be inhibited by addition of blocking antibodies to known cytokines, the activity may result from the action of an unknown cytokine. Following costimulation, this cytokine could be purified from the media by conventional methods and its activity measured by its ability to induce T cell proliferation.

To identify cytokines which prevent the induction of tolerance, an in vitro T cell costimulation assay as described above can be used. In this case, T cells would be given the primary activation signal and contacted with a selected cytokine, but would not be given the costimulatory signal. After washing and resting the T cells, the cells would be rechallenged with both a primary activation signal and a costimulatory signal. If the T cells do not respond (e.g., proliferate or produce IL-2) they have become tolerized and the cytokine has not prevented the induction of tolerance. However, if the T cells respond, induction of tolerance has been prevented by the cytokine. Those cytokines which are capable of preventing the induction of tolerance can be targeted for blockage in vivo in conjunction with reagents which block B lymphocyte antigens as a more efficient means to induce tolerance in transplant recipients or subjects with autoimmune diseases. For example, one could administer a B7-2 blocking reagent together with a cytokine blocking antibody to a subject.

I. Identification of Molecules which Inhibit Costimulation

Another application of the peptide having the activity of a novel B lymphocyte antigen of the invention (e.g., B7-2 and B7-3) is the use of one or more of these peptides in screening assays to discover as yet undefined molecules which are inhibitors of costimulatory ligand binding and/or of intracellular signaling through T cells following costimulation. For example, a solid-phase binding assay using a peptide having the activity of a B lymphocyte antigen, such as B7-2, could be used to identify molecules which inhibit binding of the antigen with the appropriate T cell ligand (e.g., CTLA4, CD28). In addition, an in vitro T cell costimulation a&say as described above could be used to identify molecules which interfere with intracellular signaling through the T cells following costimulation as determined by the ability of these molecules to inhibit T cell proliferation and/or cytokine production (yet which do not prevent binding of B lymphocyte antigens to their receptors). For example, the compound cyclosporine A inhibits T cell activation through stimulation via the T cell receptor pathway but not via the CD28/CTLA4 pathway. Therefore, a different intracellular signaling pathway is involved in costimulation. Molecules which interfere with intracellular signaling via the CD28/CTLA4 pathway may be effective as immunosuppressive agents in vivo (similar to the effects of cyclosporine A).

J. Identification of Molecules which Modulate B Lymphocyte Antigen Expression

The monoclonal antibodies produced using the proteins and peptides of the current invention can be used in a screening assay for molecules which modulate the expression of B lymphocyte antigens on cells. For example, molecules which effect intracellular signaling which leads to induction of B lymphocyte antigens, e.g. B7-2 or B7-3, can be identified by assaying expression of one or more B lymphocyte antigens on the cell surface. Reduced immunofluorescent staining by an anti-B7-2 antibody in the presence of the molecule would indicate that the molecule inhibits intracellular signals. Molecules which upregulate B lymphocyte antigen expression result in an increased immunofluorescent staining. Alternatively, the effect of a molecule on expression of a B lymphocyte antigen, such as B7-2, can be determined by detecting cellular B7-2 mRNA levels using a B7-2 cDNA as a probe. For example, a cell which expresses a peptide having B7-2 activity can be contacted with a molecule to be tested, and an increase or decrease in B7-2 MRNA levels in the cell detected by standard technique, such as Northern hybridization analysis or conventional dot blot of mRNA or total poly(A+)RNAs using a B7-2 cDNA probe labeled with a detectable marker. Molecules which modulate B lymphocyte antigen expression may be useful therapeutically for either upregulating or downregulating immune responses alone or in conjunction with soluble blocking or stimulating reagents. For instance, a molecule which inhibits expression of B7-2 could be administered together with a B7-2 blocking reagent for immunosuppressive purposes. Molecules which can be tested in the above-described assays include cytokines such as IL-4, γINF, IL-10, IL-12, GM-CSF and prostagladins.

This invention is further illustrated by the following examples which should not be construed as limiting. The contents of all references and published patent applications cited throughout this application are hereby incorporated by reference.

The following methodology was used in Examples 1, 2 and 3.

Method and Materials

A. Cells

Mononuclear cells were isolated by Ficoll-Hypaque density gradient centrifugation from single cell suspensions of normal human spleens and were separated into E− and E+ fractions by resetting with sheep red blood cells (Boyd, A. W., et al. (1985) *J. Immunol.* 134, 1516). B cells were purified from the E− fraction by adherence of monocytes on plastic and depletion of residual T, natural killer cells (NK) and residual monocytes by two treatments with anti-MsIgG and anti-MsIgM coated magnetic beads (Advanced Magnetics, Cambridge, Mass.), using monoclonal antibodies: anti-CD4, -CD8, -CD11b, -CD14 and -CD16. CD4+ T cells were isolated from the E+ fraction of the same spleens after adherence on plastic and depletion of NK, B cells and residual monocytes with magnetic beads and monoclonal antibodies: anti-CD20, -CD11b, -CD8 and -CD16. CD28+ T cells were identically isolated from the E+ fraction using anti-CD20, -CD11b, -CD14 and -CD16 monoclonal antibodies. The efficiency of the purification was analyzed by indirect immunofluorescence and flow cytometry using an EPICS flow cytometer (Coulter). B cell preparations were >95% CD20+, <2% CD3+, <1% CD14+. CD4+ T cell preparations were >98% CD3+, >98% CD4+, <1% CD8+, <1% CD20+, <1% CD14+. CD28+ T cell preparations were >98% CD3+, >98% CD28+, <1% CD20+, <1% CD14+.

B. Monoclonal Antibodies and Fusion Proteins

Monoclonal antibodies were used as purified Ig unless indicated otherwise: anti-B7:133, IgM is a blocking antibody and has been previously described (Freedman, A. S. et al. (1987) *Immunol.* 137, 3260–3267); anti-B7:B1.1, IgG1 (RepliGen Corp., Cambridge, Mass.) (Nickoloff, B., et al (1993) *Am. J. Pathol.* 142, 1029–1040) is a non-blocking monoclonal antibody; BB-1: IgM is a blocking antibody (Dr. E. Clark, University of Washington, Seattle, Wash.) (Yokochi, T., et al. (1982) *J. Immunol.* 128, 823–827); anti-CD20: B1, IgG2a (Stashenko, P., et al.(1980) *J. Immunol.* 125, 1678–1685); anti-B5: IgM (Freedman, A., et al. (1985) *J. Immunol.* 134, 2228–2235); anti-CD8: 7PT 3F9, IgG2a; anti-CD4: 19Thy5D7, IgG2a; anti-CD11b: Mo1, IgM and anti-CD14: Mo2, IgM (Todd, R, et al. (1981) *J. Immunol.* 126, 1435–1442); anti-MHC class II: 9–49, IgG2a (Dr R. Todd, University of Michigan, Ann Arbor) (Todd, R. I., et al. (1984) *Hum Immunol.* 10, 23–40; anti-CD28: 9.3, IgG2a (Dr. C. June, Naval Research Institute, Bethesda) (Hansen, J. A., et al. (1980) *Immunogenetics.* 10, 247–260); anti-CD16: 3G8, IgG1 (used as ascites) (Dr. J. Ritz, Dana-Farber Cancer Institute, Boston); anti-CD3: OKT3, IgG2a hybridoma was obtained from the American Type Culture Collection and the purified monoclonal antibody was adhered on plastic plates at a concentration of 1 µg/ml; anti-CD28 Fab fragments were generated from the 9.3 monoclonal antibody, by papain digestion and purification on a protein A column, according to the manufacturer's instructions (Pierce, Rockford, Ill.). Human CTLA4 fusion protein (CTLA4Ig) and control fusion protein (control-Ig) were prepared as previously described (Gimmi, C. D., et al. (1993) *Proc. Natl. Acad. Sci USA* 90:65866590); Boussiotis, V., et al *J Exp. Med.* (accepted for publication)).

C. CHO Cell Transfection

B7-1 transfectants (CHO-B7) were prepared from the B7-1 negative chinese hamster ovary (CHO) cell line, fixed with paraformaldehyde and used as previously described (Gimmi, C. D., et al.*Proc. Natl. Acad. Sci USA* 88, 6575–6579).

D. In Vitro B Cell Activation and Selection of B7+ and B7− Cells

Splenic B cells were cultured at $2 \times 10^6$ cells/ml in complete culture media, {RPMI 1640 with 10% heat inactivated fetal calf serum (FCS), 2mM glutamine, 1 mM sodium pyruvate, penicillin (100 units/ml), streptomycin sulfate (100 µg/ml) and gentamycin sulfate (5 µg/ml)}, in tissue culture flasks and were activated by crosslinking of sIg with affinity purified rabbit anti-human IgM coupled to Affi-Gel 702 beads (Bio-Rad), Richmond, Calif.) (Boyd, A. W., et al., (1985) *J. Immunol.* 134,1516) or by crosslinking of MHC class II with 9–49 antibody coupled to Affi-Gel 702 beads. B cells activated for 72 hours, were used as total activated B cell populations or were indirectly stained with anti-B7 (131.1) monoclonal antibody and fluoroscein isothiocyanate (FITC) labeled goat anti-mouse immunoglobulin (Fisher, Pittsburgh, Pa.), and fractionated into B7-1+ and B7-1− populations by flow cytometric cell sorting (EPICS Elite flow cytometer, Coulter).

E. Immunofluorescence and Flow Cytometry

For surface phenotype analysis populations of B cells activated by either sIg or MHC class II crosslinking for 6, 12, 24, 48, 72 and 96 hours were stained with either anti-B7 (133), BB-1 monoclonal antibodies, control IgM antibody, CTLA4Ig or control-Ig. Cell suspensions were stained by two step indirect membrane staining with 10 µg/ml of primary monoclonal antibody followed by the appropriate secondary reagents. Specifically, immunoreactive with anti-B7 (133) and BB-1 monoclonal antibodies was studied by indirect staining using goat anti-mouse Ig or immunoglobulin FITC (Fisher) as secondary reagent and immunoreactivity with fusion proteins was studied using biotinylated CTLA4Ig or biotinylated control-Ig and streptavidin-phycoerythrin as secondary reagent. PBS containing 10% AB serum was used as diluent and wash media. Cells were fixed with 0.1% paraformaldehyde and analyzed on a flow cytometer (EPICS Elite Coulter).

F. Proliferation Assay

T cells were cultured at a concentration of $1 \times 10^5$ cells per well in 96-well flat bottom microtiter plate at 37° C. for 3 days in 5% $CO_2$. Syngeneic activated B cells (total B cell population or B7+ and B7− fractions) were irradiated (2500 rad) and added into the cultures at a concentration of $1 \times 10^5$ cells per well. Factors under study were added to the required concentration for a total final volume of 200 µl per well. When indicated, T cells were incubated with anti-CD28 Fab (final concentration of 10 µg/ml), for 30 minutes at 4° C., prior to addition in experimental plates. Similarly, CHO-B7 or B cells were incubated with CTLA4Ig or control-Ig (10 µg/ml) for 30 minutes at 4° C. Thymidine incorporation as an index of mitogenic activity, was assessed after incubation with 1 µCi (37 kBg) of {methyl-$^3$H} thymidine (Du Pont, Boston, Mass.) for the last 15 hours of the culture. The cells were harvested onto filters and the radioactivity on the dried filters was measured in a Pharmacia beta plate liquid scintillation counter.

G. IL-2 and IL-4 Assay

IL-2 and IL-4 concentrations were assayed by ELISA (R&D Systems, Minneapolis, Minn. and BioSource, Camarillo, Calif.) in culture supernatants collected at 24 hours after initiation of the culture.

EXAMPLE 1

Figure 1B:
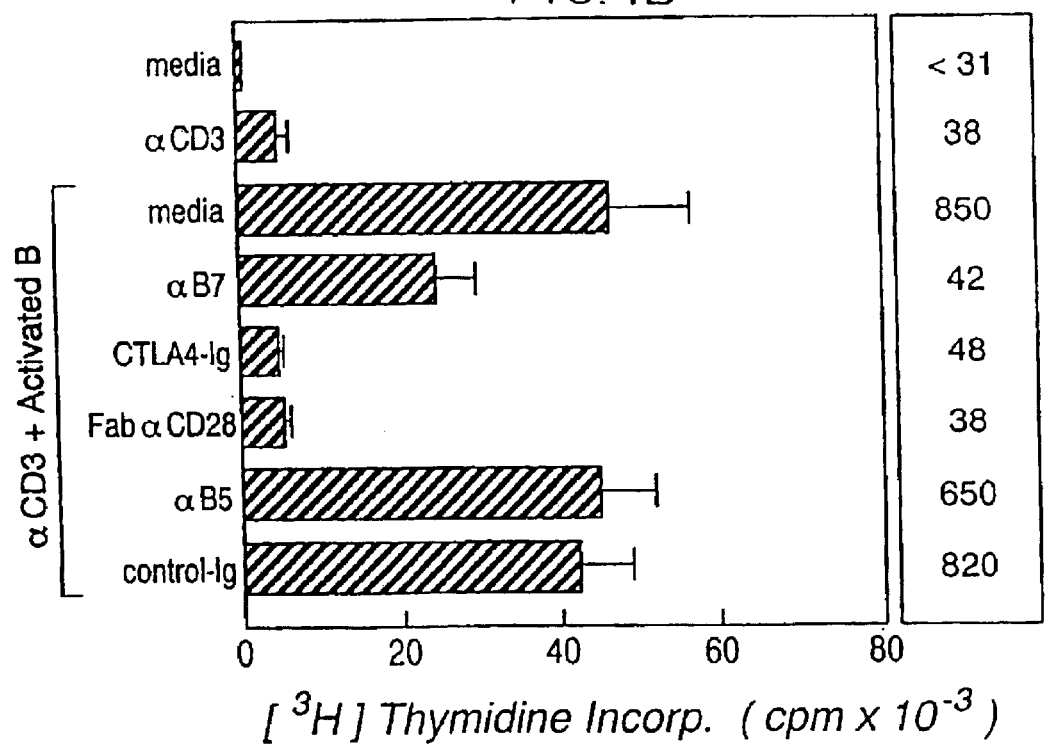

Expression of a Novel CTLA4 Ligand on Activated B Cells Which Induces T Cell Proliferation Since crosslinking surface Ig induces human resting B cells to express B7-1 maximally (50–80%) at 72 hours, the ability of activated human B lymphocytes to induce submitogenically activated T cells to proliferate and secrete IL-2 was determined. FIG. 1 depicts the costimulatory response of human splenic CD28+T cells, submitogenically activated with anti-CD3 monoclonal antibody, to either B7 (B7-1) transfected CHO cells (CHO-B7) or syngeneic splenic B cells activated with anti-Ig for 72 hours. $^3$H-Thymidine incorporation was assessed for the last 15 hours of a 72 hours culture. IL-2 was assessed by ELISA in supernatants after 24 hours of culture (Detection limits of the assay: 31–2000 pg/ml). FIG. 1 is representative of seventeen experiments.

Submitogenically activated CD28+ T cells proliferated and secreted high levels of IL-2 in response to B7-1 costirnulation provided by CHO-B7 (FIG. 1, panel a). Both proliferation and IL-2 secretion were totally inhibited by blocking the B7-1 molecule on CHO cells with either anti-B7-1 monoclonal antibody or by a fusion protein for its high affinity receptor, CTLA4. Similarly, proliferation and IL-2 secretion were abrogated by blocking B7-1 signalling via CD28 with Fab anti-CD28 monoclonal antibody. Control monoclonal antibody or control fusion protein had no effect. Nearly identical costimulation of proliferation and IL-2 secretion was provided by splenic B cells activated with anti-Ig for 72 hours (panel b). Though anti-B7-1 monoclonal antibody could completely abrogate both proliferation and IL-2 secretion delivered by CHO-B7, anti-B7-1 monoclonal antibody consistently inhibited proliferation induced by activated B cells by only 50% whereas IL-2 secretion was totally inhibited. In contrast to the partial blockage of proliferation induced by anti-B7-1 monoclonal antibody, both CTLA4Ig and Fab anti-CD28 monoclonal antibody completely blocked proliferation and IL-2 secretion. These results are consistent with the hypothesis that activated human B cells express one or more additional CTLA4/CD28 ligands which can induce T cell proliferation and IL-2 secretion.

EXAMPLE 2

Activated Human Splenic B Cells Express CTLA4 Ligand(s) Distinct from B7-1

Figure 2A:
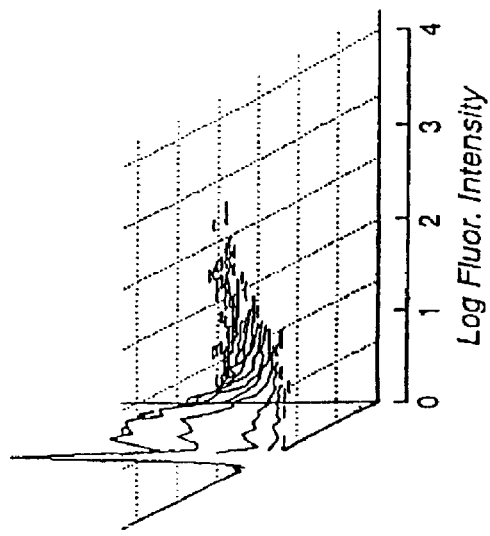
FIGS. 2A–C are graphs of log fluorescence intensity of cell surface expression of B7-1 on splenic B cells activated with surface immunoglobulin (sIg) crosslinking. The total (panel a), B7-1 positive (B7-1$^+$, panel b) and B7-1 negative (B7-1$^-$, panel c) activated B cells were stained with anti-B7-1 monoclonal antibody (133) and fluoroscein isothiocyanate (FITC) labeled goat anti-mouse immunoglobulin and analyzed by flow cytometry.
Figure 2B:
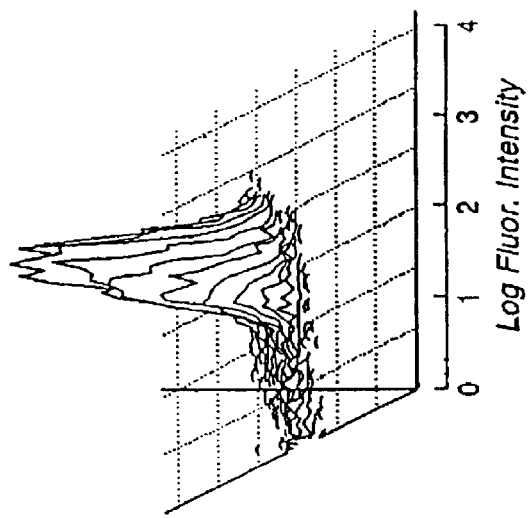
Figure 2C:
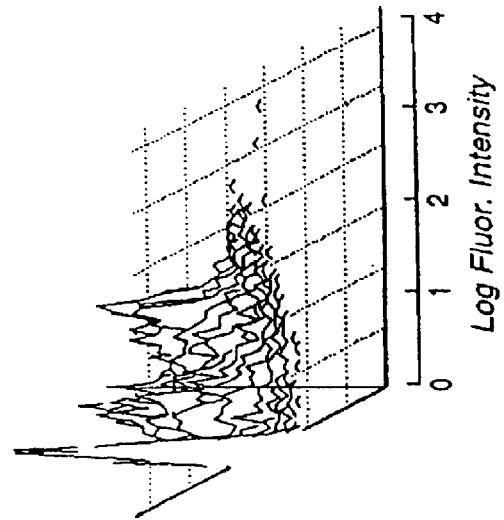

In light of the above observations, whether other CTLA4 binding counter-receptors were expressed on activated B cells was determined. To this end, human splenic B cells were activated for 72 hours with anti-Ig and then stained with an anti-B7-1 monoclonal antibody (B1.1) which does not inhibit B7-1 mediated costimulation. Fluoroscein isothiocyanate (FITC) and mAb B 1.1 were used with flow cytometric cell sorting to isolate B7-1$^+$ and B7-1$^-$ fractions. The resulting post-sort positive population was 99% B7-1$^+$ and the post-sort negative population was 98% B7-1$^-$ (FIG. 2).

Figure 3A:
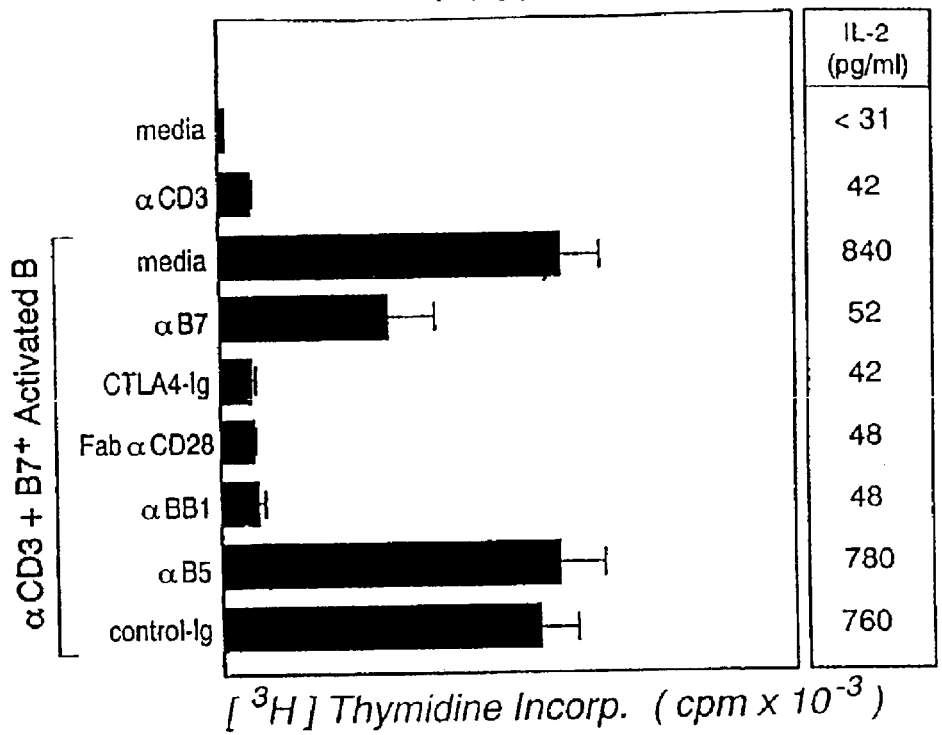
FIGS. 3A–B are graphic representations of the responses of CD28$^+$ T cells, as assessed by $^3$H-thymidine incorporation and IL-2 secretion, to costimulation provided by B7-1$^+$ (panel a) or B7-1$^-$(panel b) activated syngeneic B lymphocytes cultured in media, anti-CD3 alone, or anti-CD3 in the presence of the following monoclonal antibodies or recombinant proteins: αBB-1 (133, anti-B7-1 and anti-B7-3); αB7 (anti-B7-1); CTLA4Ig; Fab αCD28; control Ig fusion protein or αB5 (anti-B5).
Figure 3B:
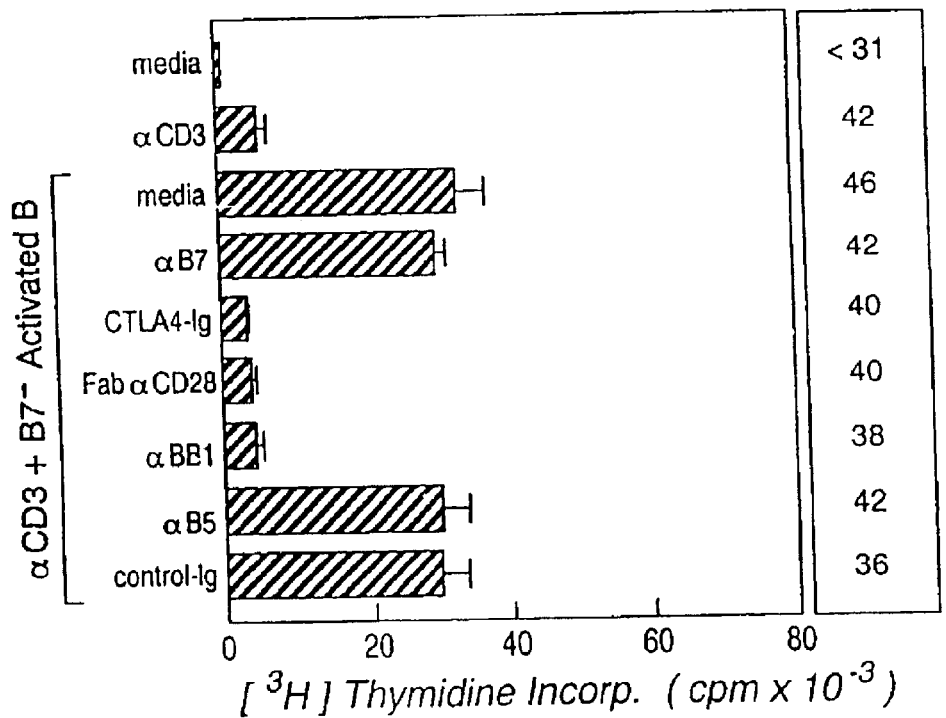

To examine the costimulatory potential of each population, human splenic CD28+ T cells were submitogenically stimulated with anti-CD3 monoclonal antibody in the presence of irradiated B7-1+ or B7-1– anti-Ig activated (72 hours) splenic B cells. $^3$H-Thymidine incorporation was assessed for the last 15 hours of a 72 hours culture. IL-2 was assessed by ELISA in supernatants after 24 hours of culture (Detection limits of the assay: 31–2000 pg/ml). The results of FIG. 3 are representative of ten experiments. B7-1+ B cells induced anti-CD3 activated T cells to proliferate and secrete IL-2 (FIG. 3a) but not IL-4. As was observed with the unfractionated activated B cell population, anti-B7-1 monoclonal antibody (133) inhibited proliferation only 50% but consistently abrogated IL-2 secretion. As above, CTLA4Ig binding or blockade of CD28 with Fab anti-CD28 monoclonal antibody completely inhibited both proliferation and IL-2 secretion. Control monoclonal antibody and control-Ig were not inhibitory. In an attempt to identify other potential CTLA4/CD28 binding costimulatory ligand(s) which might account for the residual, non-B7 mediated proliferation delivered by B7+ B cells, the effect of BB-1 monoclonal antibody on proliferation and IL-2 secretion was examined. As seen, BB-1 monoclonal antibody completely inhibited both proliferation and IL-2 secretion (FIG. 3a). FIG. 3b displays the costimulatory potential of B7-1– activated human splenic B cells. Irradiated B7-1– activated (72 hr) B cells could also deliver a significant costimulatory signal to submitogenically activated CD4+ lymphocytes. This costimulation was not accompanied by detectable IL-2 (FIG. 3b)or IL-4 accumulation and anti-B7-1 monoclonal antibody did not inhibit proliferation. However, CTLA4Ig, Fab anti-CD28 monoclonal antibody, and BB- I monoclonal antibody all completely inhibited proliferation.

Figure 4:
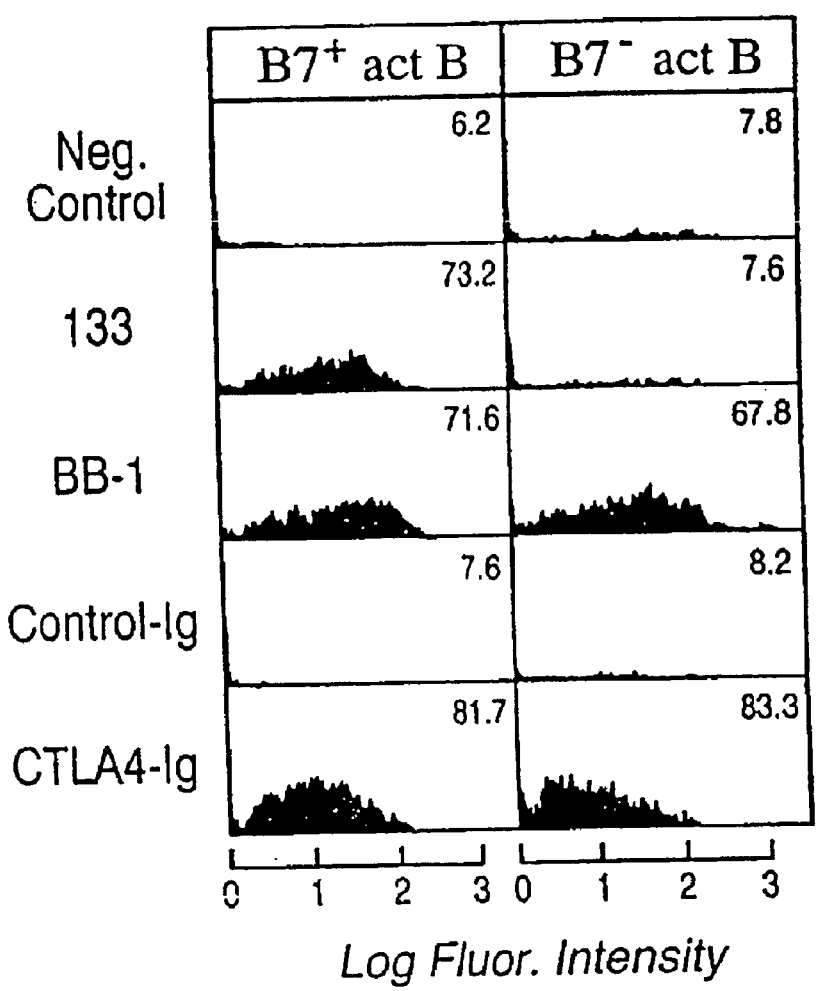
FIG. 4 is a graphic representation of the cell surface expression of B7-1, B7-3 and total CTLA4 counter-receptors on fractionated B7-1$^+$ and B7-1$^-$ activated B lymphocytes.

Phenotypic analysis of the B7-1$^+$ and B7-1 activated splenic B cells confirmed the above functional results. FIG. 4 shows the cell surface expression of B7-1, B7-2 and B7-3 on fractionated B7-1$^+$ and B7-1$^-$ activated B cell. As seen in FIG. 4, B7-1+ activated splenic B cells stained with anti-B7-1 (133) monoclonal antibody, BB-1 monoclonal antibody, and bound CTLA4-Ig. In contrast, B7- activated splenic B cells did not stain with anti-B7-1 (133) monoclonal antibody but did stain with BB-1 monoclonal antibody and CTLA4Ig. These phenotypic and functional results demonstrate that both B7-1+ and B7-1– activated (72 hours) human B lymphocytes express CTLA4 binding counter-receptor(s) which: 1) can induce submitogenically activated T cells to proliferate without detectable IL-2 secretion; and 2) are identified by the BB-1 monoclonal antibody but not anti-B7-1 monoclonal antibody. Thus, these CTLA4/CD28 ligands can be distinguished on the basis of their temporal expression after B cell activation and their reactivity with CTLA4Ig and anti-B7 monoclonal antibodies. The results of FIG. 4 are representative of five experiments.

EXAMPLE 3

Figure 5:
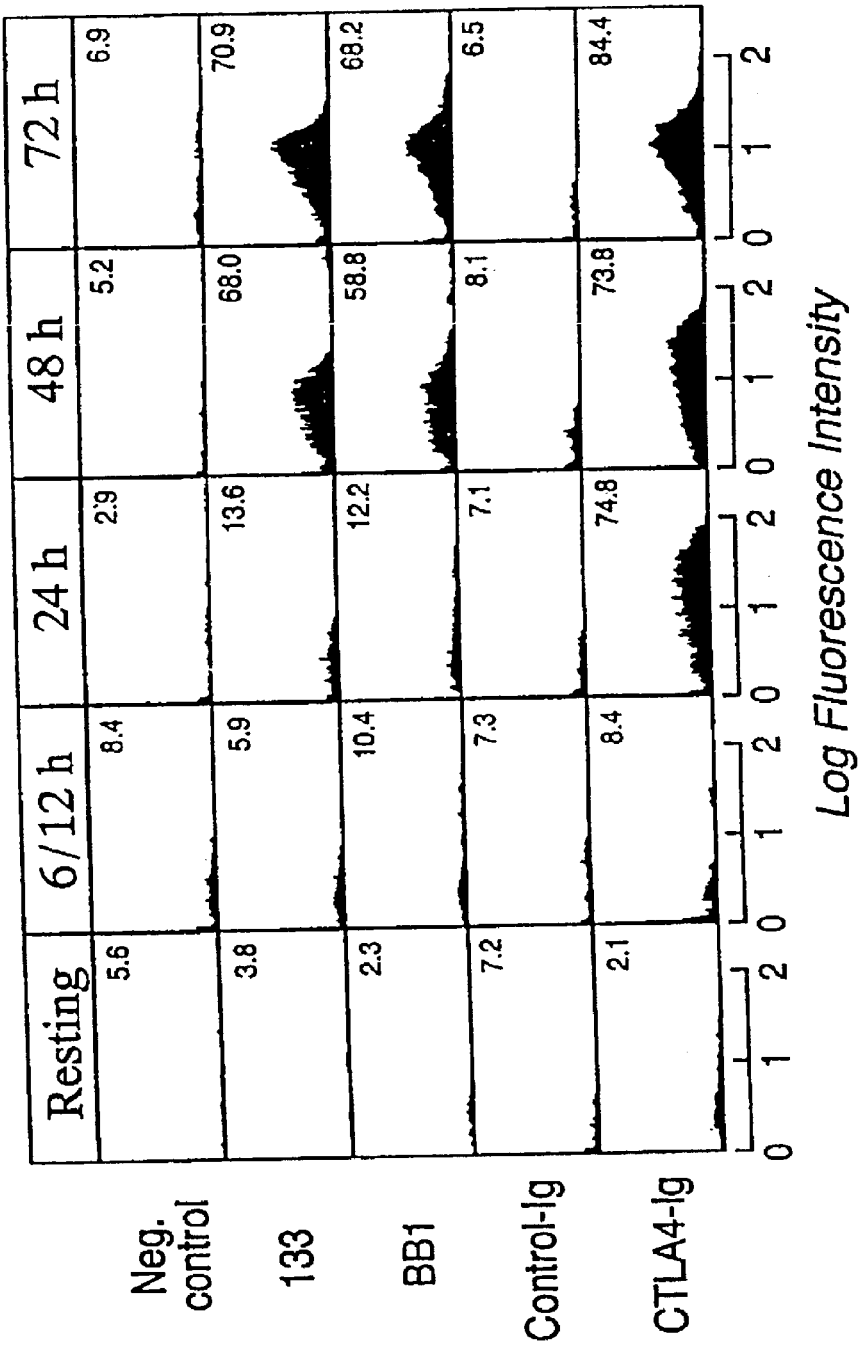
FIG. 5 is a graphic representation of temporal surface expression of B7-1 (CTLA4Ig and mAbs BB-1 and 133), B7-3 (CTLA4Ig and mAb BB1) and B7-2 (CTLA4Ig) counter-receptors on splenic B cells activated by sIg crosslinking.
Figure 6:
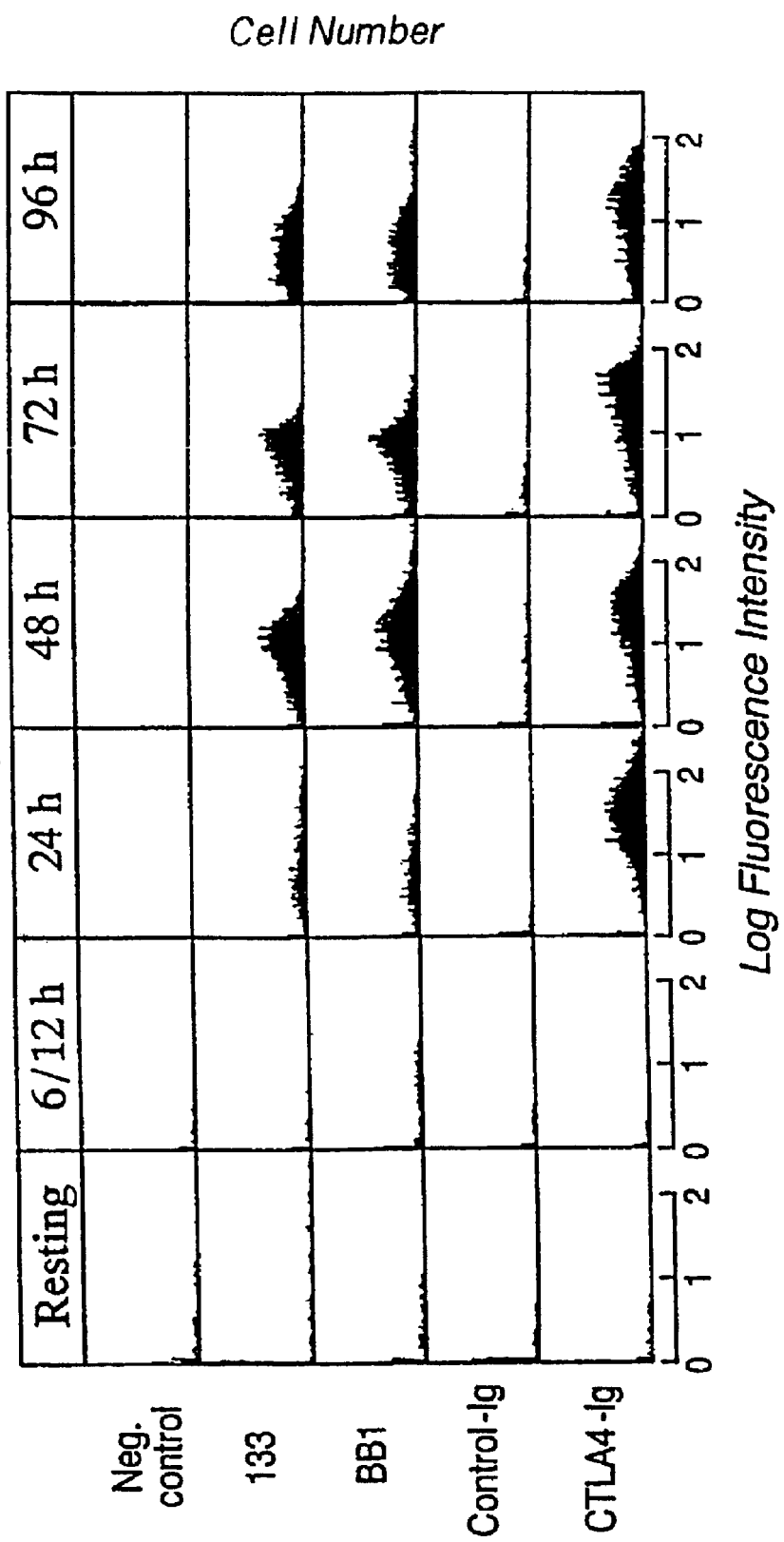
FIG. 6 is a graphic representation of temporal surface expression of B7-1 (CTLA4Ig and mAbs BB-1 and 133), B7-3 (CTLA4Ig and mAb BB1) and B7-2 (CTLA4Ig) counter-receptors on splenic B cells activated by MHC class II crosslinking.

Three Distinct CTLA4/CD28 Ligands Are Expressed Following Human B Cell Activation To determine the sequential expression of CTLA4 binding counter-receptors following activation, human splenic B cells were activated by crosslinking of either surface Ig or MHC class II and the expression of B7-1, B7-3 and B7-2 binding proteins were examined by flow cytometric analysis. Ig or MHC class II crosslinking induced a similar pattern of CTLA4Ig binding (FIGS. 5 and 6). FIG. 5 is representative of the results of 25 experiments for anti-B7-1 and BB-1 binding and 5 experiments for CTLA4Ig binding. FIG. 6 is representative of 25 experiments for anti-B7-1 binding and 5 experiments for CTLA4Ig binding. The results of these experiments indicate that prior to 24 hours, none of these molecules are expressed. At 24 hours post-activation, the majority of cells express a protein that binds CTLA4Ig (B7-2), however, fewer than 20% express either B7-1 or B7-3. Crosslinking of MHC class II induces maximal expression and intensity of B7-1 and B7-3 at 48 hours whereas crosslinking of Ig induces maximal expression at 72 hours and expression declines thereafter. These results suggest that an additional CTLA4 binding counter-receptor is expressed by 24 hours and that the temporal expression of the distinct B7-1 and B7-3 proteins appears to coincide.

Figure 7A:
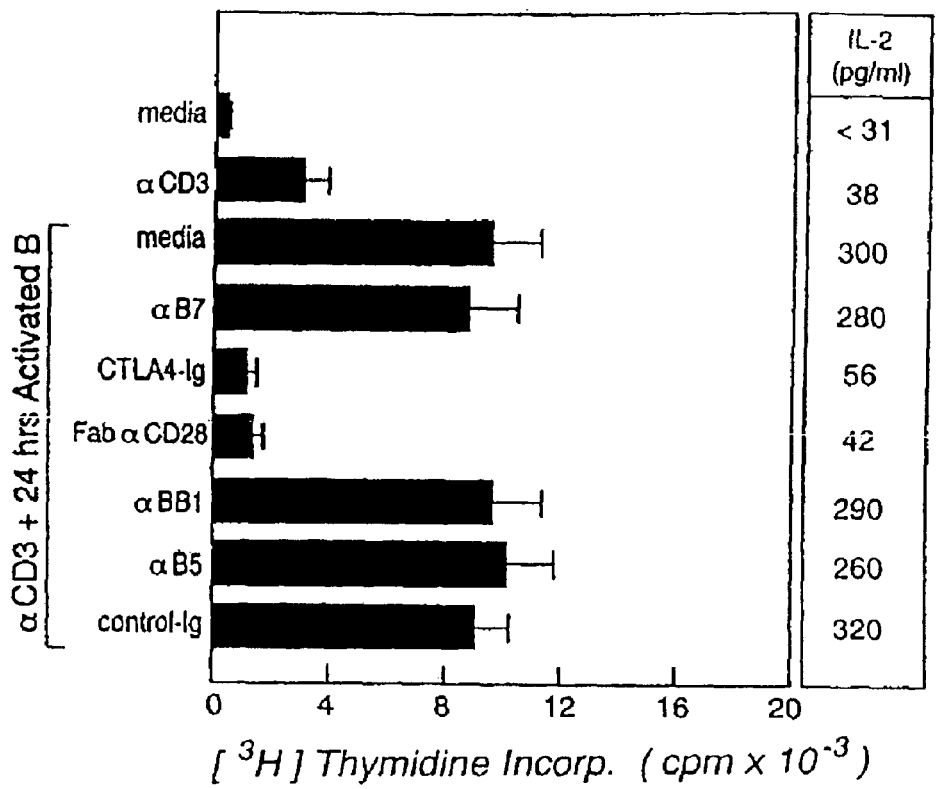
FIGS. 7A–B are graphic representations of the response of CD28$^+$T cells, as assessed by $^3$H-thymidine incorporation and IL-2 secretion, to costimulation provided by syngeneic B lymphocytes activated by sIg crosslinking for 24 hours (panel a) or 48 hours (panel b) and cultured in media, anti-CD3 alone, or anti-CD3 in the presence of the following monoclonal antibodies or recombinant protein: αB7(133, anti-B7-1); αBB1 (anti-B7-1, anti-B7-3) CTLA4Ig; Fab αCD28; and αB5(anti-B5).
Figure 7B:
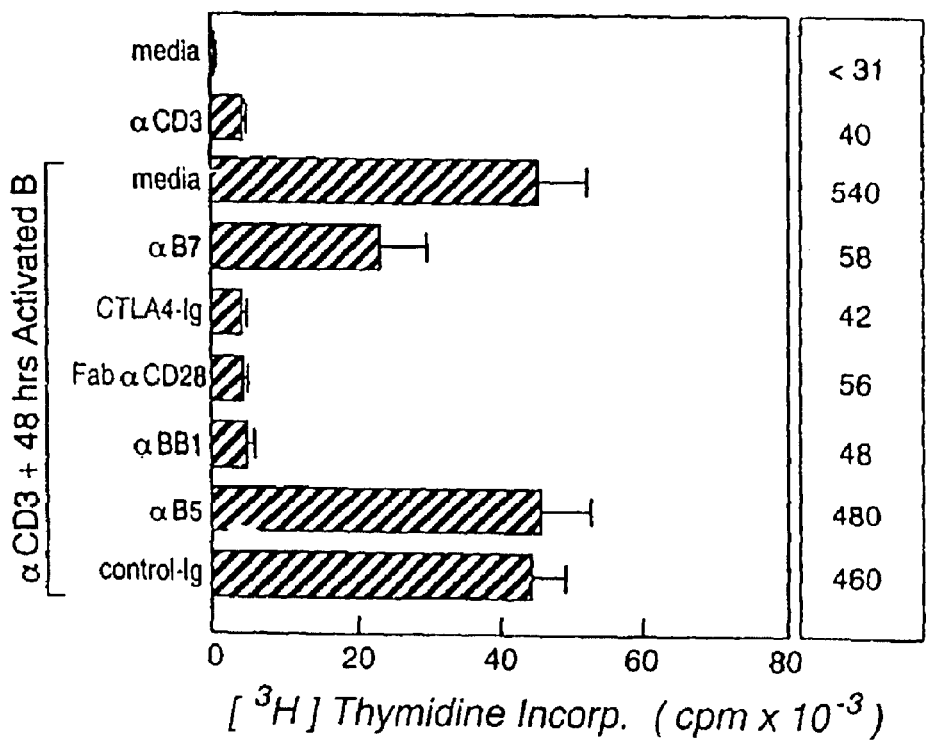
Figure 24:
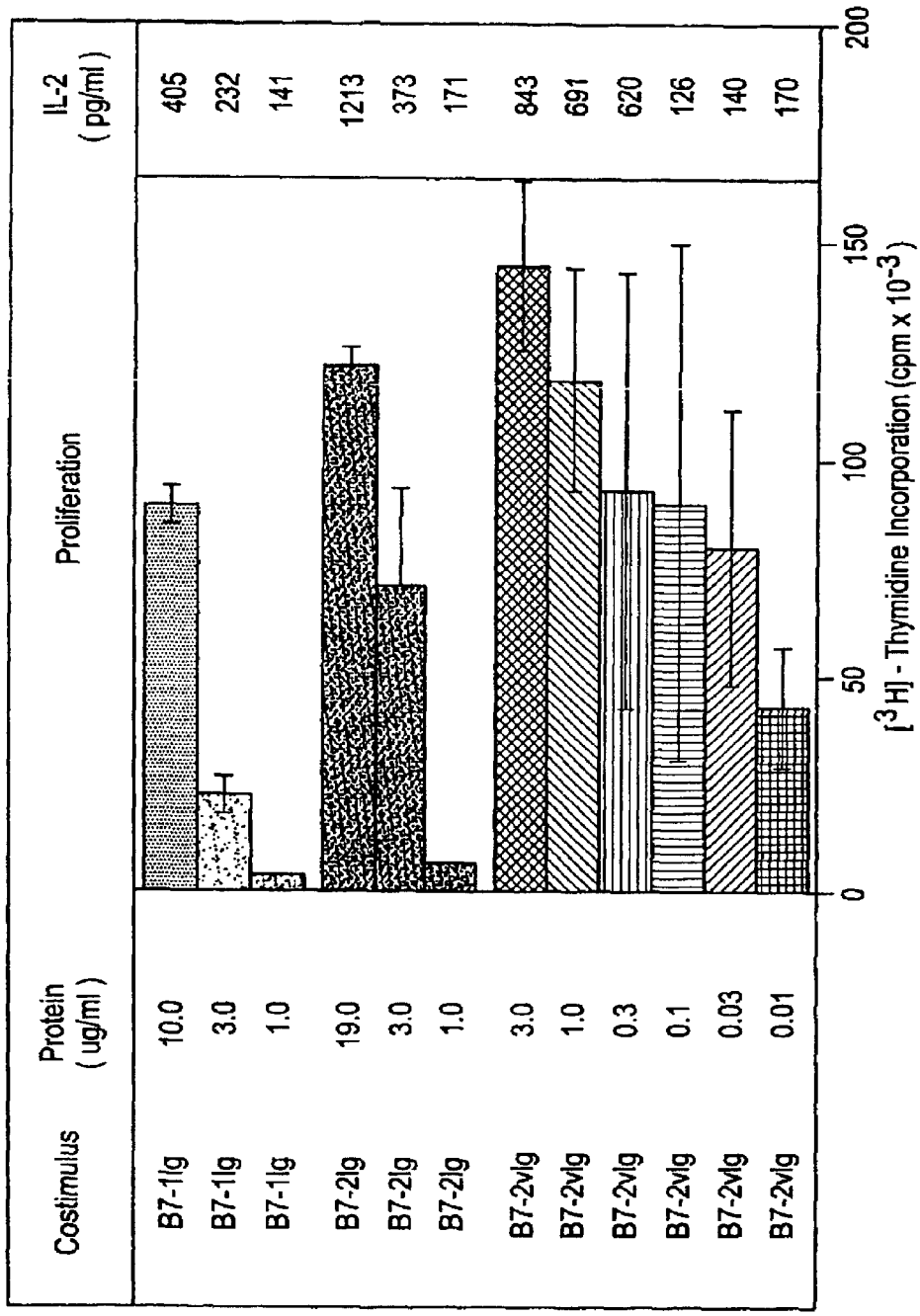
FIG. 24 represents a histogram showing proliferation of, and IL-2 production by CD28+ T cells incubated with anti-CD3 attached to plates and B7-1Ig (10, 3 or 1 μg/ml) or B7-2Ig (19, 3 or 1 μIg/ml) or B7-2VIg (3.0–0.01 μg/ml).

A series of experiments was conducted to determine whether the temporal expression of CTLA4 binding counterreceptors differentially correlated with their ability to costimulate T cell proliferation and/or IL-2 secretion. Human splenic CD28+ T cells submitogenically stimulated with anti-CD3 were cultured for 72 hours in the presence of irradiated human splenic B cells that had been previously activated in vitro by sIg crosslinking for 24, 48, or 72 hours. IL-2 secretion was assessed by ELISA in supernatants after 24 hours and T cell proliferation as assessed by $^3$H-thymidine incorporation for the last 15 hours of a 72 hour culture. The results of FIG. 7 are representative of 5 experiments. As seen in FIG. 7a, 24 hour activated B cells provided a costimulatory signal which was accompanied by modest levels of IL-2 production, although the magnitude of proliferation was significantly less than observed with 48 and 72 hours activated human B cells (note differences in scale for $^3$H-Thymidine incorporation). Neither proliferation nor IL-2 accumulation was inhibited by anti-B7-1 (133) or BB-1. In contrast, with CTLA4Ig and anti-CD28 Fab monoclonal antibody totally abrogated proliferation and IL-2 accumulation. B cells activated for 48 hours, provided costimulation which resulted in nearly maximal proliferation and IL-2 secretion (FIG. 7b). Here, anti-B7-1 (133) monoclonal antibody, inhibited proliferation approximately 50% but totally blocked IL-2 accumulation. BB-l monoclonal antibody totally inhibited both proliferation and IL-2 secretion. As above, CTLA4Ig and Fab anti-CD28 also totally blocked proliferation and IL-2 production. Finally, 72 hour activated B cells induced T cell response identical to that induced by 48 hour activated B cells. Similar results are observed if the submitogenic signal is delivered by phorbol myristic acid (PMA) and if the human splenic B cells are activated by MHC class II rather than Ig crosslinking. These results indicate that there are three CTLA4 binding molecules that are temporarily expressed on activated B cells and each can induce submitogenically stimulated T cells to proliferate. Two of these molecules, the early CTLA4 binding counter-receptor (B7-2) and B7-1 (133) induce IL-2 production whereas B7-3 induces proliferation without detectable IL-2 production.

Previous studies provided conflicting evidence whether the anti-B7 monoclonal antibody, 133 and monoclonal antibody BB-1 identified the same molecule (Freedman, A. S. et al. (1987) *Immunol.* 137, 3260–3267; Yokochi, T., et al. (1982) *J. Immunol.* 128, 823–827; Freeman, G. J., et al. (1989) *J. Immunol.* 143, 2714–2722.). Although both monoclonal antibodies identified molecules expressed 48 hours following human B-cell activation, several reports suggested that B7 (B7-1) and the molecule identified by monoclonal antibody BB-1 were distinct since they were differentially expressed on cell lines and B cell neoplasms (Freedman, A. S. et al. (1987) *Immunol.* 137, 3260–3267; Yokochi, T., et al. (1982) *J. Immunol.* 128, 823–827; Freeman, G. J., et al. (1989) *J. Immunol.* 143, 2714–2722; Clark, E and Yokochi, T. (1984) *Leukocyte Typing, 1st International References Workshop.* 339–346; Clark, E., et al. (1984) *Leukocyte Typing, 1st International References Workshop.* 740). In addition, immunoprecipitation and Western Blotting with these IgM monoclonal antibodies suggested that they identified different molecules (Clark, E and Yokochi, T. (1984) *Leukocyte Typing, 1st International References Workshop.* 339–346; Clark, E., et al. (1984) *Leukocyte Typing, 1st International References Workshop.* 740). The original anti-B7 monoclonal antibody, 133, was generated by immunization with anti-immunoglobulin activated human B lymphocytes whereas the BB-1 monoclonal antibody was generated by immunization with a baboon cell line. Thus, the BB-1 monoclonal antibody must identify an epitope on human cells that is conserved between baboons and humans.

Following the molecular cloning and expression of the human B7 gene (B7-1), B7 transfected COS cells were found to be identically stained with the anti-B7 (133) and BB-1 monoclonal antibodies and that they both precipitated the identical broad molecular band (44–54kD) strongly suggesting that they identified the same molecule (Freeman, G. J., et al. (1989) *J. Immunol.* 143, 2714–2722). This observation was unexpected since the gene encoding the molecule identified by the BB-1 monoclonal antibody had been previously mapped to chromosome 12 (Katz, F. E., et al. (1985) *Eur. J. Immunol.* 103–6), whereas the B7 gene was located by two groups on chromosome 3 (Freeman, G. J., et al. (1992) *Blood.* 79, 489–494; Selvakumar, A., et al. (1992) *Immunogenetics* 36, 175–181.). Subsequently, additional discrepancies between the phenotypic expression of B7 (B7-1) and the molecule identified by the BB-1 monoclonal antibody were noted. BB-1 monoclonal antibody stained thymic epithelial cells (Turka, L. A., et al. (1991) *J. Immunol.* 146, 1428–36; Munro, J. M., et al. *Blood* submitted.) and keratinocytes (Nickoloff, B., et al (1993) *Am. J. Pathol.* 142, 1029–1040; Augustin, M., et al. (1993) *J. Invest. Dermatol.* 100, 275–281.) whereas anti-B7 did not. Recently, Nickoloffet al. (1993) *Am. J. Pathol.* 142, 1029–1040, reported discordant expression of the molecule identified by the BB-1 monoclonal antibody and B7 on keratinocytes using a BB-1 and anti-B7 (B1.1 and 133) monoclonal antibodies. Nickoloff et al. also demonstrated that these BB-1 positive cells did not express B7 mRNA yet bound CD28 transfected COS cells providing further support for the existence of a distinct protein which binds monoclonal antibody BB-1.

The present findings confirm that there is an additional CTLA4 counter-receptor identified by the BB-1 monoclonal antibody, B7-3, and that this protein appears to be functionally distinct from B7-1 (133). Although the expression of B7-1 and B7-3 following B cell activation appears to be concordant on B7 positive B cells, these studies demonstrate that the B7-3 molecule is also expressed on B7 negative activated B cells. More importantly, the B7-3 molecule appears to be capable of inducing T cell proliferation without detectable IL-2 or IL4 production. This result is similar to the previous observation that ICAM-1 could costimulate T cell proliferation without detectable IL-2 or IL4 production (Boussiotis, V., et al *J. Exp. Med.* (accepted for publication)). These data indicate that the BB-1 monoclonal antibody recognizes an epitope on the B7-1 protein and that this epitope is also found on a distinct B7-3 protein, which also has costimulatory function. Phenotypic and blocking studies demonstrate that the BB-1 monoclonal antibody could detect one (on B7 negative cells) or both (on B7 positive cells) of these proteins. In contrast, the anti-B7 monoclonal antibodies, 133 and B1.1 detect only the B7-1 protein. Taken together, these results suggest that by 48 hours post B-cell activation by crosslinking of surface immunoglobulin or MHC class II, B cells express at least two distinct CTLA4 binding counter-receptors, one identified by both anti-B7 and BB-1 monoclonal antibodies and the other identified only by BB-1 monoclonal antibody.

The B7-2 antigen is not detectable on activated B cells after 12 hours, but by 24 hours it is strongly expressed and functional. This molecule appears to signal via CD28 since proliferation and IL-2 production are completely blocked by Fab anti-CD28 monoclonal antibody. At 48 hours post activation, IL-2 secretion seems to be accounted for by B7-1 costimulation, since anti-B7 monoclonal antibody completely inhibits IL-2 production.

Previous studies and results presented here demonstrate that B7 (B7-1) is neither expressed (Freedman, A. S. et al.

(1987) *Immunol.* 137, 3260–3267; Freedman, A. S., et al. (1991) *Cell. Immunol.* 137, 429–437) nor capable of costimulating T cell proliferation or IL-2 secretion until 48 hours post B-cell activation. Previous studies have shown that activation of T cells via the TCR in the absence of costimulation (Gimmi, C. D., et al. (1993) *Proc. Natl. Acad. Sci USA* 90:6586–6590; Schwartz, R. H., et al. (1989) *Cold Spring Harb. Symp. Quant. Biol* 54,605–10; Beverly, B., et al. (1992) *Int. Immunol.* 4,661–671.) and lack of IL-2 (Boussiotis, V., et al *J. Exp. Med.* (submitted); Beverly, B., et al. (1992) *Int. Immunol.* 4, 661–671; Wood, M., et al. (1993) *J. Exp. Med.* 177,597–603) results in anergy. If B7-1 were the only costimulatory molecule capable of inducing IL-2 secretion, T cells would be anergized within the first 24 hours following activation since there is no B7-1 present to costimulate IL-2 production. Therefore, the existence of another, early inducible costimulatory molecule, which can costimulate IL-2 secretion during the first 24 hours would be necessary to induce an effective immune response rather than anergy. The appearance of the early CTLA4 binding counter-receptor, B7-2, between 12 and 24 hours post B cell activation, fulfills this function.

Two observations shed light on the biologic and potential clinical significance of these two additional CTLA4 binding counter-receptors. First, B7 (B7-1) deficient mouse has been developed and its antigen presenting cells were found to still bind CTLA4Ig (Freeman and Sharpe manuscript in preparation). This mouse is viable and isolated mononuclear cells induce detectable levels of IL-2 when cultured with T cells in vitro. Therefore, an alternative CD28 costimulatory counter-receptor or an alternative IL-2 producing pathway must be functional. Second, thus far the most effective reagents to induce antigen specific anergy in murine and human systems are CTLA4Ig and Fab anti-CD28, whereas anti-B7 monoclonal antibodies have been much less effective (Harding, F. A., et al. (1992) *Nature.* 356, 607–609; Lenschow, D. J., et al. (1992) *Science.* 257, 789–792; Chen, L., et al. (1992) *Cell.* 71, 1093–1102; Tan, P., et al. (1993) *J. Exp. Med.* 177, 165–173.). These observations are also consistent with the hypothesis that alternative CTLA4/CD28 ligands capable of inducing IL-2 exist, and taken together with the results presented herein, suggest that all three CTLA4 binding counter-receptors may be critical for the induction of T cell immunity. Furthermore, their blockade will likely be required for the induction of T cell anergy. Identical results have been observed in the murine system with the identification of two CTLA4 binding ligands, corresponding to the human B7-1 and B7-2 molecules. APCs in the B7 deficient mouse bind to the CTLA4 and can induce IL-2 secretion. Taken together, these observations indicate that multiple CTLA4 binding counter-receptors exist and sequentially costimulate T cell activation in the murine system.

EXAMPLE 4

Cloning, Sequencing and Expression of the B7-2 Antigen

A. Construction of cDNA Library

A cDNA library was constructed in the pCDM8 vector (Seed, *Nature*, 329:840 (1987)) using poly (A)$^+$ RNA from the human anti-IgM activated B cells as described (Aruffo et al, *Proc. Natl. Acad. Sci. USA*, 84:3365 (1987)). Splenic B cells were cultured at 2×10$^6$ cells/ml in complete culture media, {RPMI 1640 with 10% heat inactivated fetal calf serum (FCS), 2 mM glutamine, 1 mM sodium pyruvate, penicillin (100 units/ml), streptomycin sulfate (100 μg/ml) and gentamycin sulfate (5 μg/ml)}, in tissue culture flasks and were activated by crosslinking of sIg with affinity purified rabbit anti-human IgM coupled to Affi-Gel 702 beads (Bio-Rad), Richmond, Calif.) (Boyd, A. W., et al., (1985) *J. Immunol.* 134,1516). Activated B cells were harvested after 1/6, 1/2, 4, 8 12,24,48, 72 and 96 hours.

RNA was prepared by homogenizing activated B cells in a solution of 4M guanidine thiocyanate, 0.5% sarkosyl, 25mM EDTA, pH 7.5, 0.13% Sigma anti-foam A, and 0.7% mercaptoethanol. RNA-was purified from the homogenate by centrifugation for 24 hour at 32,000 rpm through a solution of 5.7M CsCl, 10 mM EDTA, 25 mM Na acetate, pH 7. The pellet of RNA was dissolved in 5% sarkosyl, 1 mM EDTA, 10 mM Tris, pH 7.5 and extracted with two volumes of 50% phenol, 49% chloroform, 1% isoamyl alcohol. RNA was ethanol precipitated twice. Poly (A)$^+$ RNA used in cDNA library construction was purified by two cycles of oligo (dT)-cellulose selection.

Complementary DNA was synthesized from 5.5 μg of anti-IgM activated human B cell poly(A)$^+$ RNA in a reaction containing 50 mM Tris, pH 8.3, 75mM KCl, 3 mM MgCl$_2$, 10 mM dithiothreitol, 500 μM dATP, dCTP, dGTP, dTTP, 50μg/ml oligo(dT)1218, 180 units/ml RNasin, and 10,000 units/ml Moloney-MLV reverse transcriptase in a total volume of 55 μl at 37 for 1 hr. Following reverse transcription, the cDNA was converted to double-stranded DNA by adjusting the solution to 25 mM Tris, pH 8.3, 100 mM KCl, 5 mM MgCl$_2$, 250 μM each dATP, dCTP, dGTP, dTTP, 5 mM dithiothreitol, 250 units/ml DNA polymerase I, 8.5 units/ml ribonuclease H and incubating at 16° for 2 hr. EDTA was added to 18 mM and the solution was extracted with an equal volume of 50% phenol, 49% chloroform, 1% isoamyl alcohol. DNA was precipitated with two volumes of ethanol in the presence of 2.5M ammonium acetate and with 4 micrograms of linear polyacrylamide as carrier. In addition, cDNA was synthesized from 4 μg of anti-IgM activated human B cell poly(A)$^+$ RNA in a reaction containing 5 0 mM Tris, pH 8.8, 50 μg/ml oligo(dT)$_{12-18}$, 327 units/ml RNasin, and 952 units/ml AMV reverse transcriptase in a total volume of 100 μl at 42° for 0.67 hr. Following reverse transcription, the reverse transcriptase was inactivated by heating at 70° for 10 min. The cDNA was converted to double-stranded DNA by adding 320 μl H$_2$O and 80 μl of a solution of 0.1M Tris, pH 7.5, 25mM MgCl$_2$, 0.5M KCl, 250 μg/ml bovine serum albumin, and 50 mM dithiothreitol, and adjusting the solution to 200 μM each dATP, dCTP, dGTP, dTTP, 50 units/ml DNA polymerase I, 8 units/ml ribonuclease H and incubating at 16° C. for 2 hours. EDTA was added to 18 mM and the solution was extracted with an equal volume of 50% phenol, 49% chloroform, 1% isoamyl alcohol. DNA was precipitated with two volumes of ethanol in the presence of 2.5M ammonium acetate and with 4 micrograms of linear polyacrylamide as carrier.

The DNA from 4Ig of AMV reverse transcription and 2 μg of Moloney MLV reverse transcription was combined. Non-selfcomplementary BstXI adaptors were added to the DNA as follows: The double-stranded cDNA from 6 μg of poly (A)$^+$ RNA was incubated with 3.6 μg of a kinased oligonucleotide of the sequence CTTTAGAGCACA (SEQ ID NO: 15) and 2.4 μg of a kinased oligonucleotide of the sequence CTCTAAAG (SEQ ID NO: 16) in a solution containing 6 mM Tris, pH 7.5, 6 mM MgCl$_{2, 5}$ mM NaCl, 350 μg/ml bovine serum albumin, 7 mM mercaptoethanol, 0.1 mM ATP, 2 mM dithiothreitol, 1 mM spermidine, and 600 units T4 DNA ligase in a total volume of 0.45ml at 15° C. for 16 hours. EDTA was added to 34 mM and the solution was extracted with an equal volume of 50% phenol, 49% chloroform, 1% isoamyl alcohol. DNA was precipitated with two volumes of ethanol in the presence of 2.5M ammonium acetate.

DNA larger than 600 bp was selected as follows: The adaptored DNA was redissolved in 10 mM Tris, pH 8, 1 mM EDTA, 600 mM NaCl, 0.1% sarkosyl and chromatographed on a Sepharose CL-4B column in the same buffer. DNA in the void volume of the column (containing DNA greater than 600bp) was pooled and ethanol precipitated.

The pCDMS vector was prepared for cDNA cloning by digestion with BstXI and purification on an agarose gel. Adaptored DNA from 6 µg of poly(A)⁺ RNA was ligated to 2.25 µg of BstXI cut pCDM8 in a solution containing 6 mM Tris, pH 7.5, 6 mM $MgCl_{2,5}$ mM NaCl, 350 µg/ml bovine serum albumin, 7 mM mercaptoethanol, 0/1 mM ATP, 2 mM dithiothreitol, I1 mM spermidine, and 600 units T4 DNA ligase in a total volume of 1.5ml at 15° for 24 hr. The ligation reaction mixture was transformed into competent *E. coli* MC1061/P3 and a total of 4,290,000 independent cDNA clones were obtained.

Plasmid DNA was prepared from a 500 ml culture of the original transformation of the cDNA library. Plasmid DNA was purified by the alkaline lysis procedure followed by twice banding in CsCl equilibrium gradients (Maniatis et al, *Molecular Cloning: A Laboratory Manual*, Cold Spring Harbor, N.Y. (1987)).

B. Cloning Procedure

In the first round of screening, thirty 100 mm dishes of 50% confluent COS cells were transfected with 0.05 µg/ml anti-IgM activated human B cells library DNA using the DEAE-Dextran method (Seed et al, *Proc. Natl. Acad. Sci. USA*, 84:3365 (1987)). The cells were trypsinized and re-plated after 24 hours. After 47 hours, the cells were detached by incubation in PBS/0.5 mM EDTA, pH 7.4/ 0.02% Na azide at 37° C. for 30 min. The detached cells were treated with 10 µg/ml/CTLA4Ig and CD28Ig for 45 minutes at 4° C. Cells were washed and distributed into panning dishes coated with affinity-purified Goat anti-human IgG antibody and allowed to attach at room temperature. After 3 hours, the plates were gently washed twice with PBS/0.5 mM EDTA, pH 7.4/0.02% Na azide, 5% FCS and once with 0.15M NaCl, 0.01 M Hepes, pH 7.4, 5% FCS. Episomal DNA was recovered from the panned cells and transformed into *E. coli* DH10B/P3. The plasmid DNA was re-introduced into COS cells via spheroplast fusion as described (Seed et al, *Proc. Natl. Acad. Sci. USA*, 84:3365 (1987)) and the cycle of expression and panning was repeated twice. In the second and third rounds of selection, after 47 hours, the detached COS cells were first incubated with α-B7-1 mAbs (133 and B1.1, 10 µg/ml), and COS cells expressing B7-1 were removed by α-mouse IgG and IgM coated magnetic beads. COS cells were then treated with 10 µg/ml of human CTLA4Ig (hCTLA4Ig) and human CD28Ig (hCD28Ig) and human B7-2 expressing COS cells were selected by panning on dishes with goat anti-human IgG antibody plates. After the third round, plasmid DNA was prepared from individual colonies and transfected into COS cells by the DEAE-Dextran method. Expression of B7-2 on transfected COS cells was analyzed by indirect immunofluorescence with CTLA4Ig.

After the final round of selection, plasmid DNA was prepared from individual colonies. A total of 4 of 48 candidate clones contained a cDNA insert of approximately 1.2 kb. Plasmid DNA from these four clones was transfected into COS cells. All four clones were strongly positive for B7-2 expression by indirect immunofluorescence using CTLA4Ig and flow cytometric analysis.

C. Sequencing

The B7-2 cDNA insert in clone29 was sequenced in the pCDM8 expression vector employing the following strategy. Initial sequencing was performed using sequencing primers T7, CDM8R (Invitrogen) homologous to pCDM8 vector sequences adjacent to the cloned B7-2 cDNA (see Table 1). Sequencing was performed using dye terminator chemistry and an ABI automated DNA sequencer. (ABI, Foster City, Calif.). DNA sequence obtained using these primers was used to design additional sequencing primers (see Table 1). This cycle of sequencing and selection of additional primers was continued until the B7-2 cDNA was completely sequenced on both strands.

TABLE I

| | | |
|---|---|---|
| T7(F) | (SEQ ID NO:3) | 5'd[TAATACGACTCACTATAGGG]3' |
| CDM8(R) | (SEQ ID NO:4) | 5'd[TAAGGTTCCTTCACAAAG]3' |
| CDM8 RGV(2) | (SEQ ID NO:5) | 5'd[ACTGGTAGGTATGGAAGATCC]3' |
| HBX29-5P (2R) | (SEQ ID NO:6) | 5'd[ATGCGAATCATTCCTGTGGGC]3' |
| RBX29-5P (2F) | (SEQ ID NO:7) | 5'd[AAAGCCCACAGGAATGATTCG]3' |
| HBX29-5P | (SEQ ID NO:8) | 5'd[CTCTCAAAACCAAABCCTGAG]3' |
| 5PA | (SEQ ID NO:9) | 5'd[TTAGGTCACAGCAGAAGCAGC]3' |
| 5PA (3FA) | (SEQ ID NO:10) | 5'd[TCTGGAAACTGACAAGACGCG]3' |
| HBX29-5P(1R) | (SEQ ID NO:11) | 5'd[CTCAGGCTTTGGTTTTGAGAG]3' |
| HBX29-3P(1R) | (SEQ ID NO:12) | 5'd[CACTCTCTTCCCTCTCCATTG]3' |
| HBX29-5P(3R) | (SEQ ID NO:13) | 5'd[GACAAGCTGATGGAAACGTCG]3' |
| HBX29-3P(1P) | (SEQ ID NO:14) | 5'd[CAATGGAGAGGGAAGAGAGTG]3' |

The human B7-2 clone 29 contained an insert of 1,120 base pairs with a single long open reading frame of 987 nucleotides and approximately 27 nucleotides of 3' noncoding sequences (FIG. 8 (SEQ ID NO:1)). The predicted amino acid sequence encoded by the open reading frame of the protein is shown below the nucleotide sequence in FIG. 8. The encoded protein, human B7-2, is predicted to be 329 amino acids in length (SEQ ID NO:2). This protein sequence exhibits many features common to other type 1 Ig superfamily membrane proteins. Protein translation is predicted to begin at the ATG codon (nucleotide 107–109) based on DNA homology in this region with the consensus eukaryotic translation initiation site (Kozak, M. (1987) *Nucl. Acids Res.* 15:8125–8148). The amino terminus of the human B7-2 protein (amino acids I to 23) has the characteristics of a secretory signal peptide with a predicted cleavage between the alanines at positions 23 and 24 (von Heijne (1986) *Nucl. Acids Res.* 14:4683). Processing at this site would result in a human B7-2 membrane bound protein of 306 amino acid with an unmodified molecular weight of approximately 34 kDa. This protein would consist of an extracellular Ig superfamily V and C like domains, of from about amino acid residue 24–245, a hydrophobic transmembrane domain of from about amino acid residue 246–268 and a long cytoplasmic domain of from about amino acid residue 269–329. The homologies to the Ig superfamily are due to the two contiguous Ig-like domains in the extracellular region bound by the cysteines at positions 40 to 110 and 157 to 218. The extracellular domain also contains eight potential N-linked glycosylation sites. E. coli transfected with a vector containing the cDNA insert of clone 29, encoding the human B7-2 protein, was deposited with the American Type Culture Collection (ATCC) on Jul. 26, 1993 as Accession No. 69357.

Comparison of both the nucleotide and amino acid sequences of human B7-2 with the GenBank and EMBL databases showed that only the human and murine B7-1 proteins are related. Alignment of the three B7 protein sequences (see FIG. 13) shows that human B7-2 has approximately 26% amino acid identity with human B7-1. FIG. 13 represents the comparison of the amino acid sequences for human B7-2 (hB7-2) (SEQ ID NO:2), human B7-1 (hB7-1) (SEQ ID NO: 28 and 29) and murine B7 (mB7) (SEQ ID NO: 30 and 31). The amino acid sequences for the human B7-1 and murine B7 (referred to herein as murine B7-1) can be found in Genbank at Accession #M27533 and X60958 respectively. Vertical lines in FIG. 13 show identical amino acids between the hB7-2 and hB7-1 or mB7. Identical amino acids between hB7-1 and mB7 are not shown. The hB7-2 protein exhibits the same general structure as hB7-l as defined by the common cysteines (positions 40 and 110, IgV domains; positions 157 and 217, IgC domain) which the Ig superfamily domains and by many other common amino acids. Since both hB7-1 and mB7 have been shown to bind to both human CTLA4 and human CD28, the amino acids in common between these two related proteins will be those necessary to comprise a CTLA4 or CD28 binding sequence. An example of such a sequence would be the KYMGRTSFD (position 81–89, hB7-2) (SEQ ID NO:17) or KSQDNVELYDVS (position 188–200, hB7-2) (SEQ ID NO: 18). Additional related sequences are evident from the sequence comparison and others can be inferred by considering homologous related amino acids such as aspartic acid and glutamic acid, alanine and glycine and other recognized functionally related amino acids. The B7 sequences share a highly positive charged domain with the cytoplasmic portion WKWKKKKRPRNSYKC (position 269–282, hB7-2) (SEQ ID NO:19) which is probably involved in intracellular signaling.

EXAMPLE 5

Characterization of the Recombinant B7-2 Antigen

A. B7-2 Binds CTLA4Ig and Not Anti-B7-1 and Anti-B7-3 Monoclonal Antibodies

Figure 9:
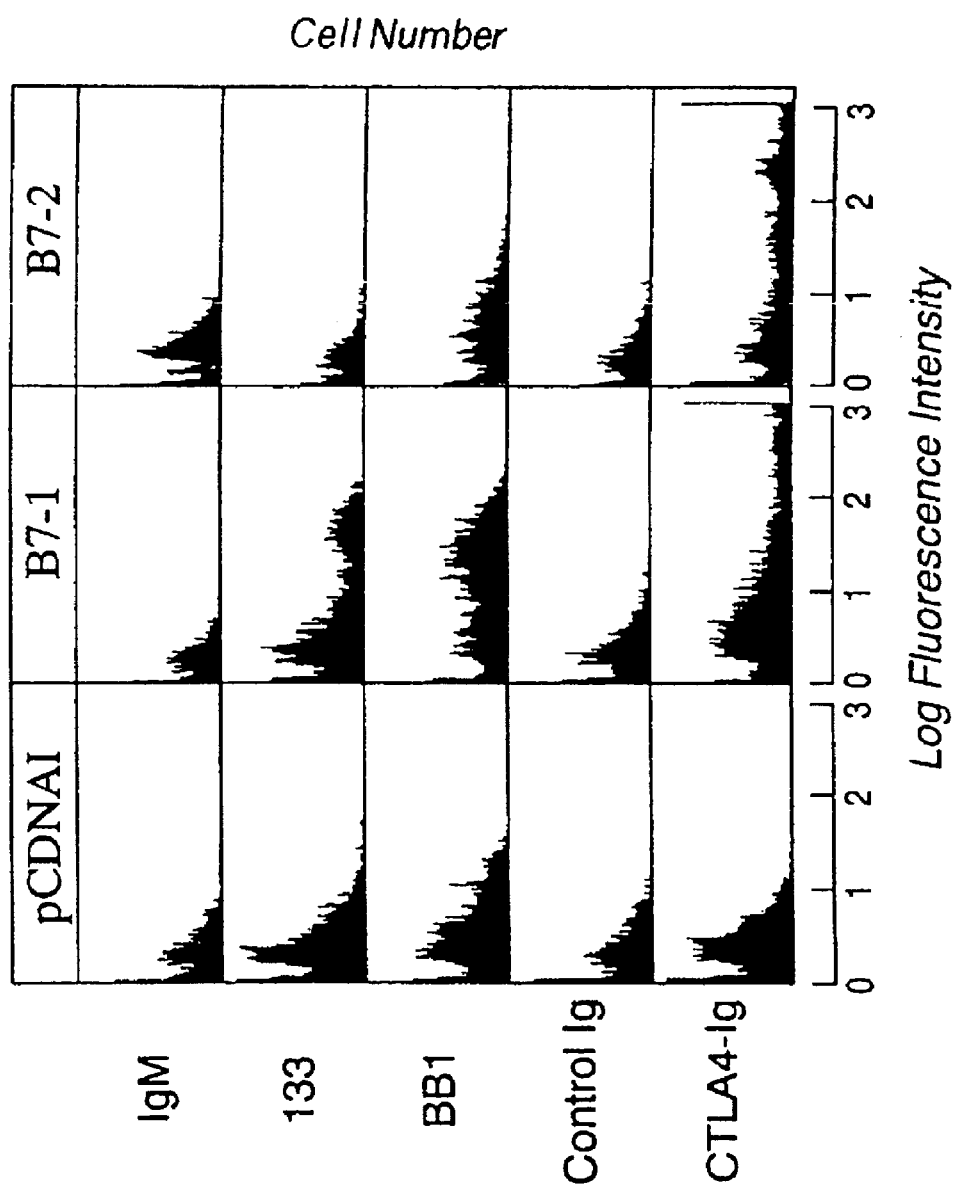
FIG. 9 is a graphic representation of COS cells transfected with control plasmid (pCDNAI), plasmid expressing B7-1 (B7-1), or plasmid expressing B7-2 (B7-2) stained with either control mAb (IgM), anti-B7-1 (mAbs 133 and BB-1), recombinant protein CTLA4Ig, or isotype matched control Ig protein followed by the appropriate second FITC labelled immunoglobulin and analyzed by flow cytometry.

COS cells transfected with either vector DNA (pCDNAI), or an expression plasmid containing B7-1 (B7-1) or B7-2 (B7-2) were prepared. After 72 hours, the transfected COS cells were detached by incubation in PBS containing 0.5 mM EDTA and 0.02% Na azide for 30 min. at 37° C. Cells were analyzed for cell surface expression by indirect immunofluorescence and flow cytometric analysis using fluorescein isothiocyanate conjugated (FITC) goat-anti-mouse Ig or goat-anti-human IgG FITC (FIG. 9). Cell surface expression of B7-1 was detected with mAbs 133 (anti-B7-1) and BB-1 (anti-B7-1 and anti-B7-3) and with CTLA4Ig, whereas B7-2 reacted only with CTLA4Ig. Neither of the B7 transfectants showed any staining with the isotype controls (IgM or control Ig). The vector transfected COS cells showed no staining with any of the detection reagents. In addition, none of the cells showed any staining with the FITC labeled detection reagents and alone. This demonstrates that B7-2 encodes a protein that is a CTLA4 counter-receptor but is distinct from B7-1 and B7-3.

Figure 10A:
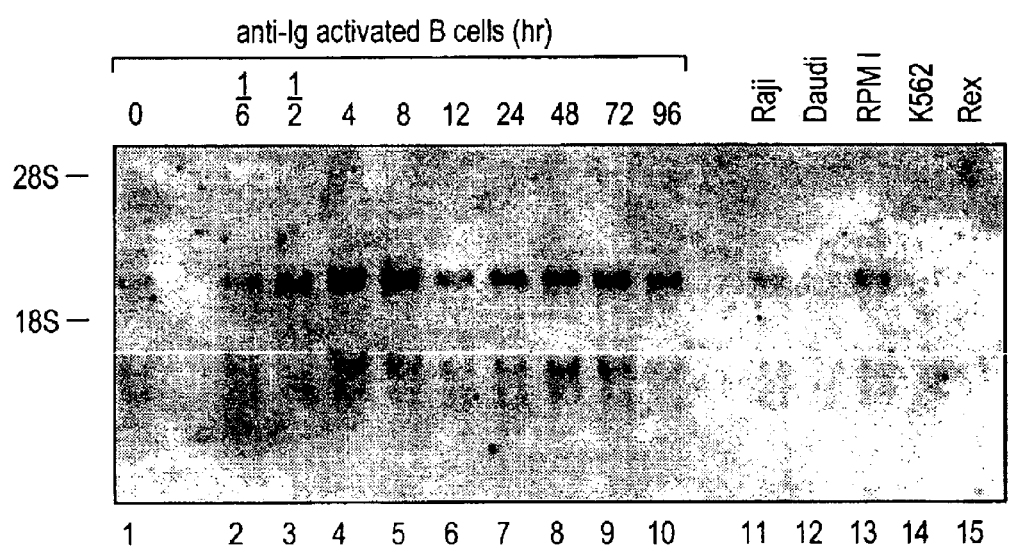
FIGS. 10A–B show RNA blot analyses of B7-2 expression in unstimulated and anti-Ig activated human splenic B cells and cell lines (panel a) and human myelomas (panel b).
Figure 10B:
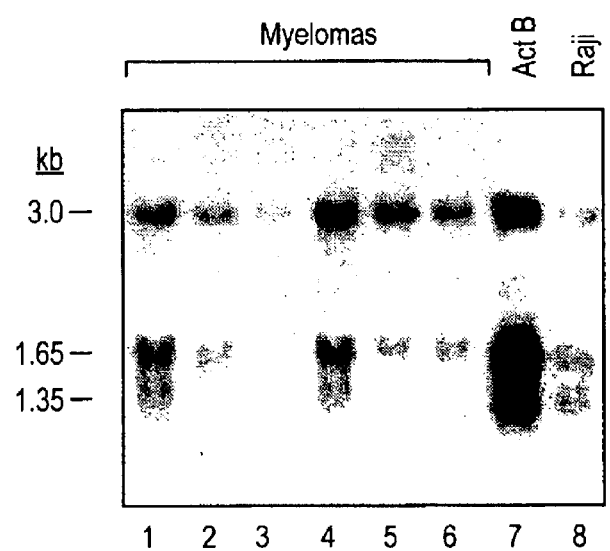

B. RNA Blot Analysis of B7-2 Expression in Unstimulated and Activated Human B Cells, Cell Lines, and Myelomas Human splenic B cells were isolated by removing T cells and monocytes as previously described (Freedman, A. S., Freeman, G. J., Horowitz, J. C., Daley, J., Nadler, L. M., *J. Immunol.* (1987) 137:3260–3267). Splenic B cells were activated using anti-Ig beads and cells were harvested at the indicated times (Freedman et al., (1987), cited supra). Human myelomas from bone marrow specimens were enriched by removing T cells and monocytes using E rosettes and adherence as previously described (Freeman, G. J., et al., *J. Immunol.* (1989) 143:2714–2722). RNA was prepared by guanidine thiocyanate homogenization and cesium chloride centrifugation. Equal amounts of RNA (20 μg) were electrophoresed on an agarose gel, blotted, and hybridized to $^{32}$P-labelled B7-2 cDNA. FIG. 10, panel a, shows RNA blot analysis of unstimulated and anti-Ig activated human splenic B cells and of cell lines including Raji (B cell Burkitt's lymphoma), Daudi (B cell Burkitt's lymphoma), RPMI 8226 (myeloma), K562 (erythroleukemia), and REX (T cell acute lymphoblastic leukemia). FIG. 10, panel b shows RNA blot analysis of human myeloma specimens.

Three mRNA transcripts of 1.35, 1.65 and 3.0 kb were identified by hybridization to the B7-2 cDNA (FIG. 10, panel b). RNA blot analysis demonstrated that B7-2 mRNA is expressed in unstimulated human splenic B cells and increases 4-fold following activation (FIG. 10, panel a). B7-2 mRNA was expressed in B cell neoplastic lines (Raji, Daudi) and a myeloma (RPMI 8226) but not in the erythroleukemia K562 and the T cell line REX. In contrast, we have previously shown that B7-1 mRNA is not expressed in resting B cells and is transiently expressed following activation (G. J. Freeman et al. (1989) supra). Examination of mRNA isolated from human myelomas demonstrates that B7-2 mRNA is expressed in 6 of 6 patients, whereas B7-1 was found in only 1 of these 6 (G. J. Freeman et al. (1989) supra). Thus, B7-1 and B7-2 expression appears to be independently regulated.

C. Costimulation

Figure 11A:
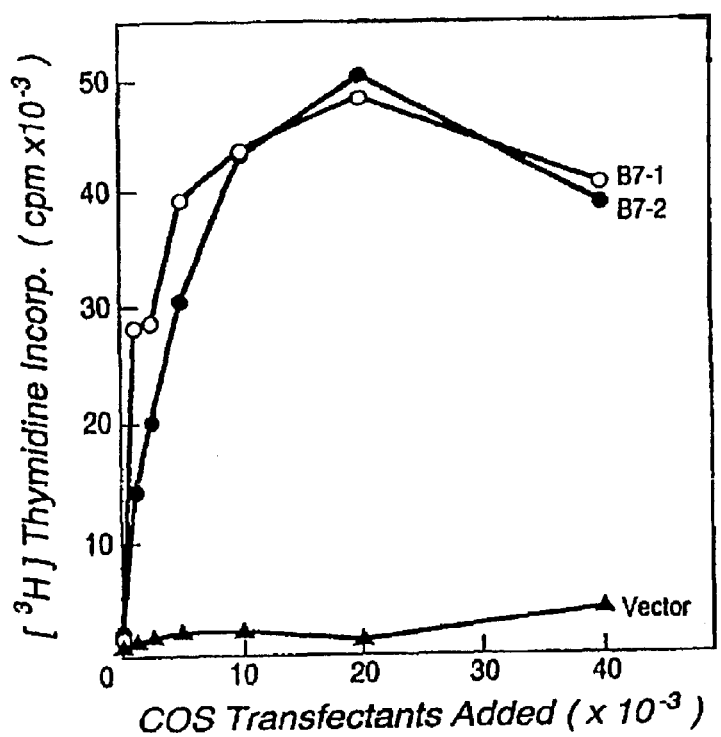
FIG. 11 is a graphic representation of the proliferation of CD28$^+$T cells, as assessed by $^3$H-thymidine incorporation or IL-2 secretion, to submitogenic stimulation with phorbol myristic acid (PMA) and COS cells transfected with vector alone or vectors directing the expression of either B7-1 or B7-2.
Figure 11B:
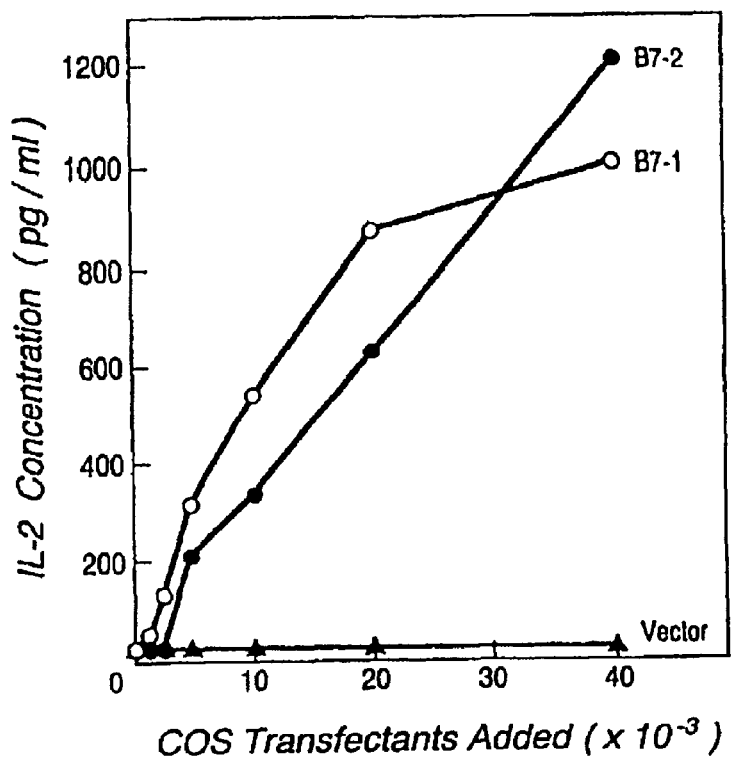

Human CD28$^+$ T cells were isolated by immunomagnetic bead depletion using monoclonal antibodies directed against B cells, natural killer cells and macrophages as previously described (Gimmi, C. D., et al. (1993) *Proc. Natl. Acad. Sci. USA* 90, 6586–6590). B7-1, B7-2 and vector transfected COS cells were harvested 72 hours after transfection, incubated with 25 μg/ml of mitomycin-C for 1 hour, and then extensively washed. $10^5$ CD28$^+$ and T cells were incubated with 1 ng/ml of phorbol myristic acid (PMA) and the indicated number of COS transfectants (FIG. 11). As shown in FIG. 11, panel a, T cell proliferation was measured by 3H-thymidine (1 μCi) incorporated for the last 12 hours of a 72 hour incubation. Panel b of FIG. 11 shows IL-2 production by T cells as measured by ELISA (Biosource, CA) using supernatants harvested 24 hours after the initiation of culture.

Figures 12E, 12F, 12G:
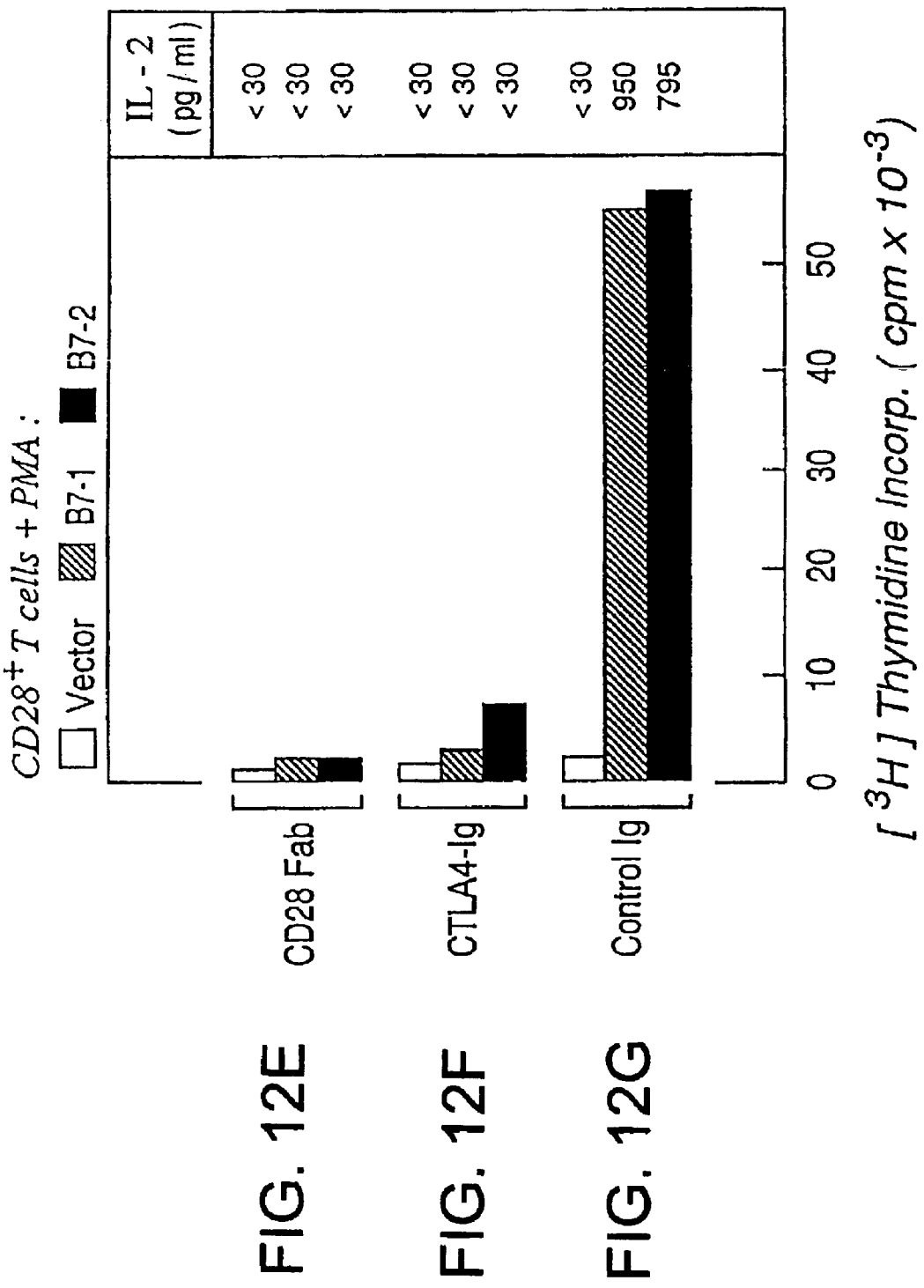
FIG. 12 is a graphic representation of the inhibition by mAbs and recombinant proteins of the proliferation of CD28+ T cells, as assessed by $^3$H-thymidine incorporation and IL-2 secretion, to stimulation by PMA and COS cells transfected with vector alone (vector), or with a vector expressing B7-1 (B7-1) or B7-2 (B7-2). Inhibition studies were performed with the addition of either no antibody (no mAb), anti-B7 mAb 133 (133), anti-B7 mAb BB-1 (BB1), anti-B5 mAb (B5), Fab fragment of anti-CD28 (CD28 Fab), CTLA4Ig (CTLA4Ig), or Ig control protein (control Ig) to the PMA stimulated COS cell admixed CD28$^+$ T cells.

D. B7-2 Costimulation is not Blocked by Anti-B7-1 and Anti-B7-3 mAbs but is Blocked by CTLA4-Ig and Anti-CD28 Fab Human CD28$^+$ T cells were isolated by immunomagnetic bead depletion using mAbs directed against B cells, natural killer cells, and macrophages as previously described (Gimmi, C. D., Freeman, G. J., Gribben, J. G., Gray, G., Nadler, L. M. (1993) *Proc. Natl. Acad Sci USA* 90, 6586–6590). B7-1, B7-2, and vector transfected COS cells were harvested 72 hours after transfection, incubated with 25 μg/ml of mitomycin-C for 1 hour, and then extensively washed. $10^5$ CD28$^+$ T cells were incubated with 1 ng/ml of phorbol myristic acetate (PMA) and $2 \times 10^4$ COS transfectants. Blocking agents (10 μg/ml) are indicated on the left side of FIG. 12 and include: 1) no monoclonal antibody (no blocking agents), 2) mAb 133 (anti-B7-1 mAb), 3) mAb BB1 (anti-B7-1 and anti-B7-3 mAb), 4) mAb B5 (control IgM mAb), 5) anti-CD28 Fab (mAb 9.3), 6) CTLA-Ig, and 7) control Ig. Panel a of FIG. 12 shows proliferation measured by $^3$H-thymidine (1 μCi) incorporation for the last 12 hours of a 72 hour incubation. FIG. 12, panel b, shows IL-2 production as measured by ELISA (Biosource, CA) using supernatants harvested 24 hours after the initiation of culture.

B7-1 and B7-2 transfected COS cells costimulated equivalent levels of T cell proliferation when tested at various stimulator to responder ratios (FIG. 11). Like B7-1, B7-2 transfected COS cell costimulation resulted in the production of IL-2 over a wide range of stimulator to responder cell ratios (FIG. 11). In contrast, vector transfected COS cells did not costimulate T cell proliferation or IL-2 production.

E. B7-2 Costimulation is not Blocked by Anti-B7-1 and Anti-B7-3 mAbs but is Blocked by CTLA4-Ig and Anti-CD28 Fab Human CD28$^+$ T cells were isolated by immunomagnetic bead depletion using mAbs directed against B cells, natural killer cells, and macrophages as previously described (Gimmi, C. D., Freeman, G. J., Gribben, J. G., Gray, G., Nadler, L. M. (1993) Proc. Natl. Acad. Sci USA 90, 65866590). B7-1, B7-2, and vector transfected COS cells were harvested 72 hours after transfection, incubated with 25 μg/ml of mitomycin-C for 1 hour, and then extensively washed. $10^5$ CD28$^+$ T cells were incubated with 1 ng/ml of phorbol myristic acetate (PMA) and $2 \times 10^4$ COS transfectants. Blocking agents (10 μg/ml) are indicated on the left side of FIG. 12 and include: 1) no monoclonal antibody (no blocking agents), 2) mAb 133 (anti-B7-1 mAb), 3) mAb BB1 (anti-B7-1 and anti-B7-3 mAb), 4) mAb B5 (control IgM mAb), 5) anti-CD28 Fab (mAb 9.3), 6) CTLA-Ig, and 7) control Ig. Panel a of FIG. 12 shows proliferation measured by $^3$H-thymidine (1 μCi) incorporation for the last 12 hours of a 72 hour incubation. FIG. 12, panel b, shows IL-2 production as measured by ELISA (Biosource, CA) using supernatants harvested 24 hours after the initiation of culture.

To distinguish B7-2 from B7-1 and B7-3, mAbs directed against B7-1 and B7-3 were used to inhibit proliferation and IL-2 production of submitogenically activated human CD28$^+$ T cells. Both B7-1 and B7-2 COS transfectants costimulated T cell proliferation and IL-2 production (FIG. 12). MAbs 133 (Freedman, A. S. et al. (1987) supra) (anti-B7-1) and BB1(Boussiotis, V. A., et al., (in review) Proc. Natl. Acad. Sci. USA; Yokochi, T., Holly, R. D., Clark, E. A. (1982) J. Immunol. 128, 823–827) (anti-B7-1 and anti-B7-3) completely inhibited proliferation and IL-2 secretion induced by B7-1 but had no effect upon costimulation by B7-2 transfected COS cells. Isotype matched control B5 mAb had no effect. To determine whether B7-2 signals via the CD28/CTLA4 pathway, anti-CD28 Fab and CTLA4-Ig fusion protein were tested to determine whether they inhibited B7-2 costimulation. Both anti-CD28 Fab and CTLA4-Ig inhibited proliferation and IL-2 production induced by either B7-1 or B7-2 COS transfectants whereas control Ig fusion protein had no effect (FIG. 12). While CTLA4-Ig inhibited B7-2 costimulation of proliferation by only 90%, in other experiments inhibition was more pronounced (98–100%). None of the blocking agents inhibited T cell proliferation or IL-2 production induced by the combination of PMA and phytohemagglutinin.

Like B7-1, B7-2 is a counter-receptor for the CD28 and CTLA4 T cell surface molecules. Both proteins are similar in that they are: 1) expressed on the surface of APCs; 2) structurally related to the Ig supergene family with an IgV and IgC domain which share 26% amino acid identity, and 3) capable of costimulating T cells to produce IL-2 and proliferate. However, B7-1 and B7-2 differ in several fundamental ways. First, B7-2 mRNA is constitutively expressed in unstimulated B cells, whereas B7-1 mRNA does not appear until 4 hours and cell surface protein is not detected until 24 hours (Freedman, A. S., et al. (1987) supra; Freeman, G. J., et al. (1989) supra). Unstimulated human B cells do not express CTLA4 counter-receptors on the cell surface and do not costimulate T cell proliferation (Boussiotis, V. A., et al. supra). Therefore, expression of B7-2 mRNA in unstimulated B cells would allow rapid expression of B7-2 protein on the cell surface following activation, presumably from stored mRNA or protein. Costimulation by B7-2 transfectants is partially sensitive to paraformaldehyde fixation, whereas B7-2 costimulation is resistant (Gimmi, C. D., et al. (1991) Proc. Natl. Acad. Sci. USA 88, 6575–6579). Second, expression of B7-1 and B7-2 in cell lines and human B cell neoplasms substantially differs. Third, B7-2 protein contains a longer cytoplasmic domain than B7-1 and this could play a role in signaling B-cell differentiation. These phenotypic and functional differences suggest that these homologous molecules may have biologically distinct functions.

EXAMPLE 6

Cloning and Sequencing of the Murine B7-2 Antigen

A. Construction of cDNA Library

A cDNA library was constructed in the pCDM8 vector (Seed, Nature, 329:840 (1987)) using poly (A)$^+$RNA from dibutryl cyclic AMP (cAMP) activated M12 cells (a murine B cell tumor line) as described (Aruffo et al, Proc. Natl. Acad. Sci. USA, 84:3365 (1987)).

M12 cells were cultured at $1 \times 10^6$ cells/ml in complete culture media, {RPMI 1640 with 10% heat inactivated fetal calf serum (FCS), 2 mM glutamine, 1 mM sodium pyruvate, penicillin (100 units/ml), streptomycin sulfate (100 μg/ml) and gentamycin sulfate (5 μg/ml)}, in tissue culture flasks and were activated by 300 μg/ml dibutryl cAMP (Nabavi, N., et al. (1992) Nature 360, 266–268). Activated M12 cells were harvested after 0, 6, 12, 18, 24 and 30 hours.

RNA was prepared by homogenizing activated M12 cells in a solution of 4M guanidine thiocyanate, 0.5% sarkosyl, 25 mM EDTA, pH 7.5, 0.13% Sigma anti-foam A, and 0.7% mercaptoethanol. RNA was purified from the homogenate by centrifugation for 24 hour at 32,000 rpm through a solution of 5.7M CsCl, 10 mM EDTA, 25 mM Na acetate, pH 7. The pellet of RNA was dissolved in 5% sarkosyl, 1 mM EDTA, 10 mM Tris, pH 7.5 and extracted with two volumes of 50% phenol, 49% chloroform, 1% isoamyl alcohol. RNA was ethanol precipitated twice. Poly (A)$^+$ RNA used in cDNA library construction was purified by two cycles of oligo (dT)-cellulose selection.

Complementary DNA was synthesized from 5.5 μg of dibutryl cAMP activated murine M12 cell poly(A)$^+$ RNA in a reaction containing 50 mM Tris, pH 8.3, 75 mM KCl, 3 mM MgCl$_2$, 10 mM dithiothreitol, 500 μM dATP, dCTP, dGTP, dTTP, 50 μg/ml oligo(dT)$_{12-18}$, 180 units/ml RNasin, and 10,000 units/ml Moloney-MLV reverse transcriptase in a total volume of 55 μl at 37° C. for 1 hr. Following reverse transcription, the cDNA was converted to double-stranded DNA by adjusting the solution to 25 mM Tris, pH 8.3, 100 mM KCl, 5 mM MgCl$_2$, 250 μM each dATP, dCTP, dGTP, dTTP, 5 mM dithiothreitol, 250 units/ml DNA polymerase I, 8.5 units/ml ribonuclease H and incubating at 16° C. for 2 hr. EDTA was added to 18 mM and the solution was extracted with an equal volume of 50% phenol, 49% chloroform, 1% isoamnyl alcohol. DNA was precipitated with two volumes of ethanol in the presence of 2.5M ammonium acetate and with 4 micrograms of linear polyacrylamide as carrier. Following reverse transcription, the reverse transcriptase was inactivated by heating Mat 70° C. for 10 min. The cDNA was converted to double-stranded DNA by adding 320 μl H$_2$O and 80 μl of a solution of 0.1M Tris, pH 7.5, 25 mM MgCl$_2$, 0.5M KCl, 250 μg/ml bovine serum albumin, and 50 mM dithiothreitol, and adjusting the solution to 200 μM each DATP, dCTP, dGTP, dTTP, 50 units/ml DNA polymerase I, 8 units/ml ribonuclease H and incubating at 16° C. for 2 hours. EDTA was added to 18 mM and the solution was extracted with an equal volume of 50% phenol, 49% chloroform, 1% isoamyl alcohol. DNA was precipitated with two volumes of ethanol in the presence of 2.5M ammonium acetate and with 4 micrograms of linear polyacrylamide as carrier.

2 μg of non-selfcomplementary BstXI adaptors were added to the DNA as follows: The double-stranded cDNA from 5.5 μg of poly(A)$^+$ RNA was incubated with 3.6 μg of a kinased oligonucleotide of the sequence CTTTAGAGCACA (SEQ ID NO:15) and 2.4 μg of a kinased oligonucleotide of the sequence CTCTAAAG (SEQ ID NO:16) in a solution containing 6 mM Tris, pH 7.5, 6 mM MgCl$_2$, 5 mM NaCl, 350 μg/ml bovine serum albumin, 7 mM mercaptoethanol, 0.1 mM ATP, 2 mM dithiothreitol, 1 mM spermidine, and 600 units T4 DNA ligase in a total volume of 0.45ml at 150 for 16 hours. EDTA was added to 34 mM and the solution was extracted with an equal volume of 50% phenol, 49% chloroform, 1% isoamyl alcohol. DNA was precipitated with two volumes of ethanol in the presence of 2.5M ammonium acetate.

DNA larger than 600 bp was selected as follows: The adaptored DNA was redissolved in 10 mM Tris, pH 8, 1 mM EDTA, 600 mM NaCl, 0.1% sarkosyl and chromatographed on a Sepharose CL-4B column in the same buffer. DNA in the void volume of the column (containing DNA greater than 600bp) was pooled and ethanol precipitated.

The pCDM8 vector was prepared for cDNA cloning by digestion with BstXI and purification on an agarose gel. Adaptored DNA from 5.5 μg of poly(A)$^+$ RNA was ligated to 2.25 μg of BstXI cut pCDM8 in a solution containing 6 mM Tris, pH 7.5, 6 mM MgCl$_2$, 5 mM NaCl, 350 μg/ml bovine serum albumin, 7 mM mercaptoethanol, 0.1 mM ATP, 2 mM dithiothreitol, 1 mM spermidine, and 600 units T4 DNA ligase in a total volume of 1.5 ml at 15° for 24 hr. The ligation reaction mixture was transformed into competent *E. coli* MC1061/P3 and a total of 200×10$^6$ independent cDNA clones were obtained.

Plasmid DNA was prepared from a 500 ml culture of the original transformation of the cDNA library. Plasmid DNA was purified by the alkaline lysis procedure followed by twice banding in CsCl equilibrium gradients (Maniatis et al, *Molecular Cloning: A Laboratory Manual*, Cold Spring Harbor, N.Y. (1987)).

B. Cloning Procedure

In the first round of screening, thirty 100 mm dishes of 50% confluent COS cells were transfected with 0.05 μg/ml activated M12 murine B cell library DNA using the DEAE-Dextran method (Seed et al, *Proc. Natl. Acad. Sci. USA*, 84:3365 (1987)). The cells were trypsinized and re-plated after 24 hours. After 47 hours, the cells were detached by incubation in PBS/0.5 mM EDTA, pH 7.4/0.02% Na azide at 37° C. for 30 min. The detached cells were treated with 10 μg/ml/human CTLA4Ig and murine CD28Ig for 45 minutes at 4° C. Cells were washed and distributed into panning dishes coated with affinity-purified Goat anti-human IgG antibody and allowed to attach at room temperature. After 3 hours, the plates were gently washed twice with PBS/0.5 mM EDTA, pH 7.4/0.02% Na azide, 5% FCS and once with 0.15M NaCl, 0.01 M Hepes, pH 7.4, 5% FCS. Episdmal DNA was recovered from the panned cells and transformed into *E. coli* DH10B/P3. T he plasmid DNA was re-introduced into COS cells via spheroplast fusion as described (Seed et al, *Proc. Natl. Acad. Sci. USA*, 84:3365 (1987)) and the cycle of expression and panning was repeated twice. In the second and third rounds of selection, after 47 hours, the detached COS cells were first incubated with α-murine B7-1 mAb (16-10A1, 10 μg/ml), and COS cells expressing B7-1 were removed by α-mouse IgG and IgM coated magnetic beads. COS cells were then treated with 10 μg/ml of human CTLA4Ig and murine CD28Ig and murine B7-2 expressing COS cells were selected by panning on dishes coated with goat anti-human IgG antibody. After the third round, plasmid DNA was prepared from individual colonies and transfected into COS cells by the DEAE-Dextran method. Expression of B7-2 on transfected COS cells was analyzed by indirect immunofluorescence with CTLA4Ig.

After the final round of selection, plasmid DNA was prepared from individual colonies. A total of 6, of 8 candidate clones contained a cDNA insert of approximately 1.2 kb. Plasmid DNA from these eight clones was transfected into COS cells. All six clones with the 1.2 Kb cDNA insert were strongly positive for B7-2 expression by indirect immunofluorescence using CTLA4Ig and flow cytometric analysis.

C. Sequencing

The B7-2 cDNA insert in clone4 was sequenced in the pCDM8 expression vector employing the following strategy. Initial sequencing was performed using sequencing primers T7, CDM8R (Invitrogen) homologous to pCDM8 vector sequences adjacent to the cloned B7-2 cDNA (see Table II). Sequencing was performed using dye terminator chemistry and an ABI automated DNA sequencer. (ABI, Foster City, Calif.). DNA sequence obtained using these primers was used to design additional sequencing primers (see Table II). This cycle of sequencing and selection of additional primers was continued until the murine B7-2 cDNA was completely sequenced on both strands.

TABLE II

| | | |
|---|---|---|
| T7(F) | (SEQ ID NO:3) | 5'd[TAATACGACTCACTATAGGG]3' |
| CDM8(R) | (SEQ ID NO:4) | 5'd[TAAGGTTCCTTCACAAAG]3' |
| MBX4-1F | (SEQ ID NO:24) | 5'd[ACATAAGCCTGAGTGAGCTGG]3' |
| MBX4-2R | (SEQ ID NO:25) | 5'd[ATGATGAGCAGCATCACAAGG]3' |
| MBX4-14 | (SEQ ID NO:26) | 5'd[TGGTCGAGTGAGTCCGAATAC]3' |
| MBX4-2F | (SEQ ID NO:27) | 5'd[GACGAGTAGTAACATACAGTG]3' |

A murine B7-2 clone (mB7-2, clone 4) was obtained containing an insert of 1,163 base pairs with a single long open reading frame of 927 nucleotides and approximately 126 nucleotides of 3' noncoding sequences (FIG. 14, SEQ ID NO:22). The predicted amino acid sequence encoded by the open reading frame of the protein is shown below the nucleotide sequence in FIG. 14. The encoded murine B7-2 protein, is predicted to be 309 amino acid residues in length (SEQ ID NO:23). This protein sequence exhibits many features common to other type I Ig superfamily membrane proteins. Protein translation is predicted to begin at the methionine codon (ATG, nucleotides 111 to 113) based on the DNA homology in this region with the consensus eucaryotic translation initiation site (see Kozak, M. (1987) *Nucl. Acids Res.* 15:8125–8148). The amino terminus of the murine B7-2 protein (amino acids 1 to 23) has the characteristics of a secretory signal peptide with a predicted cleavage between the alanine at position 23 and the valine at position 24 (von Heijne (1987) *Nucl. Acids Res.* 14:4683). Processing at this site would result in a murine B7-2 membrane bound protein of 286 amino acids having an unmodified molecular weight of approximately 32 kDa. This protein would consist of an approximate extracellular Ig superfamily V and C like domains of from about amino acid residue 24 to 246, a hydrophobic transmembrane domain of from about amino acid residue 247 to 265, and a long cytoplasmic domain of from about amino acid residue 266 to 309. The homologies to the Ig superfamily are due to the two contiguous Ig-like domains in the extracellular region bound by the cysteines at positions 40 to 110 and 157 to 216. The extracellular domain also contains nine potential N-linked glycosylation sites and, like murine B7-1, is probably glycosylated. Glycosylation of the murine B7-2 protein may increase the molecular weight to about 50–70 kDa. The cytoplasmic domain of murine B7-2 contains a common region which has a cysteine followed by positively charged amino acids which presumably functions as signaling or regulatory domain within an APC. Comparison of both the nucleotide and amino acid sequences of murine B7-2 with the GenBank and EMBL databases yielded significant homology (about 26% amino acid sequence identity) with human and murine B7-1. Murine B7-2 exhibits about 50% identity and 67% similarity with its human homologue, hB7-2. *E. coli* (DH106/p3) transfected with a vector (plasmid pmBx4) containing a cDNA insert encoding murine B7-2 (clone 4) was deposited with the American Type Culture Collection (ATCC) on Aug. 18, 1993 as Accession No. 69388.

D. Costimulation

CD4+ murine T cells were purified by first depleting red blood cells by treatment with Tris-NH$_4$Cl. T cells were enriched by passage over a nylon wool column. CD4+ T cells were purified by two-fold treatment with a mixture of anti-MHC class II and anti-CD28 mAbs and rabbit complement. Murine B7-1 (obtained from Dr. Gordon Freeman, Dana-Farber Cancer Institute, Boston, Mass.; see also, Freeman, G. J. et al (1991) *J. Exp. Med.* 174, 625–631) murine B7-2, and vector transfected COS cells were harvested 72 hours after transfection, incubated with 25 µg/ml mitomycin-C for one hour, and then extensively washed. $10^5$ murine CD4+ T cells were incubated with 1 ng/ml of phorbol myristic acid (PMA) and $2 \times 10^4$ COS transfectants (Table III). T cell proliferation was measured by $^3$H-thymidine (1 µCi) incorporated for the last 12 hours of a 72 hour incubation.

TABLE III

| | 3M-Thymidine Incorporation (cpm) |
|---|---|
| CD4+ T cells | 175 |
| CD4+ T cells + 1 ng/ml PMA | 49 |
| CD4+ T cells + COS-vector | 1750 |
| CD4+ T cells + COS-B7-1 | 4400 |
| CD4+ T cells + COS-B7-2 | 2236 |
| CD4+ T cells + 1 ng/ml PMA + COS-vector | 2354 |
| CD4+ T cells + 1 ng/ml PMA + COS-B7-1 | 67935 |
| CD4+ T cells + 1 ng/ml PMA + COS-B7-2 | 43847 |

EXAMPLE 7

Construction and Characterization of Human B7-2 Immunoglobulin Fusion Proteins

A. Preparation Of Human B7-2Ig Fusion Proteins

The extracellular portion of human B7-2 was prepared as a fusion protein coupled to an immunoglobulin constant region. The immunoglobulin constant region may contain genetic modifications including those which reduce or eliminate effector activity inherent in the immunoglobulin structure. Briefly, DNA encoding the extracellular portion of hB7-2 was joined to DNA encoding the hinge, CH2 and CH3 regions of human IgCγ1 or IgCγ4 modified by directed mutagenesis. This was accomplished as described in the following subsections.

B. Preparation of Gene Fusions

DNA fragments corresponding to the DNA sequences of interest were prepared by polymerase chain reaction (PCR) using primer pairs described below. In general, PCR reactions were prepared in 100 µl final volume composed of Taq, polymerase buffer (Gene Amp PCR Kit, Perkin-Elmer/ Cetus, Norwalk, Conn.) containing primers (1 µM each), dNTPs (200 µM each) 1 ng of template DNA, and Taq, polymerase (Saiki, R. K., et al. (1988) *Science* 239:487491). PCR DNA amplifications were run on a thermocycler (Ericomp, San Diego, Calif.) for 25 to 30 cycles each composed of a denaturation step (1 minute at 94° C.), a renaturation step (30 seconds at 54° C.), and a chain elongation step (1 minute at 72° C.). The structure of each hB7-2 Ig genetic fusion consisted of a signal sequence to facilitate secretion coupled to the extracellular domain of B7-2 and the hinge, CH2 and CH3 domains of human IgCγ1 or IgCγ4. The IgC gamma 1 and IgC gamma 4 sequences contained nucleotide changes within the hinge region to replace cysteine residues available for disulfide bond formation with serine residues and may contain nucleotide changes to replace amino acids within the CH2 domain thought to be required for IgC binding to Fc receptors and complement activation.

Sequence analysis confirmed structures of both $m\gamma_4$ and $\gamma_1$ clones, and each construct was used to transfect 293 cells to test transient expression. hIgG ELISA measured/ confirmed transient expression levels approximately equal to 100 ng protein/ml cell supernatant for both constructs. NSO cell lines were transfected for permanent expression of the fusion proteins.

C. Genetic Construction of hB7-2Ig Fusion Proteins (1). Preparation of Signal Sequence PCR amplification was used to generate an immunoglobulin signal sequence suitable for secretion of the B7-2Ig fusion protein from mammalian cells. The Ig signal sequence was prepared from a plasmid containing the murine IgG heavy chain gene (Orlandi, R. et al. (1989) *Proc. Natl. Acad. Sci. USA* 86:3833–3837) using the oligonucleotide 5'-GGCACTAGGTCTCCAGCTTGAGATCACAGTTCT CTCTAC-3' (#01) (SEQ ID NO: 32) as the forward primer and the oligonucleotide 5'-GCTTGAATCTTCAGAGGAGCGGAGTGGACACC TGTGG-3' (#02) (SEQ ID NO: 33) as the reverse PCR primer. The forward PCR primer (SEQ ID NO: 32) contains recognition sequences for restriction enzymes BsaI and is homologous to sequences 5' to the initiating methionine of the Ig signal sequence. The reverse PCR primer (SEQ ID NO: 33) is composed of sequences derived from the 5' end of the extracellular domain of hB7-2 and the 3' end of the Ig signal sequence. PCR amplification of the murine Ig signal template DNA using these primers resulted in a 224 bp product which is composed of BsaI restriction sites followed by the sequence of the Ig signal region fused to the first 20 nucleotides of the coding sequence of the extracellular domain of hB7-2. The junction between the signal sequence and hB7-2 is such that protein translation beginning at the signal sequence will continue into and through hB7-2 in the correct reading frame.

(2). Preparation of the hB7-2 Gene Segment

The extracellular domain of the hB7.2 gene was prepared by PCR amplification of plasmid containing the hB7-2 cDNA inserted into expression vector pCDNAI (Freeman et al., *Science* 262:909–11 (1994)):

The extracellular domain of hB7-2 was prepared by PCR amplification using oligonucleotide 5'-GCTCCTCTGAAGATTCAAGC-3' (#03) (SEQ ID NO: 34) as the forward primer and oligonucleotide 5'-GGCACTATGATCAGGGGGAGGCTGAGGTCC-3' (#04) (SEQ ID NO: 35) as the reverse primer. The forward PCR primer contained sequences corresponding to the first 20 nucleotides of the B7-2 extracellular domain and the reverse PCR primer contained sequences corresponding to the last 22 nucleotides of the B7-2 extracellular domain followed by a Bcl I restriction site and 7 noncoding nucleotides. PCR amplification with primer #03 (SEQ ID NO: 34) and #04 (SEQ ID NO: 35) yields a 673 bp product corresponding to the extracellular IgV and IgC like domains of hB7-2 followed by a unique Bcl I restriction site.

The signal sequence was attached to the extracellular portion of hB7-2 by PCR as follows. DNA-PCR products obtained above corresponding to the signal sequence and the hB7-2 extracellular domain were mixed in equimolar amounts, denatured by heating to 100° C., held at 54° C. for 30° C. to allow the complementary ends to anneal and the strands were filled in using dNTPs and Taq polymerase. PCR primers #01 (SEQ ID NO: 32) and #04 (SEQ ID NO: 35) were added and the entire fragment produced by PCR amplification to yield a ~880 fragment composed of a BsaI restriction site followed by the signal sequence fused to the extracellular domain of hB7-2, followed by a Bcl I restriction site.

(3). Cloning and Modification of Immunoglobulin Fusion Domain

Plasmid pSP72IgG1 was prepared by cloning the 2000 bp segment of human IgG1 heavy chain genomic DNA (Ellison, J. W., et al. (1982) *Nucl. Acids. Res.* 10:4071–4079) into the multiple cloning site of cloning vector pSP72 (Promega, Madison, Wis.). Plasmid pSP72IgG1 contained genomic DNA encoding the CH1, hinge, CH2 and CH3 domains of the heavy chain human IgCγ1 gene. PCR primers designed to amplify the hinge-CH2-CH3 portion of the heavy chain along with the intervening DNA were prepared as follows. The forward PCR primer 5'-GCATTTTAAGCTTTTCCTGATCAGGAGCCCAAA TCTTCT GACAAAACTCACACATCTCCACCGTCTC-CAGGTA AGCC-3' (SEQ ID NO: 36) contained HindIII and Bcl I restriction sites and was homologous to the hinge domain sequence except for five nucleotide substitutions which would change the three cysteine residues to serines. The reverse PCR primer 5'TAATACGACTCACTATAGGG-3' (SEQ ID NO: 37) was identical to the commercially available T7 primer (Promega, Madison, Wis.). Amplification with these primers yielded a 1050 bp fragment bounded on the 5' end by HindIII and Bcl I restriction sites and on the 3' end by BamH1, Sma1, Kpn1, Sac1, EcoR1, Cla1, EcoR5 and BglII restriction sites. This fragment contained the IgC hinge domain in which the three cysteine codons had been replaced by serine codons followed by an intron, the CH2 domain, an intron, the CH3 domain and additional 3' sequences. After PCR amplification, the DNA fragment was digested with HindIII and EcoR1 and cloned into expression vector pNRDSH digested with the same restriction enzymes. This created plasmid pNRDSH/IgG1.

A similar PCR based strategy was used to clone the hinge-CH2-CH3 domains of human IgCgamma4 constant regions. A plasmid, p428D Medical Research Council, London, England) containing the complete IgCgamina4 heavy chain genomic sequence (Ellison, J. Buxbaum, J. and Hood, L. E. (1981) *DNA* 1: 11–18) was used as a template for PCR amplification using oligonucleotide 5'GAGCAT-FTCCTGATCAGGA GTCCAAATATGGTCCCCCATC-CCATCATCCCCAGG TAAGCCAACCC-3' (SEQ ID NO: 38) as the forward PCR primer and oligonucleotide 5'GCAGAGGAATC-GAGCTCGGTACCCGGGGATCCCCAGT-GTGGGGACAGTGGGA CCGCTCTGCCTCCC-3' (SEQ ID NO: 39) as the reverse PCR primer. The forward PCR primer (SEQ ID NO: 38) contains a Bcl I restriction site followed by the coding sequence for the hinge domain of IgCgamma4. Nucleotide substitutions have been made in the hinge region to replace the cysteine residues with serines. The reverse PCR primer (SEQ ID NO:39) contains a PspAI restriction site (5' CCCGGG-3'). PCR amplification with these primers results in a 1179 bp DNA fragment. The PCR product was digested with BclI and PspAI and ligated to pNRDSH/IgG1 digested with the same restriction enzymes to yield plasmid pNRDSH/IgG4. In this reaction, the IgCγ4 domain replaced the IgCγ1 domain present in pNRDSH/IgG1.

Modification of the CH2 domain in IgC to replace amino acids thought to be involved in binding to Fc receptor was accomplished as follows. Plasmid pNRDSH/IgG1 served as template for modifications of the IgCγ1 CH2 domain and plasmid pNRDSH/IgG4 served as template for modifications of the IgCγ4 CH2 domain. Plasmid pNRDSH/IgG1 was PCR amplified using a forward PCR primer (SEQ ID NO: 36) and oligonucleotide 5'-GGGTTTT GGGGGGAA-GAGGAAGACTGACGGTGCCCCC TCGGCTTCAGGTGCTGAGGAAG-3' (SEQ ID NO: 40) as the reverse primer. The forward PCR primer (SEQ ID NO: 36) has been previously described and the reverse PCR primer (SEQ ID NO: 40) was homologous to the amino terminal portion of the CH2 domain of IgG I except for five nucleotide substitutions designed to change amino acids 234, 235, and 237 (Canfield, S. M. and Morrison, S. L. (1991) *J. Exp. Med.* 173: 1483–1491.) from Leu to Ala, Leu to Glu, and Gly to Ala, respectively. Amplification with these PCR primers will yield a 239 bp DNA fragment consisting of a modified hinge domain, an intron and modified portion of the CH2 domain. Plasmid pNRDSH/IgG1 was also PCR amplified with the oligonuclcotide 5'-CATCTCTTCCTCAGCACCTGAAGCCGAGGGGC ACCGTCAGTCTTCCTCTTCCC CC-3' (SEQ ID NO: 41) as the forward primer and oligonucleotide (SEQ ID NO: 37) as the reverse PCR primer. The forward PCR primer (SEQ ID NO: 41) is complementary to primer (SEQ ID NO: 40) and contains the five complementary nucleotide changes necessary for the CH2 amino acid replacements. The reverse PCR primer (SEQ ID NO: 37) has been previously described. Amplification with these primes yields a 875 bp fragment consisting of the modified portion of the CH2 domain, an intron, the CH3 domain, and 3' additional sequences. The complete IgCγ1 segment consisting of modified hinge domain, modified CH2 domain and CH3 domain was prepared by an additional PCR reaction. The purified products of the two PCR reactions above were mixed, denatured (95° C., 1 minute) and then renatured (54° C., 30 seconds) to allow complementary ends of the two fragments to anneal. The strands were filled in using dNTP and Taq polymerase and the entire fragment amplified using forward PCR primer (SEQ ID NO: 36) and reverse PCR primer (SEQ ID NO: 37). The resulting fragment of 1050 bp was purified, digested with HindIII and EcoR1 and ligated to pNRDSH previously digested with the same restriction enzymes to yield plasmid pNRDSHIgG1 m.

Two amino acids at immunoglobulin positions 235 and 237 were changed from Leu to Glu and Gly to Ala, respectively, within the IgCγ4 CH2 domain to eliminate Fc receptor binding. Plasmid pNRDSH/IgG4 was PCR amplified using the forward primer (SEQ ID NO: 38) and the oligonucleotide 5'-CGCACGTGACCTCAGGGGTCCGGGAGATCATGA GAGTGTCCTTGGGTITTGGGG GGAACAGGAA-GACTGATGGTGCCCCCTCGAACTC AGGTGCTGAGG-3 ' (SEQ ID NO: 42) as the reverse primer. The forward primer has been previously described and the reverse primer was homologous to the amino terminal portion of the CH2 domain, except for three nucleotide substitutions designed to replace the amino acids described above. This primer also contained a PmlI restriction site for subsequent cloning. Amplification with these primers yields a 265 bp fragment composed of the modified hinge region, and intron, and the modified 5' portion of the CH2 domain.

Plasmid pNRDSH/IgG4 was also PCR amplified with the oligonucleotide 5'-CCTCAGCACCTGAGTTCGAGGGGGCACCATCA GTCTCCTGTTCCCCCC AAAACCCAAGGACACTCT-CATGATCTCCCGGACC CCTGAGGTCACGTGCG-3' (SEQ ID NO: 43) as the forward primer and oligonucleotide (SEQ ID NO:39) as the reverse PCR primer. The forward PCR primer (SEQ ID NO: 43) is complementary to primer (SEQ ID NO: 42) and contains the three complementary nucleotide changes necessary for the CR2 amino acid replacements. The reverse PCR primer (SEQ ID NO: 39) has been previously described. Amplification with these primers yields a 1012 bp fragment consisting of the modified portion of the CH2 domain, an intron, the CH3 domain, and 3' additional sequences. The complete IgCγ4 segment consisting of modified hinge domain, modified CH2 domain and CH3 domain was prepared by an additional PCR reaction. The purified products of the two PCR reactions above were mixed, denatured (95° C., 1 minute) and then renatured (54° C., 30 seconds) to allow complementary ends of the two fragments to anneal. The strands were filled in using dNTP and Taq polymerase and the entire fragment amplified using forward PCR primer (SEQ ID NO: 38) and reverse PCR primer (SEQ ID NO:39). The resulting fragment of 1179 bp was purified, digested with BclI and PspAI and ligated to pNRDSH previously digested with the same restriction enzymes to yield plasmid pNRDSH/IgG4m.

(4). Assembly of Final hB7-2Ig Genes

The PCR fragment corresponding to the Ig signal-hB7-2 gene fusion prepared above was digested with BsaI and Bcl I restriction enzymes and ligated to pNRDSH/IgG1, pNRDSH/IgG1m, pNRDSH/IgG4, and pNRDSH/IgG4m previously digested with Hind III and BclI. The ligated plasmids were transformed into *E. coli* JM109 using CaCl2 competent cells and transformants were selected on L-agar containing ampicillin (50 µg/ml; Molecular Cloning: A Laboratory Manual (1982) Eds. Maniatis, T., Fritsch, E. E., and Sambrook, J. Cold Spring Harbor Laboratory). Plasmids isolated from the transformed *E. coli* were analyzed by restriction enzyme digestion. Plasmids with the expected restriction plasmid were sequenced to verify all portions of the signal-hB7-2-IgG gene fusion segments.

D. Expression Cloning of hB7-2V-IgG1 and hB7-2C IgG1

The variable and constant domains of human B7-2 were separately cloned into pNRDSH/IgG1. These clonings were accomplished using PCR. The portions of hB7-2 corresponding to the variable and constant regions were determined from intron/exon mapping and previously published gene structure analysis.

```
Human B7-2 Variable Domain
    5'GCTCCTCTGAAGATT...................GAACTGTCAGTGCTT3'      (SEQ ID NO:44)
       A  P  L  K  I                      E   L    S V  L      (SEQ ID NO:45)

Human B7-2 Constant Domain
    5'GCTAACTTCAGTCAA...................CCTTTCTCTATAGAG3'      (SEQ ID NO:46)
       A  N  F  S  Q                      P    F   S I  E      (SEQ ID NO:47)
```

(1). Assembly of hB7-2VIg

The hB7-2V domain Ig sequence was assembled using a PCR strategy similar to that shown above. The signal sequence was derived from the onco M gene by PCR amplification of a plasmid containing the onco M gene using oligonucleotide 5'-GCAACCGGAAGCTTGCCACCATGGGGGTACTG CTCACACAGAGGACG-3' (#05) (SEQ ID NO: 48) as the forward PCR primer and 5'-AGTCTCATTGAAATAAGCTTGAATCTTCAGAGG AGCCATGCTGGCCATGCTTGGAAACAGGAG-3' (#06) (SEQ ID NO: 49) as the reverse primer. The forward PCR primer (#05) (SEQ ID NO: 48) contains a Hind III restriction site and the amino terminal portion of the onco M signal sequence. The reverse PCR (#06) (SEQ ID NO: 49) contains the sequence corresponding to the 3' portion of the onco M signal sequence fused to the 5' end of the hB7-2 IgV like domain.

The hB7-2 IgV like domain was obtained by PCR amplification of the hB7-2 cDNA using oligonucleotide 5'-CTCCTGTMTCCAAGCATGGCCAGCATGGCTCC TCTGAA GATTCAGGCTTATTTCAATGAGAC-3' (#07) (SEQ ID NO: 50) as the forward and oligonucleotide 5'-TGTGTGTGGAATTCTCATTACTGATCAAGCACT GACAGTTCAGAATTCATC-3' (#08) (SEQ ID NO: 51) as the reverse PCR primer. PCR amplification with these primers yields the hB7-2 IgV domain with a portion of the 3' end of the onco M signal sequence on the 5' end and a Bcl I restriction site on the 3' end. The signal and IgV domain were linked together in a PCR reaction in which equimolar amounts of the onco M signal and IgV domain DNA fragments were mixed, denatured, annealed, and the strands filled in. Subsequent PCR amplification using forward primer #05 (SEQ ID NO:48) and reverse primer #08 (SEQ ID NO: 51) yielded a DNA fragment containing a Hind III restriction site, followed by the onco M signal fused to the B7-2 IgV domain followed by a Bcl I restriction site. This PCR fragment was digested with Hind II and Bcl I and cloned into expression vector pNRDSH/IgG1 digested with the same restriction enzymes to yield pNRDSH/B7-2CIg.

(2). Assembly of hB7-2CIg

The expression plasmid for hB7-2IgC domain was prepared as described above for the IgV domain except for using PCR primers specific for the IgC domain. The onco M signal sequence was prepared using oligonucleotide #05 (SEQ ID NO: 48) as the forward PCR primer and oligonucleotide 5'-AGAAATTGGTACTATTTCAGGTTGACTGAAGTT AGCCATGCTGGCCATGCTTGGAAACAGGAG-3' (#09) (SEQ ID NO: 52) as the reverse PCR primer. The hB7-2 IgC domain was prepared using oligonucleotide 5'-CTCCTGTTmCCAAGCATGGCCAGCATGGCTAA CTTCAGTC AACCTGAAATAGTACCAATTTC-3' (#11) (SEQ ID NO: 53) as the reverse PCR primer. The two PCR products were mixed and amplified with primers #05 (SEQ ID NO: 48) and #11 (SEQ ID NO: 53) to assemble the onco M signal sequence with the hB7-2IgC domain. The PCR product was subsequently digested with Hind III and BclI and ligated to pNRDSH/IgG1 digested with similar restriction enzymes to yield the final expression plasmid pNRDSH/hB7-2CIgG1.

E. Competitive Binding Assays with Human B7-2Ig Fusion Proteins

To determine the affinity of binding of different forms of soluble B7-1 and B7-2 proteins to CTLA4, competitive binding assays were performed with these proteins. The soluble B7-2VIg, B7-2CIg, B7-2Ig, and B7-1Ig fusion proteins used in these assays were expressed and purified as follows.

The preparation of expression vectors encoding human B7-2VIg, B7-2CIg, and B7-2Ig fusion proteins is described above. The expression vector encoding the B7-1Ig fusion protein, containing an OncoM leader sequence linked the extracellular domain of B7-1 was prepared similarly, using the PCR primers OncoMB71F (5'CTCAAGCTTGCCACCATGGGGGTACTGCTCACA CAGAGGACG CTGCTCAGTCTGGTCCTTGCACTC-CTGTTTCCGAGCATGGCGAGCATGGGTCTTTC TCACTFC3'; SEQ ID NO: 54) and B71/BclI (5'TGTGTGTGGAATTCTCATTACTGATCAGGAAAAT-GCTCTTGCTTG3'; SEQ ID NO: 55). The plasmid pKShB7-1, containing the OncoM leader sequence linked to the human B7-1 cDNA sequence (the nucleotide sequence of the human B7-1 cDNA is disclosed in Freeman, G. J. et al., (1989) *J. Immunol.* 143:2714–2722) was used as a template in this PCR reaction.

The B7Ig fusion proteins were prepared by transfection of COS cells or Chinese Hamster Ovary (CHO) cells and purification of the protein from the supernatant of the cultures.

Cell culture reagents were obtained from Gibco-BRL, Gaithersburg, Md. CHO cells were maintained in alpha MEM supplemented with 10% Fetal bovine serum (FB S) and glutamine. Penicillin, streptomycin, and fungi zone were typically added. COS cells were maintained in DMEM with 10% FBS and supplemented as described for CHO cells. All cells were kept at 5% CO2 at 37° C. in a humidified incubator.

All fusion constructs except the hB7-1Ig construct were expressed transiently in COS cells. Typical transient transfections were done using 200 µgs/ml of DEAE-dextran, 100 µM chloroquine and 5 µgs of DNA per 10 cm dish in serum-free DMEM. The cells were treated until vacuoles were noted and the cells appeared distressed (about 3 hours). Cells were shocked with 10% DMSO/PBS for 2 minutes, then incubated with DMEM/10%FBS overnight. The following morning the media was changed to DMEM/serum free and left until harvest at 72 hours post transfection. The hB7-1Ig construct was transfected into CHO cells by calcium phosphate transfection. The line was made stable using Geneticin (G418) resistance selection, and expression was amplified using methotrexate and alpha MEM lacking nucleosides.

For all transiently transfected constructs (i.e., all constructs except hB7-1Ig) media enriched for Ig fusion proteins produced by the transiently transfected host cells was harvested 72 hours post-transfection. The amount of Ig fusion proteins produced by the host cells was measured by performing an anti-human IgG Elisa assay with the supernatant of the cultures. For this assay, Maxisorp plates (Nunc, Denmark) were coated overnight with 20 µgs/ml of goat anti-human IgG (H+L) (Zymed, San Francisco, Calif.) in PBS. The plates were blocked for 1 hour with PBS/0.1% BSA and then incubated for an additional hour with cell culture supernatants from the transfected cells. After 5 washes with PBS/0.05% Tween, HRP-coupled goat anti-human IgG(H+L) (Zymed) was added as a 1:1000 dilution in PBS. After a 1 hour incubation the plates were washed again, then enzymatically developed using an ABTS kit (Zymed) as described above.

Expression levels were approximately 3 µg/ml for the constructs. The B7Ig fusion proteins were purified from the supernatant of transfected host cells by protein A purification as follows. Protein A Sepharose IPA300 (Repligen, Cambridge, Mass.) was washed in OBB (1.5 M glycine, 3 M NaCl, pH 8.9), resuspended in DMEM, and added to cell culture supernatant at 1 ml/liter of supernatant. The solution was left to mix gently overnight at 4° C. The Protein A sepharose was then pelleted, the majority of the supernatant was removed, and the remaining supernatant was used to resuspend the Protein-A Sepharose prior to loading onto a Poly-prep column (BioRad, Hercules, Calif.). The column was washed extensively with OBB and the immunoglobulin fusion protein was eluted in 0.1 M sodium citrate. Half volume column washes were collected into ⅒th volume 1 M Tris (pH9.0). Protein containing fractions were identified by a standard colorimetric reaction (BioRad), pooled, and dialyzed overnight against PBS in 6000–8000 KD dialysis tubing. The purified proteins were of the expected size and high purity, representing >90% of total protein stained with Coomassie Blue on acrylamide gels.

The ability of various B7 family-Ig fusion proteins to competitively inhibit the binding of biotinylated-CTLA4Ig to immobilized B7-2Ig was determined. Competition binding assays were done as follows and analyzed according to McPherson (McPherson, G. A. (1985) *J. Pharmacol. Methods* 14:213–228). Soluble hCTLA4Ig was labelled with 1251 to a specific activity of approximately $2 \times 10^6$ cpm/pmol. hB7-2-Ig fusion protein was coated overnight onto microtiter plates at 10 mg/ml in 10 mM Tris-HCl, pH8.0, 50 ml /well. The wells were blocked with binding buffer (DMEM containing 10% heat-inactivated FBS, 0.1% BSA, and 50 mM BES, pH 6.8) for 2 h at room temperature. The labeled CTLA4-Ig (4 nM) was added to each well in the presence or absence of unlabeled competing Ig fusion proteins, including fill-length B7-2 (hB7-2Ig), full-length B7-1 (hB7-1Ig), the variable region-like domain of B7-2 (hB7-2VIg) and the constant region-like domain of B7-2 (hB7-2CIg) and allowed to bind for 2.5 h at room temperature. The wells were washed once with ice-cold binding buffer and then four times with ice-cold PBS. Bound radioactivity was recovered by treatment of the wells with 0.5 N NaOH for 5 min and the solubilized material removed and counted in a gamma counter.

Figure 15:
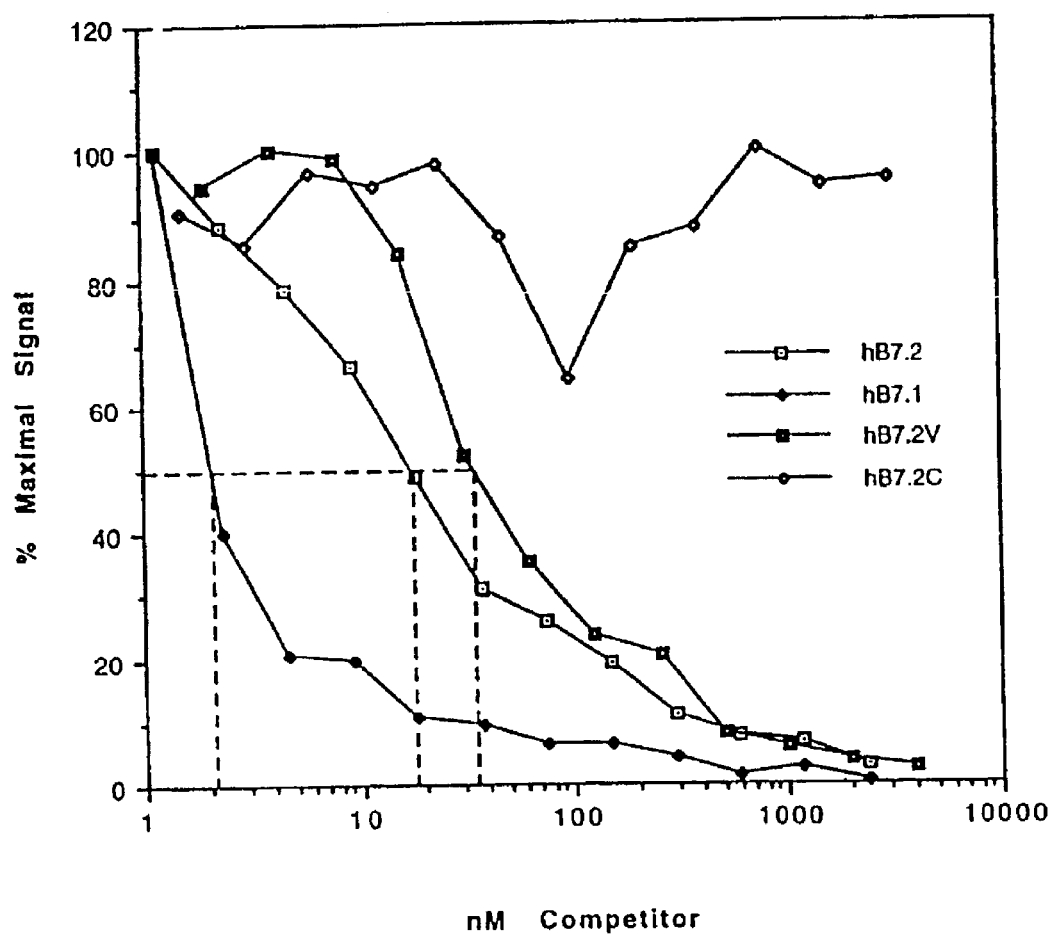
FIG. 15 is a graphic representation of the competitive inhibition of binding of biotinylated-CTLA4Ig to immobilized B7-2 Ig by B7 family-Ig fusion proteins. The Ig fusion proteins examined as competitors were: full-length B7-2 (hB7.2), full-length B7-1 (hB7.1), the variable region-like domain of B7-2 (hB7.2V) or the constant region-like domain of B7-2 (hB7.2C).

The results of these assays are shown in FIG. 15 in which both hB7-2Ig (10–20 nM) and hB7-2VIg (30–40 nM) competitively inhibit the binding of CTLA4Ig to immobilized B7-2 protein. hB7-2CIg is unable to compete with soluble CTLA4, indicating that the B7-2 binding region is in found in the variable-region like domain.

F. Competitive Binding Assays for B7-1 and B7-2 Fusion Proteins

The ability of recombinant CTLA4Ig to bind to hB7-1 or hB7-2 was assessed in a competitive binding ELISA assay as follows. Purified recombinant CTLA4Ig (20 μg/ml in PBS) was bound to a Costar EIA/RIA 96 well microtiter dish (Costar Corp, Cambridge Mass., USA) in 50 μL overnight at room temperature. The wells were washed three times with 200 μL of PBS and the unbound sites blocked by the addition of 1% BSA in PBS (200 μl/well) for 1 hour at room temperature. The wells were washed as above. Biotinylated B7-1Ig or B7-2Ig (1 μg/ml serially diluted in twofold steps to 15.6 ng/mL; 50 μL) was added to each well and incubated for 2.5 hours at room temperature. The wells were washed as above. The bound biotinylated B7-Ig was detected by the addition of 50 μl/well of a 1:2000 dilution of streptavidin-HRP (Pierce Chemical Co., Rockford, Ill.) for 30 minutes at room temperature. The wells were washed as above and 50 μL of ABTS (Zymed, California) added and the developing blue color monitored at 405 nm after 30 min. The ability of unlabelled B7-1Ig or B7-2Ig to compete with biotinylated B7-1Ig or B7-2Ig, respectively, was assessed by mixing varying amounts of the competing protein with a quantity of biotinylated B7-1Ig or B7-2Ig shown to be non-saturating (i.e., 70 ng/mL; 1.5 nM) and performing the binding assays as described above. A reduction in the signal (Abs 405 nm) expected for biotinylated B7-1Ig or B7-2Ig indicated a competition for binding to immobilized CTLA4Ig.

Figure 16A:
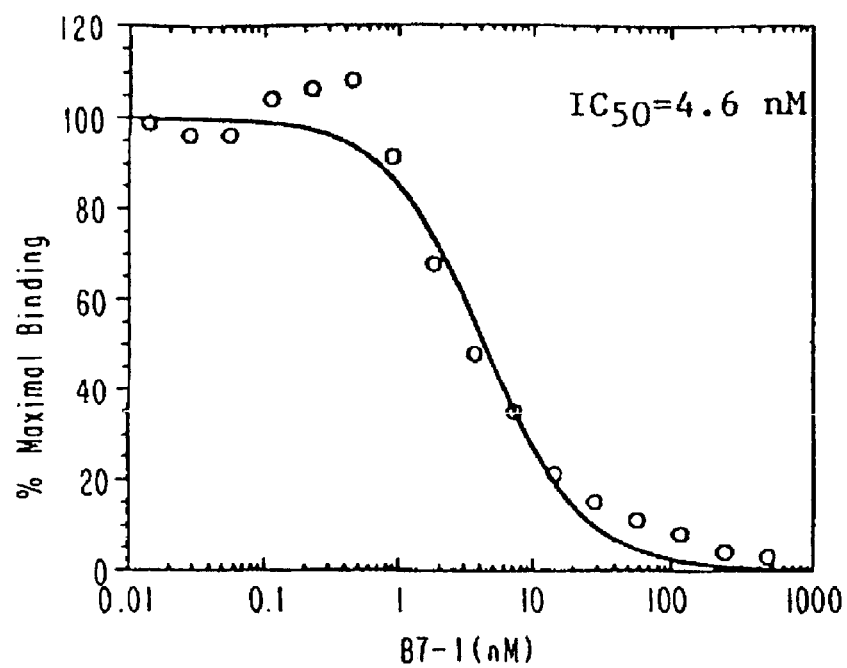
FIGS. 16A–B are graphic representations of the competitive inhibition of binding of biotinylated-B7-1-Ig (panel A) or B7-2-Ig (panel B) to immobilized CTLA4Ig by increasing concentrations of unlabelled B7-1-Ig (panel A) or B7-2-Ig (panel B). The experimentally determined IC$_{50}$ values are indicated in the upper right corner of the panels.
Figure 16B:
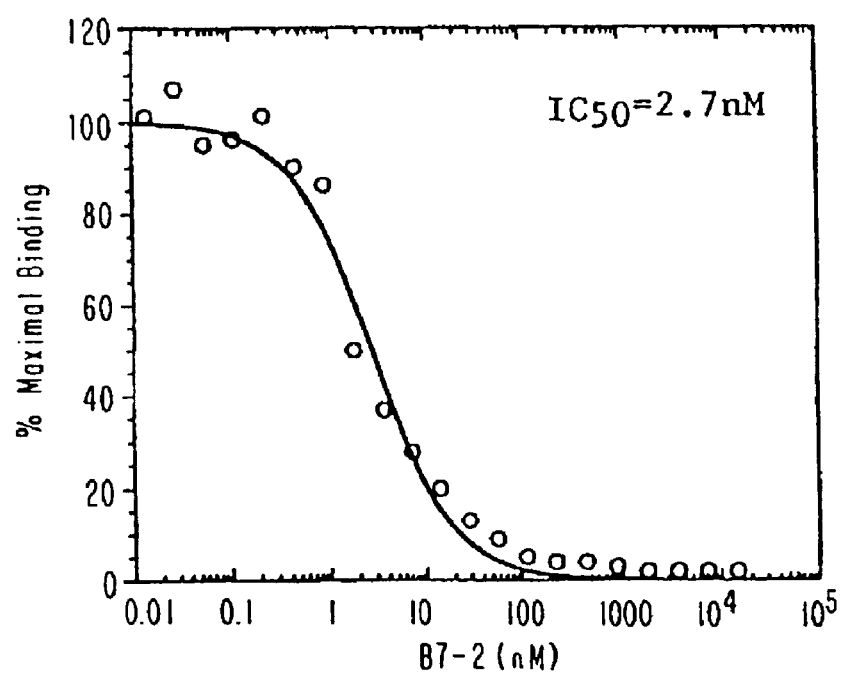

Considering the previous evidence that CTLA4 was the high affinity receptor for B7-1, the avidity of binding of CTLA4 and CD28 to B7-1 and B7-2 was compared in assays as described above. In a first experiment, B7-1Ig or B7-2-Ig was labelled with biotin and bound to immobilized CTLA4-Ig in the presence or absence of increasing concentrations of unlabeled B7-1Ig or B7-2Ig. The experiment was repeated with $^{125}$I-labeled B7-1Ig or B7-2Ig. Representative results are shown in FIG. 16 (Panel A: B7-1Ig; Panel B: B7-2Ig). Using this solid phase binding assay, the avidity of B7-2 (2.7 nM) for CTLA4 was determined to be approximately twofold lower than that observed for B7-1 (4.6 nM). The experimentally determined $IC_{50}$ values are indicated in the upper right corner of the panels. The affinity of both B7-1 and B7-2 for CD28 was lower and was difficult to confidently determine.

G. Direct Binding Assays of modified forms of B7 family members to CTLA4Ig

Direct binding ELISA assays were performed to determine the level of binding of B7 family members as Ig fusions proteins to CTLA4. For these assays, the immunoglobulin fusion proteins were attached to plates and the amount of biotinylated CTLA4 binding to the plates was determined as described below.

Nunc Maxisorp plates were coated overnight at room temperature with 50 μl per well of a 20 μg/ml stock of the various B7Ig fusion proteins, or purified human IgG (Zymed) in PBS as described above. Human CTLA4Ig (Repligen) was biotinylated using NHS-LC-biotin (Pierce, Rockford, Ill.). Varying amounts of biotinylated CTLA4Ig were added to the plates and incubated for 2 hours at room temperature. The plates were washed five times with PBS and then a 1:1000 dilution of streptavidin-HRP (Zymed) was added and left for 30' minutes on the plates. After another series of washes with PBS, the HRP reactivity was measured using an ABTS kit (Zymed) as described above.

Figure 20:
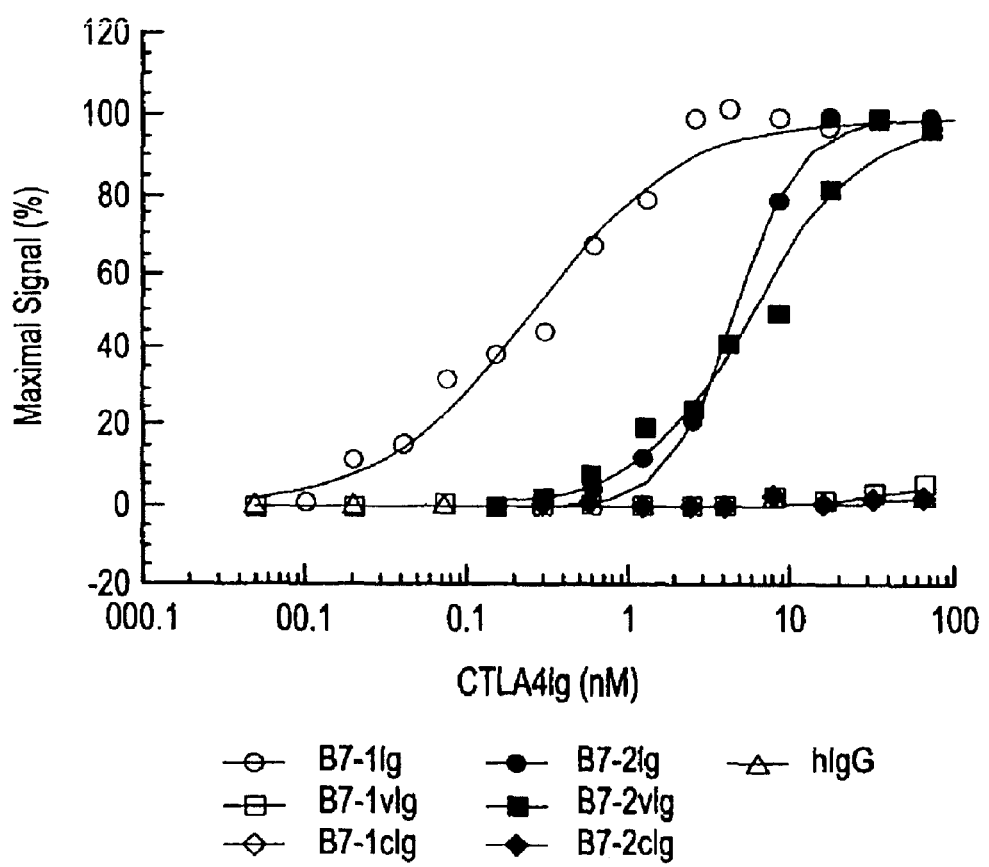
FIG. 20 is a graphic representation of the direct binding of soluble biotinylated CTLA4Ig to B7-1Ig, B7-1VIg, B7-1 CIg, B7-2Ig, B7-2VIg, B7-2CIg, or human IgG (hIgG) bound to plates.
Figure 21A:
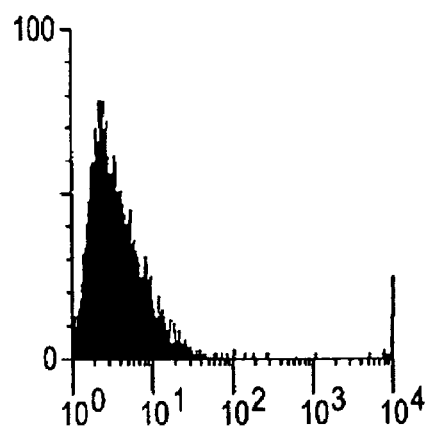
FIGS. 21A–E depict flow cytometric profiles of binding of B7-2Ig (Panel C), B7-2VIg (Panel D), B7-1Ig (Panel E), or secondary antibody alone (Panel B) to CTLA4+ CHO cells. Panel A is a negative control representing untransfected CHO cells.
Figure 21B:
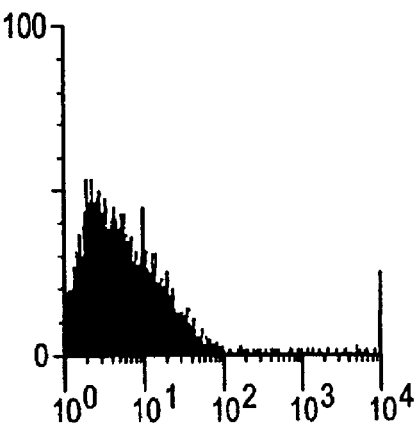
Figure 21C:
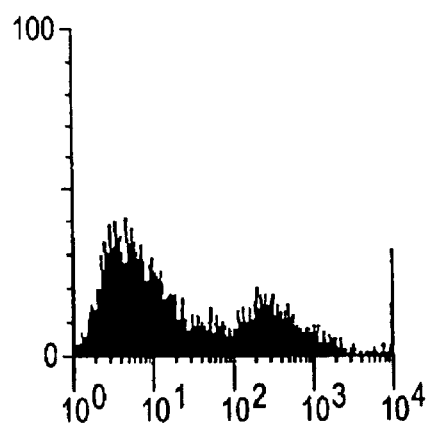
Figure 21D:
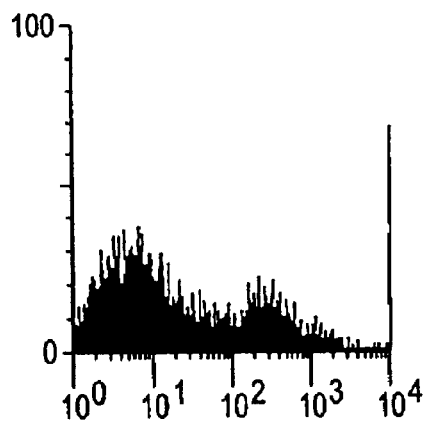
Figure 21E:
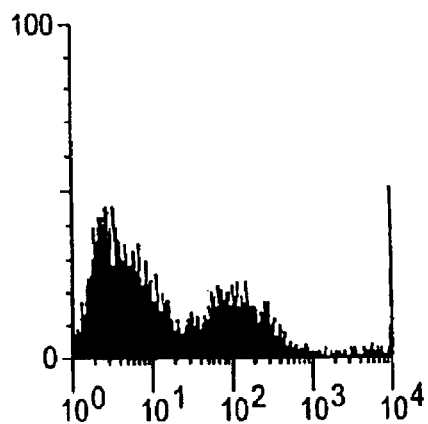

The results, presented in FIG. 20, show that half-saturation occurred at 500 pM for B7-1Ig, and at 5 nM and 8 nM for B7-2VIg and B7-2Ig, respectively. Thus, CTLA4Ig binds to a similar extent to the B7-2VIg and B7-2Ig fusion proteins. CTLA4 does not, however bind to B7-2CIg. Thus, the variable domain of B7-2 is sufficient for binding to CTLA4.

H. Binding of B7-2VIg, B7-2Ig, and B7-1Ig to CHO-CTLA4 cells

The examples presented in section F and G of Example 7 showed that B7-2VIg and B7-2Ig bind soluble CTLA4Ig. The present example shows that B7-2VIg and B7-2Ig also bind to CTLA4 expressed on a cell.

For this example, labeled B7-1Ig and B7-2Ig fusion proteins were incubated with CHO cells transfected to express CTLA4 and binding was measured by flow cytometry as follows.

B7-1 and B7-2 immunoglobulin fusion proteins, prepared as described above, were diluted to 20 μg/ml in PBS/1% BSA and incubated with $10^6$ CHO cells transfected to express CTLA4 on their surface (CHO/CTLA4 cells) for 30 minutes on ice. The cells were washed twice with cold PBS/BSA and incubated with a 1:50 dilution of goat anti-human IgG-FITC (Zymed) for 30 minutes on ice. The cells were washed once with cold PBS/BSA, once with cold PBS and then resuspended in 250 μl cold PBS. The cells were then fixed by adding 250 μl of a 2% paraformaldehyde solution in PBS and incubation for at least 1 hour and the fluorescence analyzed using a FACS (Becton Dickinson, San Jose, Calif.). Similarly treated CHO/CTLA4 cells which received the secondary antibody alone served to measure background staining.

The results of the flow cytometric analysis are presented in FIG. 21. The results show that hB7-2Ig and hB7-2VIg fusion proteins bind to a similar extent to CTLA4 positive cells (FIG. 21, panels C and D, respectively) and that the binding is stronger than binding of hB7-1Ig to CHO/CTLA4 cells (panel E).

I. B7-2VIg binds with stronger affinity to CD28 than B7-1Ig and B7-2Ig

The Example shown in the previous section showed that B7-2VIg and B7-2Ig fusion proteins bind with similar affinity to cell membrane bound CTLA4. This example shows that the fusion proteins bind with different affinities to CD28 and in particular, that B7-2VIg binds with higher affinity to CD28 than B7-2Ig.

B7-1 and B7-2 immunoglobulin fusion proteins diluted at 20 µg/ml in PBS/1% BSA were incubated with $10^6$ CHO cells transfected to express CD28 on their surface (CHO/CD28 cells) for 30 minutes on ice. The cells were washed twice with cold PBS/BSA and incubated with a 1:50 dilution of goat anti-human IgG-FITC (Zymed) for 30 minutes on ice. The cells were washed once with cold PBS/BSA, once with cold PBS and then resuspended in 250 µl cold PBS. The cells were then fixed by adding 250 µl of a 2% paraformaldehyde solution in PBS and incubation for at least 1 hour and the fluorescence analyzed using a FACS (Becton Dickinson, San Jose, Calif.).

Figure 22:
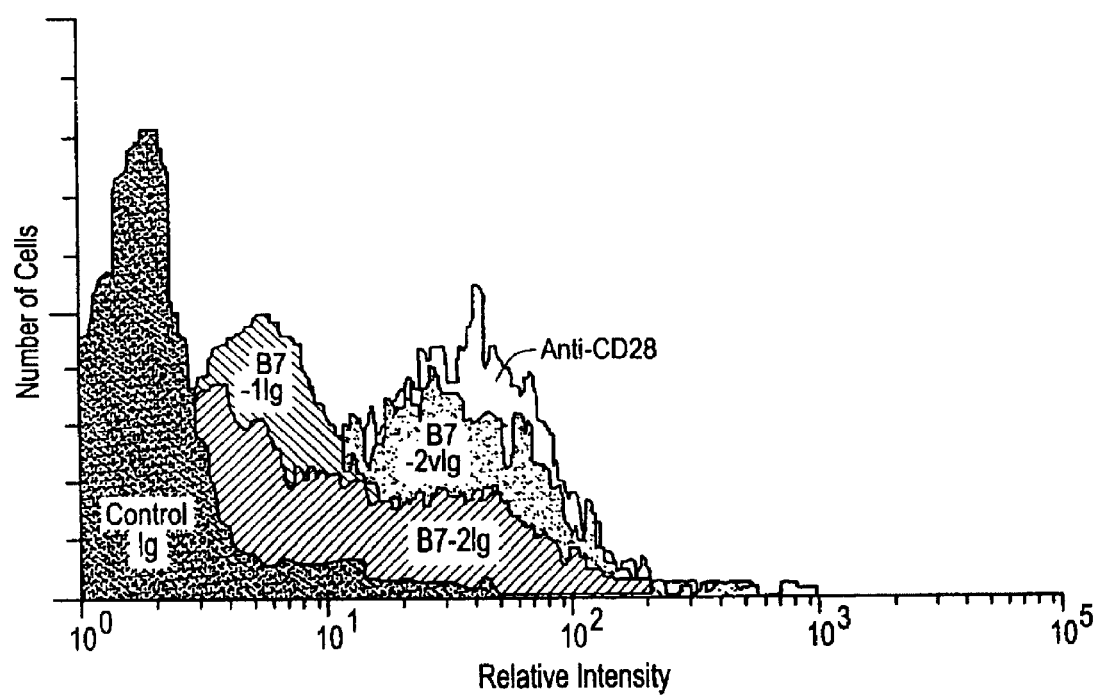
FIG. 22 depicts flow cytometric profiles of binding of control Ig, B7-1Ig, B7-2Ig, B7-2VIg, and anti-CD28 to CHO cells expressing CD28.

Representative results, as presented in FIG. 22, indicate that B7-2Ig and B7-2VIg fusion proteins bind specifically to CHO-CD28 cells. The results further indicate that B7-2VIg protein binds to CD28 with stronger affinity than does B7-2Ig and B7-1Ig.

Thus, B7-2VIg fusion protein binds with higher affinity than B7-2Ig to CD28, whereas both fusion proteins bind with similar affinity to CTLA4.

J. B7-2VIg is more potent than B7-2Ig and B7-1Ig at costimulating proliferation of CD28+ T cells Since B7-2VIg binds with higher affinity to CD28 than B7-2Ig, it was next investigated whether B7-2VIg fusion protein is also more potent at stimulating T cell proliferation than B7-2Ig fusion protein.

CD28+ T cells were isolated from peripheral blood leukocytes (PBLs) as described above. For measuring T cell proliferation, $1.2 \times 10^5$ CD28+ T cells were incubated in 200 µl of culture media in 96 well plates and stimulated with PMA at I ng/ml and either of the following costimulatory signals: $6 \times 10^4$ CHO/B7-1 or CHO/B7-2 cells (pretreated overnight with mitomycin C and then extensively washed), 30 or 100 µg/ml of B7-1Ig, B7-2Ig, or B7-2VIg. Alternatively, the fusion proteins can first be incubated with a 3 fold excess (w/w)of affinity purified goat anti-human IgGFc (Cappel) for 30 minutes prior to use. After 60 hours of incubation, the T cells were pulsed overnight with $^3$H-thymidine (Dupont/NEN) and harvested for counting, as described above.

Figure 23:
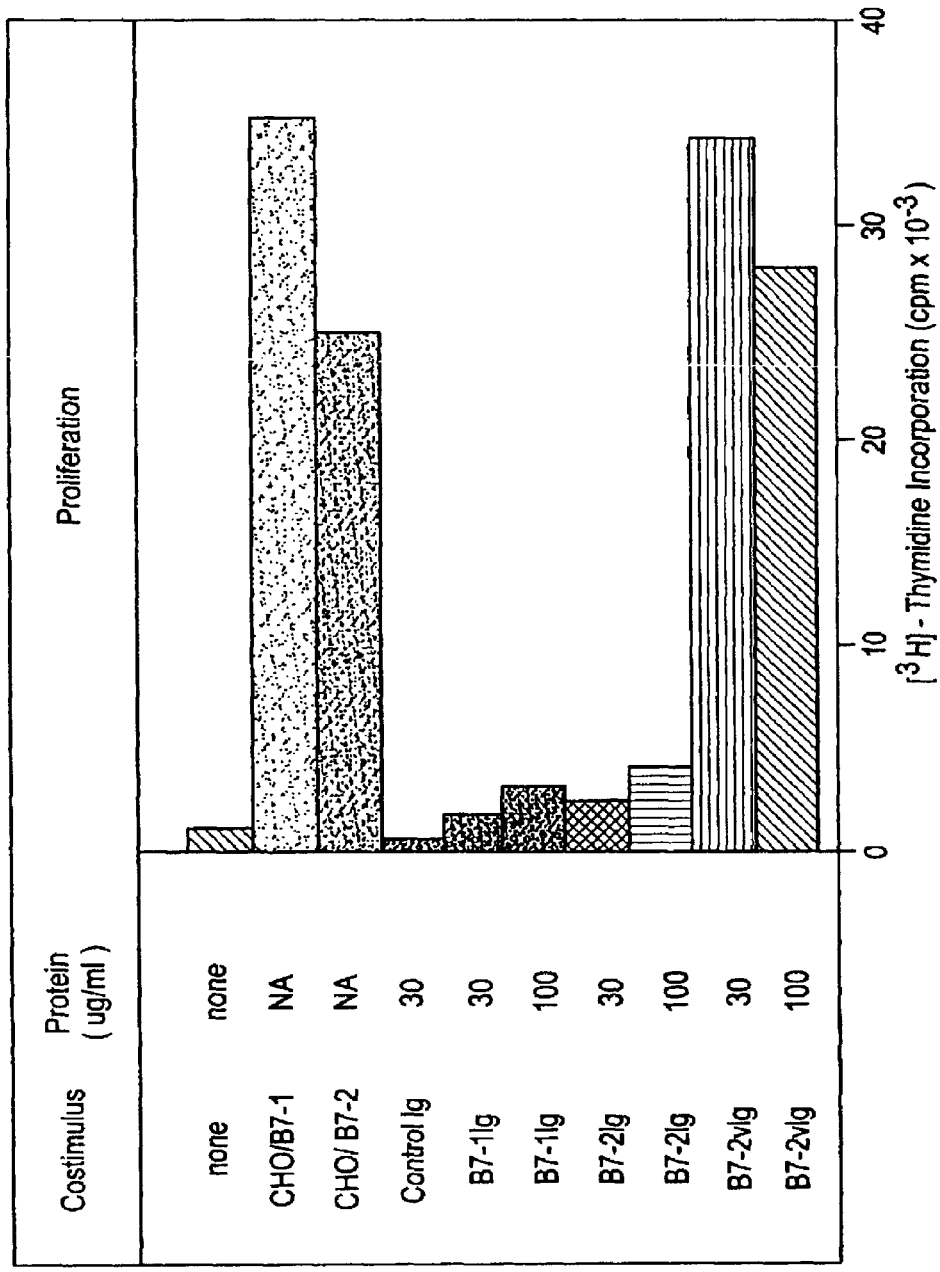
FIG. 23 represents a histogram showing proliferation of CD28+ T cells stimulated with 1 ng/ml PMA alone or with either of the following costimulatory signals: CHO/B7-1 cells, CHO/B7-2 cells, control Ig (30μg/ml), or B7-1Ig, B7-2Ig, or B7-2VIg (30μg or 100)μg/ml each).

The results of the proliferation assay are represented graphically in FIG. 23. The results indicate that CHO expressed B7-1 and B7-2 strongly induced T cell proliferation.

Purified B7-1Ig and B7-2Ig also induced proliferation, although not as potently as the CHO/B7-1 and CHO/B7-2 cells. However, B7-2VIg induced proliferation to the same extent as the CHO/B7-1 and CHO/B7-2 cells. Thus, B7-2VIg is as potent as CHO/B7-1 and CHO/B7-2 cells in costimulating proliferation of T cells.

It another example, CD28+ T cells were activated with anti-CD3 coated plates prepared as described above and costimulated with various amounts of B7-1Ig, B7-2Ig, and B7-2VIg. Proliferation of the CD28+ T cells was measured after 60 hours and overnight pulsing of the cells with $^3$H-thymidine. The results, presented graphically in FIG. 24 indicate that B7-2VIg fusion protein is also more potent than B7-2Ig and B7-1Ig at costimulating CD28+ T cells when anti-CD3 is used as the primary activating agent. Moreover, the results indicate that B7-2VIg is more potent than B7-2Ig and B7-1Ig at costimulating proliferation of CD28+ T cells when low concentrations of the proteins are used. This is apparent when comparing the amount of thymidine incorporated in cells incubated with 1 µg/ml of costimulatory fusion protein. In addition, B7-2VIg costimulates proliferation of the T cells at doses as low as 10 ng/ml (250 pM).

Thus, the higher binding affinity of B7-2VIg versus B7-2Ig fusion protein for CD28 (Example7, section 1) correlates with a higher costimulatory activity of B7-2VIg versus B7-2Ig for proliferation of the T cells.

K. B7-2VIg is more potent than B7-1Ig and B7-2Ig at costimulating production of IL-2 by CD28+ T cells It was next investigated whether B7-2VIg was also more potent than B7-1Ig and B7-2Ig at costimulating activated T cells for the production of IL-2.

In the second example described in the previous section (Section J. of Example 7), in which CD28+ T cells were activated with anti-CD3 and costimulated with various amounts of B7-1Ig, B7-2Ig, and B7-2VIg, and cell proliferation measured, the level of IL-2 in the supernatant was determined after 18 hours of stimulation using an ELISA kit (Endogen, Cambridge, Mass.). The results, presented in FIG. 24 show that more IL-2 is produced: by T cells costimulated with B7-2VIg than by T cells costimulated with B7-1Ig or B7-2Ig. This was most apparent at low concentrations of costimulatory proteins (for example at 1 µg/ml of the fusion proteins).

Figure 25:
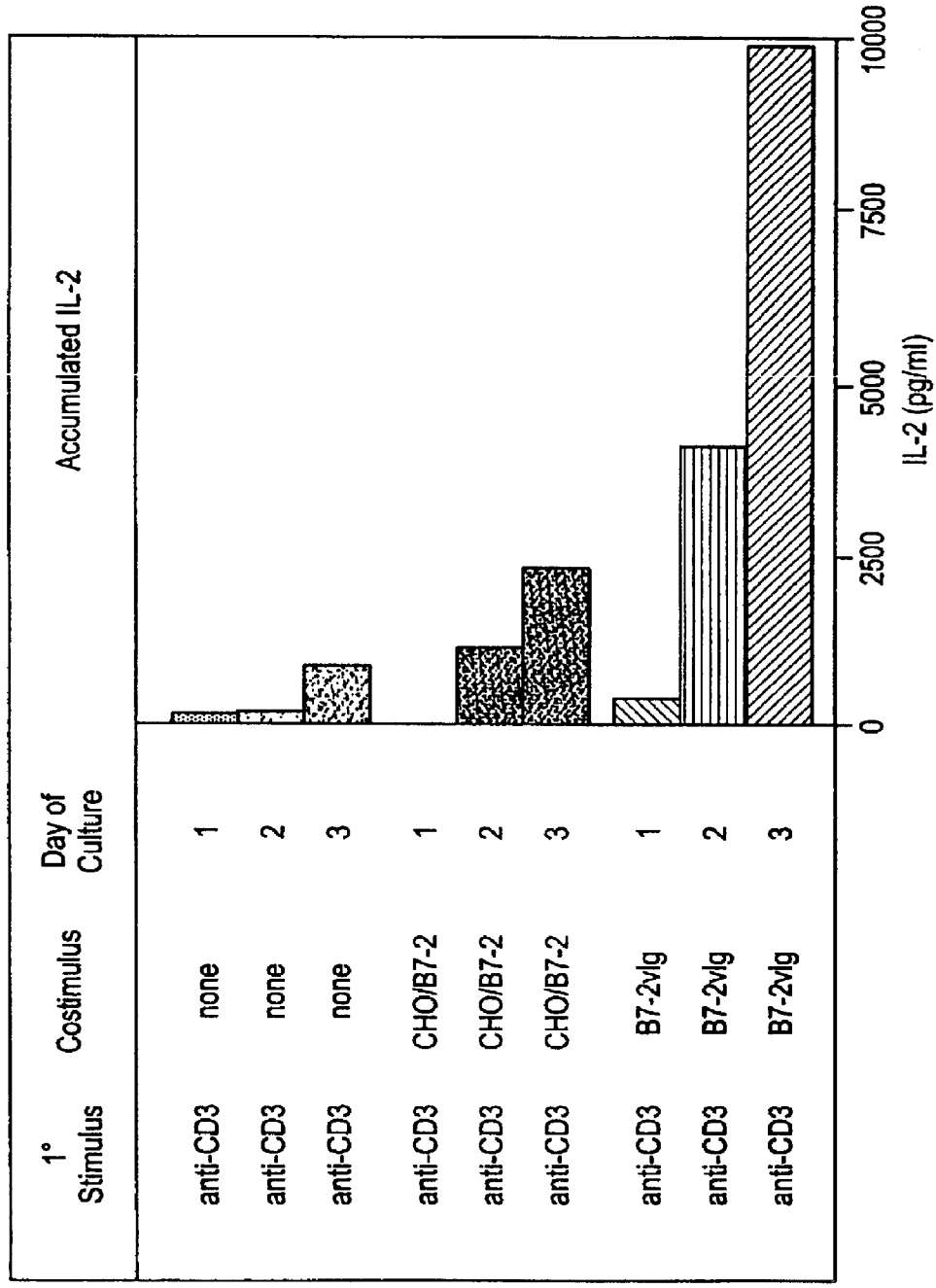
FIG. 25 represents the amount of IL-2 produced by CD28+ T cells after 1, 2, or 3 days of incubation of the cells with anti-CD3 alone or together with either CHO/B7-2 cells or B7-2VIg fusion protein.

Another example was performed to compare production of IL-2 from CD28+ T cells costimulated with CHO/B7-2 cells or costimulated with B7-2VIg protein. CD28+ T cells were incubated in anti-CD3 coated plates in the presence of CHO/B7-2 cells or B7-2VIg protein for 1, 2, or 3 days, and the amount of IL-2 was measured in the supernatant. The results, presented in FIG. 25, show that B7-2VIg is more potent at costimulating T cells for the production of IL-2 than CHO/B7-2 cells.

Figure 26:
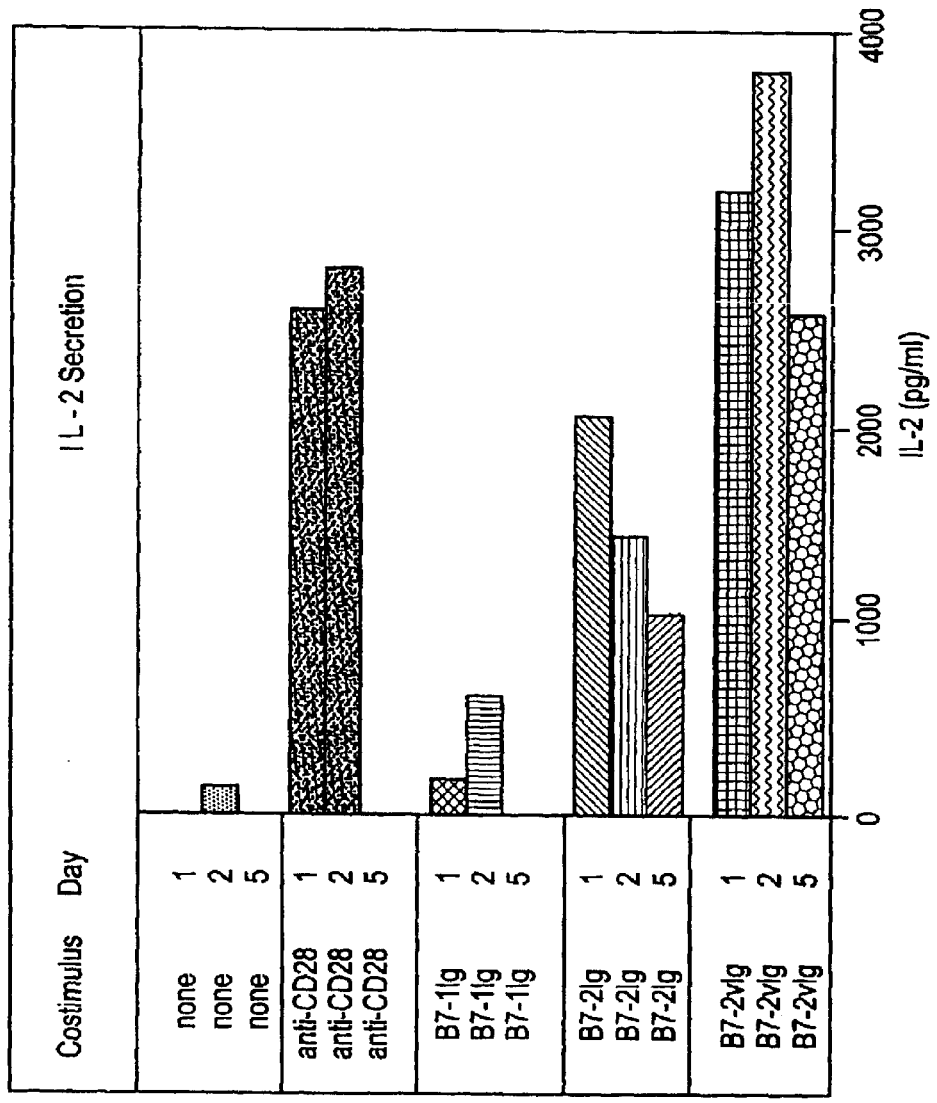
FIG. 26 represents the amount of IL-2 secreted by CD28+ T cells after 1, 2, or 5 days of incubation of the cells with anti-CD3 alone or with either anti-CD28, B7-1Ig, B7-2Ig, or B7-2VIg.

In a further example, the amount of IL-2 produced by CD28+ T cells costimulated with anti-CD28, B7-1Ig, B7-2Ig, or B7-2VIg was compared after 1, 2, or 5 days of costimulation. CD28+ T cells were activated and costimulated with anti-CD28 antibody, or with B7-1Ig, B7-2Ig, or B7-2VIg fusion protein. The amount of IL-2 in the supernatant was measured after 1, 2, and 5 days of costimulation. FIG. 26, representing graphically the amount of IL-2 produced by the T cells, indicate that B7-2IVIg is more potent than B7-2Ig and B7-1Ig at stimulating production of IL-2 by CD28+ T cells and further, that after 5 days of culture, only T cells costimulated with B7-2Ig or B7-2VIg fusion proteins were producing IL-2. Moreover, T cells costimulated with B7-2VIg produce more IL-2 than T cells costimulated with B7-2Ig after 5 days of culture.

Thus, B7-2VIg costimulate T cells to produce high levels of IL-2, even after at least 5 days of culture.

L. B7-2VIg is a potent costimulator of activated CD4+ T cells for the production of cytokines.

In this example, the amount of IL-2, IL-4, IFN-γ, and GM-CSF produced by T cells costimulated with B7-2VIg, B7-2Ig, or B7-1Ig was compared.

CD4+CD28-+ T cells were cultured at $2\times10^6$ cells/ml in T75 flasks coated with anti-CD3 antibody alone, or with anti-CD28 mAb 9.3, or one of the fusion proteins B7-1Ig, B7-2Ig, or B7-2VIg. After 18 hours of culture, the amount of IL-2, IL-4, interferon-γ (IFN-γ), and granulocyte macrophage-colony stimulating factor (GM-CSF) was measured by ELISA using commercially available kits (IL-2 (BioSource, Camarillo, Calif.), IL-4 (Endogen, Cambridge, Mass.), IFN-γ (Bio-Source, Camarillo, Calif.), and GM-CSF (R&D Systems, Minneapolis, Min.)). The amount of IL-2 and IL4 was also measured in cell costimulated for 120 hours.

The results are presented in Table VI. The results indicate that costimulation with B7-2VIg leads to production of high levels of IL-2, IL4, IFN-γ, and. GM-CSF. Moreover, the amount of all 4 cytokines produced from T cells costimulated with B7-2VIg was higher than the amount of cytokines produced from T cells costimulated with B7-1Ig. Compared to B7-2Ig, B7-2VIg also costimulated the production of higher amounts of IL-2, IL4 and GM-CSF and similar amounts of IFN-γ. Thus, B7-2VIg is a potent costimulator for production of cytokines by T cells.

Moreover, after 120 hours of culture, the T cells costimulated with B7-2VIg produced more than twice the amount of IL-4 produced by T cells costimulated with B7-2Ig and approximately 8 fold the amount of IL4 produced by T cells costimulated with B7-1Ig. Thus, T cells costimulated with B7-2VIg fusion protein induces production of high levels of IL-4 and this production is longlasting. Costimulation of T cells with B7-2VIg could thus drive T cells to a T helper 2 (Th2) state in long term culture.

TABLE VI

Cytokine production by CD4 + CD28 + T cells costimulated with
B7-2VIg, B7-2Ig, B7-1Ig or anti-CD28 antibody

| costimulus | IL-2 18 hr | IL-2 120 hr | IL-4 18 hr | IL-4 120 hr | IFN-g 18 hr | GM-CSF 18 hr |
|---|---|---|---|---|---|---|
| none | 19 | 0 | 6.5 | 0 | 27.6 | 0 |
| anti-CD28 | 2412 | N.D. | 83.2 | 0 | 28 | 25 |
| B7-1Ig | 734 | 0 | 10.4 | 5.7 | 27.8 | 10 |
| B7-2Ig | 1557 | 104 | 10.8 | 18.6 | 42.6 | 12 |
| B7-2vIg | 3073 | 262 | 29.8 | 40.8 | 37.5 | 30 |

M. B7-2Ig and B7-2VIg, but not B7-1Ig promote sustained T cell growth.

In this example, the capability of B7Ig fusion proteins to promote growth of T cells for extended periods was analyzed.

Figure 27:
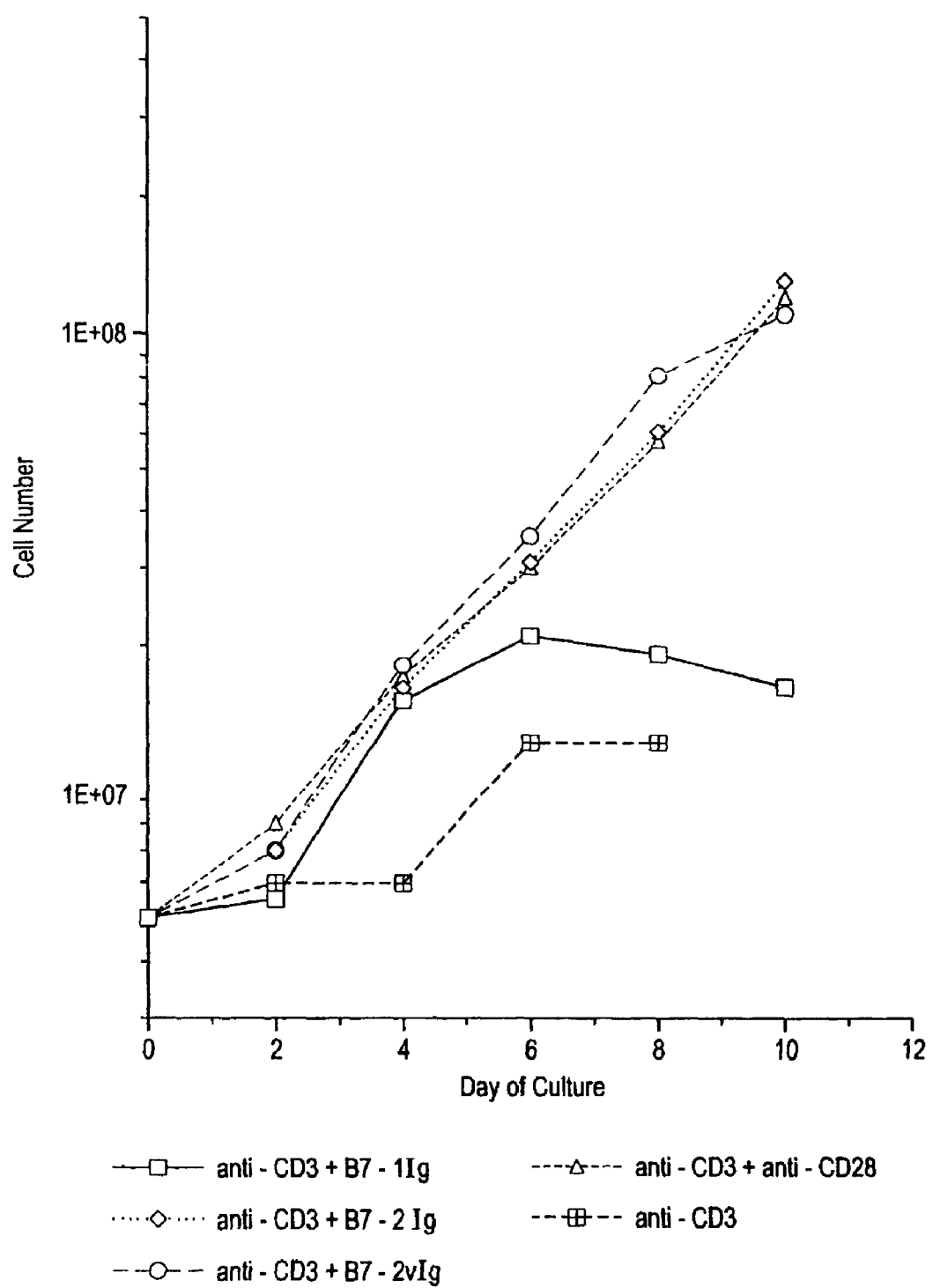
FIG. 27 is a graphical representation of the growth of CD28+ T cells incubated with anti-CD3 alone, or with B7-1Ig, B7-2Ig, B7-2VIg, or together with either anti-CD28.

CD28+ T lymphocytes were incubated in the presence of anti-CD3 plus anti-CD28, or B7-1Ig, B7-2Ig, or B7-2VIg immobilized on beads and the total cell numbers monitored over a period of 12 days. The results are presented in FIG. 27. Cells stimulated with anti-CD3 alone fail to proliferate, and die. Cells stimulated with anti-CD3 plus B7-2Ig go through one cycle of replication and then apoptose. Cells stimulated with anti-CD3 plus anti-CD28 or B7-2Ig or B7-2vIg continue to replicate. Thus, B7-2Ig and B7-2VIg fusion proteins, but not B7-1Ig, are capable of stimulating prolonged growth of CD28+ T cells.

EXAMPLE 8

Production and Characterization of Monoclonal Antibodies to Human B7-2

A. Immunizations and Cell Fusions

Balb/c female mice (obtained from Taconic Labs, Germantown, N.Y.) were immunized intraperitoneally with 50 μg human B7.2-Ig emulsified in complete Freund's adjuvant (Sigma Chemical Co., St. Louis, Mo.) or $10^6$ CHO-human B7.2 cells per mouse. The mice were given two booster immunizations with 10–25 μg human B7.2-Ig emulsified in incomplete Freund's adjuvant (Sigma Chemical Co., St. Louis, Mo.) or CHO-human B7.2 cells at fourteen day intervals following the initial immunization for the next two months. The mice were bled by retroorbital bleed and the sera assayed for the presence of antibodies reactive to the immunuogen by ELISA against human B7.2-Ig. ELISA against hCTLA4-Ig was also used to control for Ig tail directed antibody responses. Mice showing a strong serological response were boosted intravenously via the tail vein with 25 μg human hB7.2-Ig diluted in phosphate-buffered saline (PBS), pH 7.2 (GIBCO, Grand Island, N.Y.). Three to four days following this boost, the spleens from these mice were fused 5:1 with SP 2/0 myeloma cells (American Type Culture Collection, Rockville, Md., No. CRL8006), which are incapable of secreting both heavy and light immunoglobulin chains (Kearney et al. (1979) *J. Immunol.* 123:1548). Standard methods based upon those developed by Kohler and Milstein (*Nature* (1975) 256:495) were used.

B. Antibody Screening

After 10–21 days, supernatants from wells containing hybridoma colonies from the fusion were screened for the presence of antibodies reactive to human B7.2 as follows: Each well of a 96 well flat bottomed plate (Costar Corp., Cat. #3590) was coated with 50 μl per well of a 1 μg/ml human B7.2-Ig solution or $5\times10^4$ 3T3-hB7.2 cells on lysine coated plates in phosphate-buffered saline, pH 7.2, overnight at 4° C. The human B7.2-Ig solution was aspirated off, or the cells were cross-linked to the plates with glutaraldehyde, and the wells were washed three times with PBS, then blocked with 1% BSA solution (in PBS) (100 μl/well) for one hour at room temperature. Following this blocking incubation, the wells were washed three times with PBS and 50 μl of hybridoma supernatant was added per well and incubated for 1.5 hours at room temperature. Following this incubation, the wells were washed three times with PBS and then incubated for 1.5 hours at room temperature with 50 μl per well of a 1:4000 dilution of horseradish peroxidase-conjugated, affinity purified, goat anti-mouse IgG or IgM heavy and light chain-specific antibodies (HRP; Zymed Laboratories, San Francisco, Calif.). The wells were then washed three times with PBS, followed by a 30 minute incubation in 50 μl per well of 1 mM 2,2-azino-bis-3-ethylbenzthiazoline-6-sulfonic acid (ABTS) in 0.1 M Na-Citrate, pH 4.2 to which a 1:1000 dilution of 30% hydrogen peroxide had been added as a substrate for HRP to detect bound antibody. The absorbance was then determined at $OD_{410}$ on a spectrophotometric autoreader (Dynatech, Virginia).

Three hybridomas, HA3.1F9, HA5.2B7 and HF2.3D1, were identified that produced antibodies to human B7.2-Ig. HA3.1F9 was determined to be of the IgG1 isotype, HA5.2B7 was determined to be of the IgG2b isotype and HF2.3D1 as determined to be of the IgG2a isotype. Each of these hybridomas were subcloned two additional times to insure that they were monoclonal. Hybridoma cells were deposited with the American Type Culture Collection, which meets the requirements of the Budapest Treaty, on Jul. 19, 1994 as ATCC Accession No. HB11688 (hybridoma HA3.1F9), ATCC Accession HB11687 (HA5.2B7) and ATCC Accession HB11686 (HF2.3D1).

C. Competitive ELISA

Supernatants from the hybridomas HA3.1F9, HA5.2B7 and HF2.3D1 were further characterized by competitive ELISA, in which the ability of the monoclonal antibodies to inhibit the binding of biotinylated hCTLA4Ig to immobilized hB7-2 immunoglobulin fusion proteins was examined. Biotinylation of hCTLA4Ig was performed using Pierce Immunopure NHS-LC Biotin (Cat. No. 21335). B7-2 immunoglobulin fusion proteins used were: hB7.2-Ig (full-length hB7-2), hB7.2-VIg (hB7-2 variable domain only) and hB7.2-CIg (B7-2 constant domain only). A hB7.1-Ig fusion protein was used as a control. For the ELISA, 96 well plates were coated with the Ig fusion protein (50 µl/well of a 20 µg/ml solution) overnight at room temperature. The wells were washed three times with PBS, blocked with 10% fetal bovine serum (FBS), 0.1% bovine serum albumin (BSA) in PBS for 1 hour at room temperature, and washed again three times with PBS. To each well was added 50 pi of Bio-hCTLA4-Ig (70 ng/ml) and 50 µl of competitor monoclonal antibody supernatant. Control antibodies were an anti-B7.1 mAb (EW3.5D12) and the anti-hB7-2 mAb B70 (IgG2bκ, obtained from Pharmingen). The wells were washed again and streptavidin-conjugated horse radish peroxidase (from Pierce, Cat. No. 21126; 1:2000 dilution, 50 µl/well) was added and incubated for 30 minutes at room temperature. The wells were washed again, followed by a 30 minute incubation in 50 µl per well of ABTS in 0.1 M Na-Citrate, pH 4.2 to which a 1:1000 dilution of 30% hydrogen peroxide had been added as a substrate for HRP to detect bound antibody. The absorbance was then determined at $OD_{410}$ on a spectrophotometric autoreader (Dynatech, Virginia). The results, shown in Table IV below, demonstrate that each of the mAbs produced by the hybridomas HA3.1F9, HA5.2B7 and HF2.3D1 are able to competitively inhibit the binding of hCLTA4Ig to full-length hB7.2-Ig or hB7.2-VIg (hCTLA4Ig does not bind to hB7.2CIg).

TABLE IV

| | Blocking of Binding | | | |
|---|---|---|---|---|
| | hB7.1-Ig | hB7.2-Ig | hB7.2-VIg | hB7.2-CIg |
| EW3.5D12 (anti-hB7.1 mAb) | Yes | No | No | No |
| B70 (anti-hB7-2) | No | Yes | Yes | No |
| HA3.1F9 (anti-hB7-2) | No | Yes | Yes | No |
| HA5.2B7 (anti-hB7-2) | No | Yes | Yes | No |
| HF2.3D1 (anti-hB7-2) | No | Yes | Yes | No |

D. Flow Cytometry

Supernatants from the hybridomas HA3.1F9, HA5.2B7 and HF2.3D1 were also characterized by flow cytometry. Supernatants collected from the clones were screened by flow cytometry on CHO and 3T3 cells transfected to express hB7.2 (CHO-hB7.2 and 3T3-hB7.2, respectively) or control transfected 3T3 cells (3T3-Neo). Flow cytometry was performed as follows: $1 \times 10^6$ cells were washed three times in 1% BSA in PBS, then the cells were incubated in 50 µl hybridoma supernatant or culture media per $1 \times 10^6$ cells for 30 minutes at 4° C. Following the incubation, the cells were washed three times with 1% BSA in PBS, then incubated in 50 µl fluorescein-conjugated goat anti-mouse IgG or IgM antibodies (Zymed Laboratories, San Francisco, Calif.) at 1:50 dilution per $1 \times 10^6$ cells for 30 minutes at 4° C. The cells were then washed three times in 1% BSA in PBS and fixed with 1% paraformaldehyde solution. The cell samples were then analyzed on a FACScan flow cytometer (Becton Dickinson, San Jose Calif.). The results, shown in FIGS. 17, 18 and 19, demonstrate the monoclonal antibodies produced by the hybridomas HA3.1F9, HA5.2B7 and HF2.3D1 each bind to hB7-2 on the surface of cells.

E. Inhibition of Proliferation of Human T Cells by Anti-hB7-2 mAbs

Hybridoma supernatants containing anti-human B7-2 mAbs were tested for their ability to inhibit hB7-2 costimulation of human T cells. In this assay, purified $CD28^+$ human T cells were treated with submitogenic amounts of PMA (1 ng/ml) to deliver the primary signal and with CHO cells expressing hB7-2 on their surface to deliver the costimulatory signal. Proliferation of the T cells was measured after three days in culture by the addition of $^3H$-thymidine for the remaining 18 hours. As shown in Table V, resting T cells show little proliferation as measured by $^3H$-thymidine incorporation (510 pm). Delivery of signal 1 by PMA results in some proliferation (3800 pm) and T cells receiving both the primary (PMA) and costimulatory (CHO/hB7-2) signals proliferate maximally (9020 cpm). All three anti-hB7-2 mAbs tested reduce the costimulatory signal induced proliferation to that found for PMA treated cells alone showing that these mAbs can inhibit T cell proliferation by blocking the B7/CD28 costimulatory pathway.

TABLE V

| Addition to $CD28^+$ T Cells | hB7-2 mAb | CPM |
|---|---|---|
| — | — | 510 |
| +PMA | — | 3800 |
| +PMA + CHO/hB7-2 | — | 9020 |
| +PMA + CHO/hB7-2 | HF2.301 | 3030 |
| — | HA5.2B7 | 1460 |
| — | RA3.1F9 | 2980 |

F. Antibodies to the B7-2 Variable domain block B7-2 function

In this example, the ability of a series of monoclonal antibodies to B7-2 to bind to the Ig-variable or Ig-constant domains of B7-2, an to inhibit T cell proliferation was analyzed.

Monoclonal antibodies to human B7-1 and B7-2 were prepared from Balb/c mice using SP2/0 cells and standard protocols. Briefly, Balb/c female mice (Taconic Labs, Germantown, N.Y.) were immunized intraperitoneally with either 50 µgs B7-2Ig emulsified in CFA (Sigma, St. Louis, Mo.) or $10^6$ CHO/B7-2 cells. The mice were boosted twice at 14 day intervals following the initial immunization and once with B7-2Ig protein in PBS. Hybridoma colonies were established in 96 well tissue culture plates and the culture supernatants were assayed for direct binding to B7-2Ig. All mAbs were purified from ascites fluid on Protein-A sepharose as described above. MAb B70 was purchased from PharMingen (San Diego, Calif.).

Purified mAbs were tested for their ability to bind to the various B7-Ig forms as follows. Maxisorp plates (Nunc) were coated overnight at room temperature with 20 µg/ml of purified B7-2Ig protein in PBS. The plates were then blocked with PBS/0.1% BSA for 1 h. Purified antibody (5 µgs/ml in PBS) was added to the test wells, the plates incubated for I hour, and then washed 5 times with PBS/0.05% Tween20. Goat anti-mouse IgG-HRP (Zymed) was added and allowed to react for 1 hour, followed by 5 washes. The plates were developed as described above.

The binding characteristics of the antibodies is indicated in Table VII under the heading "Recognition". As indicated in Table VII, all antibodies recognized B7-2Ig. Binding of the antibodies to B7-2VIg and B7-2CIg fusion proteins indicated that the antibodies recognize either the variable region construct or the constant region construct, but not both constructs.

The antibodies were further analyzed for their ability to inhibit binding of B7-2Ig to CTLA4 and to CD28 and to inhibit T cell proliferation. Using a competition ELISA format, varying amounts of mAbs were added to wells coated B7-2Ig and containing 35 ngs/ml biotinylated CTLA4Ig or CD28Ig. The ability of mAbs to disrupt the binding was measured as a decrease in the specific signal of captured biotinylated CTLA4Ig or CD28Ig. The capability of the antibodies to inhibit proliferation of T cells was determined by performing proliferation assays, as described above in which one of the antibodies was added.

The results are presented in Table VII under the heading "Inhibition". In general, antibodies to the V-domain of B7-2 inhibit binding of the B7-2Ig to CD28 and CTLA4 and also inhibit CHO/B7-2 driven T cell proliferation. Antibodies to the C-domain are not inhibitory suggesting that the functionality of B7-2 resides in the V-domain.

TABLE VII

Characterization of anti-B7-2 antibodies

| Anti-B7-2 mAbs | | B7 | Recognition B7v domain | B7c domain | Inhibition CTLA4 binding | CD28 binding | T cell prolif. |
|---|---|---|---|---|---|---|---|
| HA5.1F9 | IgG1 | + | − | − | + | + | + |
| HA5.2B7 | IgG2b | + | + | − | + | + | + |
| HF2.3D11 | IgG2a | + | + | − | + | + | + |
| HF4.3C11 | IgG1 | + | + | − | + | + | + |
| HF4.3E8 | IgG1 | + | + | − | + | +/− | +/− |
| HF4.5B4 | IgG1 | + | − | + | nd | − | − |
| HF4.5H12 | IgM | + | − | + | − | − | − |
| HF4.6B1 | IgG2a | + | − | + | − | − | − |
| HF4.6H4 | IgG1 | + | + | − | + | + | + |
| B70 | IgG2b | + | + | − | + | + | + |

Moreover, all of the anti-B7-1 and anti-B7-2 mAbs tested also recognized their respective ligand when expressed on the surface of CHO cells and on the surface of activated human B cells where tested. None of the anti-B7-1 or anti-B7-2 mAbs showed any crossreactivity with the other B7 protein.

Equivalent

Those skilled in the art will recognize, or be able to ascertain using no more than routine experimentation, many equivalents to the specific embodiments of the invention described herein. Such equivalents are intended to be encompassed by the following claims.

SEQUENCE LISTING (1) GENERAL INFORMATION:

(iii) NUMBER OF SEQUENCES: 55

(2) INFORMATION FOR SEQ ID NO:1:

(i) SEQUENCE CHARACTERISTICS:
      (A) LENGTH: 1120 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 107..1093

(xi) SEQUENCE DESCRIPTION: SEQ ID NO:1:

```
CACAGGGTGA AAGCTTTGCT TCTCTGCTGC TGTAACAGGG ACTAGCACAG ACACACGGAT        60

GAGTGGGGTC ATTTCCAGAT ATTAGGTCAC AGCAGAAGCA GCCAAA ATG GAT CCC          115
                                                Met Asp Pro
                                                  1

CAG TGC ACT ATG GGA CTG AGT AAC ATT CTC TTT GTG ATG GCC TTC CTG         163
Gln Cys Thr Met Gly Leu Ser Asn Ile Leu Phe Val Met Ala Phe Leu
      5                  10                  15

CTC TCT GGT GCT GCT CCT CTG AAG ATT CAA GCT TAT TTC AAT GAG ACT         211
Leu Ser Gly Ala Ala Pro Leu Lys Ile Gln Ala Tyr Phe Asn Glu Thr
 20                  25                  30                  35

GCA GAC CTG CCA TGC CAA TTT GCA AAC TCT CAA AAC CAA AGC CTG AGT         259
Ala Asp Leu Pro Cys Gln Phe Ala Asn Ser Gln Asn Gln Ser Leu Ser
```

-continued

```
             40                    45                    50
GAG CTA GTA GTA TTT TGG CAG GAC CAG GAA AAC TTG GTT CTG AAT GAG       307
Glu Leu Val Val Phe Trp Gln Asp Gln Glu Asn Leu Val Leu Asn Glu
             55                    60                    65

GTA TAC TTA GGC AAA GAG AAA TTT GAC AGT GTT CAT TCC AAG TAT ATG       355
Val Tyr Leu Gly Lys Glu Lys Phe Asp Ser Val His Ser Lys Tyr Met
             70                    75                    80

GGC CGC ACA AGT TTT GAT TCG GAC AGT TGG ACC CTG AGA CTT CAC AAT       403
Gly Arg Thr Ser Phe Asp Ser Asp Ser Trp Thr Leu Arg Leu His Asn
         85                    90                    95

CTT CAG ATC AAG GAC AAG GGC TTG TAT CAA TGT ATC ATC CAT CAC AAA       451
Leu Gln Ile Lys Asp Lys Gly Leu Tyr Gln Cys Ile Ile His His Lys
100                   105                   110                115

AAG CCC ACA GGA ATG ATT CGC ATC CAC CAG ATG AAT TCT GAA CTG TCA       499
Lys Pro Thr Gly Met Ile Arg Ile His Gln Met Asn Ser Glu Leu Ser
                 120                   125                   130

GTG CTT GCT AAC TTC AGT CAA CCT GAA ATA GTA CCA ATT TCT AAT ATA       547
Val Leu Ala Asn Phe Ser Gln Pro Glu Ile Val Pro Ile Ser Asn Ile
                 135                   140                   145

ACA GAA AAT GTG TAC ATA AAT TTG ACC TGC TCA TCT ATA CAC GGT TAC       595
Thr Glu Asn Val Tyr Ile Asn Leu Thr Cys Ser Ser Ile His Gly Tyr
                 150                   155                   160

CCA GAA CCT AAG AAG ATG AGT GTT TTG CTA AGA ACC AAG AAT TCA ACT       643
Pro Glu Pro Lys Lys Met Ser Val Leu Leu Arg Thr Lys Asn Ser Thr
165                   170                   175

ATC GAG TAT GAT GGT ATT ATG CAG AAA TCT CAA GAT AAT GTC ACA GAA       691
Ile Glu Tyr Asp Gly Ile Met Gln Lys Ser Gln Asp Asn Val Thr Glu
180                   185                   190                195

CTG TAC GAC GTT TCC ATC AGC TTG TCT GTT TCA TTC CCT GAT GTT ACG       739
Leu Tyr Asp Val Ser Ile Ser Leu Ser Val Ser Phe Pro Asp Val Thr
                 200                   205                   210

AGC AAT ATG ACC ATC TTC TGT ATT CTG GAA ACT GAC AAG ACG CGG CTT       787
Ser Asn Met Thr Ile Phe Cys Ile Leu Glu Thr Asp Lys Thr Arg Leu
                 215                   220                   225

TTA TCT TCA CCT TTC TCT ATA GAG CTT GAG GAC CCT CAG CCT CCC CCA       835
Leu Ser Ser Pro Phe Ser Ile Glu Leu Glu Asp Pro Gln Pro Pro Pro
                 230                   235                   240

GAC CAC ATT CCT TGG ATT ACA GCT GTA CTT CCA ACA GTT ATT ATA TGT       883
Asp His Ile Pro Trp Ile Thr Ala Val Leu Pro Thr Val Ile Ile Cys
245                   250                   255

GTG ATG GTT TTC TGT CTA ATT CTA TGG AAA TGG AAG AAG AAG CGG           931
Val Met Val Phe Cys Leu Ile Leu Trp Lys Trp Lys Lys Lys Arg
260                   265                   270                275

CCT CGC AAC TCT TAT AAA TGT GGA ACC AAC ACA ATG GAG AGG GAA GAG       979
Pro Arg Asn Ser Tyr Lys Cys Gly Thr Asn Thr Met Glu Arg Glu Glu
                 280                   285                   290

AGT GAA CAG ACC AAG AAA AGA GAA AAA ATC CAT ATA CCT GAA AGA TCT      1027
Ser Glu Gln Thr Lys Lys Arg Glu Lys Ile His Ile Pro Glu Arg Ser
                 295                   300                   305

GAT GAA GCC CAG CGT GTT TTT AAA AGT TCG AAG ACA TCT TCA TGC GAC      1075
Asp Glu Ala Gln Arg Val Phe Lys Ser Ser Lys Thr Ser Ser Cys Asp
                 310                   315                   320

AAA AGT GAT ACA TGT TTT TAATTAAAGA GTAAAGCCCA AAAAAA                 1120
Lys Ser Asp Thr Cys Phe
325
```

(2) INFORMATION FOR SEQ ID NO:2:

(i) SEQUENCE CHARACTERISTICS:
        (A) LENGTH: 329 amino acids

-continued

```
            (B) TYPE: amino acid
            (D) TOPOLOGY: linear (ii) MOLECULE TYPE: protein (xi) SEQUENCE DESCRIPTION: SEQ ID NO:2:

Met Asp Pro Gln Cys Thr Met Gly Leu Ser Asn Ile Leu Phe Val Met
 1               5                  10                  15

Ala Phe Leu Leu Ser Gly Ala Ala Pro Leu Lys Ile Gln Ala Tyr Phe
                20                  25                  30

Asn Glu Thr Ala Asp Leu Pro Cys Gln Phe Ala Asn Ser Gln Asn Gln
            35                  40                  45

Ser Leu Ser Glu Leu Val Val Phe Trp Gln Asp Gln Glu Asn Leu Val
        50                  55                  60

Leu Asn Glu Val Tyr Leu Gly Lys Glu Lys Phe Asp Ser Val His Ser
 65                  70                  75                  80

Lys Tyr Met Gly Arg Thr Ser Phe Asp Ser Asp Ser Trp Thr Leu Arg
                85                  90                  95

Leu His Asn Leu Gln Ile Lys Asp Lys Gly Leu Tyr Gln Cys Ile Ile
            100                 105                 110

His His Lys Lys Pro Thr Gly Met Ile Arg Ile His Gln Met Asn Ser
        115                 120                 125

Glu Leu Ser Val Leu Ala Asn Phe Ser Gln Pro Glu Ile Val Pro Ile
        130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
                165                 170                 175

Asn Ser Thr Ile Glu Tyr Asp Gly Ile Met Gln Lys Ser Gln Asp Asn
            180                 185                 190

Val Thr Glu Leu Tyr Asp Val Ser Ile Ser Leu Ser Val Ser Phe Pro
        195                 200                 205

Asp Val Thr Ser Asn Met Thr Ile Phe Cys Ile Leu Glu Thr Asp Lys
    210                 215                 220

Thr Arg Leu Leu Ser Ser Pro Phe Ser Ile Glu Leu Glu Asp Pro Gln
225                 230                 235                 240

Pro Pro Pro Asp His Ile Pro Trp Ile Thr Ala Val Leu Pro Thr Val
                245                 250                 255

Ile Ile Cys Val Met Val Phe Cys Leu Ile Leu Trp Lys Trp Lys Lys
            260                 265                 270

Lys Lys Arg Pro Arg Asn Ser Tyr Lys Cys Gly Thr Asn Thr Met Glu
        275                 280                 285

Arg Glu Glu Ser Glu Gln Thr Lys Lys Arg Glu Lys Ile His Ile Pro
    290                 295                 300

Glu Arg Ser Asp Glu Ala Gln Arg Val Phe Lys Ser Ser Lys Thr Ser
305                 310                 315                 320

Ser Cys Asp Lys Ser Asp Thr Cys Phe
                325

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(ii) MOLECULE TYPE: oligonucleotide (xi) SEQUENCE DESCRIPTION: SEQ ID NO:3:

TAATACGACT CACTATAGGG                                                    20

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:4:

TAAGGTTCCT TCACAAAG                                                      18

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:5:

ACTGGTAGGT ATGGAAGATC C                                                  21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:6:

ATGCGAATCA TTCCTGTGGG C                                                  21

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:7:

AAAGCCCACA GGAATGATTC G                                                  21

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:8:

```
CTCTCAAAAC CAAAGCCTGA G                                              21

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:9:

TTAGGTCACA GCAGAAGCAG C                                              21

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:10:

TCTGGAAACT GACAAGACGC G                                              21

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:11:

CTCAGGCTTT GGTTTTGAGA G                                              21

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:12:

CACTCTCTTC CCTCTCCATT G                                              21

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:13:

GACAAGCTGA TGGAAACGTC G                                              21

(2) INFORMATION FOR SEQ ID NO:14:
```

```
        (i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:14:

CAATGGAGAG GGAAGAGAGT G                                                  21

(2) INFORMATION FOR SEQ ID NO:15:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:15:

CTTTAGAGCA CA                                                            12

(2) INFORMATION FOR SEQ ID NO:16:

(i) SEQUENCE CHARACTERISTICS:
            (A) LENGTH: 8 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:16:

CTCTAAAG                                                                  8

(2) INFORMATION FOR SEQ ID NO:17:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (xi) SEQUENCE DESCRIPTION: SEQ ID NO:17:

Lys Tyr Met Gly Arg Thr Ser Phe Asp
                 5

(2) INFORMATION FOR SEQ ID NO:18:

(i) SEQUENCE CHARACTERISTICS:
            (A) LENGTH: 13 amino acids
            (B) TYPE: amino acid
            (D) TOPOLOGY: linear (ii) MOLECULE TYPE: peptide (xi) SEQUENCE DESCRIPTION: SEQ ID NO:18:

Lys Ser Gln Asp Asn Val Thr Glu Lys Tyr Asp Val Ser
                 5                  10

(2) INFORMATION FOR SEQ ID NO:19:

(i) SEQUENCE CHARACTERISTICS:
            (A) LENGTH: 15 amino acids
            (B) TYPE: amino acid
```

(D) TOPOLOGY: linear (ii) MOLECULE TYPE: peptide (xi) SEQUENCE DESCRIPTION: SEQ ID NO:19:

Trp Lys Trp Lys Lys Lys Lys Arg Pro Arg Asn Ser Tyr Lys Cys
              5                   10                  15

(2) INFORMATION FOR SEQ ID NO:20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:20:

TGGCCCATGG CTTCAGA                                                      17

(2) INFORMATION FOR SEQ ID NO:21:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:21:

GCCAAAATGG ATCCCCA                                                      17

(2) INFORMATION FOR SEQ ID NO:22:

(i) SEQUENCE CHARACTERISTICS:
        (A) LENGTH: 1163 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 111..1040

(xi) SEQUENCE DESCRIPTION: SEQ ID NO:22:

CCCACGCGTC CGGGAGCAAG CAGACGCGTA AGAGTGGCTC CTGTAGGCAG CACGGACTTG        60

AACAACCAGA CTCCTGTAGA CGTGTTCCAG AACTTACGGA AGCACCCACG ATG GAC         116
                                                        Met Asp
                                                          1

CCC AGA TGC ACC ATG GGC TTG GCA ATC CTT ATC TTT GTG ACA GTC TTG        164
Pro Arg Cys Thr Met Gly Leu Ala Ile Leu Ile Phe Val Thr Val Leu
        5                  10                  15

CTG ATC TCA GAT GCT GTT TCC GTG GAG ACG CAA GCT TAT TTC AAT GGG        212
Leu Ile Ser Asp Ala Val Ser Val Glu Thr Gln Ala Tyr Phe Asn Gly
     20                  25                  30

ACT GCA TAT CTG CCG TGC CCA TTT ACA AAG GCT CAA AAC ATA AGC CTG        260
Thr Ala Tyr Leu Pro Cys Pro Phe Thr Lys Ala Gln Asn Ile Ser Leu
 35                  40                  45                  50

AGT GAG CTG GTA GTA TTT TGG CAG GAC CAG CAA AAG TTG GTT CTG TAC        308
Ser Glu Leu Val Val Phe Trp Gln Asp Gln Gln Lys Leu Val Leu Tyr
             55                  60                  65

GAG CAC TAT TTG GGC ACA GAG AAA CTT GAT AGT GTG AAT GCC AAG TAC        356

```
                                                                                      -continued Glu His Tyr Leu Gly Thr Glu Lys Leu Asp Ser Val Asn Ala Lys Tyr
             70                  75                  80

CTG GGC CGC ACG AGC TTT GAC AGG AAC AAC TGG ACT CTA CGA CTT CAC        404
Leu Gly Arg Thr Ser Phe Asp Arg Asn Asn Trp Thr Leu Arg Leu His
             85                  90                  95

AAT GTT CAG ATC AAG GAC ATG GGC TCG TAT GAT TGT TTT ATA CAA AAA        452
Asn Val Gln Ile Lys Asp Met Gly Ser Tyr Asp Cys Phe Ile Gln Lys
        100                 105                 110

AAG CCA CCC ACA GGA TCA ATT ATC CTC CAA CAG ACA TTA ACA GAA CTG        500
Lys Pro Pro Thr Gly Ser Ile Ile Leu Gln Gln Thr Leu Thr Glu Leu
115                 120                 125                 130

TCA GTG ATC GCC AAC TTC AGT GAA CCT GAA ATA AAA CTG GCT CAG AAT        548
Ser Val Ile Ala Asn Phe Ser Glu Pro Glu Ile Lys Leu Ala Gln Asn
                135                 140                 145

GTA ACA GGA AAT TCT GGC ATA AAT TTG ACC TGC ACG TCT AAG CAA GGT        596
Val Thr Gly Asn Ser Gly Ile Asn Leu Thr Cys Thr Ser Lys Gln Gly
            150                 155                 160

CAC CCG AAA CCT AAG AAG ATG TAT TTT CTG ATA ACT AAT TCA ACT AAT        644
His Pro Lys Pro Lys Lys Met Tyr Phe Leu Ile Thr Asn Ser Thr Asn
        165                 170                 175

GAG TAT GGT GAT AAC ATG CAG ATA TCA CAA GAT AAT GTC ACA GAA CTG        692
Glu Tyr Gly Asp Asn Met Gln Ile Ser Gln Asp Asn Val Thr Glu Leu
    180                 185                 190

TTC AGT ATC TCC AAC AGC CTC TCT CTT TCA TTC CCG GAT GGT GTG TGG        740
Phe Ser Ile Ser Asn Ser Leu Ser Leu Ser Phe Pro Asp Gly Val Trp
195                 200                 205                 210

CAT ATG ACC GTT GTG TGT GTT CTG GAA ACG GAG TCA ATG AAG ATT TCC        788
His Met Thr Val Val Cys Val Leu Glu Thr Glu Ser Met Lys Ile Ser
                215                 220                 225

TCC AAA CCT CTC AAT TTC ACT CAA GAG TTT CCA TCT CCT CAA ACG TAT        836
Ser Lys Pro Leu Asn Phe Thr Gln Glu Phe Pro Ser Pro Gln Thr Tyr
            230                 235                 240

TGG AAG GAG ATT ACA GCT TCA GTT ACT GTG GCC CTC CTC CTT GTG ATG        884
Trp Lys Glu Ile Thr Ala Ser Val Thr Val Ala Leu Leu Leu Val Met
        245                 250                 255

CTG CTC ATC ATT GTA TGT CAC AAG AAG CCG AAT CAG CCT AGC AGG CCC        932
Leu Leu Ile Ile Val Cys His Lys Lys Pro Asn Gln Pro Ser Arg Pro
260                 265                 270

AGC AAC ACA GCC TCT AAG TTA GAG CGG GAT AGT AAC GCT GAC AGA GAG        980
Ser Asn Thr Ala Ser Lys Leu Glu Arg Asp Ser Asn Ala Asp Arg Glu
                275                 280                 285                 290

ACT ATC AAC CTG AAG GAA CTT GAA CCC CAA ATT GCT TCA GCA AAA CCA       1028
Thr Ile Asn Leu Lys Glu Leu Glu Pro Gln Ile Ala Ser Ala Lys Pro
            295                 300                 305

AAT GCA GAG TGAAGGCAGT GAGAGCCTGA GGAAAGAGTT AAAAATTGCT               1077
Asn Ala Glu

TTGCCTGAAA TAAGAAGTGC AGAGTTTCTC AGAATTCAAA AATGTTCTCA GCTGATTGGA     1137

ATTCTACAGT TGAATAATTA AAGAAC                                          1163

(2) INFORMATION FOR SEQ ID NO:23:

(i) SEQUENCE CHARACTERISTICS:
        (A) LENGTH: 309 amino acids
        (B) TYPE: amino acid
        (D) TOPOLOGY: linear (ii) MOLECULE TYPE: protein (xi) SEQUENCE DESCRIPTION: SEQ ID NO:23:

Met Asp Pro Arg Cys Thr Met Gly Leu Ala Ile Leu Ile Phe Val Thr
```

```
          1               5                 10                  15
        Val Leu Leu Ile Ser Asp Ala Val Ser Val Glu Thr Gln Ala Tyr Phe
                        20                  25                  30

Asn Gly Thr Ala Tyr Leu Pro Cys Pro Phe Thr Lys Ala Gln Asn Ile
                        35                  40                  45

Ser Leu Ser Glu Leu Val Val Phe Trp Gln Asp Gln Lys Leu Val
                50                  55                  60

Leu Tyr Glu His Tyr Leu Gly Thr Glu Lys Leu Asp Ser Val Asn Ala
        65                      70                  75                  80

Lys Tyr Leu Gly Arg Thr Ser Phe Asp Arg Asn Asn Trp Thr Leu Arg
                        85                  90                  95

Leu His Asn Val Gln Ile Lys Asp Met Gly Ser Tyr Asp Cys Phe Ile
                        100                 105                 110

Gln Lys Lys Pro Pro Thr Gly Ser Ile Ile Leu Gln Gln Thr Leu Thr
                        115                 120                 125

Glu Leu Ser Val Ile Ala Asn Phe Ser Glu Pro Glu Ile Lys Leu Ala
                130                 135                 140

Gln Asn Val Thr Gly Asn Ser Gly Ile Asn Leu Thr Cys Thr Ser Lys
        145                     150                 155                 160

Gln Gly His Pro Lys Pro Lys Lys Met Tyr Phe Leu Ile Thr Asn Ser
                        165                 170                 175

Thr Asn Glu Tyr Gly Asp Asn Met Gln Ile Ser Gln Asp Asn Val Thr
                        180                 185                 190

Glu Leu Phe Ser Ile Ser Asn Ser Leu Ser Leu Ser Phe Pro Asp Gly
                        195                 200                 205

Val Trp His Met Thr Val Val Cys Val Leu Glu Thr Glu Ser Met Lys
        210                     215                 220

Ile Ser Ser Lys Pro Leu Asn Phe Thr Gln Glu Phe Pro Ser Pro Gln
        225                     230                 235                 240

Thr Tyr Trp Lys Glu Ile Thr Ala Ser Val Thr Val Ala Leu Leu Leu
                        245                 250                 255

Val Met Leu Leu Ile Ile Val Cys His Lys Lys Pro Asn Gln Pro Ser
                        260                 265                 270

Arg Pro Ser Asn Thr Ala Ser Lys Leu Glu Arg Asp Ser Asn Ala Asp
                        275                 280                 285

Arg Glu Thr Ile Asn Leu Lys Glu Leu Glu Pro Gln Ile Ala Ser Ala
                        290                 295                 300

Lys Pro Asn Ala Glu
        305
```

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:24:

ACATAAGCCT GAGTGAGCTG G                                         21

(2) INFORMATION FOR SEQ ID NO:25:

(i) SEQUENCE CHARACTERISTICS:
        (A) LENGTH: 21 base pairs

```
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:25:

ATGATGAGCA GCATCACAAG G                                              21

(2) INFORMATION FOR SEQ ID NO:26:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:26:

TGGTCGAGTG AGTCCGAATA C                                              21

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:27:

GACGAGTAGT AACATACAGT G                                              21

(2) INFORMATION FOR SEQ ID NO:28:

(i) SEQUENCE CHARACTERISTICS:
        (A) LENGTH: 1491 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: no (iv) ANTI-SENSE: no (vi) ORIGINAL SOURCE:
        (A) ORGANISM: Homo sapien
        (F) TISSUE TYPE: lymphoid
        (G) CELL TYPE: B cell
        (H) CELL LINE: Raji (vii) IMMEDIATE SOURCE:
        (A) LIBRARY: cDNA in pCDM8 vector
        (B) CLONE: B7, Raji clone #13

(viii) POSITION IN GENOME:
        (A) CHROMOSOME/SEGMENT: 3

(ix) FEATURE:
        (A) NAME/KEY:  Open reading frame (translated region)
        (B) LOCATION:  318 to 1181 bp
        (C) IDENTIFICATION METHOD: similarity to other pattern (ix) FEATURE:
        (A) NAME/KEY:  Alternate polyadenylation signal
        (B) LOCATION:  1474 to 1479 bp
        (C) IDENTIFICATION METHOD: similarity to other pattern (x) PUBLICATION INFORMATION:
```

(A) AUTHORS: FREEMAN, GORDON J.
                         FREEDMAN, ARNOLD S.
                         SEGIL, JEFFREY M.
                         LEE, GRACE
                         WHITMAN, JAMES F.
                         NADLER, LEE M.
            (B) TITLE:   B7, A New Member Of The Ig Superfamily With
                         Unique Expression On Activated And Neoplastic B Cells
            (C) JOURNAL: The Journal of Immunology
            (D) VOLUME:  143
            (E) ISSUE:   8
            (F) PAGES:   2714-2722
            (G) DATE:    15-OCT-1989
            (H) RELEVANT RESIDUES IN SEQ ID NO:28: FROM 1 TO 1491

(xi) SEQUENCE DESCRIPTION: SEQ ID NO:28:

```
CCAAAGAAAA AGTGATTTGT CATTGCTTTA TAGACTGTAA GAAGAGAACA TCTCAGAAGT      60

GGAGTCTTAC CCTGAAATCA AAGGATTTAA AGAAAAAGTG GAATTTTTCT TCAGCAAGCT     120

GTGAAACTAA ATCCACAACC TTTGGAGACC CAGGAACACC CTCCAATCTC TGTGTGTTTT     180

GTAAACATCA CTGGAGGGTC TTCTACGTGA GCAATTGGAT TGTCATCAGC CCTGCCTGTT     240

TTGCACCTGG GAAGTGCCCT GGTCTTACTT GGGTCCAAAT TGTTGGCTTT CACTTTTGAC     300

CCTAAGCATC TGAAGCC ATG GGC CAC ACA CGG AGG CAG GGA ACA TCA CCA TCC    353
                   Met Gly His Thr Arg Arg Gln Gly Thr Ser Pro Ser
                                 -30                 -25

AAG TGT CCA TAC CTG AAT TTC TTT CAG CTC TTG GTG CTG GCT GGT CTT      401
Lys Cys Pro Tyr Leu Asn Phe Phe Gln Leu Leu Val Leu Ala Gly Leu
        -20                 -15                 -10

TCT CAC TTC TGT TCA GGT GTT ATC CAC GTG ACC AAG GAA GTG AAA GAA      449
Ser His Phe Cys Ser Gly Val Ile His Val Thr Lys Glu Val Lys Glu
         -5                      1               5               10

GTG GCA ACG CTG TCC TGT GGT CAC AAT GTT TCT GTT GAA GAG CTG GCA      497
Val Ala Thr Leu Ser Cys Gly His Asn Val Ser Val Glu Glu Leu Ala
                15                  20                  25

CAA ACT CGC ATC TAC TGG CAA AAG GAG AAG AAA ATG GTG CTG ACT ATG      545
Gln Thr Arg Ile Tyr Trp Gln Lys Glu Lys Lys Met Val Leu Thr Met
                30                  35                  40

ATG TCT GGG GAC ATG AAT ATA TGG CCC GAG TAC AAG AAC CGG ACC ATC      593
Met Ser Gly Asp Met Asn Ile Trp Pro Glu Tyr Lys Asn Arg Thr Ile
            45                  50                  55

TTT GAT ATC ACT AAT AAC CTC TCC ATT GTG ATC CTG GCT CTG CGC CCA      641
Phe Asp Ile Thr Asn Asn Leu Ser Ile Val Ile Leu Ala Leu Arg Pro
    60                  65                  70

TCT GAC GAG GGC ACA TAC GAG TGT GTT GTT CTG AAG TAT GAA AAA GAC      689
Ser Asp Glu Gly Thr Tyr Glu Cys Val Val Leu Lys Tyr Glu Lys Asp
 75                  80                  85                  90

GCT TTC AAG CGG GAA CAC CTG GCT GAA GTG ACG TTA TCA GTC AAA GCT      737
Ala Phe Lys Arg Glu His Leu Ala Glu Val Thr Leu Ser Val Lys Ala
                 95                 100                 105

GAC TTC CCT ACA CCT AGT ATA TCT GAC TTT GAA ATT CCA ACT TCT AAT      785
Asp Phe Pro Thr Pro Ser Ile Ser Asp Phe Glu Ile Pro Thr Ser Asn
             110                 115                 120

ATT AGA AGG ATA ATT TGC TCA ACC TCT GGA GGT TTT CCA GAG CCT CAC      833
Ile Arg Arg Ile Ile Cys Ser Thr Ser Gly Gly Phe Pro Glu Pro His
         125                 130                 135

CTC TCC TGG TTG GAA AAT GGA GAA GAA TTA AAT GCC ATC AAC ACA ACA      881
Leu Ser Trp Leu Glu Asn Gly Glu Glu Leu Asn Ala Ile Asn Thr Thr
     140                 145                 150

GTT TCC CAA GAT CCT GAA ACT GAG CTC TAT GCT GTT AGC AGC AAA CTG      929
Val Ser Gln Asp Pro Glu Thr Glu Leu Tyr Ala Val Ser Ser Lys Leu
155                 160                 165                 170
```

```
GAT TTC AAT ATG ACA ACC AAC CAC AGC TTC ATG TGT CTC ATC AAG TAT      977
Asp Phe Asn Met Thr Thr Asn His Ser Phe Met Cys Leu Ile Lys Tyr
            175                 180                 185

GGA CAT TTA AGA GTG AAT CAG ACC TTC AAC TGG AAT ACA ACC AAG CAA     1025
Gly His Leu Arg Val Asn Gln Thr Phe Asn Trp Asn Thr Thr Lys Gln
            190                 195                 200

GAG CAT TTT CCT GAT AAC CTG CTC CCA TCC TGG GCC ATT ACC TTA ATC     1073
Glu His Phe Pro Asp Asn Leu Leu Pro Ser Trp Ala Ile Thr Leu Ile
            205                 210                 215

TCA GTA AAT GGA ATT TTT GTG ATA TGC TGC CTG ACC TAC TGC TTT GCC     1121
Ser Val Asn Gly Ile Phe Val Ile Cys Cys Leu Thr Tyr Cys Phe Ala
            220                 225                 230

CCA AGA TGC AGA GAG AGA AGG AGG AAT GAG AGA TTG AGA AGG GAA AGT     1169
Pro Arg Cys Arg Glu Arg Arg Arg Asn Glu Arg Leu Arg Arg Glu Ser
235                 240                 245                 250

GTA CGC CCT GTA   TAACAGTGTC CGCAGAAGCA AGGGGCTGAA AAGATCTGAA       1221
Val Arg Pro Val

GGTAGCCTCC GTCATCTCTT CTGGGATACA TGGATCGTGG GGATCATGAG GCATTCTTCC   1281

CTTAACAAAT TTAAGCTGTT TTACCCACTA CCTCACCTTC TTAAAAACCT CTTTCAGATT   1341

AAGCTGAACA GTTACAAGAT GGCTGGCATC CCTCTCCTTT CTCCCCATAT GCAATTTGCT   1401

TAATGTAACC TCTTCTTTTG CCATGTTTCC ATTCTGCCAT CTTGAATTGT CTTGTCAGCC   1461

AATTCATTAT CTATTAAACA CTAATTTGAG                                    1491

(2) INFORMATION FOR SEQ ID NO:29:

(i) SEQUENCE CHARACTERISTICS:
        (A) LENGTH: 288 amino acids
        (B) TYPE: amino acid
        (C) TOPOLOGY: linear (ii) MOLECULE TYPE: protein
        (A) DESCRIPTION: B cell activation antigen; natural ligand
            for CD28 T cell surface antigen; transmembrane protein (ix) FEATURE:
        (A) NAME/KEY: signal sequence
        (B) LOCATION: -34 to -1
        (C) IDENTIFICATION METHOD: amino terminal sequencing of
            soluble protein
        (D) OTHER INFORMATION: hydrophobic (ix) FEATURE:
        (A) NAME/KEY: extracellular domain
        (B) LOCATION: 1 to 208
        (C) IDENTIFICATION METHOD: similarity with known
            sequence (ix) FEATURE:
        (A) NAME/KEY: transmembrane domain
        (B) LOCATION: 209 to 235
        (C) IDENTIFICATION METHOD: similarity with known
            sequence (ix) FEATURE:
        (A) NAME/KEY: intracellular domain
        (B) LOCATION: 236 to 254
        (C) IDENTIFICATION METHOD: similarity with known
            sequence (ix) FEATURE:
        (A) NAME/KEY: N-linked glycosylation
        (B) LOCATION: 19 to 21
        (C) IDENTIFICATION METHOD: similarity with known
            sequence (ix) FEATURE:
        (A) NAME/KEY: N-linked glycosylation
        (B) LOCATION: 55 to 57
```

```
            (C) IDENTIFICATION METHOD: similarity with known
                sequence (ix) FEATURE:
            (A) NAME/KEY: N-linked glycosylation
            (B) LOCATION: 64 to 66
            (C) IDENTIFICATION METHOD: similarity with known
                sequence (ix) FEATURE:
            (A) NAME/KEY: N-linked glycosylation
            (B) LOCATION: 152 to 154
            (C) IDENTIFICATION METHOD: similarity with known
                sequence (ix) FEATURE:
            (A) NAME/KEY: N-linked glycosylation
            (B) LOCATION: 173 to 175
            (C) IDENTIFICATION METHOD: similarity with known
                sequence (ix) FEATURE:
            (A) NAME/KEY: N-linked glycosylation
            (B) LOCATION: 177 to 179
            (C) IDENTIFICATION METHOD: similarity with known
                sequence (ix) FEATURE:
            (A) NAME/KEY: N-linked glycosylation
            (B) LOCATION: 192 to 194
            (C) IDENTIFICATION METHOD: similarity with known
                sequence (ix) FEATURE:
            (A) NAME/KEY: N-linked glycosylation
            (B) LOCATION: 198 to 200
            (C) IDENTIFICATION METHOD: similarity with known
                sequence (ix) FEATURE:
            (A) NAME/KEY: Ig V-set domain
            (B) LOCATION: 1 to 104
            (C) IDENTIFICATION METHOD: similarity with known
                sequence (ix) FEATURE:
            (A) NAME/KEY: Ig C-set domain
            (B) LOCATION:  105 to 202
            (C) IDENTIFICATION METHOD: similarity with known
                sequence (x) PUBLICATION INFORMATION:
            (A) AUTHORS: FREEMAN, GORDON J.
                         FREEDMAN, ARNOLD S.
                         SEGIL, JEFFREY M.
                         LEE, GRACE
                         WHITMAN, JAMES F.
                         NADLER, LEE M.
            (B) TITLE: B7, A New Member Of The Ig Superfamily With
                 Unique Expression On Activated And Neoplastic B Cells
            (C) JOURNAL: The Journal of Immunology
            (D) VOLUME: 143
            (E) ISSUE: 8
            (F) PAGES: 2714-2722
            (G) DATE:  15-OCT-1989
            (H) RELEVANT RESIDUES IN SEQ ID NO:29: From -26 to 262

(xi) SEQUENCE DESCRIPTION: SEQ ID NO:29:

Met Gly His Thr Arg Arg Gln Gly Thr Ser Pro Ser Lys Cys Pro Tyr
            -30                 -25                 -20

Leu Asn Phe Phe Gln Leu Leu Val Leu Ala Gly Leu Ser His Phe Cys
            -15                 -10                  -5

Ser Gly Val Ile His Val Thr Lys Glu Val Lys Glu Val Ala Thr Leu
     -1   1               5                  10

Ser Cys Gly His Asn Val Ser Val Glu Glu Leu Ala Gln Thr Arg Ile
```

```
                  15                  20                  25                  30
Tyr Trp Gln Lys Glu Lys Lys Met Val Leu Thr Met Met Ser Gly Asp
                    35                  40                  45

Met Asn Ile Trp Pro Glu Tyr Lys Asn Arg Thr Ile Phe Asp Ile Thr
                    50                  55                  60

Asn Asn Leu Ser Ile Val Ile Leu Ala Leu Arg Pro Ser Asp Glu Gly
                    65                  70                  75

Thr Tyr Glu Cys Val Val Leu Lys Tyr Glu Lys Asp Ala Phe Lys Arg
                    80                  85                  90

Glu His Leu Ala Glu Val Thr Leu Ser Val Lys Ala Asp Phe Pro Thr
 95                    100                 105                 110

Pro Ser Ile Ser Asp Phe Glu Ile Pro Thr Ser Asn Ile Arg Arg Ile
                    115                 120                 125

Ile Cys Ser Thr Ser Gly Gly Phe Pro Glu Pro His Leu Ser Trp Leu
                    130                 135                 140

Glu Asn Gly Glu Glu Leu Asn Ala Ile Asn Thr Thr Val Ser Gln Asp
                    145                 150                 155

Pro Glu Thr Glu Leu Tyr Ala Val Ser Ser Lys Leu Asp Phe Asn Met
        160                 165                 170

Thr Thr Asn His Ser Phe Met Cys Leu Ile Lys Tyr Gly His Leu Arg
175                 180                 185                 190

Val Asn Gln Thr Phe Asn Trp Asn Thr Thr Lys Gln Glu His Phe Pro
                    195                 200                 205

Asp Asn Leu Leu Pro Ser Trp Ala Ile Thr Leu Ile Ser Val Asn Gly
                    210                 215                 220

Ile Phe Val Ile Cys Cys Leu Thr Tyr Cys Phe Ala Pro Arg Cys Arg
                    225                 230                 235

Glu Arg Arg Arg Asn Glu Arg Leu Arg Arg Glu Ser Val Arg Pro Val
            240                 245                 250
```

(2) INFORMATION FOR SEQ ID NO:30:

(i) SEQUENCE CHARACTERISTICS:
        (A) LENGTH: 1716 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: no (vi) ORIGINAL SOURCE:
        (A) ORGANISM: Mus musculus
        (D) DEVELOPMENTAL STAGE: germ line
        (F) TISSUE TYPE: lymphoid
        (G) CELL TYPE: B lymphocyte
        (H) CELL LINE: 70Z and A20

(vii) IMMEDIATE SOURCE:
        (A) LIBRARY: cDNA in pCDM8 vector
        (B) CLONE: B7 #'s 1 and 29

(ix) FEATURE:
        (A) NAME/KEY: translated region
        (B) LOCATION: 249 to 1166 bp
        (C) IDENTIFICATION METHOD: similarity to other pattern (ix) FEATURE:
        (A) NAME/KEY: Alternate ATG initiation codons
        (B) LOCATION: 225 to 227 and 270 to 272
        (C) IDENTIFICATION METHOD: similarity to other pattern (xi) SEQUENCE DESCRIPTION: SEQ ID NO:30:

-continued

```
GAGTTTTATA CCTCAATAGA CTCTTACTAG TTTCTCTTTT TCAGGTTGTG AAACTCAACC    60

TTCAAAGACA CTCTGTTCCA TTTCTGTGGA CTAATAGGAT CATCTTTAGC ATCTGCCGGG   120

TGGATGCCAT CCAGGCTTCT TTTTCTACAT CTCTGTTTCT CGATTTTTGT GAGCCTAGGA   180

GGTGCCTAAG CTCCATTGGC TCTAGATTCC TGGCTTTCCC CATCATGTTC TCCAAAGCAT   240

CTGAAGCT ATG GCT TGC AAT TGT CAG TTG ATG CAG GAT ACA CCA CTC CTC    290
         Met Ala Cys Asn Cys Gln Leu Met Gln Asp Thr Pro Leu Leu
                     -35             -30             -25

AAG TTT CCA TGT CCA AGG CTC AAT CTT CTC TTT GTG CTG CTG ATT CGT     338
Lys Phe Pro Cys Pro Arg Leu Ile Leu Leu Phe Val Leu Leu Ile Arg
            -20             -15             -10

CTT TCA CAA GTG TCT TCA GAT GTT GAT GAA CAA CTG TCC AAG TCA GTG     386
Leu Ser Gln Val Ser Ser Asp Val Asp Glu Gln Leu Ser Lys Ser Val
        -5              -1  1               5

AAA GAT AAG GTA TTG CTG CCT TGC CGT TAC AAC TCT CCT CAT GAA GAT     434
Lys Asp Lys Val Leu Leu Pro Cys Arg Tyr Asn Ser Pro His Glu Asp
 10              15              20              25

GAG TCT GAA GAC CGA ATC TAC TGG CAA AAA CAT GAC AAA GTG GTG CTG     482
Glu Ser Glu Asp Arg Ile Tyr Trp Gln Lys His Asp Lys Val Val Leu
             30              35              40

TCT GTC ATT GCT GGG AAA CTA AAA GTG TGG CCC GAG TAT AAG AAC CGG     530
Ser Val Ile Ala Gly Lys Leu Lys Val Trp Pro Glu Tyr Lys Asn Arg
             45              50              55

ACT TTA TAT GAC AAC ACT ACC TAC TCT CTT ATC ATC CTG GGC CTG GTC     578
Thr Leu Tyr Asp Asn Thr Thr Tyr Ser Leu Ile Ile Leu Gly Leu Val
         60              65              70

CTT TCA GAC CGG GGC ACA TAC AGC TGT GTC GTT CAA AAG AAG GAA AGA     626
Leu Ser Asp Arg Gly Thr Tyr Ser Cys Val Val Gln Lys Lys Glu Arg
 75              80              85

GGA ACG TAT GAA GTT AAA CAC TTG GCT TTA GTA AAG TTG TCC ATC AAA     674
Gly Thr Tyr Glu Val Lys His Leu Ala Leu Val Lys Leu Ser Ile Lys
 90              95              100             105

GCT GAC TTC TCT ACC CCC AAC ATA ACT GAG TCT GGA AAC CCA TCT GCA     722
Ala Asp Phe Ser Thr Pro Asn Ile Thr Glu Ser Gly Asn Pro Ser Ala
             110             115             120

GAC ACT AAA AGG ATT ACC TGC TTT GCT TCC GGG GGT TTC CCA AAG CCT     770
Asp Thr Lys Arg Ile Thr Cys Phe Ala Ser Gly Gly Phe Pro Lys Pro
             125             130             135

CGC TTC TCT TGG TTG GAA AAT GGA AGA GAA TTA CCT GGC ATC AAT ACG     818
Arg Phe Ser Trp Leu Glu Asn Gly Arg Glu Leu Pro Gly Ile Asn Thr
             140             145             150

ACA ATT TCC CAG GAT CCT GAA TCT GAA TTG TAC ACC ATT AGT AGC CAA     866
Thr Ile Ser Gln Asp Pro Glu Ser Glu Leu Tyr Thr Ile Ser Ser Gln
 155             160             165

CTA GAT TTC AAT ACG ACT CGC AAC CAC ACC ATT AAG TGT CTC ATT AAA     914
Leu Asp Phe Asn Thr Thr Arg Asn His Thr Ile Lys Cys Leu Ile Lys
170             175             180             185

TAT GGA GAT GCT CAC GTG TCA GAG GAC TTC ACC TGG GAA AAA CCC CCA     962
Tyr Gly Asp Ala His Val Ser Glu Asp Phe Thr Trp Glu Lys Pro Pro
             190             195             200

GAA GAC CCT CCT GAT AGC AAG AAC ACA CTT GTG CTC TTT GGG GCA GGA    1010
Glu Asp Pro Pro Asp Ser Lys Asn Thr Leu Val Leu Phe Gly Ala Gly
             205             210             215

TTC GGC GCA GTA ATA ACA GTC GTC GTC ATC GTT GTC ATC ATC AAA TGC    1058
Phe Gly Ala Val Ile Thr Val Val Val Ile Val Val Ile Ile Lys Cys
             220             225             230

TTC TGT AAG CAC AGA AGC TGT TTC AGA AGA AAT GAG GCA AGC AGA GAA    1106
Phe Cys Lys His Arg Ser Cys Phe Arg Arg Asn Glu Ala Ser Arg Glu
```

```
                235                 240                 245
ACA AAC AAC AGC CTT ACC TTC GGG CCT GAA GAA GCA TTA GCT GAA CAG        1154
Thr Asn Asn Ser Leu Thr Phe Gly Pro Glu Glu Ala Leu Ala Glu Gln
250                 255                 260                 265

ACC GTC TTC CTT TAGTTCTTCT CTGTCCATGT GGGATACATG GTATTATGTG            1206
Thr Val Phe Leu

GCTCATGAGG TACAATCTTT CTTTCAGCAC CGTGCTAGCT GATCTTTCGG ACAACTTGAC      1266

ACAAGATAGA GTTAACTGGG AAGAGAAAGC CTTGAATGAG GATTTCTTTC CATCAGGAAG      1326

CTACGGGCAA GTTTGCTGGG CCTTTGATTG CTTGATGACT GAAGTGGAAA GGCTGAGCCC      1386

ACTGTGGGTG GTGCTAGCCC TGGGCAGGGG CAGGTGACCC TGGGTGGTAT AAGAAAAAGA      1446

GCTGTCACTA AAAGGAGAGG TGCCTAGTCT TACTGCAACT TGATATGTCA TGTTTGGTTG      1506

GTGTCTGTGG GAGGCCTGCC CTTTTCTGAA GAGAAGTGGT GGGAGAGTGG ATGGGGTGGG      1566

GGCAGAGGAA AAGTGGGGGA GAGGGCCTGG GAGGAGAGGA GGGAGGGGGA CGGGGTGGGG      1626

GTGGGGAAAA CTATGGTTGG GATGTAAAAA CGGATAATAA TATAAATATT AAATAAAAAG      1686

AGAGTATTGA GCAAAAAAAA AAAAAAAAA                                       1716
```

(2) INFORMATION FOR SEQ ID NO:31:

(i) SEQUENCE CHARACTERISTICS:
        (A) LENGTH: 306 amino acids
        (B) TYPE: amino acid
        (C) TOPOLOGY: linear (ii) MOLECULE TYPE: protein
        (A) DESCRIPTION: B lymphocyte activation antigen; Ig
            superfamily member; T cell costimulatory signal
            via activation of CD28 pathways, binds to CD28+
            T cells, transmembrane protein (ix) FEATURE:
        (A) NAME/KEY: signal sequence
        (B) LOCATION: -37 to -1
        (C) IDENTIFICATION METHOD: similarity with known
            sequence
        (D) OTHER INFORMATION: hydrophobic (ix) FEATURE:
        (A) NAME/KEY: extracellular domain
        (B) LOCATION: 1 to 210
        (C) IDENTIFICATION METHOD: similarity with known
            sequence (ix) FEATURE:
        (A) NAME/KEY: transmembrane domain
        (B) LOCATION: 211 to 235
        (C) IDENTIFICATION METHOD: similarity with known
            sequence (ix) FEATURE:
        (A) NAME/KEY: intracellular (cytoplasmic) domain
        (B) LOCATION: 236 to 269
        (C) IDENTIFICATION METHOD: similarity with known
            sequence (ix) FEATURE:
        (A) NAME/KEY: Ig V-set domain
        (B) LOCATION: 1 to 105
        (C) IDENTIFICATION METHOD: similarity with known
            sequence (ix) FEATURE:
        (A) NAME/KEY: Ig C-set domain
        (B) LOCATION: 106 to 199
        (C) IDENTIFICATION METHOD: similarity with known
            sequence (x) PUBLICATION INFORMATION:

-continued (A) AUTHORS: FREEMAN, GORDON J.
    GRAY, GARY S.
    GIMMI, CLAUDE D.
    LOMBARD, DAVID B.
    ZHOU, LIANG-JI
    WHITE, MICHAEL
    FINGEROTH, JOYCE D.
    GRIBBEN, JOHN G.
    NADLER, LEE M.
(B) TITLE: Structure, Expression, and T Cell Costimulatory
    Activity Of The Murine Homologue Of The Human B
    Lymphocyte Activation Antigen B7
(C) JOURNAL: Journal of Experimental Medicine
(D) VOLUME:
(E) ISSUE:
(F) PAGES:
(G) DATE: IN PRESS
(H) RELEVANT RESIDUES IN SEQ ID NO:31: From -37 to 269

(xi) SEQUENCE DESCRIPTION: SEQ ID NO:31:

```
Met Ala Cys Asn Cys Gln Leu Met Gln Asp Thr Pro Leu Leu Lys Phe
        -35                 -30                 -25

Pro Cys Pro Arg Leu Ile Leu Leu Phe Val Leu Leu Ile Arg Leu Ser
    -20                 -15                 -10

Gln Val Ser Ser Asp Val Asp Glu Gln Leu Ser Lys Ser Val Lys Asp
 -5              -1   1                  5                      10

Lys Val Leu Leu Pro Cys Arg Tyr Asn Ser Pro His Glu Asp Glu Ser
             15                  20                  25

Glu Asp Arg Ile Tyr Trp Gln Lys His Asp Lys Val Val Leu Ser Val
         30                  35                  40

Ile Ala Gly Lys Leu Lys Val Trp Pro Glu Tyr Lys Asn Arg Thr Leu
     45                  50                  55

Tyr Asp Asn Thr Thr Tyr Ser Leu Ile Ile Leu Gly Leu Val Leu Ser
 60                  65                  70                  75

Asp Arg Gly Thr Tyr Ser Cys Val Val Gln Lys Lys Glu Arg Gly Thr
 80                  85                  90

Tyr Gly Val Lys His Leu Ala Leu Val Lys Leu Ser Ile Lys Ala Asp
             95                 100                 105

Phe Ser Thr Pro Asn Ile Thr Glu Ser Gly Asn Pro Ser Ala Asp Thr
            110                 115                 120

Lys Arg Ile Thr Cys Phe Ala Ser Gly Gly Phe Pro Lys Pro Arg Phe
            125                 130                 135

Ser Trp Leu Glu Asn Gly Arg Glu Leu Pro Gly Ile Asn Thr Thr Ile
140                 145                 150                 155

Ser Gln Asp Pro Glu Ser Glu Leu Tyr Thr Ile Ser Ser Gln Leu Asp
                160                 165                 170

Phe Asn Thr Thr Arg Asn His Thr Ile Lys Cys Leu Ile Lys Tyr Gly
            175                 180                 185

Asp Ala His Val Ser Glu Asp Phe Thr Trp Glu Lys Pro Pro Glu Asp
            190                 195                 200

Pro Pro Asp Ser Lys Asn Thr Leu Val Leu Phe Gly Ala Gly Phe Gly
205                 210                 215

Ala Val Ile Thr Val Val Ile Val Val Ile Ile Lys Cys Phe Cys
220                 225                 230                 235

Lys His Arg Ser Cys Phe Arg Arg Asn Glu Ala Ser Arg Glu Thr Asn
            240                 245                 250

Asn Ser Leu Thr Phe Gly Pro Glu Glu Ala Leu Ala Glu Gln Thr Val
            255                 260                 265

Phe Leu
```

(2) INFORMATION FOR SEQ ID NO:32:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:32:

GGCACTAGGT CTCCAGCTTG AGATCACAGT TCTCTCTAC                    39

(2) INFORMATION FOR SEQ ID NO:33:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:33:

GCTTGAATCT TCAGAGGAGC GGAGTGGACA CCTGTGG                      37

(2) INFORMATION FOR SEQ ID NO:34:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:34:

GCTCCTCTGA AGATTCAAGC                                      20

(2) INFORMATION FOR SEQ ID NO:35:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

GGCACTATGA TCAGGGGGAG GCTGAGGTCC                            30

(2) INFORMATION FOR SEQ ID NO:36:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:36:

GCATTTTAAG CTTTTTCCTG ATCAGGAGCC CAAATCTTCT GACAAAACTC ACACATCTCC      60

ACCGTCTCCA GGTAAGCC                                          78

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:37:

```
TAATACGACT CACTATAGGG                                           20
```

(2) INFORMATION FOR SEQ ID NO:38:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

```
GAGCATTTTC CTGATCAGGA GTCCAAATAT GGTCCCCCAT CCCATCATCC CCAGGTAAGC    60

CAACCC                                                              66
```

(2) INFORMATION FOR SEQ ID NO:39:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

```
GCAGAGGAAT CGAGCTCGGT ACCCGGGGAT CCCCAGTGTG GGGACAGTGG GACCGCTCTG    60

CCTCCC                                                              66
```

(2) INFORMATION FOR SEQ ID NO:40:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:40:

```
GGGTTTTGGG GGGAAGAGGA AGACTGACGG TGCCCCCTCG GCTTCAGGTG CTGAGGAAG     59
```

(2) INFORMATION FOR SEQ ID NO:41:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:41:

```
CATCTCTTCC TCAGCACCTG AAGCCGAGGG GGCACCGTCA GTCTTCCTCT TCCCCC        56
```

```
(2) INFORMATION FOR SEQ ID NO:42:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:42:

CGCACGTGAC CTCAGGGGTC CGGGAGATCA TGAGAGTGTC CTTGGGTTTT GGGGGGAACA      60

GGAAGACTGA TGGTGCCCCC TCGAACTCAG GTGCTGAGG                            99

(2) INFORMATION FOR SEQ ID NO:43:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:43:

CCTCAGCACC TGAGTTCGAG GGGGCACCAT CAGTCTCCTG TTCCCCCCAA AACCCAAGGA      60

CACTCTCATG ATCTCCCGGA CCCCTGAGGT CACGTGCG                             98

(2) INFORMATION FOR SEQ ID NO:44:

(i) SEQUENCE CHARACTERISTICS:
        (A) LENGTH: 330 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..330

(xi) SEQUENCE DESCRIPTION: SEQ ID NO:44:

GCT CCT CTG AAG ATT CAA GCT TAT TTC AAT GAG ACT GCA GAC CTG CCA       48
Ala Pro Leu Lys Ile Gln Ala Tyr Phe Asn Glu Thr Ala Asp Leu Pro
 1               5                  10                  15

TGC CAA TTT GCA AAC TCT CAA AAC CAA AGC CTG AGT GAG CTA GTA GTA       96
Cys Gln Phe Ala Asn Ser Gln Asn Gln Ser Leu Ser Glu Leu Val Val
                20                  25                  30

TTT TGG CAG GAC CAG GAA AAC TTG GTT CTG AAT GAG GTA TAC TTA GGC      144
Phe Trp Gln Asp Gln Glu Asn Leu Val Leu Asn Glu Val Tyr Leu Gly
            35                  40                  45

AAA GAG AAA TTT GAC AGT GTT CAT TCC AAG TAT ATG GGC CGC ACA AGT      192
Lys Glu Lys Phe Asp Ser Val His Ser Lys Tyr Met Gly Arg Thr Ser
    50                  55                  60

TTT GAT TCG GAC AGT TGG ACC CTG AGA CTT CAC AAT CTT CAG ATC AAG      240
Phe Asp Ser Asp Ser Trp Thr Leu Arg Leu His Asn Leu Gln Ile Lys
65                  70                  75                  80

GAC AAG GGC TTG TAT CAA TGT ATC ATC CAT CAC AAA AAG CCC ACA GGA      288
Asp Lys Gly Leu Tyr Gln Cys Ile Ile His His Lys Lys Pro Thr Gly
                85                  90                  95

ATG ATT CGC ATC CAC CAG ATG AAT TCT AGG CTG TCA GTG CTT              330
Met Ile Arg Ile His Gln Met Asn Ser Arg Leu Ser Val Leu
            100                 105                 110
```

(2) INFORMATION FOR SEQ ID NO:45:

(i) SEQUENCE CHARACTERISTICS:
        (A) LENGTH: 110 amino acids
        (B) TYPE: amino acid
        (D) TOPOLOGY: linear (ii) MOLECULE TYPE: protein (xi) SEQUENCE DESCRIPTION: SEQ ID NO:45:

```
Ala Pro Leu Lys Ile Gln Ala Tyr Phe Asn Glu Thr Ala Asp Leu Pro
  1               5                  10                  15

Cys Gln Phe Ala Asn Ser Gln Asn Gln Ser Leu Ser Glu Leu Val Val
             20                  25                  30

Phe Trp Gln Asp Gln Glu Asn Leu Val Leu Asn Glu Val Tyr Leu Gly
         35                  40                  45

Lys Glu Lys Phe Asp Ser Val His Ser Lys Tyr Met Gly Arg Thr Ser
 50                  55                  60

Phe Asp Ser Asp Ser Trp Thr Leu Arg Leu His Asn Leu Gln Ile Lys
 65                  70                  75                  80

Asp Lys Gly Leu Tyr Gln Cys Ile Ile His His Lys Lys Pro Thr Gly
                 85                  90                  95

Met Ile Arg Ile His Gln Met Asn Ser Arg Leu Ser Val Leu
                100                 105                 110
```

(2) INFORMATION FOR SEQ ID NO:46:

(i) SEQUENCE CHARACTERISTICS:
        (A) LENGTH: 306 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..310

(xi) SEQUENCE DESCRIPTION: SEQ ID NO:46:

```
GCT AAC TTC AGT CAA CCT GAA ATA GTA CCA ATT TCT AAT ATA ACA GAA      48
Ala Asn Phe Ser Gln Pro Glu Ile Val Pro Ile Ser Asn Ile Thr Glu
  1               5                  10                  15

AAT GTG TAC ATA AAT TTG ACC TGC TCA TCT ATA CAC GGT TAC CCA GAA      96
Asn Val Tyr Ile Asn Leu Thr Cys Ser Ser Ile His Gly Tyr Pro Glu
             20                  25                  30

CCT AAG AAG ATG AGT GTT TTG CTA AGA ACC AAG AAT TCA ACT ATC GAG     144
Pro Lys Lys Met Ser Val Leu Leu Arg Thr Lys Asn Ser Thr Ile Glu
         35                  40                  45

TAT GAT GGT ATT ATG CAG AAA TCT CAA GAT AAT GTC ACA GAA CTG TAC     192
Tyr Asp Gly Ile Met Gln Lys Ser Gln Asp Asn Val Thr Glu Leu Tyr
 50                  55                  60

GAC GTT TCC ATC AGC TTG TCT GTT TCA TTC CCT GAT GTT ACG AGC AAT     240
Asp Val Ser Ile Ser Leu Ser Val Ser Phe Pro Asp Val Thr Ser Asn
 65                  70                  75                  80

ATG ACC ATC TTC TGT ATT CTG GAA ACT GAC AAG ACG CGG CTT TTA TCT     288
Met Thr Ile Phe Cys Ile Leu Glu Thr Asp Lys Thr Arg Leu Leu Ser
                 85                  90                  95

TCA CCT TTC TCT ATA GAG                                             306
Ser Pro Phe Ser Ile Glu
                100
```

(2) INFORMATION FOR SEQ ID NO:47:

(i) SEQUENCE CHARACTERISTICS:
    (A) LENGTH: 102 amino acids
    (B) TYPE: amino acid
    (D) TOPOLOGY: linear (ii) MOLECULE TYPE: protein (xi) SEQUENCE DESCRIPTION: SEQ ID NO:47:

| Ala | Asn | Phe | Ser | Gln | Pro | Glu | Ile | Val | Pro | Ile | Ser | Asn | Ile | Thr | Glu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asn | Val | Tyr | Ile | Asn | Leu | Thr | Cys | Ser | Ser | Ile | His | Gly | Tyr | Pro | Glu |
|     |     |     | 20  |     |     |     |     | 25  |     |     |     |     | 30  |     |     |

| Pro | Lys | Lys | Met | Ser | Val | Leu | Leu | Arg | Thr | Lys | Asn | Ser | Thr | Ile | Glu |
|     |     | 35  |     |     |     |     | 40  |     |     |     |     | 45  |     |     |     |

| Tyr | Asp | Gly | Ile | Met | Gln | Lys | Ser | Gln | Asp | Asn | Val | Thr | Glu | Leu | Tyr |
|     | 50  |     |     |     |     | 55  |     |     |     |     | 60  |     |     |     |     |

| Asp | Val | Ser | Ile | Ser | Leu | Ser | Val | Ser | Phe | Pro | Asp | Val | Thr | Ser | Asn |
| 65  |     |     |     |     | 70  |     |     |     |     | 75  |     |     |     |     | 80  |

| Met | Thr | Ile | Phe | Cys | Ile | Leu | Glu | Thr | Asp | Lys | Thr | Arg | Leu | Leu | Ser |
|     |     |     |     | 85  |     |     |     |     | 90  |     |     |     |     | 95  |     |

Ser Pro Phe Ser Ile Glu
            100

(2) INFORMATION FOR SEQ ID NO:48:

(i) SEQUENCE CHARACTERISTICS:
       (A) LENGTH: 47 base pairs
       (B) TYPE: nucleic acid
       (C) STRANDEDNESS: single
       (D) TOPOLOGY: linear (ii) MOLECULE TYPE: oligonucleotide (xi) SEQUENCE DESCRIPTION: SEQ ID NO:48:

GCAACCGGAA GCTTGCCACC ATGGGGGTAC TGCTCACACA GAGGACG          47

(2) INFORMATION FOR SEQ ID NO:49:

(i) SEQUENCE CHARACTERISTICS:
       (A) LENGTH: 63 base pairs
       (B) TYPE: nucleic acid
       (C) STRANDEDNESS: single
       (D) TOPOLOGY: linear (ii) MOLECULE TYPE: oligonucleotide (xi) SEQUENCE DESCRIPTION: SEQ ID NO:49:

AGTCTCATTG AAATAAGCTT GAATCTTCAG AGGAGCCATG CTGGCCATGC TTGGAAACAG     60

GAG                                                                   63

(2) INFORMATION FOR SEQ ID NO:50:

(i) SEQUENCE CHARACTERISTICS:
       (A) LENGTH: 62 base pairs
       (B) TYPE: nucleic acid
       (C) STRANDEDNESS: single
       (D) TOPOLOGY: linear (ii) MOLECULE TYPE: oligonucleotide (xi) SEQUENCE DESCRIPTION: SEQ ID NO:50:

CTCCTGTTTC CAAGCATGGC CAGCATGGCT CCTCTGAAGA TTCAGGCTTA TTTCAATGAG     60

AC                                                                   62

(2) INFORMATION FOR SEQ ID NO:51:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:51:

```
TGTGTGTGGA ATTCTCATTA CTGATCAAGC ACTGACAGTT CAGAATTCAT C            51
```

(2) INFORMATION FOR SEQ ID NO:52:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:52:

```
AGAAATTGGT ACTATTTCAG GTTGACTGAA GTTAGCCATG CTGGCCATGC TTGGAAACAG   60

GAG                                                                63
```

(2) INFORMATION FOR SEQ ID NO:53:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:53:

```
CTCCTGTTTC CAAGCATGGC CAGCATGGCT AACTTCAGTC AACCTGAAAT AGTACCAATT   60

TC                                                                 62
```

(2) INFORMATION FOR SEQ ID NO:54:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:54:

```
CTCAAGCTTG CCACCATGGG GGTACTGCTC ACACAGAGGA CGCTGCTCAG TCTGGTCCTT   60

GCACTCCTGT TTCCGAGCAT GGCGAGCATG GGTCTTTCTC ACTTC                  105
```

(2) INFORMATION FOR SEQ ID NO:55:

(i) SEQUENCE CHARACTERISTICS:
        (A) LENGTH: 45 base pairs
        (B) TYPE: nucleic acid
        (C) STRANDEDNESS: single
        (D) TOPOLOGY: linear -continued (ii) MOLECULE TYPE: oligonucleotide (xi) SEQUENCE DESCRIPTION: SEQ ID NO:55:

TGTGTGTGGA ATTCTCATTA CTGATCAGGA AAATGCTCTT GCTTG    45

What is claimed is:

1. A method for blocking binding interactions of B7-2 with CD28 or CTLA4 an immune cell, comprising contacting the immune cell with an antibody that recognizes the polypeptide shown in SEQ ID NO:2 to thereby block the binding interactions of B7-2 with the CD28 or CTLA4 on the immune cell.

2. The method of claim 1, wherein the antibody is a polyclonal antibody.

3. The method of claim 1, wherein the antibody is a monoclonal antibody.

4. The method of claim 1, wherein the antibody is a chimeric antibody.

5. The method of claim 1, wherein the antibody is a humanized antibody.

6. The method of claim 1, wherein the antibody is a human antibody.

7. The method of claim 1, wherein the antibody is a F(ab')$_2$ or an Fab' fragment.

8. The method of claim 1, wherein the antibody is produced by a hybridoma selected from the group consisting of: ATCC accession number HB 11688, ATCC accession number HB 11687, and ATCC accession number 11686.

9. The method of claim 1, wherein the step of contacting is performed in vitro.

10. The method of claim 1, wherein the step of contacting is performed in vivo.

11. The method of claim 1, wherein the B7-2 is human B7-2.

12. A method for inhibiting proliferation of a T cell comprising contacting a cell bearing B7-2 an antibody that recognize the polypeptide shown in SEQ ID NO:20 to thereby inhibit the proliferation of the cell.

13. The method of claim 12, wherein the step of contacting is performed in vitro.

14. The method of claim 12, wherein the step of contacting is performed in vivo.

15. The method of claim 12, wherein the B7-2 is human B7-2.

16. The method of claim 12, wherein the antibody is a polyclonal antibody.

17. The method of claim 12, wherein the antibody is a monoclonal antibody.

18. The method of claim 12, wherein the antibody is a chimeric antibody.

19. The method of claim 12, wherein the antibody is a humanized antibody.

20. The method of claim 12, wherein the antibody is a human antibody.

21. The method of claim 12, wherein the antibody is a F(ab')$_2$ or an Fab' fragment.

22. The method of claim 12, wherein the antibody is produced by a hybridoma selected from the group consisting of: ATCC accession number HB 11688, ATCC accession number HB 11687, and ATCC accession number HB 11686.

23. A method for inhibiting cytokine production by a T cell comprising contacting cell bearing B7-2 with an antibody that recognize the polypeptide shown in SEQ ID NO:2, thereby inhibiting cytokine production by the T cell.

24. The method of claim 23, wherein the step of contacting is performed in vitro.

25. The method of claim 23, wherein the step of contacting is performed in vivo.

26. The method of claim 23, wherein the B7-2.

27. The method of claim 23, wherein the antibody is a polyclonal antibody.

28. The method of claim 23, wherein the antibody is a monoclonal antibody.

29. The method of claim 23, wherein the antibody is a chimeric antibody.

30. The method of claim 23, wherein the antibody is a humanized antibody.

31. The method of claim 23, wherein the antibody is a human antibody.

32. The method of claim 23, wherein the antibody is a F(ab')$_2$ or an Fab' fragment.

33. The method of claim 23, wherein the antibody is a produced by a hybridoma selected from the group consisting of: ATCC accession number HB 11688, ATCC accession number HB 11687, and ATCC accession number HB 11686.

34. A method for downregulating an immune response comprising administering an antibody that recognizes the polypeptide shown in SEQ ID NO:2 to a subject, such that an immune response is downregulated.

35. The method of claim 34, wherein the antibody is administered prophylactically.

36. The method of claim 34, wherein the antibody is administered therapeutically.

37. The method of claim 34, wherein the subject is a human subject.

38. The method of claim 34, wherein the antibody is a polyclonal antibody.

39. The method of claim 34, wherein the antibody is a monoclonal antibody.

40. The method of claim 34, wherein the antibody is a chimeric antibody.

41. The method of claim 34, wherein the antibody is a humanized antibody.

42. The method of claim 34, wherein the antibody is a human antibody.

43. The method of claim 34, wherein the antibody is a F(ab')$_2$ or an Fab' fragment.

44. The method of claim 34, wherein the antibody is a produced by a hybridoma selected from the group consisting of: ATCC accession number HB 11688, ATCC accession number HB 11687, and ATCC accession number HB 11686.

45. A method for blocking binding interactions of B7-2 with CD28 or CTLA4 on an immune cell, comprising contacting the immune cell with an antibody that recognizes the polypeptide shown in SEQ ID NO:23 to thereby block the binding interactions of B7-2 with the ligand on the immune cell.

46. A method for inhibiting proliferation of a T cell comprising contacting the T cell with an antibody that recognizes the polypeptide shown in SEQ ID NO:23 to thereby inhibit the proliferation of the T cell.

47. A method for inhibiting cytokine production by a T cell comprising contacting the T cell with an antibody that recognizes the polypeptide shown in SEQ ID NO:23, thereby inhibiting cytokine production by the T cell.

* * * * *

UNITED STATES PATENT AND TRADEMARK OFFICE
CERTIFICATE OF CORRECTION

PATENT NO. : 6,824,779 B1
DATED : November 30, 2004
INVENTOR(S) : Gordon J. Freeman et al.

It is certified that error appears in the above-identified patent and that said Letters Patent is hereby corrected as shown below:

Column 119,
Line 12, add -- on -- after "CTLA4".
Line 39, add -- with -- after "B7-2".
Lines 40 and 64, replace "recognize", for -- recognizes --.
Line 40, replace "20" for -- 2 --.
Line 63, add -- a -- after "contacting"

Column 120,
Line 12, after "B7-2", add -- is human B7-2 --.

Signed and Sealed this

Thirty-first Day of May, 2005

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,824,779 B1 | Page 1 of 1 |
| APPLICATION NO. | : 09/425516 | |
| DATED | : November 30, 2004 | |
| INVENTOR(S) | : Gordon J. Freeman et al. | |

It is certified that error appears in the above-identified patent and that said Letters Patent is hereby corrected as shown below:

On the Title Page, Item (63)

(a) "Continuation of application No. 08/479,744, filed on Jun. 5, 1995, now Pat. No. 6,084,067, which is a continuation-in-part of application No. 08/280,757, filed on Jul. 26, 1994, now Pat. No. 6,130,316, which is a continuation-in-part of application No. 08/109,393, filed on Aug. 19, 1993, now abandoned, which is a continuation-in-part of application No. 08/101,624, filed on Jul. 26, 1993, now Pat. No. 5,942,607, which is a continuation-in-part of application No. 08/147,773, filed on Nov. 3, 1993, now abandoned." should be On the Title Page, Item (63)

--Continuation of application No. 08/479,744, filed on Jun. 5, 1995, now Pat. No. 6,084,067, which is a continuation-in-part of application No. 08/280,757, filed on Jul. 26, 1994, now Pat. No. 6,130,316, which is a continuation-in-part of application No. 08/109,393, filed on Aug. 19, 1993, now abandoned, which is a continuation-in-part of application No. 08/101,624, filed on Jul. 26, 1993, now Pat. No. 5,942,607. U.S. Ser. No. 08/479,744, filed on Jun. 5, 1995, now Pat. No. 6,084,067, is also a continuation-in-part of application No. 08/147,773, filed on Nov. 3, 1993, now abandoned.--

Signed and Sealed this

Eighth Day of July, 2008

JON W. DUDAS
*Director of the United States Patent and Trademark Office*